(12) United States Patent
Gorodeski et al.

(10) Patent No.: US 7,767,789 B2
(45) Date of Patent: Aug. 3, 2010

(54) TRUNCATED PROTEINS AS CANCER MARKERS

(75) Inventors: George Gorodeski, Beachwood, OH (US); Ying-Hong Feng, Germantown, MD (US); Xin Li, Solon, OH (US)

(73) Assignees: University Hopitals of Cleveland, Cleveland, OH (US); The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 0 days.

(21) Appl. No.: 11/446,420

(22) Filed: Jun. 2, 2006

(65) Prior Publication Data

US 2007/0020706 A1 Jan. 25, 2007

Related U.S. Application Data

(60) Provisional application No. 60/686,770, filed on Jun. 2, 2005, provisional application No. 60/778,993, filed on Mar. 3, 2006.

(51) Int. Cl.
*C07K 14/82* (2006.01)
*C12P 21/06* (2006.01)
*C07K 16/30* (2006.01)
*G01N 33/574* (2006.01)
*A61K 30/00* (2006.01)

(52) U.S. Cl. ................................ 530/350
(58) Field of Classification Search ................ 530/350
See application file for complete search history.

(56) References Cited

U.S. PATENT DOCUMENTS

| | | | |
|---|---|---|---|
| 4,357,272 A | 11/1982 | Polson | 260/112 |
| RE33,994 E | 7/1992 | Baker et al. | 424/465 |
| 5,194,596 A * | 3/1993 | Tischer et al. | 530/399 |
| 5,260,203 A | 11/1993 | Lander et al. | 435/172.3 |
| 5,350,836 A * | 9/1994 | Kopchick et al. | 530/399 |
| 5,565,332 A | 10/1996 | Hoogenboom et al. | 435/69.1 |
| 5,585,089 A | 12/1996 | Queen et al. | 424/133.1 |
| 5,658,727 A | 8/1997 | Barbas et al. | 435/6 |
| 5,904,922 A | 5/1999 | Carroll | 424/130.1 |
| 6,150,420 A | 11/2000 | Houdi et al. | 514/649 |
| 6,294,192 B1 | 9/2001 | Patel et al. | 424/451 |
| 6,369,113 B2 | 4/2002 | Young | 514/649 |
| 6,835,810 B2 | 12/2004 | Hwu | 530/324 |
| 6,866,845 B1 | 3/2005 | Ward et al. | 424/139.1 |

OTHER PUBLICATIONS

Cheewatrakoolpong et al. (Biochem. Biophys. Res. Commun. 332:17-27 (2005)).*
Georgio et al. (J. Invest. Dermatol. 125:482-490 (2005).*
Benjamin et al., 1998, Development 125:1591-1598.*
Vukicevic et al. (1996, PNAS USA 93:9021-9026).*
Massague, 1987, Cell 49:437-438.*
Pilbeam et al., 1993, Bone 14:717-720.*
Skolnick et al. (2000, Trends in Biotech. 18:34-39).*
Bork (2000, Genome Research 10:398-400).*
Doerks et al. (1998, Trends in Genetics 14:248-250).*
Smith et al. (1997, Nature Biotechnology 15:1222-1223).*
Brenner (1999, Trends in Genetics 15:132-133).*
Bork (1996, Trends in Genetics 12:425-427).*
Bowie et al. (1990, Science 247:1306-1310).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987)).*
Lin et al Biochemistry USA vol. 14:1559-1563 (1975).*
Dunnen et al., Hum. Mutat. 14(2): 95-102 (1999), Abstract.*
Stedman's Medical Dictionary, 27th Ed. definition for "gene" (p. 1, Dec. 27, 2008).*
yourdictionary.com definition for "gene" (p. 1, Dec. 27, 2008).*
Ashkenazi et al., "Death receptors: signaling and modulation" *Science* 281:1305-1308, 1998.
Barak et al., "A β-arrestin/green fluorescent protein biosensor for detecting G protein-coupled receptor activation" *J Biol Chem* 272:27497-27500, 1997.
Bardini et al., "Distribution of P2X receptor subtypes in the rat female reproductive tract at late pro-oestrus/early oestrus" *Cell Tissue Res* 299:105-113, 2000.
P. Calabresi and B.A. Chabner, In: Goodman and Gilman The Pharmacological Basis of Therapeutics. Pergamon Press, 8th Edition, pp. 1209-1240.
Di Virgilio et al., "Cytolytic P2X purinoceptors" *Cell Death Differ* 5:191-199, 1998.
Di Virgilio et al., "Nucleotide receptors: an emerging family of regulatory molecules in blood cells" *Blood* 97:587-600; 2001.
Dubyak et al., "Signal transduction via P2-purinergic receptors for extracellular ATP and other nucleotides" *Am J Physiol* 265:C577-C606, 1993.
Ellis et al., "Mechanisms and functions of cell death" *Annul Rev Cell Biol* 7:663-698, 1991.
Elzaim et al., "Generation of Neutralizing Antipeptide Antibodies to the Enzymatic Domain of *Pseudomonas aeruginosa* Exotoxin A" *Infect Immun.* 66:2170-2179, 1998.
Feng et al., "ATP stimulates GRK-3-phosphorylation and b-arrestin-2-dependent internalization of the P2X7 receptor" *Am J Physiol Cell Physiol* 288(6):C1342-C1356, 2005.
Gerlach, J.H. et al., "Multidrug resistance" *Canver Surveys*, 5:25-46, 1986.

(Continued)

*Primary Examiner*—Lynn Bristol
(74) *Attorney, Agent, or Firm*—Medlen & Carroll, LLP

(57) ABSTRACT

Methods/reagents for detecting and/or treating cancers or potential cancers are disclosed. In one embodiment, methods and reagents for detecting truncated forms of P2X$_7$ protein in cells are described. In one embodiment, methods and reagents for increasing the amount and/or activity of full-length P2X$_7$ in cells are described. In one embodiment, methods and reagents for decreasing the amount and/or activity of truncated P2X$_7$ in cells are described.

4 Claims, 63 Drawing Sheets
(1 of 63 Drawing Sheet(s) Filed in Color)

OTHER PUBLICATIONS

Goldie, J.H. and Coldman, Andrew J., "The Genetic Origin of Drug Resistance in Neoplams: Implications for Systemic Therapy" *Cancer Research*, 44:3643-3653, 1984.

Gorodeski et al., "A novel fluorescence chamber for the determination of volume changes in human CaSki cell cultures attached on filters" *Cell Biochem Biophys* 29:307-332, 1998.

Gorodeski, G.I. "Expression regulation and function of P2X4 receptor in human cervical epithelial cells" *Am J Physiol* 282:C84-C93, 2002.

Gorodeski et al., "Human uterine cervical epithelial ceils grown permeable support- a model for the study of differentiation and transepthelial transport" *Differentiation* 56:107-118, 1994.

Gorodeski et al., "Maintenance of in vivo-like keratin expression, sex steroid responsiveness and estrogen receptor expression in cultured human ectocervical epithelial cells" *Endocrinology* 126:399-406, 1990.

Humphreys et al., "Induction of the P2z/P2X7 nucleotide receptor and associated phospholipase D activity by lipopolysaccharide and IFN-γ in the human THP-1 monocytic cell line" *J Immunol* 157:5627-5637, 1996.

Jacobberger et al., "Transforming growth factor β regulation of epidermal growth factor receptor in ectocervical epithelial cells" *Exp Cell Res* 220:390-396, 1995.

Kennet, R.H., "Ch 10- Monoclonal Antibodies against Human Tumor-Associated Antigens" *In: Monoclonal Antibodies, Hybridoma- A New Dimension in Biological Analysis*, Plenum Press, pp. 155-168, 1980.

Kettleborough et al., "Humanization of a mouse monoclonal antibody by CDR-grafting: the importance of framework residues on loop conformation" *Protein Engineering* 4:773-783, 1991.

Köhler et al., "Continuous cultures of fused cells secreting antibody of predefined specificity" *Nature* 256: 495, 1975.

Kozbor et al., "The production of monoclonal antibodies from human lymphocytes" *Immunol. Today* 4:72-79, 1983.

Lohse et al., "Receptor specific desensitizations with purified proteins. Kinase dependence and receptor specificity of β-arrestin and arrestin in the β2-adrenergic receptor and rhodospin systems" *J Biol Chem* 267:8558-8564, 1993.

Lohse et al., "β-arrestin: a protein that regulates β-adrenergic receptor function" *Science* 248:1547-1550, 1990.

Luttrell et al., "The role of β-arrestins in the termination and transduction of G-protein-coupled receptor signals" *J Cell Sci* 115:455-465, 2002.

MacKenzie et al., "Rapid secretion of interleukin-1β by microvesicle shedding" *Immunity* 15:825-834, 2001.

Mandelblatt, "Squamous cell of the cervix, immune and HPV: is cervical age-related neoplasm?" *Adv Exp Med Biol* 330:13-26, 1993.

McPherson et al., "Signaling on the Endocytic Pathway" *Traffic* 2:375-384, 2001.

Murgia et al., "Characterization of the cytotoxic effect of extracellular ATP in J774 mouse macrophages" *Biochem J* 288:897-901, 1992.

Nicke et al., "P2X1 and P2X3 receptors form stable trimers: a novel structural motif of ligand-gated tion channels" *EMBO J* 17:3016-3028, 1998.

Oakley et al. "Molecular Determinants Underlying the Formation of Stable Intracellular G Protein-coupled Receptor-β-Arrestin Complexes after Receptor Endocytosis" *J Biol Chem* 276:19452-19460, 2001.

Ralevie et al., "Receptors for purines and pyrimidines" *Pharmacol Rev* 50:413-492, 1998.

Ramirez et al., "P2X purinergic receptor channel expression and function in bovine aortic endothelium" *Am J Physiol* 282:H2106-H2116, 2002.

Schachter et al., "HEK293 human embryonic kidney cells endogenously express the P2Y1 and P2Y2 receptors" *Neuropharmacology* 36:1181-1187, 1997.

Sime et al., "Methods for the growth of equine airway epithelial cells in culture" *Res Vet Sci* 62:30-33, 1997.

Smart et al., "Pore formation is not associated with macroscopic redistribution of P2X7-receptors" *Am J Physiol* 283:C77-C84, 2002.

Suh et al., "P2X7 nucleotide receptor mediation of membrane pore formation and superoxide generation in human promyelocytes and neutrophils" *J Immunol* 166:6754-6764, 2001.

Torres et al., "Hetero-oligomeric assembly of P2X receptor subunits" *J Biol Chem* 274:6653-6659, 1999.

Vijayalakshmi et al., "Estradiol-regulated transamidation of keratins by vaginal epithelial cell transglutaminase" *Exp Cell Res* 214:358-366, 1994.

Wang et al., "Antiapoptic Effects of estrogen in normal and cancer human cervical epithelia cells" *Endocrinol* 145:5568-5579, 2004.

Wang et al., "EGF facilities epinephrine inhibition of P2X7-receptor mediated pore formation and apoptosis: a novel signaling network" *Endocrinology* 146:164-174, 2005.

Wang et al., "P2X7-receptor mediated apoptosis of human cervical epithelial cells" *Am J Physiol Cell Physiol* 287:C1349-C1358, 2004.

Wells "EGF receptor" *Int Biochem Cell Biol* 31:637-643, 1999.

Zastrow, M, "Mechanisms regulating membrane trafficking of G protein-coupled receptors in the endocytic pathway" *Life Sci* 74:217-224, 2003.

* cited by examiner

P2X7 RECEPTOR: FULL LENGTH: MARKED EXONS MARKED TRANSMEMBRANE SEGMENTS

```
        1 ATGCCGGCCTGCTGCAGCTGCAGTGATGTTTTCCAGTATGAGACGAACAA
  1 (+1)   M  P  A  C  C  S  C  S  D  V  F  Q  Y  E  T  N  K
       51 AGTCACTCGGATCCAGAGCATGAATTATGGCACCATTAAGTGGTTCTTCC
 18 (+1)   V  T  R  I  Q  S  M  N  Y  G  T  I  K  W  F  F
      101 ACGTGATCATCTTTTCCTACGTTTGCTTTGCTCTGGTGAGTGACAAGCTG
 34 (+1)   H  V  I  I  F  S  Y  V  C  F  A  L  V  S  D  K  L
      151 TACCAGCGGAAAGAGCCTGTCATCAGTTCTGTGCACACCAAGGTGAAGGG
 51 (+1)   Y  Q  R  K  E  P  V  I  S  S  V  H  T  K  V  K  G
      201 GATAGCAGAGGTGAAAGAGGAGATCGTGGAGAATGGAGTGAAGAAGTTGG
 68 (+1)   I  A  E  V  K  E  E  I  V  E  N  G  V  K  K  L
      251 TGCACAGTGTCTTTGACACCGCAGACTACACCTTCCCTTTGCAGGGGAAC
 84 (+1)   V  H  S  V  F  D  T  A  D  Y  T  F  P  L  Q  G  N
      301 TCTTTCTTCGTGATGACAAACTTTCTAAAACAGAAGGCCAAGAGCAGCG
101 (+1)   S  F  F  V  M  T  N  F  L  K  T  E  G  Q  E  Q  R
      351 GTTGTGTCCCGAGTATCCCACCCGCAGGACGCTCTGTTCCTCTGACCGAG
118 (+1)   L  C  P  E  Y  P  T  R  R  T  L  C  S  S  D  R
      401 GTTGTAAAAAGGGATGGATGGACCCGCAGAGCAAAGGAATTCAGACCGGA
134 (+1)  G  C  K  K  G  W  M  D  P  Q  S  K  G  I  Q  T  G
      451 AGGTGTGTAGTGCATGAAGGGAACCAGAAGACCTGTGAAGTCTCTGCCTG
151 (+1)   R  C  V  V  H  E  G  N  Q  K  T  C  E  V  S  A  W
      501 GTGCCCCATCGAGGCAGTGGAAGAGGCCCCCCGGCCTGCTCTCTTGAACA
168 (+1)   C  P  I  E  A  V  E  E  A  P  R  P  A  L  L  N
      551 GTGCCGAAAACTTCACTGTGCTCATCAAGAACAATATCGACTTCCCCGGC
184 (+1)  S  A  E  N  F  T  V  L  I  K  N  N  I  D  F  P  G
      601 CACAACTACACCACGAGAAACATCCTGCCAGGTTTAAACATCACTTGTAC
201 (+1)   H  N  Y  T  T  R  N  I  L  P  G  L  N  I  T  C  T
      651 CTTCCACAAGACTCAGAATCCACAGTGTCCCATTTTCCGACTAGGAGACA
218 (+1)   F  H  K  T  Q  N  P  Q  C  P  I  F  R  L  G  D
      701 TCTTCCGAGAAACAGGCGATAATTTTTCAGATGTGGCAATTCAGGGCGGA
234 (+1)  I  F  R  E  T  G  D  N  F  S  D  V  A  I  Q  G  G
      751 ATAATGGGCATTGAGATCTACTGGGACTGCAACCTAGACCGTTGGTTCCA
251 (+1)   I  M  G  I  E  I  Y  W  D  C  N  L  D  R  W  F  H
      801 TCACTGCCATCCCAAATACAGTTTCCGTCGCCTTGACGACAAGACCACCA
268 (+1)   H  C  H  P  K  Y  S  F  R  R  L  D  D  K  T  T
      851 ACGTGTCCTTGTACCCTGGCTACAACTTCAGATACGCCAAGTACTACAAG
284 (+1)  N  V  S  L  Y  P  G  Y  N  F  R  Y  A  K  Y  Y  K
      901 GAAAACAATGTTGAGAAACGGACTCTGATAAAAGTCTTCGGGATCCGTTT
301 (+1)   E  N  N  V  E  K  R  T  L  I  K  V  F  G  I  R  F
      951 TGACATCCTGGTTTTTGGCACCGGAGGAAAATTTGACATTATCCAGCTGG
318 (+1)   D  I  L  V  F  G  T  G  G  K  F  D  I  I  Q  L
     1001 TTGTGTACATCGGCTCAACCCTCTCCTACTTCGGTCTGGCCGCTGTGTTC
334 (+1)  V  V  Y  I  G  S  T  L  S  Y  F  G  L  A  A  V  F
     1051 ATCGACTTCCTCATCGACACTTACTCCAGTAACTGCTGTCGCTCCCATAT
351 (+1)   I  D  F  L  I  D  T  Y  S  S  N  C  C  R  S  H  I
     1101 TTATCCCTGGTGCAAGTGCTGTCAGCCCTGTGTGGTCAACGAATACTACT
```

FIG. 2A

```
368 (+1)     Y  P  W  C  K  C  C  Q  P  C  V  V  N  E  Y  Y
     1151 ACAGGAAGAAGTGCGAGTCCATTGTGGAGCCAAAGCCGACATTAAAGTAT
384 (+1) Y  R  K  K  C  E  S  I  V  E  P  K  P  T  L  K  Y
     1201 GTGTCCTTTGTGGATGAATCCCACATTAGGATGGTGAACCAGCAGCTACT
401 (+1)  V  S  F  V  D  E  S  H  I  R  M  V  N  Q  Q  L  L
     1251 AGGGAGAAGTCTGCAAGATGTCAAGGGCCAAGAAGTCCCAAGACCTGCGA
418 (+1)    G  R  S  L  Q  D  V  K  G  Q  E  V  P  R  P  A
     1301 TGGACTTCACAGATTTGTCCAGGCTGCCCCTGGCCCTCCATGACACACCC
434 (+1) M  D  F  T  D  L  S  R  L  P  L  A  L  H  D  T  P
     1351 CCGATTCCTGGACAACCAGAGGAGATACAGCTGCTTAGAAAGGAGGCGAC
451 (+1)  P  I  P  G  Q  P  E  E  I  Q  L  L  R  K  E  A  T
     1401 TCCTAGATCCAGGGATAGCCCCGTCTGGTGCCAGTGTGGAAGCTGCCTCC
468 (+1)    P  R  S  R  D  S  P  V  W  C  Q  C  G  S  C  L
     1451 CATCTCAACTCCCTGAGAGCCACAGGTGCCTGGAGGAGCTGTGCTGCCGG
484 (+1) P  S  Q  L  P  E  S  H  R  C  L  E  E  L  C  C  R
     1501 AAAAAGCCGGGGGCCTGCATCACCACCTCAGAGCTGTTCAGGAAGCTGGT
510 (+1)    K  K  P  G  A  C  I  T  T  S  E  L  F  R  K  L  V
     1551 CCTGTCCAGACACGTCCTGCAGTTCCTCCTGCTCTACCAGGAGCCCTTGC
518 (+1)  L  S  R  H  V  L  Q  F  L  L  L  Y  Q  E  P  L
     1601 TGGCGCTGGATGTGGATTCCACCAACAGCCGGCTGCGGCACTGTGCCTAC
534 (+1) L  A  L  D  V  D  S  T  N  S  R  L  R  H  C  A  Y
     1651 AGGTGCTACGCCACCTGGCGCTTCGGCTCCCAGGACATGGCTGACTTTGC
551 (+1)    R  C  Y  A  T  W  R  F  G  S  Q  D  M  A  D  F  A
     1701 CATCCTGCCCAGCTGCTGCCGCTGGAGGATCCGGAAAGAGTTTCCGAAGA
568 (+1)     I  L  P  S  C  C  R  W  R  I  R  K  E  F  P  K
     1751 GTGAAGGGCAGTACAGTGGCTTCAAGAGTCCTTACTGA
584 (+1)S  E  G  Q  Y  S  G  F  K  S  P  Y  *
```

FIG. 2B

P2X7-RECEPTOR: TRUNCATED: MARKED EXONS MARKED TRANSMEMBRANE SEGMENTS

```
        1 ATGCCGGCCTGCTGCAGCTGCAGTGATGTTTTCCAGTATGAGACGAACAA
  1 (+1)   M  P  A  C  C  S  C  S  D  V  F  Q  Y  E  T  N  K
       51 AGTCACTCGGATCCAGAGCATGAATTATGGCACCATTAAGTGGTTCTTCC
 18 (+1)   V  T  R  I  Q  S  M  N  Y  G  T  I  K  W  F  F
      101 ACGTGATCATCTTTTCCTACGTTTGCTTTGCTCTGGTGAGTGACAAGCTG
 34 (+1)   H  V  I  I  F  S  Y  V  C  F  A  L  V  S  D  K  L
      151 TACCAGCGGAAAGAGCCTGTCATCAGTTCTGTGCACACCAAGGTGAAGGG
 51 (+1)   Y  Q  R  K  E  P  V  I  S  S  V  H  T  K  V  K  G
      201 GATAGCAGAGGTGAAAGAGGAGATCGTGGAGAATGGAGTGAAGAAGTTGG
 68 (+1)   I  A  E  V  K  E  E  I  V  E  N  G  V  K  K  L
      251 TGCACAGTGTCTTTGACACCGCAGACTACACCTTCCCTTTGCAGGGGAAC
 84 (+1)  V  H  S  V  F  D  T  A  D  Y  T  F  P  L  Q  G  N
      301 TCTTTCTTCGTGATGACAAACTTTCTCAAAACAGAAGGCCAAGAGCAGCG
101 (+1)   S  F  F  V  M  T  N  F  L  K  T  E  G  Q  E  Q  R
      351 GTTGTGTCCCGAGTATCCCACCCGCAGGACGCTCTGTTCCTCTGACCGAG
118 (+1)   L  C  P  E  Y  P  T  R  R  T  L  C  S  S  D  R
      401 GTTGTAAAAAGGGATGGATGGACCCGCAGAGCAAAGGAATTCAGACCGGA
134 (+1)  G  C  K  K  G  W  M  D  P  Q  S  K  G  I  Q  T  G
      451 AGGTGTGTAGTGCATGAAGGCAACCAGAAGACCTGTGAAGTCTCTGCCTG
151 (+1)   R  C  V  V  H  E  G  N  Q  K  T  C  E  V  S  A  W
      501 GTGCCCCATCGAGGCAGTGGAAGAGGCCCCCCGGCCTGCTCTCTTGAACA
168 (+1)   C  P  I  E  A  V  E  E  A  P  R  P  A  L  L  N
      551 GTGCCGAAAACTTCACTGTGCTCATCAAGAACAATATCGACTTCCCCGGC
184 (+1)  S  A  E  N  F  T  V  L  I  K  N  N  I  D  F  P  G
      601 CACAACTACACCACGAGAAACATCCTGCCAGGTTTAAACATCACTTGTAC
201 (+1)   H  N  Y  T  T  R  N  I  L  P  G  L  N  I  T  C  T
      651 CTTCCACAAGACTCAGAATCCACAGTGTCCATTTTCCGACTAGGAGACA
218 (+1)   F  H  K  T  Q  N  P  Q  C  P  I  F  R  L  G  D
      701 TCTTCCGAGAAACAGGCGATAATTTTTCAGATGTGGCAATTCAGATACGC
234 (+1) I  F  R  E  T  G  D  N  F  S  D  V  A  I  Q  I  R
      751 CAAGTACTACAAGGAAAACAATGT TGA
251 (+1)   Q  V  L  Q  G  K  Q  C  *
```

FIG. 2C

RT-PCR FOR FULL-LENGTH ($P2X_7$) AND TRUNCATED ($P2X_{7-j}$) RECEPTORS:

FORWARD PRIMER P2X7d+ (TTCCGACTAGGAGACATCTTCC)
REVERSE PRIMER P2X7d- (AAGTAGGAGAGGGTTGAGCC).
IN THEORY, THIS PRIMER PAIR COULD AMPLIFY BOTH RECEPTOR FORMS.
EXPECTED RT-PCT PRODUCTS:
    336 bp (695-1031) FOR THE FULL-LENGTH
    195 bp FOR THE TRUNCATED.
PCR PROTOCOL:
    94°C 2 MIN, 94°C 1 MIN / 60°C 20 SEC / 72°C 35 SEC 35 CYCLES.

RT-PCR FOR TRUNCATED ($P2X_{7-j}$) RECEPTOR:

FORWARD PRIMER 2P2X7+ (GGTTGTAAAAGGGATGGATGGAC)
REVERSE PRIMER 3tP2X7d- (AGTACTTGGGCGTATCTGAATTG).
THIS PRIMER PAIR DID NOT AMPLIFY THE FULL-LENGTH $P2X_7$- RECEPTOR.
EXPECTED RT-PCR PRODUCTS:
    361 bp FOR THE TRUNCATED $P2X_7$- RECEPTOR
PCR PROTOCOL:
    94°C 2 MIN, 94°C 1 MIN / 62°C 20 SEC / 72°C 40 SEC 40 CYCLES.

FIG. 4

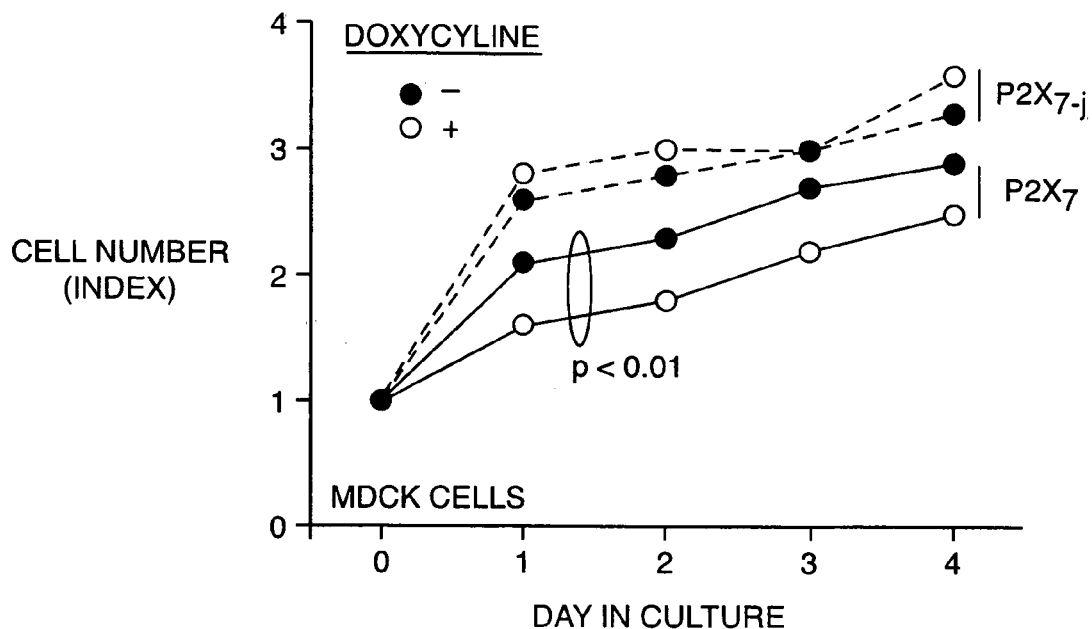
PANEL A
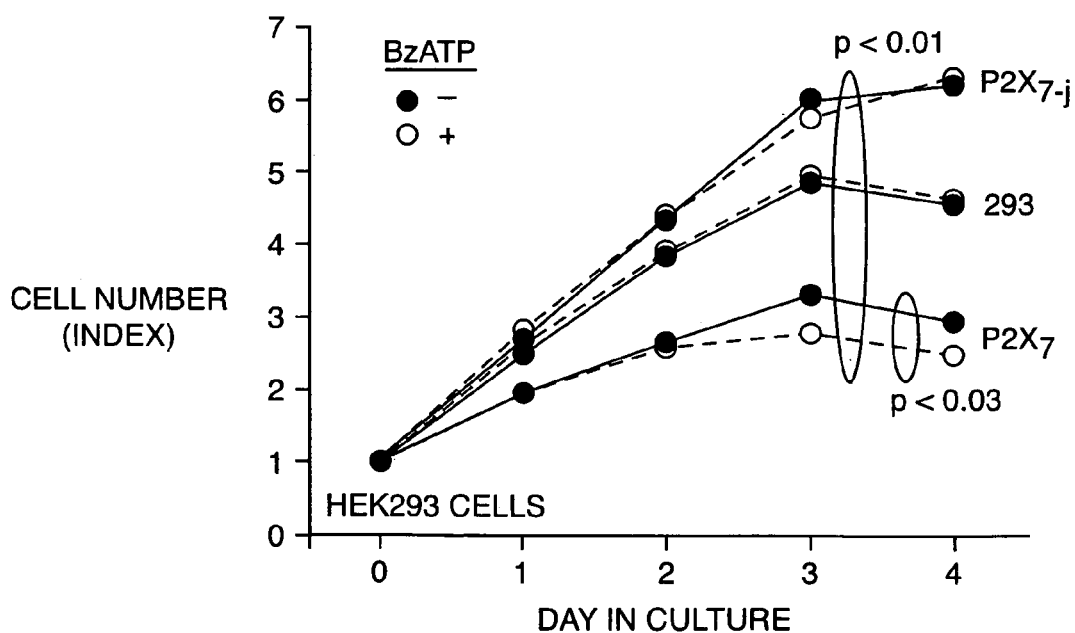
PANEL B
FIG. 15

PANEL A

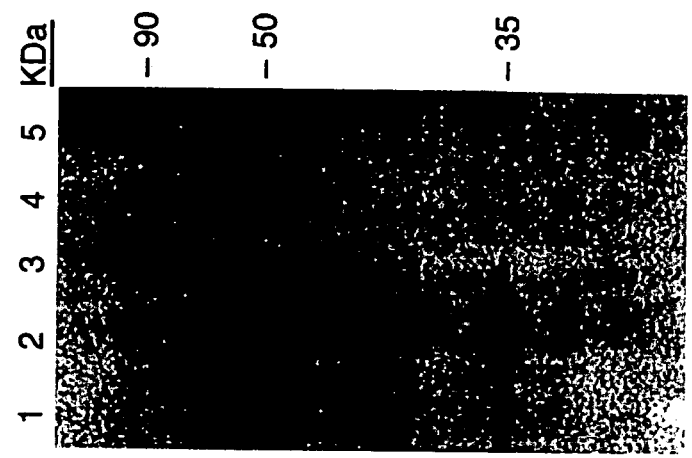
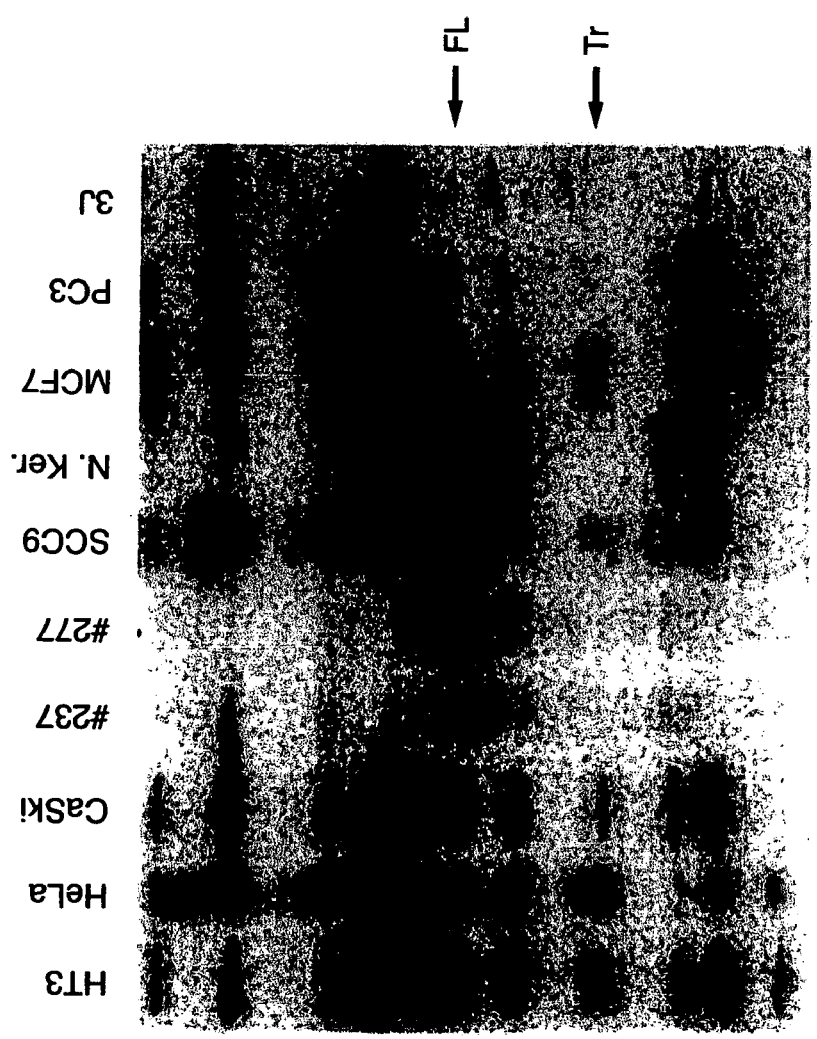
FIG. 21
FIG. 20

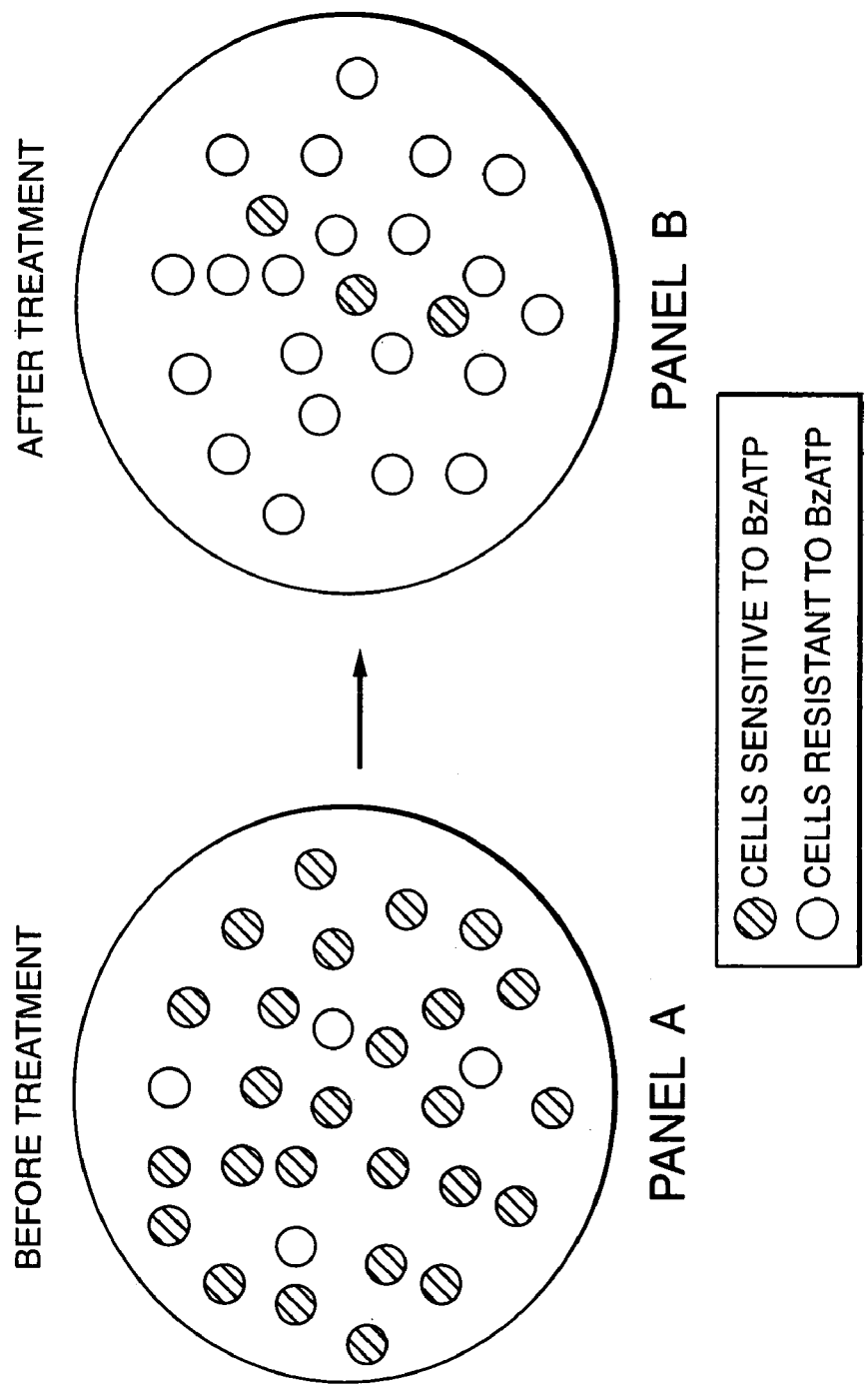

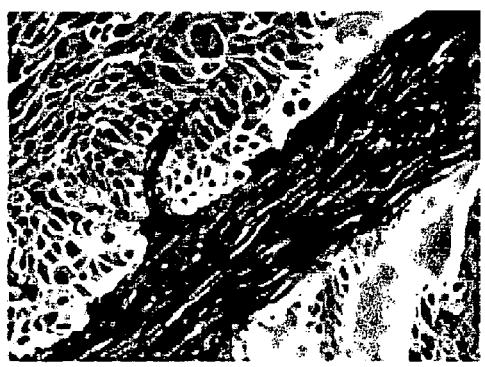
PANEL A
PANEL B
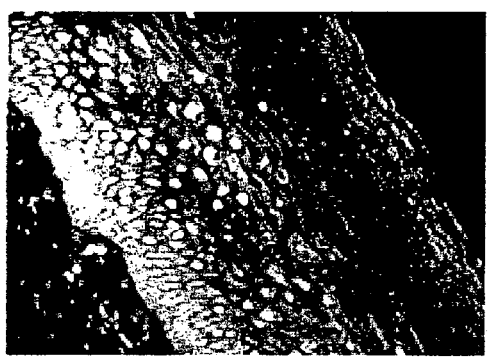
PANEL C
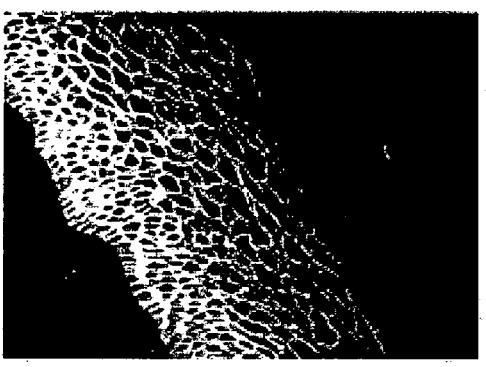
PANEL D
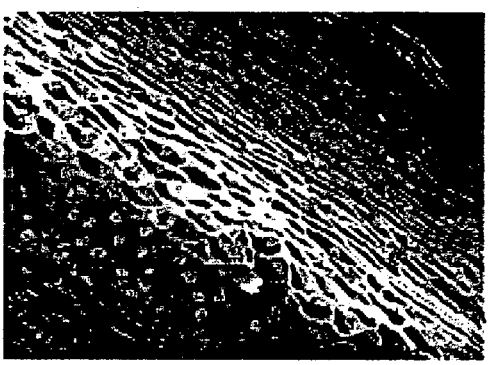
PANEL E
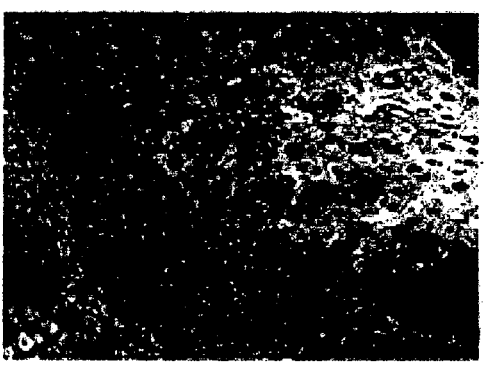
PANEL F
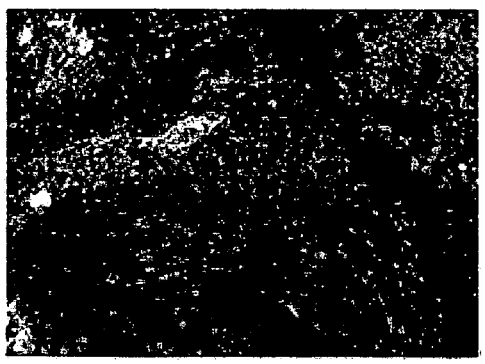
PANEL G
PANEL H
FIG. 24

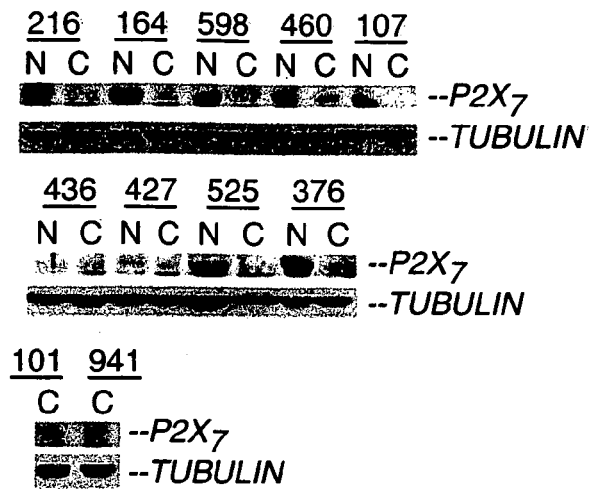
PANEL A
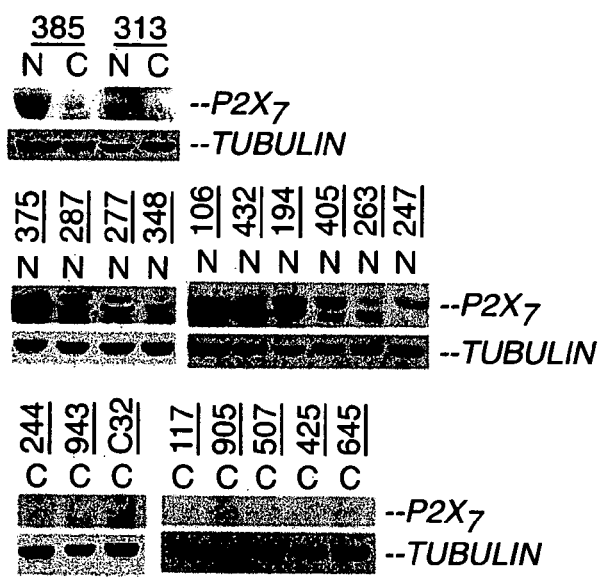
PANEL B
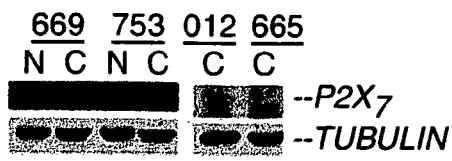
PANEL C
FIG. 27

| RNA | CANCER | NORMAL | TOTAL |
|---|---|---|---|
| POSITIVE | 34 TP | 0 FP | 34 |
| NEGATIVE | 2 FN | 15 TN | 17 |
| TOTAL | 36 | 15 | 51 |

FIG. 30

| PROTEIN | CANCER | NORMAL | TOTAL |
|---|---|---|---|
| POSITIVE | 25 TP | 3 FP | 28 |
| NEGATIVE | 0 FN | 20 TN | 20 |
| TOTAL | 25 | 23 | 48 |

FIG. 31

| | RNA | | PROTEIN | |
|---|---|---|---|---|
| SENSITIVITY | (34/36) | 94% | (25/25) | 100% |
| SPECIFICITY | (15/15) | 100% | (20/23) | 87% |
| POSITIVE PREDICTIVE VALUE | (34/34) | 100% | (25/28) | 89% |
| NEGATIVE PREDICTIVE VALUE | (15/17) | 88% | (20/20) | 100% |
| FALSE POSITIVE | (0/34) | 0 | (3/28) | 11% |
| FALSE NEGATIVE | (2/17) | 12% | (0/20) | 0 |
| LIKELIHOOD RATIO | (94/[100-100])$inf$ | | (100/[100-87])0 7.7 | |
| 95% CONFIDENCE INTERVAL | 2.31-31.26 | | $-inf$ to $+inf$ | |
| $X^2$ (FISHER'S EXACT TEST) | p<0.0001 | | p<0.0001 | |

FIG. 32

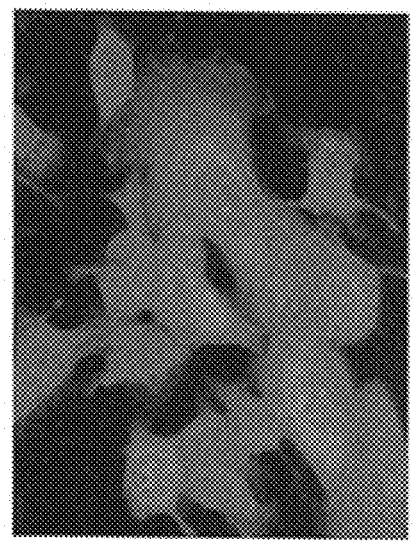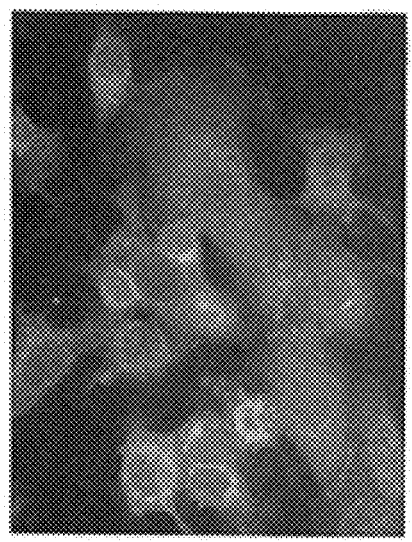
FIG. 33

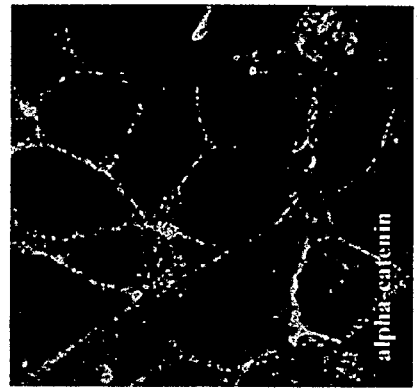
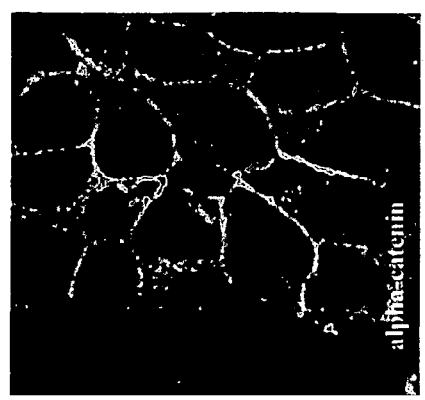
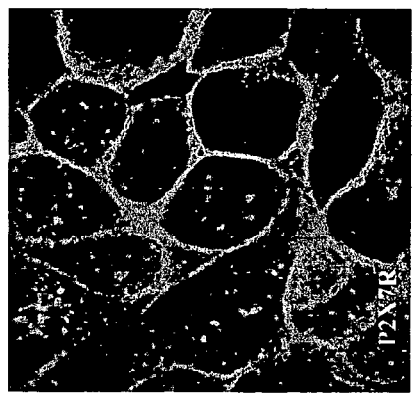
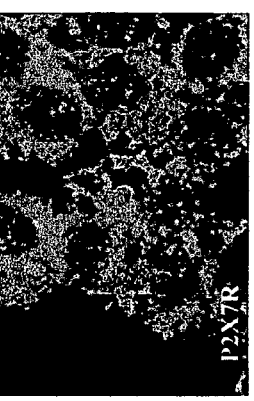
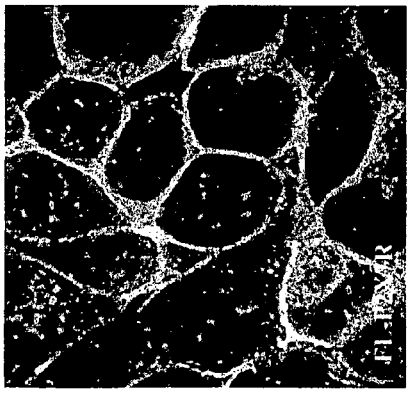
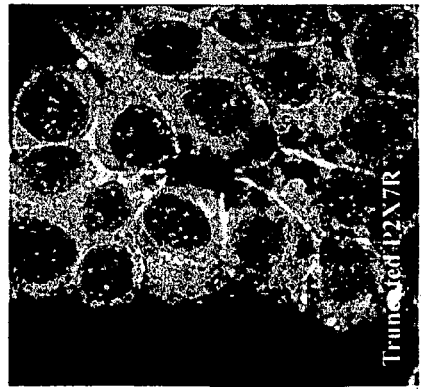
FIG. 35

P2X7 RECEPTOR: FULL STRENGTH; MARKED EXONS;
MARKED TRANSMEMBRANE SEGMENTS

```
   1 ATGCCGGCCTGCTGCAGCTGCAGTGATGTTTTCCAGTATGAGACGAACAA
1(+1) M  P  A  C  C  S  C  S  D  V  F  Q  Y  E  T  N  K
  51 AGTCACTCGGATCCAGAGCATGAATTATGGCACCATTAAGTGGTTCTTCC
18(+1) V  T  R  I  Q  S  M  N  Y  G  T  I  K  W  F  F
 101 ACGTGATCATCTTTTCCTACGTTTGCTTTGCTCTGGTGAGTGACAAGCTG
34(+1) H  V  I  I  F  S  Y  V  C  F  A  L  V  S  D  K  L
 151 TACCAGCGGAAAGAGCCTGTCATCAGTTCTGTGCACACCAAGGTGAAGGG
51(+1) Y  Q  R  K  E  P  V  I  S  S  V  H  T  K  V  K  G
 201 GATAGCAGAGGTGAAAGAGGAGATCGTGGAGAATGGAGTGAAGAAGTTGG
68(+1) I  A  E  V  K  E  E  I  V  E  N  G  V  K  K  L
 251 TGCACAGTGTCTTTGACACCGCAGACTACACCTTCCCTTTGCAGGGGAAC
84(+1) V  H  S  V  F  D  T  A  D  Y  T  F  P  L  Q  G  N
 301 TCTTTCTTCGTGATGACAAACTTTCTCAAAACAGAAGGCCAAGAGCAGCG
101(+1) S  F  F  V  M  T  N  F  L  K  T  E  G  Q  E  Q  R
 351 GTTGTGTCCCGAGTATCCCACCCGCAGGACGCTCTGTTCCTCTGACCGAG
118(+1) L  C  P  E  Y  P  T  R  R  T  L  'C  S  S  D  R
 401 GTTGTAAAAGGGATGGATGGACCCGCAGAGCAAAGGAATTCAGACCGGA
134(+1)G  C  K  K  G  W  M  D  P  Q  S  K  G  I  Q  T  G
 451 AGGTGTGTAGTGCATGAAGGGAACCAGAAGACCTGTGAAGTCTCTGCCTG
151(+1) R  C  V  V  H  E  G  N  Q  K  T  C  E  V  S  A  W
 501 GTGCCCCATCGAGGCAGTGGAAGAGGCCCCCCGGCCTGCTCTCTTGAACA
168(+1) C  P  I  E  A  V  E  E  A  P  R  P  A  L  L  N
 551 GTGCCGAAAACTTCACTGTGCTCATCAAGAACAATATCGACTTCCCCGGC
184(+1)S  A  E  N  F  T  V  L  I  K  N  N  I  D  F  P  G
 601 CACAACTACACCACGAGAAACATCCTGCCAGGTTTAAACATCACTTGTAC
201(+1) H  N  Y  T  T  R  N  I  L  P  G  L  N  I  T  C  T
 651 CTTCCACAAGACTCAGAATCCACAGTGTCCCATTTTCCGACTAGGAGACA
218(+1) F  H  K  T  Q  N  P  Q  C  P  I  F  R  L  G  D
 701 TCTTCCGAGAAACAGGCGATAATTTTTCAGATGTGGCAATTCAGGGCGGA
234(+1)I  F  R  E  T  G  D  N  F  S  D  V  A  I  Q  G  G
 751 ATAATGGGCATTGAGATCTACTGGGACTGCAACCTAGACCGTTGGTTCCA
251(+1) I  M  G  I  E  I  Y  W  D  C  N  L  D  R  W  F  H
 801 TCACTGCCATCCCAAATACAGTTTCCGTCGCCTTGACGACAAGACCACCA
268(+1) H  C  H  P  K  Y  S  F  R  R  L  D  D  K  T  T
 851 ACGTGTCCTTGTACCCTGGCTACAACTTCAGATACGCCAAGTACTACAAG
284(+1)N  V  S  L  Y  P  G  Y  N  F  R  Y  A  K  Y  Y  K
 901 GAAAACAATGTTGAGAAACGGACTCTGATAAAAGTCTTCGGGATCCGTTT
301(+1) E  N  N  V  E  K  R  T  L  I  K  V  F  G  I  R  F
 951 TGACATCCTGGTTTTTGGCACCGGAGGAAAATTTGACATTATCCAGCTGG
318(+1) D  I  L  V  F  G  T  G  G  K  F  D  I  I  Q  L
1001 TTGTGTACATCGGCTCAACCCTCTCCTACTTCGGTCTGGCCGCTGTGTTC
334(+1)V  V  Y  I  G  S  T  L  S  Y  F  G  L  A  A  V  F
1051 ATCGACTTCCTCATCGACACTTACTCCAGTAACTGCTGTCGCTCCCATAT
```

FIG. 39A

```
351(+1)  I  D  F  L  I  D  T  Y  S  S  N  C  C  R  S  H  I
   1101 TTATCCCTGGTGCAAGTGCTGTCAGCCCTGTGTGGTCAACGAATACTACT
368(+1)  Y  P  W  C  K  C  C  Q  P  C  V  V  N  E  Y  Y
   1151 ACAGGAAGAAGTGCGAGTCCATTGTGGAGCCAAAGCCGACATTAAAGTAT
384(+1) Y  R  K  K  C  E  S  I  V  E  P  K  P  T  L  K  Y
   1201 GTGTCCTTTGTGGATGAATCCCACATTAGGATGGTGAACCAGCAGCTACT
401(+1)  V  S  F  V  D  E  S  H  I  R  M  V  N  Q  Q  L  L
   1251 AGGGAGAAGTCTGCAAGATGTCAAGGGCCAAGAAGTCCCAAGACCTGCGA
418(+1)  G  R  S  L  Q  D  V  K  G  Q  E  V  P  R  P  A
   1301 TGGACTTCACAGATTTGTCCAGGCTGCCCCTGGCCCTCCATGACACACCC
434(+1) M  D  F  T  D  L  S  R  L  P  L  A  L  H  D  T  P
   1351 CCGATTCCTGGACAACCAGAGGAGATACAGCTGCTTAGAAAGGAGGCGAC
451(+1)  P  I  P  G  Q  P  E  E  I  Q  L  L  R  K  E  A  T
   1401 TCCTAGATCCAGGGATAGCCCCGTCTGGTGCCAGTGTGGAAGCTGCCTCC
468(+1)  P  R  S  R  D  S  P  V  W  C  Q  C  G  S  C  L
   1451 CATCTCAACTCCCTGAGAGCCACAGGTGCCTGGAGGAGCTGTGCTGCCGG
484(+1) P  S  Q  L  P  E  S  H  R  C  L  E  L  C  C  R
   1501 AAAAAGCCGGGGGCCTGCATCACCACCTCAGAGCTGTTCAGGAAGCTGGT
510(+1)  K  K  P  G  A  C  I  T  T  S  E  L  F  R  K  L  V
   1551 CCTGTCCAGACACGTCCTGCAGTTCCTCCTGCTCTACCAGGAGCCCTTGC
518(+1)  L  S  R  H  V  L  Q  F  L  L  L  Y  Q  E  P  L
   1601 TGGCGCTGGATGTGGATTCCACCAACAGCCGGCTGCGGCACTGTGCCTAC
534(+1) L  A  L  D  V  D  S  T  N  S  R  L  R  H  C  A  Y
   1651 AGGTGCTACGCCACCTGGCGCTTCGGCTCCCAGGACATGGCTGACTTTGC
551(+1)  R  C  Y  A  T  W  R  F  G  S  Q  D  M  A  D  F  A
   1701 CATCCTGCCCAGCTGCTGCCGCTGGAGGATCCGGAAAGAGTTTCCGAAGA
568(+1)  I  L  P  S  C  C  R  W  R  I  R  K  E  F  P  K
   1751 GTGAAGGGCAGTACAGTGGCTTCAAGAGTCCTTACTGA
584(+1) S  E  G  Q  Y  S  G  F  K  S  P  Y  *
```

FIG. 39B

P2X7 RECEPTOR: TRUNCATED; MARKED EXONS;
MARKED TRANSMEMBRANE SEGMENTS

```
    1 ATGCCGGCCTGCTGCAGCTGCAGTGATGTTTTCCAGTATGAGACGAACAA
 1(+1) M  P  A  C  C  S  C  S  D  V  F  Q  Y  E  T  N  K
   51 AGTCACTCGGATCCAGAGCATGAATTATGGCACCATTAAGTGGTTCTTCC
18(+1)  V  T  R  I  Q  S  M  N  Y  G  T  I  K  W  F  F
  101 ACGTGATCATCTTTTCCTACGTTTGCTTTGCTCTGGTGAGTGACAAGCTG
34(+1)  H  V  I  I  F  S  Y  V  C  F  A  L  V  S  D  K  L
  151 TACCAGCGGAAAGAGCCTGTCATCAGTTCTGTGCACACCAAGGTGAAGGG
51(+1)  Y  Q  R  K  E  P  V  I  S  S  V  H  T  K  V  K  G
  201 GATAGCAGAGGTGAAAGAGGAGATCGTGGAGAATGGAGTGAAGAAGTTGG
68(+1)   I  A  E  V  K  E  E  I  V  E  N  G  V  K  K  L
  251 TGCACAGTGTCTTTGACACCGCAGACTACACCTTCCCTTTGCAGGGGAAC
84(+1)  V  H  S  V  F  D  T  A  D  Y  T  F  P  L  Q  G  N
  301 TCTTTCTTCGTGATGACAAACTTTCTCAAAACAGAAGGCCAAGAGCAGCG
101(+1) S  F  F  V  M  T  N  F  L  K  T  E  G  Q  E  Q  R
  351 GTTGTGTCCCGAGTATCCCACCCGCAGGACGCTCTGTTCCTCTGACCGAG
118(+1) L  C  P  E  Y  P  T  R  R  T  L  C  S  S  D  R
  401 GTTGTAAAAAGGGATGGATGGACCCGCAGAGCAAAGGAATTCAGACCGGA
134(+1) G  C  K  K  G  W  M  D  P  Q  S  K  G  I  Q  T  G
  451 AGGTGTGTAGTGCATGAAGGGAACCAGAAGACCTGTGAAGTCTCTGCCTG
151(+1) R  C  V  V  H  E  G  N  Q  K  T  C  E  V  S  A  W
  501 GTGCCCCATCGAGGCAGTGGAAGAGGCCCCCCGGCCTGCTCTCTTGAACA
168(+1) C  P  I  E  A  V  E  E  A  P  R  P  A  L  L  N
  551 GTGCCGAAAACTTCACTGTGCTCATCAAGAACAATATCGACTTCCCCGGC
184(+1)S  A  E  N  F  T  V  L  I  K  N  N  I  D  F  P  G
  601 CACAACTACACCACGAGAAACATCCTGCCAGGTTTAAACATCACTTGTAC
201(+1) H  N  Y  T  T  R  N  I  L  P  G  L  N  I  T  C  T
  651 CTTCCACAAGACTCAGAATCCACAGTGTCCCATTTTCCGACTAGGAGACA
218(+1) F  H  K  T  Q  N  P  Q  C  P  I  F  R  L  G  D
  701 TCTTCCGAGAAACAGGCGATAATTTTCAGATGTGGCAATTCAGATACGC
234(+1)I  F  R  E  T  G  D  N  F  S  D  V  A  I  Q  I  R
  751 CAAGTACTACAAGGAAAACAATGTTGA
251(+1) Q  V  L  Q  G  K  Q  C  *
```

FIG. 40

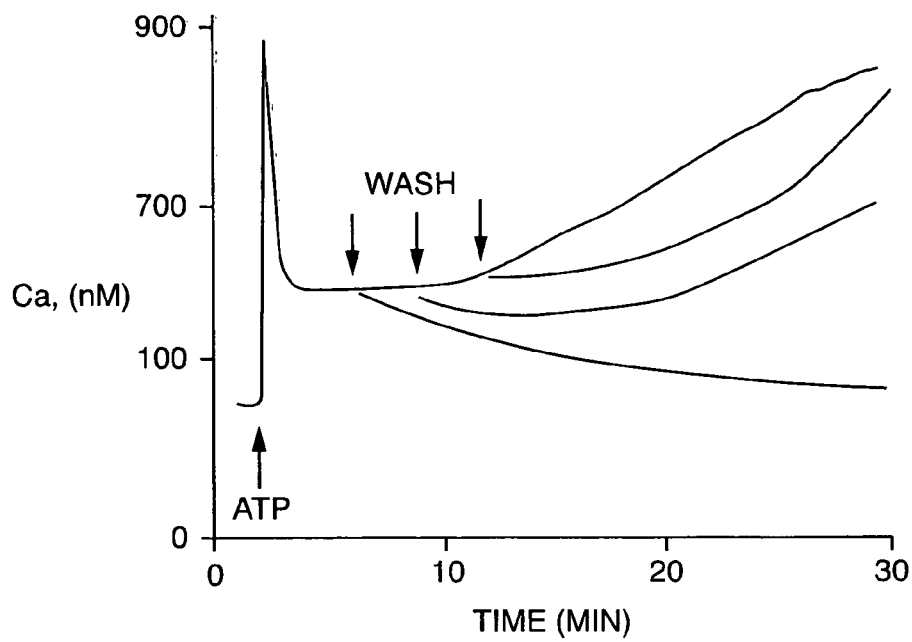
PANEL A
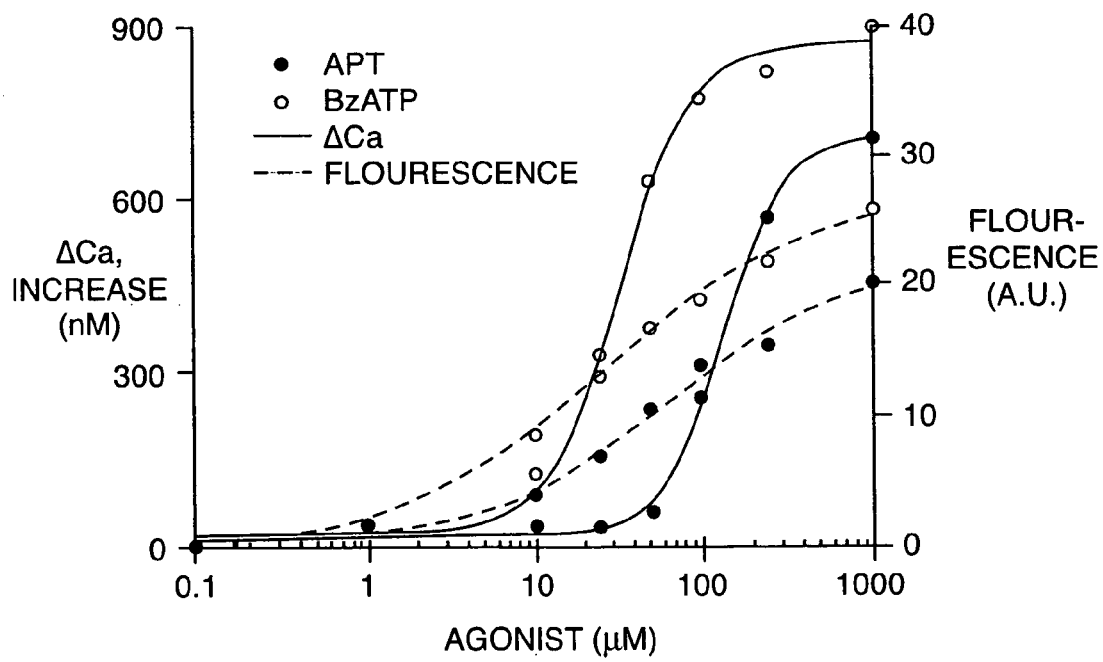
PANEL B
FIG. 43

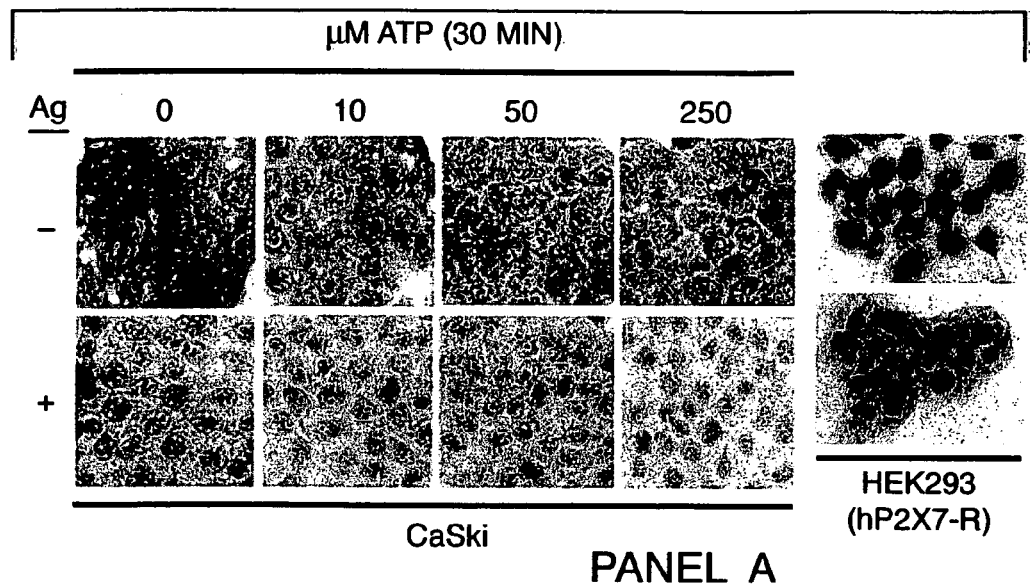
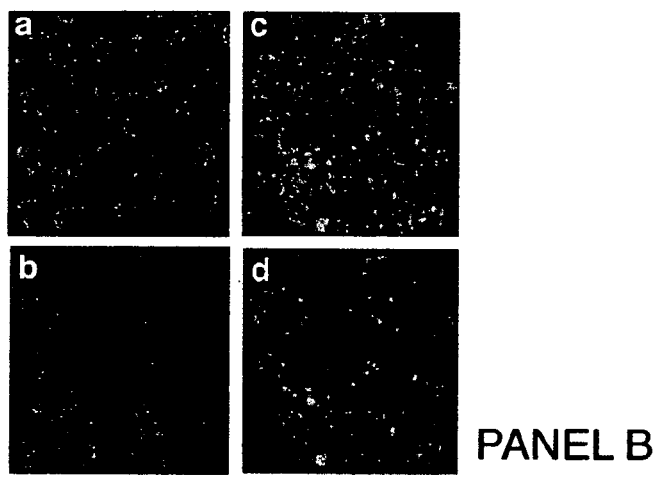
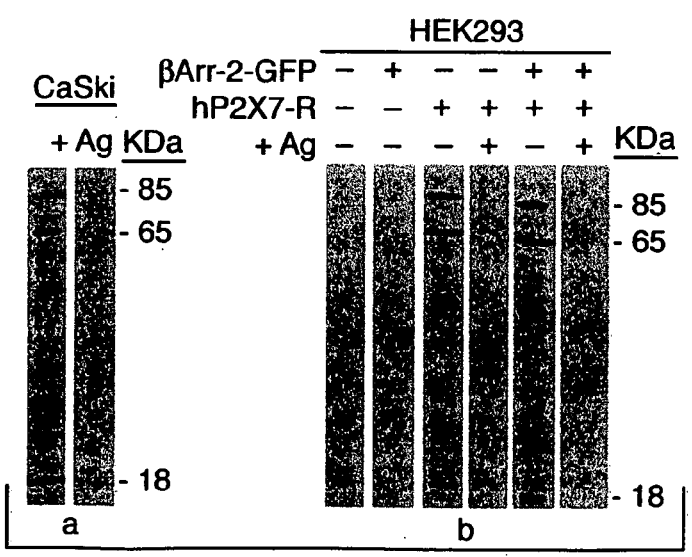
FIG. 44

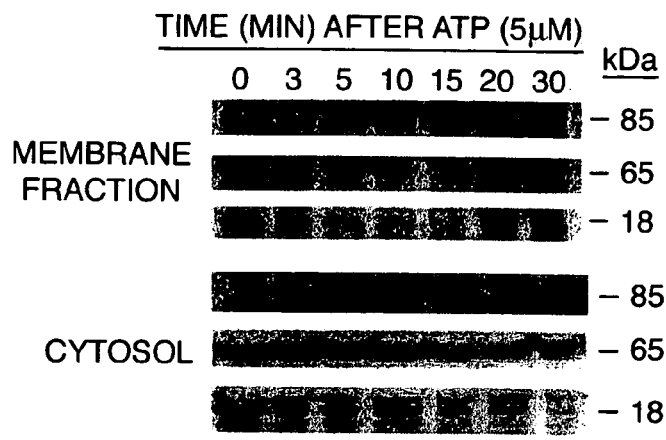
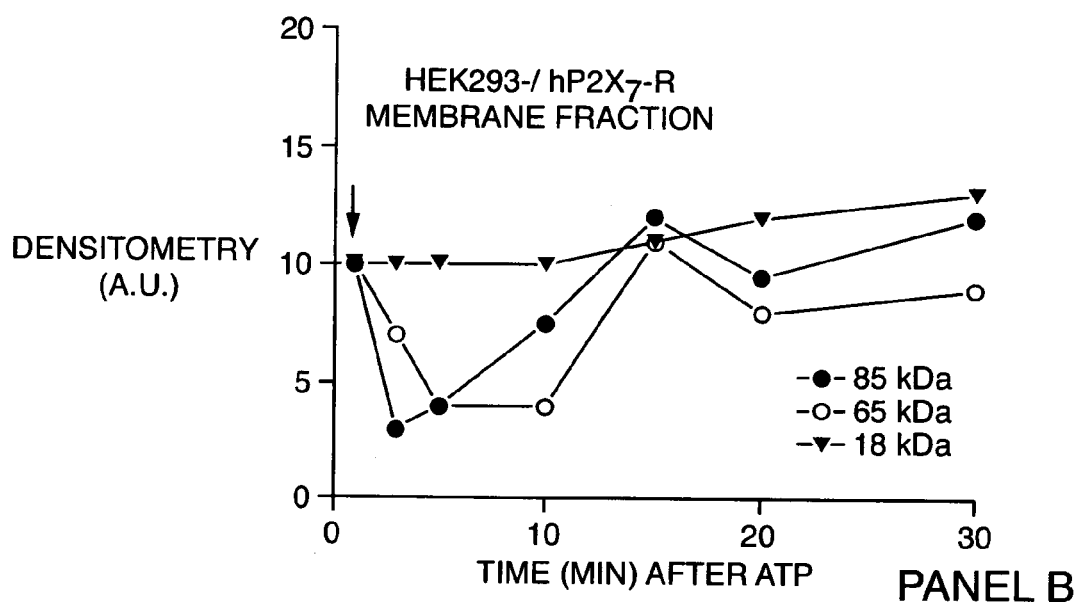
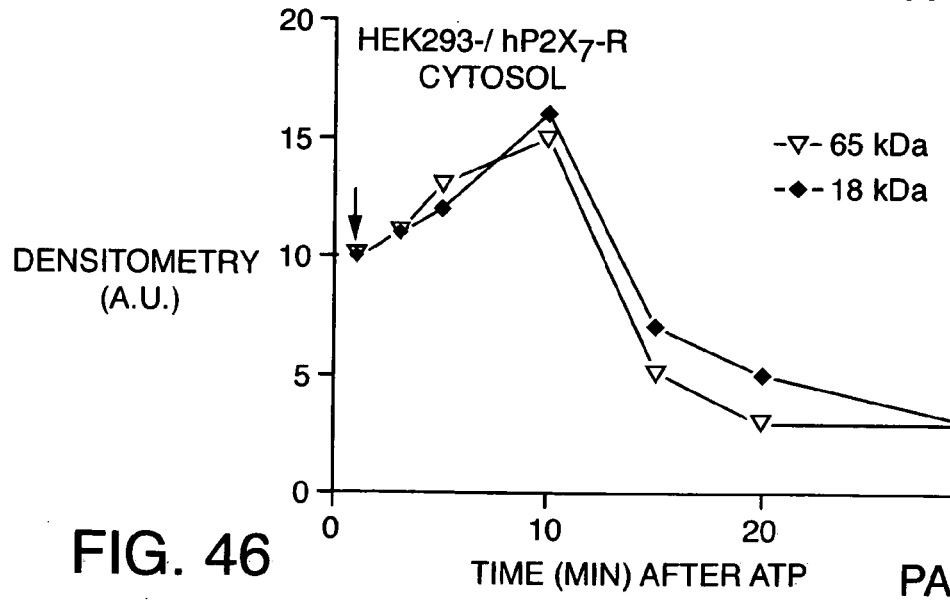
FIG. 46

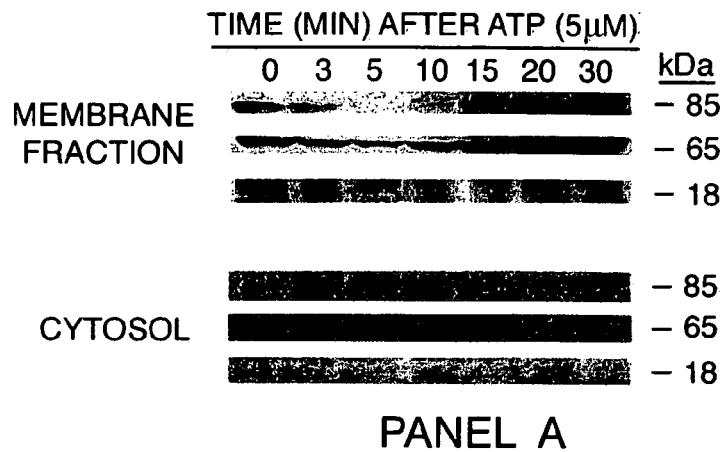
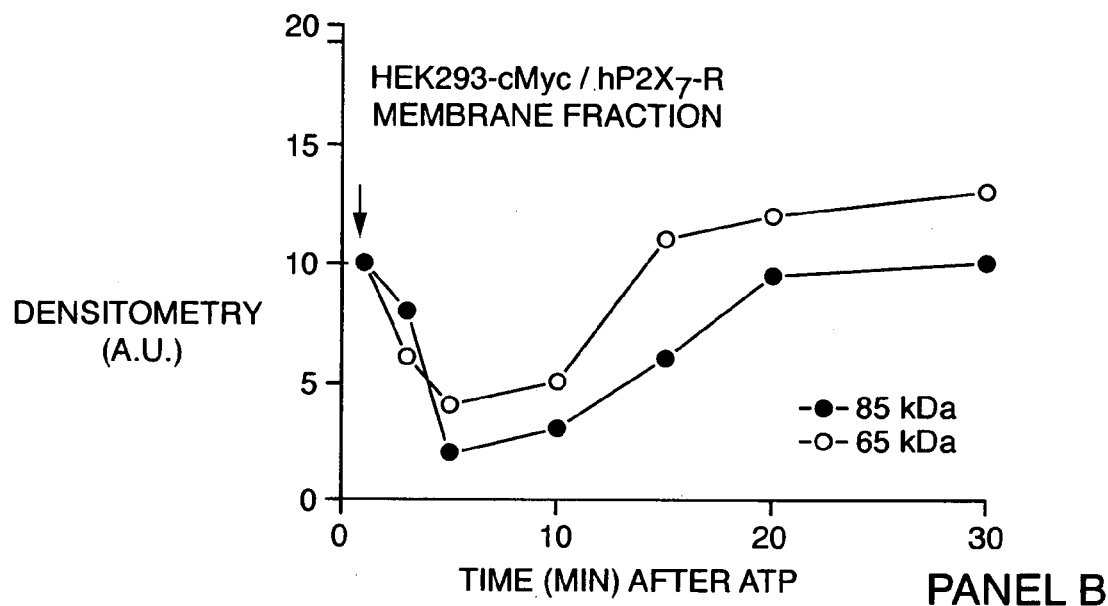
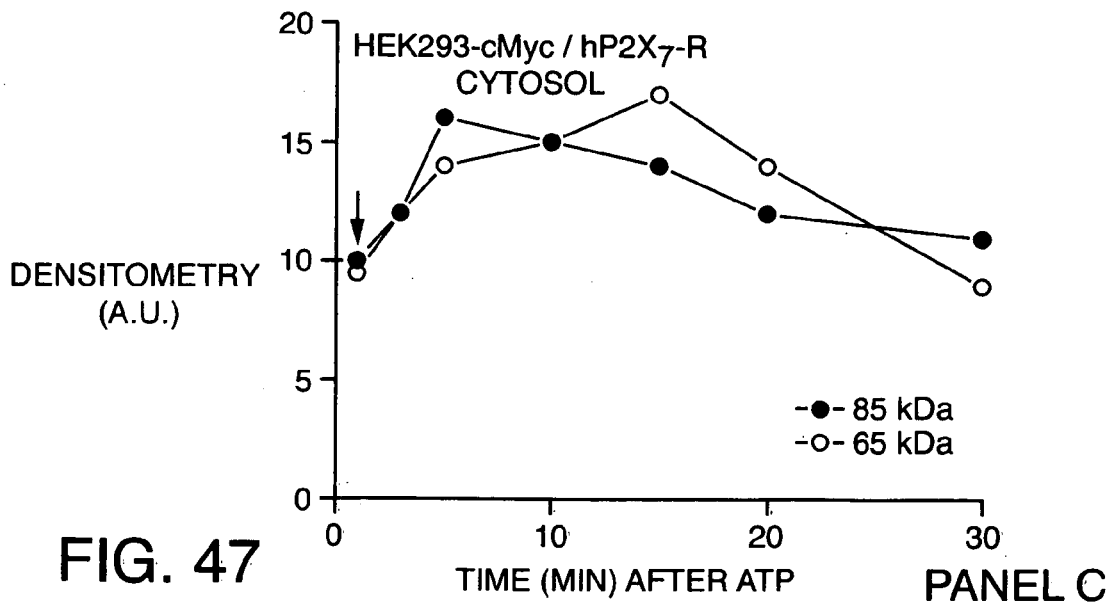
FIG. 47

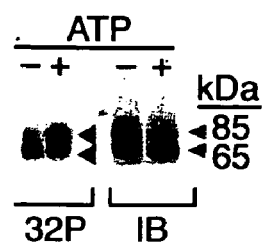
PANEL A
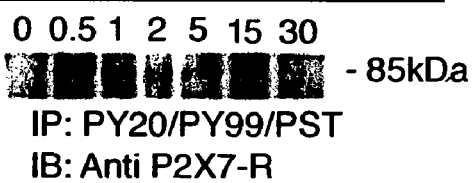
PANEL B
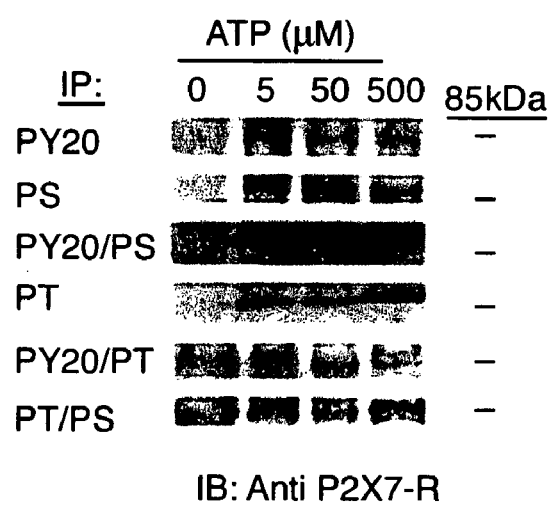
PANEL C
FIG. 48

PANEL A  PANEL B
PANEL C
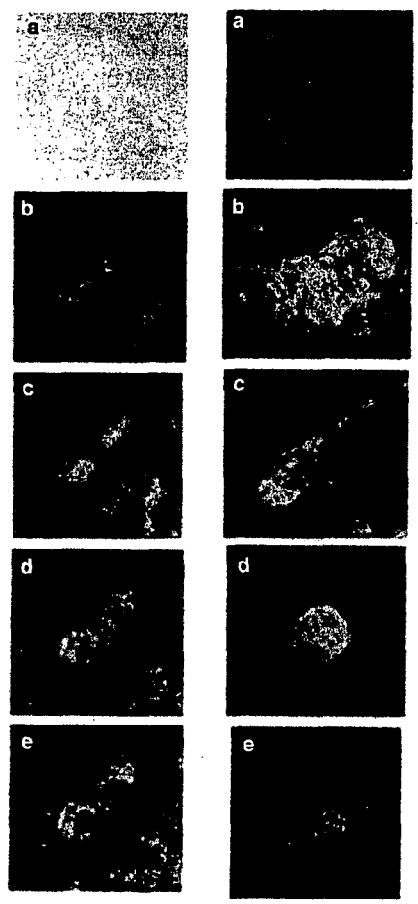
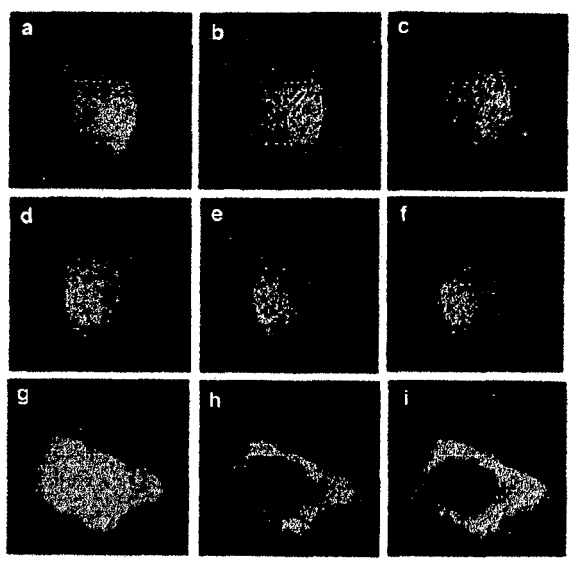
FIG. 50

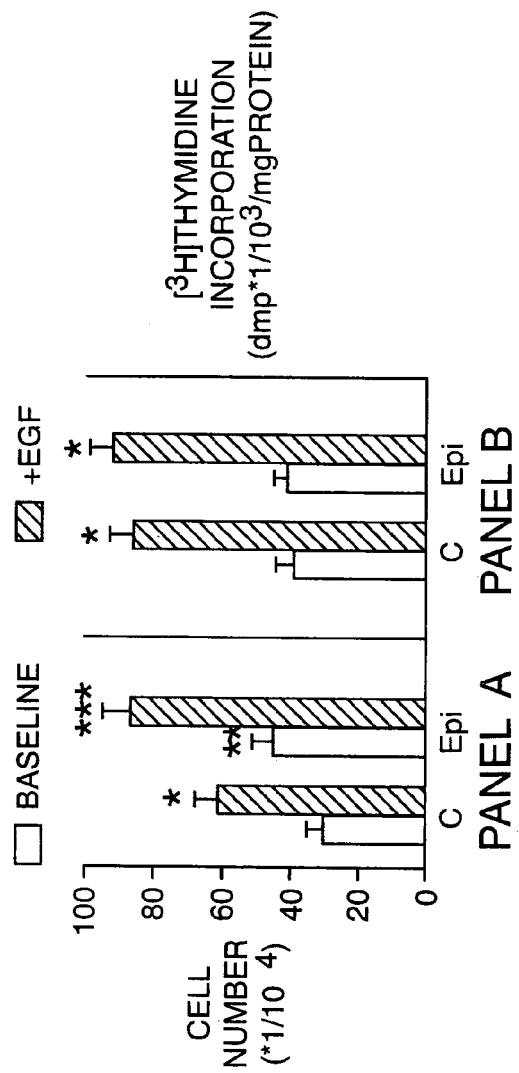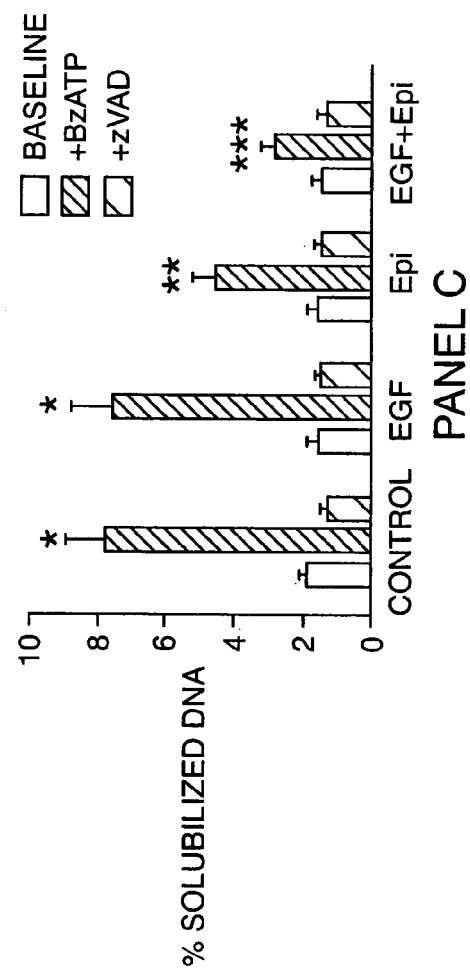
FIG. 51

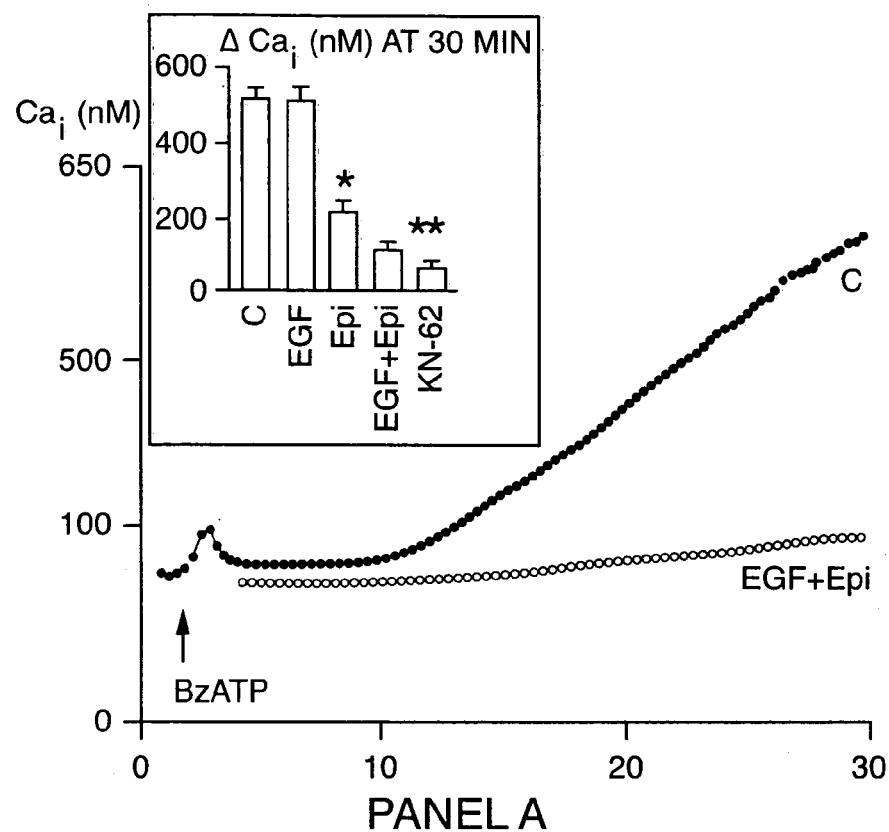
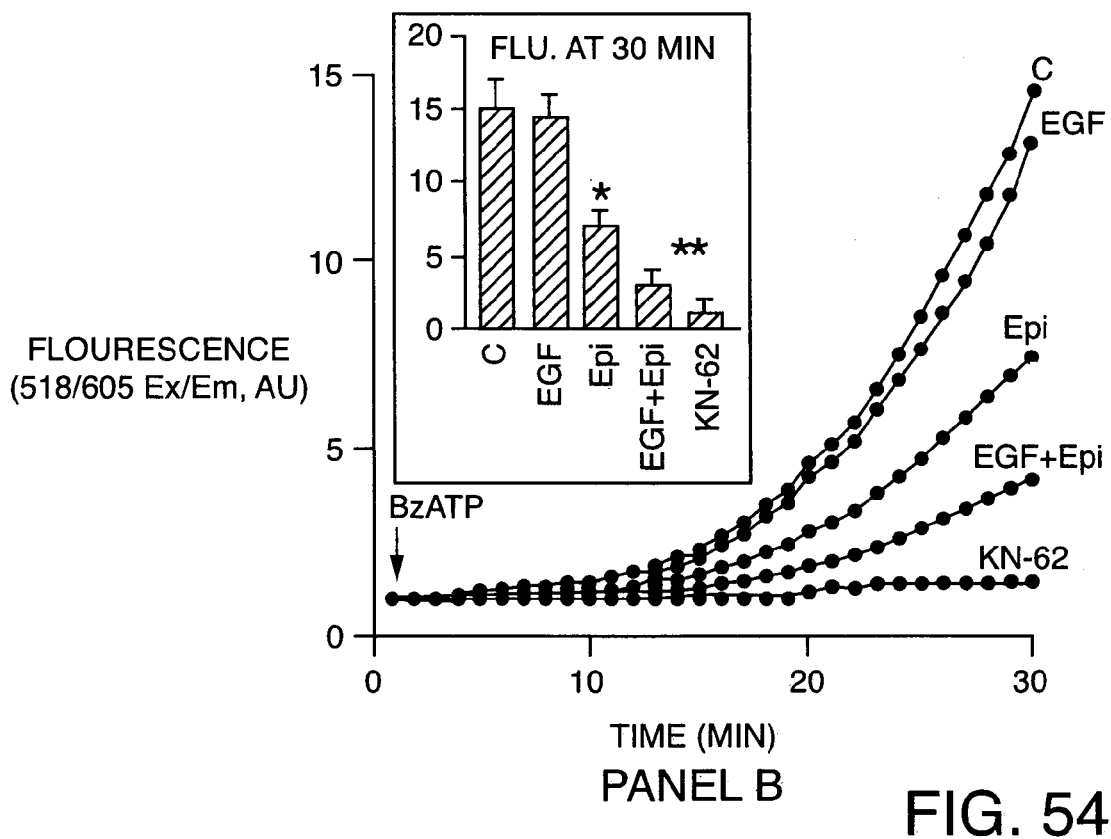
FIG. 54

SEQUENCE LISTING

```
<160> NUMBER OF SEQ ID NOS: 18

<210> SEQ ID NO 1
<211> LENGTH: 10
<212> TYPE: PRT
<213> ORGANISM: Homo sapiens

<400> SEQUENCE: 1

Ile Arg Gln Val Leu Gln Gly Lys Gln Cys
1               5                   10

<210> SEQ ID NO 2
<211> LENGTH: 20
<212> TYPE: PRT
<213> ORGANISM: Homo sapiens

<400> SEQUENCE: 2
```

Gly Asp Asn Phe Ser Asp Val Ala Ile Gln Ile Arg Gln Val Leu Gln
1               5                   10                  15

Gly Lys Gln Cys
            20

<210> SEQ ID NO 3
<211> LENGTH: 1788
<212> TYPE: DNA
<213> ORGANISM: Homo sapiens

<400> SEQUENCE: 3

| | | | | | | |
|---|---|---|---|---|---|---|
| atgccggcct | gctgcagctg | cagtgatgtt | ttccagtatg | agacgaacaa | agtcactcgg | 60 |
| atccagagca | tgaattatgg | caccattaag | tggttcttcc | acgtgatcat | cttttcctac | 120 |
| gtttgctttg | ctctggtgag | tgacaagctg | taccagcgga | agagcctgt | catcagttct | 180 |
| gtgcacacca | aggtgaaggg | gatagcagag | gtgaaagagg | agatcgtgga | gaatggagtg | 240 |
| aagaagttgg | tgcacagtgt | ctttgacacc | gcagactaca | ccttccctt | gcaggggaac | 300 |
| tctttcttcg | tgatgacaaa | ctttctcaaa | acagaaggcc | aagagcagcg | gttgtgtccc | 360 |
| gagtatccca | cccgcaggac | gctctgttcc | tctgaccgag | gttgtaaaaa | gggatggatg | 420 |
| gacccgcaga | gcaaaggaat | tcagaccgga | aggtgtgtag | tgcatgaagg | gaaccagaag | 480 |
| acctgtgaag | tctctgcctg | gtgccccatc | gaggcagtgg | aagaggcccc | ccggcctgct | 540 |
| ctcttgaaca | gtgccgaaaa | cttcactgtg | ctcatcaaga | caatatcga | cttccccggc | 600 |
| cacaactaca | ccacgagaaa | catcctgcca | ggtttaaaca | tcacttgtac | cttccacaag | 660 |
| actcagaatc | cacagtgtcc | cattttccga | ctaggagaca | tcttccgaga | aacaggcgat | 720 |
| aattttcag | atgtggcaat | tcagggcgga | ataatgggca | ttgagatcta | ctgggactgc | 780 |
| aacctagacc | gttggttcca | tcactgccat | cccaaataca | gtttccgtcg | ccttgacgac | 840 |
| aagaccacca | acgtgtcctt | gtaccctggc | tacaacttca | gatacgccaa | gtactacaag | 900 |
| gaaaacaatg | ttgagaaacg | gactctgata | aaagtcttcg | ggatccgttt | tgacatcctg | 960 |
| gttttttggca | ccggaggaaa | aatttgacatt | atccagctgg | ttgtgtacat | cggctcaacc | 1020 |
| ctctcctact | tcggtctggc | cgctgtgttc | atcgacttcc | tcatcgacac | ttactccagt | 1080 |
| aactgctgtc | gctcccatat | ttatccctgg | tgcaagtgct | gtcagccctg | tgtggtcaac | 1140 |
| gaatactact | acaggaagaa | gtgcgagtcc | attgtggagc | caaagccgac | attaaagtat | 1200 |
| gtgtcctttg | tggatgaatc | ccacattagg | atggtgaacc | agcagctact | agggagaagt | 1260 |
| ctgcaagatg | tcaagggcca | agaagtccca | agacctgcga | tggacttcac | agatttgtcc | 1320 |
| aggctgcccc | tggccctcca | tgacacaccc | ccgattcctg | gacaaccaga | ggagatacag | 1380 |
| ctgcttagaa | aggaggcgac | tcctagatcc | agggatagcc | ccgtctggtg | ccagtgtgga | 1440 |
| agctgcctcc | catctcaact | ccctgagagc | acaggtgcc | tggaggagct | gtgctgccgg | 1500 |
| aaaaagccgg | gggcctgcat | caccacctca | gagctgttca | ggaagctggt | cctgtccaga | 1560 |
| cacgtcctgc | agttcctcct | gctctaccag | gagcccttgc | tggcgctgga | tgtggattcc | 1620 |
| accaacagcc | ggctgcggca | ctgtgcctac | aggtgctacg | ccacctggcg | cttcggctcc | 1680 |
| caggacatgg | ctgactttgc | catcctgccc | agctgctgcc | gctggaggat | ccggaaagag | 1740 |
| tttccgaaga | gtgaagggca | gtacagtggc | ttcaagagtc | cttactga | 1788 |

<210> SEQ ID NO 4
<211> LENGTH: 595
<212> TYPE: PRT
<213> ORGANISM: Homo sapiens

```
<400> SEQUENCE: 4

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
            35                  40                  45

Lys Leu Tyr Gln Arg Lys Glu Pro Val Ile Ser Ser Val His Thr Lys
        50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys His Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
        355                 360                 365

Pro Trp Cys Lys Cys Cys Gln Pro Cys Val Val Asn Glu Tyr Tyr Tyr
370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
```

```
                405                 410                 415
Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
        435                 440                 445

Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 5
<211> LENGTH: 777
<212> TYPE: DNA
<213> ORGANISM: Homo sapiens

<400> SEQUENCE: 5
atgccggcct gctgcagctg cagtgatgtt ttccagtatg agacgaacaa agtcactcgg      60
atccagagca tgaattatgg caccattaag tggttcttcc acgtgatcat ctttcctac     120 gtttgctttg ctctggtgag tgacaagctg taccagcgga agagcctgt catcagttct     180 gtgcacacca aggtgaaggg gatagcagag gtgaaagagg agatcgtgga gaatggagtg     240
aagaagttgg tgcacagtgt ctttgacacc gcagactaca ccttcccttt gcagggaaac     300
tctttcttcg tgatgacaaa ctttctcaaa acagaaggcc aagagcagcg ttgtgtccc     360 gagtatccca cccgcaggac gctctgttcc tctgaccgag ttgtaaaaa gggatggatg     420 gacccgcaga gcaaaggaat tcagaccgga aggtgtgtag tgcatgaagg gaaccagaag     480
acctgtgaag tctctgcctg gtgccccatc gaggcagtgg aagaggcccc ccggcctgct     540
ctcttgaaca gtgccgaaaa cttcactgtg ctcatcaaga caatatcga cttccccggc     600 cacaactaca ccacgagaaa catcctgcca ggtttaaaca tcacttgtac cttccacaag     660
actcagaatc cacagtgtcc catttttccga ctaggagaca tcttccgaga aacaggcgat     720 aattttcag atgtggcaat tcagatacgc caagtactac aaggaaaaca atgttga      777

<210> SEQ ID NO 6
<211> LENGTH: 258
<212> TYPE: PRT
<213> ORGANISM: Homo sapiens

<400> SEQUENCE: 6
```

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
                35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Tyr Pro Thr Arg Arg Thr Leu
            115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Ile Arg Gln Val Leu Gln Gly Lys
                245                 250                 255

Gln Cys

<210> SEQ ID NO 7
<211> LENGTH: 16
<212> TYPE: PRT
<213> ORGANISM: Homo sapiens

<400> SEQUENCE: 7

Lys Lys Gly Trp Met Asp Pro Ser Lys Gly Ile Gln Thr Gly Arg Cys
1               5                   10                  15

<210> SEQ ID NO 8
<211> LENGTH: 20
<212> TYPE: PRT
<213> ORGANISM: Homo sapiens

<400> SEQUENCE: 8

Gly Asp Asn Phe Ser Asp Val Ala Ile Gln Ile Arg Gln Val Leu Gln
1               5                   10                  15

Gly Lys Gln Cys
            20

<210> SEQ ID NO 9
<211> LENGTH: 21
```

```
<212> TYPE: PRT
<213> ORGANISM: Homo sapiens

<400> SEQUENCE: 9

Cys Lys Ile Arg Lys Glu Phe Pro Lys Thr Gln Gly Gln Tyr Ser Gly
1               5                   10                  15

Phe Lys Tyr Pro Tyr
            20

<210> SEQ ID NO 10
<211> LENGTH: 21
<212> TYPE: PRT
<213> ORGANISM: Homo sapiens

<400> SEQUENCE: 10

Cys Lys Ile Arg Lys Glu Phe Pro Lys Thr Gln Gly Gln Tyr Ser Gly
1               5                   10                  15

Phe Lys Tyr Pro Tyr
            20

<210> SEQ ID NO 11
<211> LENGTH: 22
<212> TYPE: DNA
<213> ORGANISM: Homo sapiens

<400> SEQUENCE: 11
ttccgactag gagacatctt cc                                          22

<210> SEQ ID NO 12
<211> LENGTH: 20
<212> TYPE: DNA
<213> ORGANISM: Homo sapiens

<400> SEQUENCE: 12
aagtaggaga gggttgagcc                                             20

<210> SEQ ID NO 13
<211> LENGTH: 24
<212> TYPE: DNA
<213> ORGANISM: Homo sapiens

<400> SEQUENCE: 13
ggttgtaaaa agggatggat ggac                                        24

<210> SEQ ID NO 14
<211> LENGTH: 22
<212> TYPE: DNA
<213> ORGANISM: Homo sapiens

<400> SEQUENCE: 14
agtacttggc gtatctgaat tg                                          22

<210> SEQ ID NO 15
<211> LENGTH: 250
<212> TYPE: DNA
<213> ORGANISM: Homo sapiens

<400> SEQUENCE: 15
tcttccgaga aacaggcgat aatttttcag atgtggcaat tcaggcggga ataatgggca   60
ttgagatcta ctgggactgc aacctagacc gttggttcca tcactgccat cccaaataca  120
gtttccgtcg ccttgacgac aagaccacca acgtgtcctt gtaccctggc tacaacttca  180
```

```
                                                              -continued
gatacgccaa gtactacaag gaaaacaatg ttgagaaacg gactctgata aaagtcttcg        240
ggatccgttt                                                              250

<210> SEQ ID NO 16
<211> LENGTH: 77
<212> TYPE: DNA
<213> ORGANISM: Homo sapiens

<400> SEQUENCE: 16
tcttccgaga aacaggcgat aatttttcag atgtggcaat tcagatacgc caagtactac         60
aaggaaaaca atgttga                                                       77

<210> SEQ ID NO 17
<211> LENGTH: 27
<212> TYPE: PRT
<213> ORGANISM: Homo sapiens

<400> SEQUENCE: 17

Asn Phe Ser Asp Val Ala Ile Gln Gly Gly Ile Met Gly Ile Glu Ile
1               5                   10                  15

Trp Asp Cys Asn Leu Asp Arg Trp Phe His His
            20                  25

<210> SEQ ID NO 18
<211> LENGTH: 18
<212> TYPE: PRT
<213> ORGANISM: Homo sapiens

<400> SEQUENCE: 18

Asn Phe Ser Asp Val Ala Ile Gln Ile Arg Gln Val Leu Gln Gly Lys
1               5                   10                  15

Gln Cys
```

TRUNCATED PROTEINS AS CANCER MARKERS

This application for patent under 35 U.S.C. §111(a) claims priority to Provisional Application(s) Ser. No. 60/686,770 filed on Jun. 2, 2005 AND Provisional Application(s) Ser. No. 60/778,993 filed on Mar. 3, 2006 under 35 U.S.C. §111(b).

FIELD OF THE INVENTION

The present invention is related to cancer screening, diagnosis, and treatment. In one embodiment, a cell may be screened for the presence of a truncated $P2X_7$ mRNA and/or protein. In another embodiment, reagents reactive with a defective $P2X_7$ protein are provided in a kit. In another embodiment, patients are treated by increasing the amount and/or activity of a functional $P2X_7$ protein.

BACKGROUND

The term "chemotherapy" simply means the treatment of disease with chemical substances. The father of chemotherapy, Paul Ehrlich, imagined the perfect chemotherapeutic as a "magic bullet;" such a compound would kill invading organisms without harming the host. This target specificity is sought in all types of chemotherapeutics, including anticancer agents.

However, specificity has been the major problem with anticancer agents. In the case of anticancer agents, the drug needs to distinguish between host cells that are cancerous and host cells that are not cancerous. The vast bulk of anticancer drugs are indiscriminate at this level. Typically anticancer agents have negative hematological effects (e.g., cessation of mitosis and disintegration of formed elements in marrow and lymphoid tissues), and immunosuppressive action (e.g., depressed cell counts), as well as a severe impact on epithelial tissues (e.g., intestinal mucosa), reproductive tissues (e.g., impairment of spermatogenesis), and the nervous system. P. Calabresi and B. A. Chabner, In: Goodman and Gilman The Pharmacological Basis of Therapeutics (Pergamon Press, 8th Edition) (pp. 1209-1216).

Success with chemotherapeutics as anticancer agents has also been hampered by the phenomenon of multiple drug resistance, resistance to a wide range of structurally unrelated cytotoxic anticancer compounds. J. H. Gerlach et al., Cancer Surveys, 5:25-46 (1986). The underlying cause of progressive drug resistance may be due to a small population of drug-resistant cells within the tumor (e.g., mutant cells) at the time of diagnosis. J. H. Goldie and Andrew J. Coldman, Cancer Research, 44:3643-3653 (1984). Treating such a tumor with a single drug first results in a remission, where the tumor shrinks in size as a result of the killing of the predominant drug-sensitive cells. With the drug-sensitive cells gone, the remaining drug-resistant cells continue to multiply and eventually dominate the cell population of the tumor.

What is needed are compositions and methods to specifically identify biochemically altered cancer cells and correct this biochemical alteration.

SUMMARY

The present invention is related to cancer screening, diagnosis, and treatment. In one embodiment, a cell may be screened for the presence of a truncated $P2X_7$ mRNA and/or protein. In another embodiment, reagents reactive with a defective $P2X_7$ protein are provided in a kit. In another embodiment, patients are treated by increasing the amount and/or activity of a functional $P2X_7$ protein.

In one embodiment, the present invention contemplates a protein comprising a C terminus having an amino acid sequence comprising IRQVLQGKQC (SEQ ID NO:1). In one embodiment, the protein is encoded by a $P2X_{7-j}$ gene. In one embodiment, the $P2X_{7-j}$ gene comprises a frameshift mutation. In one embodiment, the frameshift creates a truncated protein.

In one embodiment, the present invention contemplates a nucleic acid encoding a C terminus having an amino acid sequence comprising IRQVLQGKQC (SEQ ID NO:1). In one embodiment, the nucleic acid comprises messenger ribonucleic acid. In one embodiment, the nucleic acid comprises deoxyribonucleic acid. In one embodiment, the nucleic acid comprises a $P2X_{7-j}$ gene. In one embodiment, the $P2X_{7-j}$ gene comprises a frameshift mutation. In one embodiment, the frameshift creates a truncated $P2X_{7-j}$ messenger ribonucleic acid.

In one embodiment, the present invention contemplates an antibody comprising reactivity with an amino acid sequence comprising GDNFSDVAIQIRQVLQGKQC (SEQ ID NO:8). In one embodiment, the antibody is polyclonal. In one embodiment, the antibody is monoclonal. In one embodiment, the amino acid sequence is derived from a $P2X_{7-j}$ protein.

In one embodiment, the present invention contemplates an antibody comprising reactivity with an amino acid sequence comprising KKGWMDPSKGIQTGRC (SEQ ID NO:7). In one embodiment, the antibody is polyclonal. In one embodiment, the antibody is monoclonal. In one embodiment, the amino acid sequence is derived from a $P2X_7$ protein.

In one embodiment, the present invention contemplates a nucleic acid encoding a an amino acid sequence comprising KKGWMDPSKGIQTGRC (SEQ ID NO:7). In one embodiment, the nucleic acid comprises messenger ribonucleic acid. In one embodiment, the nucleic acid comprises deoxyribonucleic acid. In one embodiment, the nucleic acid comprises a $P2X_7$ gene.

In one embodiment, the present invention contemplates a kit, comprising a first antibody comprising reactivity with an amino acid sequence comprising GDNFSDVAIQIRQVLQGKQC (SEQ ID NO:8). In one embodiment, the kit further comprises a non-cancer cell line derived from a mammalian tissue. In one embodiment, the kit further comprises a second antibody, wherein said second antibody has reactivity with said first antibody. In one embodiment, the first antibody is reactive with a cancer tissue biopsy sample. In one embodiment, the biopsy sample comprises epithelial tissue. In one embodiment, the amino acid sequence is derived from a $P2X_{7-j}$ receptor protein. In one embodiment, the second antibody comprises a label.

In one embodiment, the present invention contemplates a kit, comprising a first antibody comprising reactivity with an amino acid sequence comprising KKGWMDPSKGIQTGRC (SEQ ID NO:7). In one embodiment, the kit further comprises a non-cancer cell line derived from a mammalian tissue. In one embodiment, the kit further comprises a second antibody, wherein said second antibody has reactivity with said first antibody. In one embodiment, the first antibody is reactive with a cancer tissue biopsy sample. In one embodiment, the biopsy sample comprises epithelial tissue. In one embodiment, the amino acid sequence is derived from a $P2X_7$ receptor protein. In one embodiment, the second antibody comprises a label.

In one embodiment, the present invention contemplates a kit, comprising a reagent capable of amplifying a nucleic acid sequence encoding an amino acid sequence comprising IRQVLQGKQC (SEQ ID NO:1). In one embodiment, the kit further comprises a non-cancer cell line derived from a mammalian tissue. In one embodiment, the reagent comprises a forward primer and a reverse primer. In one embodiment, the forward primer comprises 2p2X₇+. In one embodiment, the reverse primer comprises 3tP2X₇d−. In one embodiment, the nucleic acid is derived from a cancer tissue biopsy sample. In one embodiment, the biopsy sample comprises epithelial tissue. In one embodiment, the nucleic acid sequence is derived from a $P2X_{7\text{-}j}$ gene. In one embodiment, the nucleic acid sequence comprises messenger ribonucleic acid.

In one embodiment, the present invention contemplates a kit, comprising a reagent capable of amplifying a nucleic acid sequence encoding an amino acid sequence comprising KKGWMDPSKGIQTGRC (SEQ ID NO:7). In one embodiment, the kit further comprises a non-cancer cell line derived from a mammalian tissue. In one embodiment, the reagent comprises a forward primer and a reverse primer. In one embodiment, the forward primer comprises $P2X_7d+$. In one embodiment, the reverse primer comprises $P2X_7d-$. In one embodiment, the nucleic acid is derived from a cancer tissue biopsy sample. In one embodiment, the biopsy sample comprises epithelial tissue.

In one embodiment, the nucleic acid sequence is derived from a $P2X_7$ gene. In one embodiment, the nucleic acid sequence comprises messenger ribonucleic acid. In one embodiment, the present invention contemplates a method, comprising: a) providing; i) a patient comprising at least one cancer cell; and ii) a composition comprising a $P2X_7$ receptor protein; and b) administering said composition to said patient under conditions such that said at least one cancer cell undergoes apoptosis. In one embodiment, the cancer cell is derived from an epithelial cell. In one embodiment, the epithelial cell is selected from the group consisting of breast, prostate, gastrointestinal, squamous skin, and cervical. In one embodiment, the administering comprises a fusion protein. In one embodiment, the fusion protein comprises a protein transduction domain. In one embodiment, the administering comprises a liposome. In one embodiment, the administering is selected from the group consisting of microinjection and electroporation.

In one embodiment, the present invention contemplates a method, comprising: a) providing; i) a patient comprising at least one cancer cell; and ii) a vector comprising a gene encoding a $P2X_7$ receptor protein amino acid sequence; and b) administering said vector to said patient under conditions such that said at least one cancer cell undergoes apoptosis. In one embodiment, the cancer cell is derived from an epithelial cell. In one embodiment, the epithelial cell is selected from the group consisting of breast, prostate, gastrointestinal, squamous skin, and cervical. In one embodiment, the apoptosis results from overexpression of the gene. In one embodiment, the administering comprises a liposome. In one embodiment, the administering is selected from the group consisting of microinjection and electroporation.

In one embodiment, the present invention contemplates a method, comprising: a) providing; i) a patient comprising at least one cancer cell; and ii) a composition comprising a $P2X_{7\text{-}j}$ receptor protein inhibitor; and b) administering said composition to said patient under conditions such that at least one cancer cell undergoes apoptosis. In one embodiment, the cancer cell is derived from an epithelial cell. In one embodiment, the epithelial cell is selected from the group consisting of breast, prostate, gastrointestinal, squamous skin, and cervical. In one embodiment, the inhibitor comprises an antibody. In one embodiment, the antibody is a monoclonal antibody. In one embodiment, the antibody is a polyclonal antibody. In one embodiment, the antibody is directed to an amino acid sequence comprising IRQVLQGKQC (SEQ ID NO:1) or a portion thereof.

In one embodiment, the present invention contemplates a method, comprising: a) providing; i) a patient comprising at least one cancer cell; and ii) a vector comprising a gene encoding a $P2X_{7\text{-}j}$ receptor protein inhibitor; and b) administering said vector to said patient under conditions such that said at least one cancer cell undergoes apoptosis. In one embodiment, the cancer cell is derived from an epithelial cell. In one embodiment, the epithelial cell is selected from the group consisting of breast, prostate, gastrointestinal, squamous skin, and cervical. In one embodiment, the gene comprises an antisense gene. In one embodiment, the vector overexpresses said gene.

In one embodiment, the present invention contemplates a method, comprising: a) providing; i) a patient suspected of developing cancer; and ii) a reagent having specificity for at least one P2X receptor protein; and iii) a sample derived from said patient comprising cells; and b) contacting said sample with said reagent under conditions such that said at least one P2X receptor protein is detected. In one embodiment, the sample is selected from the group consisting of tissue biopsies, blood samples, serum samples, plasma samples, saliva sample, and fecal samples. In one embodiment, the receptor protein comprises a $P2X_{7\text{-}j}$ receptor protein. In one embodiment, the receptor protein comprises a $P2X_7$ receptor protein. In one embodiment, the cell is diagnosed as a cancer cell when said detection identifies a low $P2X_7$ receptor protein level when compared to a normal cell. In one embodiment, a low $P2X_7$ receptor protein level is at least approximately 2-fold below a normal cell, preferably at least approximately 5-fold below a normal cell, but more preferably at least approximately 10-fold below a normal cell. In one embodiment, the cell is diagnosed as a cancer cell when said detection identifies a high $P2X_{7\text{-}j}$ receptor protein level when compared to a normal cell. In one embodiment, a high $P2X_{7\text{-}j}$ receptor protein level is at least approximately 2-fold above a normal cell, preferably at least approximately 5-fold above a normal cell, but more preferably at least approximately 10-fold above a normal cell. In one embodiment, the detection comprises an assay selected from the group consisting of immunofluorescence staining, immunoblotting, immunoprecipitation, flow cytometry, and immmunoassays such as an enzyme-linked immunoabsorbent assay. In one embodiment, the detection comprises an assay selected from the group consisting of an apoptosis assay, a cation channel formation assay, and a cation pore formation assay. In one embodiment, the detection comprises an antibody having specificity for the C-terminus of said P2X receptor protein. In one embodiment, the antibody specificity is directed to an amino acid sequence comprising IRQVLQGKQC (SEQ ID NO:1). In one embodiment, the antibody is a monoclonal antibody. In one embodiment, the antibody is a polyclonal antibody. In one embodiment, the antibody comprises a fluorescent antibody.

In one embodiment, the present invention contemplates a method, comprising: a) providing; i) a patient suspected of developing cancer; and ii) a reagent having specificity for at least one P2X nucleic acid; and iii) a sample derived from said patient comprising cells; and b) contacting said sample with said reagent under conditions such that said at least one P2X nucleic acid is detected. In one embodiment, the sample is selected from the group consisting of tissue biopsies, blood samples, serum samples, plasma samples, saliva sample, and fecal samples. In one embodiment, the nucleic acid comprises a ribonucleic acid. In one embodiment, the ribonucleic acid comprises a $P2X_{7-j}$ ribonucleic acid. In one embodiment, the ribonucleic acid comprises a $P2X_7$ ribonucleic acid. In one embodiment, the detection comprises RT-PCR (wherein RT-PCR comprises a reverse transcriptase enzyme during the performance of a polymerase chain reaction). In one embodiment, the cell is diagnosed as a cancer cell, when said detection identifies a low $P2X_7$ ribonucleic acid level when compared to a normal cell. In one embodiment, the cell is diagnosed as a cancer cell, when said detection identifies a high $P2X_{7-j}$ ribonucleic acid level when compared to a normal cell.

In one embodiment, the present invention contemplates a method, comprising: a) providing; i) a cell, wherein said cell is capable of transfection; and ii) a vector comprising a gene encoding a P2X receptor protein amino acid sequence; b) introducing said vector into said cell, wherein said cell becomes stably transfected with said gene; and c) expressing said gene under conditions such that said P2X ribonucleic acid is produced. In one embodiment, the method further comprises detecting said P2X ribonucleic acid. In one embodiment, the P2X ribonucleic acid detection comprising reverse transcriptase polymerase chain reaction. In one embodiment, the method further comprises translating said P2X nucleic acid to create a P2X receptor protein.

In one embodiment, the present invention contemplates a protein comprising a C-terminus having an amino acid sequence comprising IRQVLQGKQC (SEQ ID NO:1).

In one embodiment, the present invention contemplates an antibody comprising specificity for a protein comprising a C-terminus having an amino acid sequence comprising IRQVLQGKQC (SEQ ID NO:1).

In one embodiment, the present invention contemplates a method for detecting cancer cells or cells with potential to become cancer cells in a tissue or organ of a subject, comprising: assaying cells in a cell sample obtained from a subject for the presence of a truncated $P2X_7$ protein (i.e., for example, $P2X_{7-j}$) alone or in combination with the $P2X_7$ protein. In one embodiment, the truncated $P2X_7$ (i.e., for example, $P2X_{71}$) alone or in combination with the $P2X_7$ protein is located inside at least some of the cells. In one embodiment, the method is performed in conjunction with a Pap test. In one embodiment, the method is performed in conjunction with any other cytological screening. In one embodiment, the method is performed in conjunction with any other histological test.

In one embodiment, the present invention contemplates a method for treating a cancer or potential cancer in a patient comprising one or more of, increasing the amount and/or activity of $P2X_7$ RNA and/or protein in a cell, and decreasing the amount and/or activity of $P2X_{7-j}$ RNA and/or protein in a cell.

In one embodiment, the present invention contemplates a composition for treating cancer or potential cancer in a patient, comprising an antibody capable of specifically binding to all or part of an amino acid sequence comprising IRQVLQGKQC (SEQ ID NO:1).

Definitions

The term "tumor", "cancer", or "cancer cell" as used herein, refers to an abnormal benign or malignant growth of tissue and arises from uncontrolled usually rapid cellular proliferation.

The term "reduced in size" means any quantitative reduction of a three dimensional measurement (i.e., for example, circumference, length, width, height, density etc.) of a physical object (i.e., for example, tumor, epithelial layer etc.).

"Vector" shall be defined as a nucleic acid molecule capable of having one or more genes therein encoded transcribed when put into the appropriate environment in vivo or in vitro. In one embodiment, a vector comprises a gene encoding a P2X gene.

"Expression" shall be defined as the transcription and translation of a gene. Such transcription and translation may be in vivo or in vitro.

"Constitutive" shall be defined as the level of expression of a genomic gene in vivo.

"Overexpression" shall be defined as expression at a level above the level normally expressed by an untransfected cell and may be reflected by the combined expression level of a genomic gene along with a similar gene transfected into a cell.

"Transfect" shall be defined as the introduction of a vector into a cell by means such as, e.g., electroporation.

"In operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "compound" as used herein refers to organic or inorganic molecules. The term includes, but is not limited to polypeptides, proteins, glycoproteins (e.g. antibodies), nucleic acids, oligonucleotides, and inorganic molecules.

The term "small molecule", as used herein, refers to a compound that is an organic molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Daltons.

The term "protein" herein is meant at least two covalently attached amino acids, which includes proteins, polypeptides, oligopeptides, and peptides. The protein may be made of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline, and norleucine are considered amino acids for the purposes of this invention. "Amino acid" also includes imino acid residues such as proline and hydroxyproline. The side chains may be in either the (R) or the (S) configuration. In one embodiment, the amino acids are in the (R) or D-configuration. In one embodiment, the amino acids are in the (S) or L-configuration. If non-naturally occurring side chains are used, non-amino acid substituents may be used, for example to prevent or retard in vivo degradations.

The term "fusion protein", as used herein, refers to a chimeric protein containing the protein of interest (i.e., for example, a P2X receptor protein) joined to an exogenous protein or peptide. The fusion partner may enhance solubility of a P2X receptor protein as expressed in a host cell, may provide an affinity tag to allow purification of the recombinant fusion protein from the host cell or culture supernatant, or both.

The term "protein transduction domain", as used herein, refers to a portion of a fusion protein that possesses the ability to transverse biological membranes efficiently Hwu, "Fusion protein for use as vector" U.S. Pat. No. 6,835,810 (herein incorporated by reference).

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, including, but not limited to, phosphoramide, phosphorothioate, phosphorodithioate, O-methyiphophoroamidite linkages peptide nucleic acid backbones and linkages.

The term "antisense", as used herein, refers to any nucleic acid comprising an exogenous nucleic acid sequence having reverse complementarity to an endogenous nucleic acid sequence. An antisense sequence may then bind to an endogenous nucleic acid sequence (i.e., for example, an open reading frame) and prevent transcription of a gene of interest. Consequently, antisense nucleic acids sequences are useful as transcription inhibitors (i.e., for example, inhibition of P2X7-j transcription).

"In vivo" refers to in the living body of an organism.

"In vitro" refers to outside the living body, such as, an artificial environment, for example, a test tube or a cell or tissue culture.

The term "promote" as used herein, refers to an interaction between a molecule and a biological pathway or system, that causes a change (e.g., enhancement) in the biological pathway or system. Molecules resulting in promotion may include proteins, nucleic acids, carbohydrates, or any other molecules which bind or interact with biologically active molecules.

The term "inhibited" or "inhibit" as used herein, refer to a molecule which, when interacting with a biologically active molecule, blocks or modulates the biological activity of the biologically active molecule. Antagonists and inhibitors may include proteins, nucleic acids, carbohydrates, or any other molecules that bind or interact with biologically active molecules. Inhibitors and antagonists can effect the biology of entire cells, organs, or organisms (e.g., an inhibitor that slows tumor growth).

The term "antibody", as used herein, refers to any protein that are produced normally by specialized B cells after stimulation by an antigen and act specifically against the antigen in an immune response, and that typically consist of four sub-units including two heavy chains and two light chains.

The term "accessible", as used herein, refers to any ability to treat a solid tumor by non-surgical or minimal surgical techniques. Such techniques may include, but are not limited to, injection into the skin or injection via endoscopy, bronchoscopy, cystoscopy, colonoscopy, laparoscopy, catheterization, or topical application by a lotion, ointment or powder. For example, an ovarian solid tumor may be accessible by laparoscopy. In another example, a colon solid tumor may be accessible by colonoscopy.

The term "introducing", as used herein, refers to any method of transferring a compound into a tissue and subsequently into cells within said tissue. Such methods of introduction may include, but are not limited to, viral vectors, retroviral vectors, adenoviral vectors, biobalistics, lipofection, and many commercially available DNA vectors known in the art. Alternatively, a compound may be placed adjacent to a cell such that the compound is incorporated into the cell by physiological mechanisms (i.e., for example, hydrophobic interactions or active transport). One method of introduction comprises injection, wherein a compound is placed directly into the intercellular space within the injected tissue. Such an injection may be possible when an organ part, growth (i.e., for example, a solid tumor), or bodily cavity is "accessible".

The term "into", as used herein, refers to the successful penetration of a molecule through or within a cell membrane. For example, a molecule may be introduced into a solid tumor cell by an "intratumoral injection".

The term "regression", "is at least partially diminished in size" or "reduced", as used herein, refers to a diminution of a bodily growth, such as, for example, a solid tumor. Such a diminution may be determined by a reduction in measured parameters such as, but not limited to, diameter, mass (i.e., weight), or volume. The diminution by no means indicates that the size is completely reduced, only that a measured parameter is quantitatively less than a previous determination.

The term "apoptosis", as used herein, refers to any cellular breakdown of a cell, such as, for example, the cells of a solid tumor or a cancer cell. Intracellular apoptosis may also involve the macrophage phagocytosis such that a bodily growth becomes digested and eliminated from the body.

The term "growth", as used herein, refers to any tissue or organ that comprises a cellular mass considered to represent an abnormal proliferation. Such growths may be cancerous, non-cancerous, malignant, or non-malignant. If a growth comprises cancer, it may be a tumor. Such tumors may be solid or non-solid.

The term "accessible through the skin", as used herein, refers to any non-surgical technique that is capable of reaching an internal organ or body cavity. Such non-surgical techniques do not require conventional open site surgery comprising a scalpel incision. Non-surgical techniques include, but are not limited to, percutaneous access, or bodily orifice access to internal organs or body cavities. For example, percutaneous access may include, but is not limited to, laparoscopy and catheterization. In another example, bodily orifice access, may include, but is not limited to, endoscopy, bronchoscopy, cystoscopy, and colonoscopy.

The term "patient", as used herein, refers to any organism that is capable of developing a tumor. Such organisms include mammals, but are not limited to, human, dog, cat, horse, cow, sheep, goat, mouse, rat, guinea pig, monkey etc.

The term "liposome", as used herein, refers to any composition, mixture, or solution that contains sufficient lipids (i.e., for example, phospholipids) to attain a critical micellular concentration (CMC). When liposomes are formed in the presence of a molecule or other substance (i.e., for example, a protein or drug), the liposomes encapsulate the molecule or other substance. Consequently, the liposomal composition may be administered to a patient whereby the encapsulated contents are protected from physiological metabolic pathways before delivery to a target (i.e., for example, a cancer cell and/or tumor).

The term "isolated", as used herein, refers to any composition or mixture that has undergone a laboratory purification procedure including, but not limited to, extraction, centrifugation, chromatographic separation (i.e., for example, thin layer chromatography or high performance liquid chromatography). Usually such a purification procedures provides an isolated composition or mixture based upon physical, chemical, or electrical potential properties. Depending upon the choice of procedure an isolated composition or mixture may contain other compositions, compounds or mixtures having similar chemical properties. For example, an isolated composition or mixture may contain between 1-20%, preferably, 1-10%, but more preferably 1-5% of compositions or mixtures having similar chemical properties.

The term "molecule", as used herein, refers to the smallest particle of a composition that retains all the properties of the composition and is composed of one or more atoms. These one or more atoms are arranged such that the molecule may interact (i.e., ionically, covalently, non-covalently etc) with other molecules to form attachments and/or associations. For example, a molecule may have one or more atoms arranged to provide a capability for an interaction with a P2X receptor protein and/or gene.

The term "formulation" or "pharmaceutical formulation", as used herein, refers to any composition intended for the administration of a pharmaceutical compound, or combination, including, but not limited to, any chemical or peptide, natural or synthetic, that is administered to a patient for medicinal purposes. Specifically, a formulation may comprise either a single compound or a plurality of compounds.

The term "compounded" or "compounded formulation", as used herein, refers to any formulation containing a plurality of compounds, wherein the compounds may have the same, or different dosage ratios, and further wherein the compounds may be uniform (i.e., evenly mixed) or non-uniform (i.e., unevenly mixed, including but not limited to, separated tablet layers or separated capsule compartmentalization).

The term "tablets", as used herein, refers to any solid formulation comprising at least one pharmaceutical compound intended for oral or intrapulmonary administration to a patient. In one embodiment, "tablets" may have multiple layers (i.e., multilayered tablets), wherein each layer comprises different pharmaceutical formulation.

The term "capsules", as used herein, refers to any polymer film-based container comprising a single or plurality of compartments containing at least one pharmaceutical compound intended for oral or intrapulmonary administration to a patient. In one embodiment, "capsules" may have multiple compartments (i.e., multi-compartmentalized), wherein each compartment comprises a different pharmaceutical formulation.

The term "parenteral", refers to the administration of a molecule, composition, or formulation that does not involve the gastrointestinal system. For example, parenteral is generally referred to in regards to an injection (i.e., for example, intravenous, intraperitoneal, intramuscular, subcutaneous, or intratumoral). A topical (i.e., for example, transdermal) route of administration is also within the scope of parenteral administration.

The term "connect" or "directly connected to" or "indirectly connected to", as used herein, are interchangeable and include configurations that are connected through another component or components.

BRIEF DESCRIPTION OF THE FIGURES

This patent application contains at least one drawing executed in color. Copies of this patent or patent application publication with color drawing(s) will be provided by the Office upon request and payment of the necessary fee.

FIG. 2A-E illustrates example nucleotide sequences of the coding regions and amino acid sequences for the wild type full length P2X$_7$ (FIG. 2A-B (SEQ ID NOS:3-4)) and the truncated P2X$_7$ (FIG. 2C (SEQ ID NOS:5-6)) (which may be also referred to as P2X$_{7-j}$ or P2X$_7$-R$_{TR}$, and which designations are hereinafter used interchangeably) FIG. 2C (SEQ ID NOS:5-6) also provides one example how the P2X$_{7-j}$ is generated by near complete omission of exon 8, with the exception of Adenine-882, resulting in frameshift and stop-codon at base-pairs 775-778. The truncated P2X$_{7-j}$ receptor lacks one third of the extracellular loop, the second transmembrane domain, and the entire C terminus. FIG. 2D (SEQ ID NOS: 15-16) shows the frameshift leading to the stop codon and the truncation of the P2X$_{7-j}$. FIG. 2E (SEQ ID NOS:17-18) shows a detailed comparison of the C-terminus of the P2X$_{7-j}$ protein as compared to the respective amino acid segment of the P2X$_7$ (FIG. 2E) (further discussed below).

FIG. 4 illustrates example primers (SEQ ID NOS:11-14) and conditions for detection of the P2X$_7$ and/or P2X$_{7-j}$ mRNAs by reverse transcription-polymerase chain reaction (RT-PCR).

FIG. 15 illustrates example results of cell-number index for cells grown in culture, including MDCK cells expressing P2X$_7$(Myc) or P2X$_{7-j}$(Myc) under the control of a promoter inducible by doxycycline (Panel A); and HEK-293 cells, HEK-293 cells expressing P2X$_7$, and HEK-293 cells expressing P2X$_{7-j}$ (Panel B).

Figure 1:
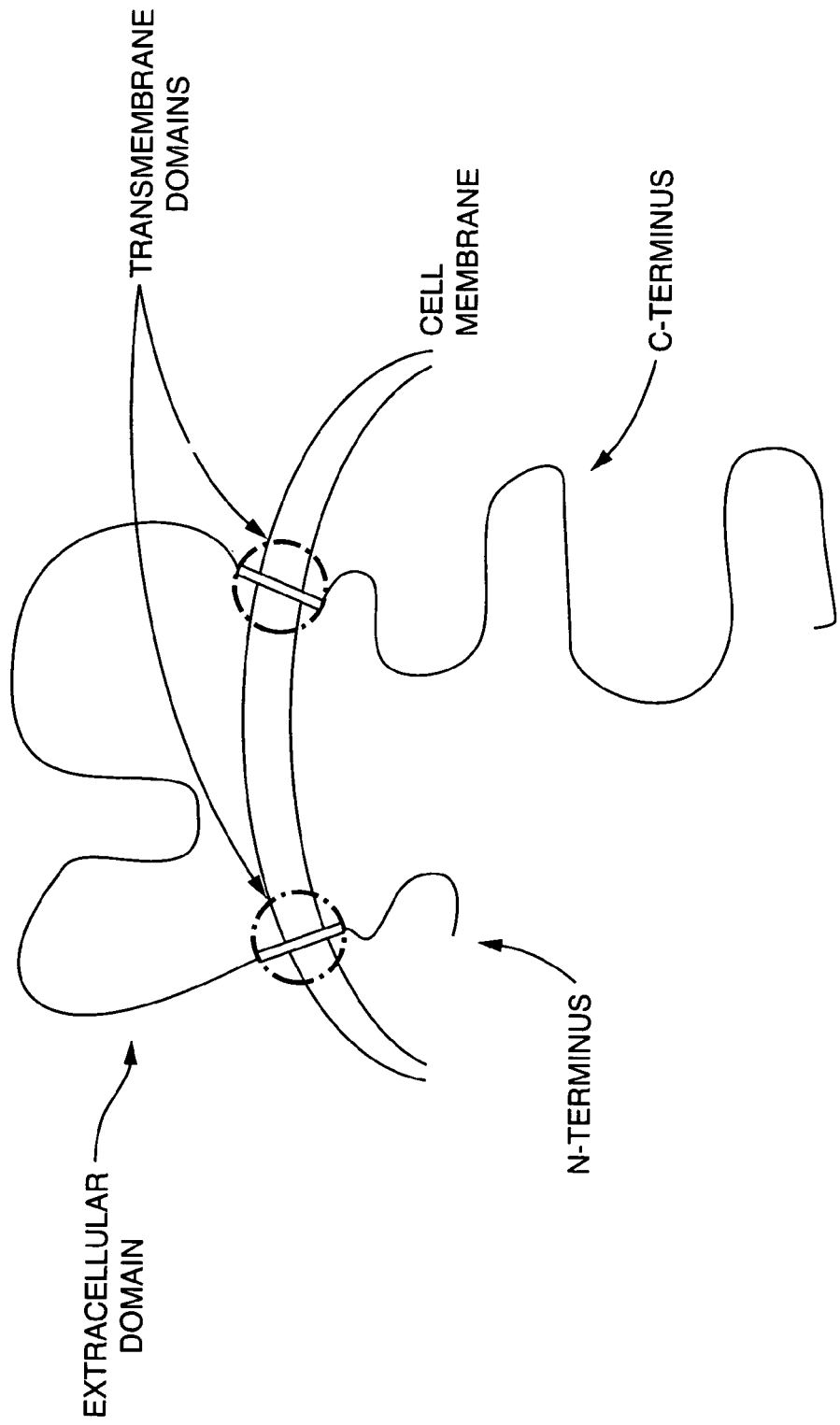
FIG. 1 illustrates an example predicted structure of a wild-type, full-length P2X$_7$ receptor (which may be also referred to as P2X$_7$-R$_{FL}$ or P2X$_7$-WT, and which designations are hereinafter used interchangeably).

Panel A: Right Lane—Shows P2X$_7$ homooligomerization banding pattern in MDCK cells transfected with Myc/HA tagged P2X$_7$ exposed to Myc-immunoprecipitation (IP) and HA immunoblotting (IB); Left Lane—Shows a control experiment where only Myc tagged proteins were detected (Myc-IP and Myc-IB).

Panel B. Right Lane—Shows P$_2$X$_{7-j}$ homooligomerization banding pattern in HEK293 cells transfected with Myc/HA P$_2$X$_{7-j}$ exposed to Myc-immunoprecipitation (IP) and HA immunoblotting (IB). Middle Lane—Shows a control experiment where only HA tagged proteins were detected. Left Lane—Shows a control experiment where only Myc tagged proteins were detected.

Panel C. Right Lane-Shows a P$_2$X$_7$/P$_2$X$_{7-j}$ heterooligomerization banding pattern in HEK293 cells transfected with HA P$_2$X$_7$ and Myc P$_2$X$_{7-j}$ exposed to Myc-immunoprecipitation (IP) and HA immunoblotting (IB). Left Lane—Shows a control experiment where only HA tagged proteins were detected (i.e., P2X$_7$ proteins). Middle Lane—Shows a control experiment where only Myc tagged proteins were detected (i.e., P2X$_{7-j}$ proteins).

Panel D. Electrophoretic separation of P2X$_7$/P2X$_{7-j}$ protein molecules on 6-8% gels. Each lane was prepared using anti-P2X$_7$ receptor antibody immunoblot (IB) on extracts from HEK293-P2X$_7$ or HEK293-P2X$_{7-j}$ cells. Left Lane—Standard markers with P2X$_7$ and P2X$_{7-j}$ with standard protein stain. Second Lane from Left: Standard markers with P2X$_7$ and P2X$_{7-j}$ stained with anti-P2X$_7$-R-Ab. Full-Length 75 kDal P2X$_7$ protein is, in fact, a complex of a native non-glycosylated 65 kDa protein and a heavier glycosylated 85 kDal protein. Third Lane from Left—Showing that in HEK293 cells expressing the P2X$_7$ alone, the 85-65 kDal form, a major 220 kDal specific P2X$_7$ as well as a minor 115 kDal form immunoreactivity could be detected. Fourth Lane from Left—Showing that in HEK293 cells expressing the P2X$_{7-j}$ alone, the 45-42 form, a major 90 kDal specific P2X$_{7-j}$, as well as a minor 135 kDal immunoreactivity could be detected.

Figure 19:
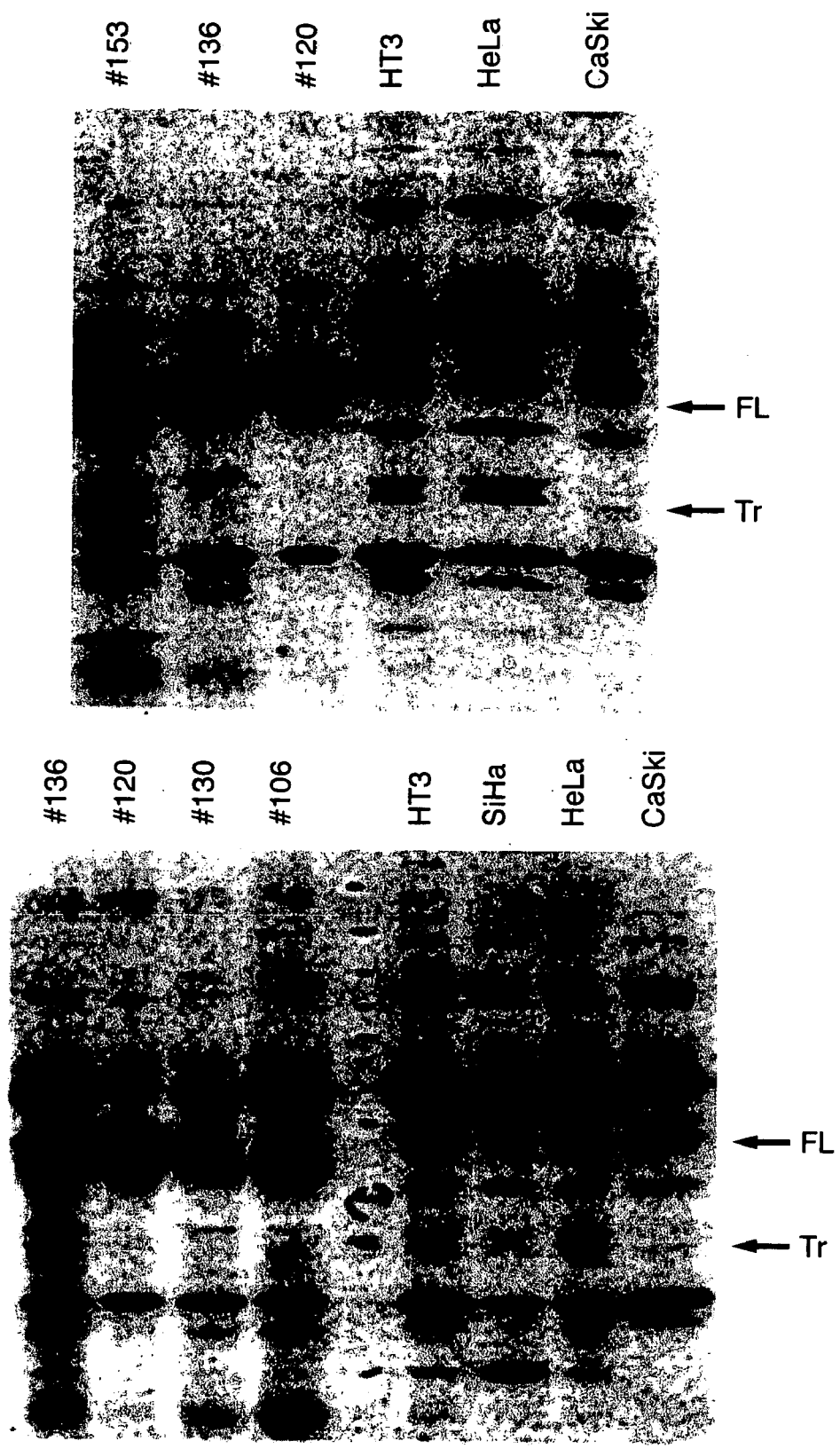

FIG. 19 illustrates example results of immunoblotting experiments using antibodies against P2X$_7$ to probe extracts from cervical cancer cell lines and from normal cervical cells.

FIG. 20 illustrates example results of immunoblotting experiments using antibodies against P2X$_7$ to probe extracts from various cancer cell lines and normal cells.

FIG. 21 illustrates example results of an immunoblotting experiment using sera from a rabbit immunized with a peptide of amino acid sequence GDNFSDVAIQIRQVLQGKQC (SEQ ID NO: 2), and with pre-immune sera, to probe extracts from HEK293 cells expressing either the P2X$_7$ or the P2X$_{7-j}$ proteins.

FIG. 22 is a schematic illustration of example results of a growth/survival experiment, showing selection of BzATP-resistant cells.

Figure 23:
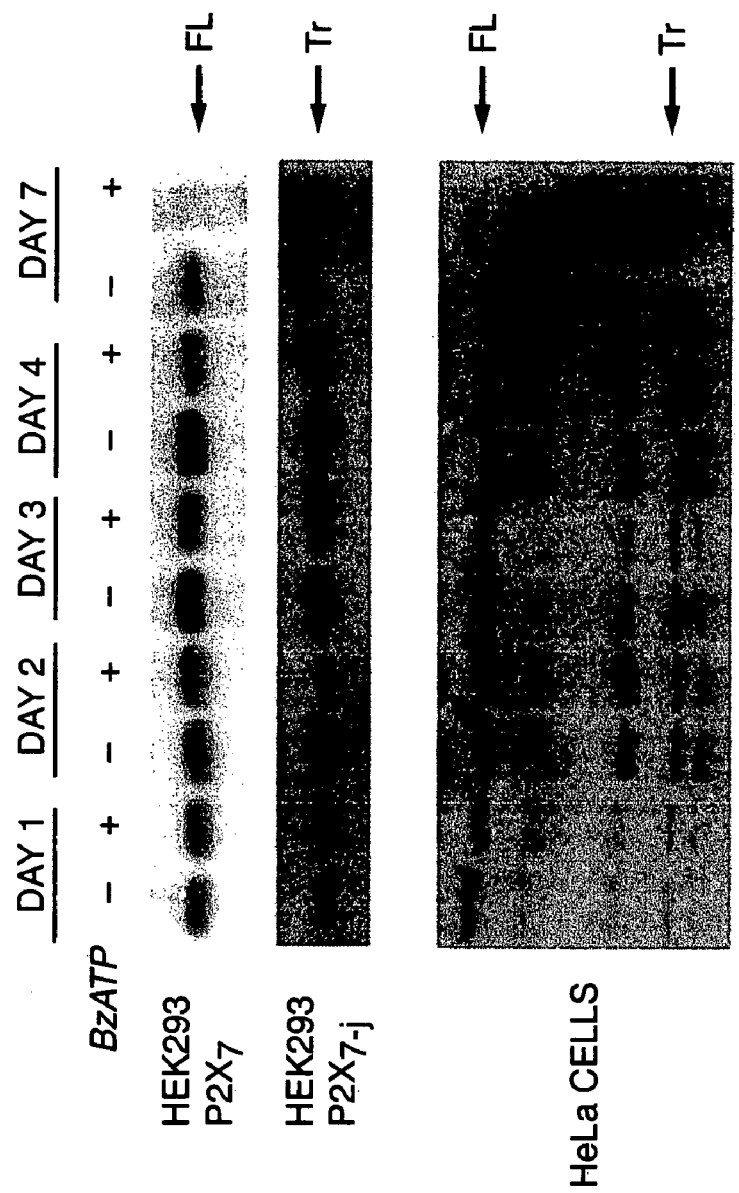

FIG. 23 illustrates example results of growth of HEK-293 cells expressing either the P2X$_7$ or the P2X$_{7-j}$ proteins, and the human cervical cancer cell line HeLa (which express endogenously both the P2X$_7$ and P2X$_{7-j}$ proteins when grown in the absence or presence or BzATP.

FIG. 24 illustrates example results of immunostaining of human cervical normal, pre-cancer and cancer tissues using commercially available anti P2X$_7$-antibody that recognizes the C-terminus. Panel A: Cross section of normal endocervix. Panel B: Cross section of normal endocervix pre-incubated with the antigen used to raise the antibody, showing no staining thus indicating antibody specificity. Panel C: A cross section of normal ectocervix stained with the anti-P2X$_7$-receptor antibody. Panel D: A cross section of normal ectocervix stained with anti-E-cadherin antibody. Panel E: A cross section of a cervix with mild dysplasia stained with the anti-P2X$_7$-receptor antibody. Panel F: A cross section of a cervix with moderate dysplasia stained with the anti P2X$_7$-receptor antibody. Panel G: A cross section of a cervix with high-grade dysplasia stained with the anti P2X$_7$-receptor antibody. Panel H: A cross section of a cervix with invasive cervical cancer stained with the anti P2X$_7$-receptor antibody. In Panels C-H, the subepithelial tissues are on the lower left, and the luminal spaces on the upper right. 20× Magnification.

Figure 25:
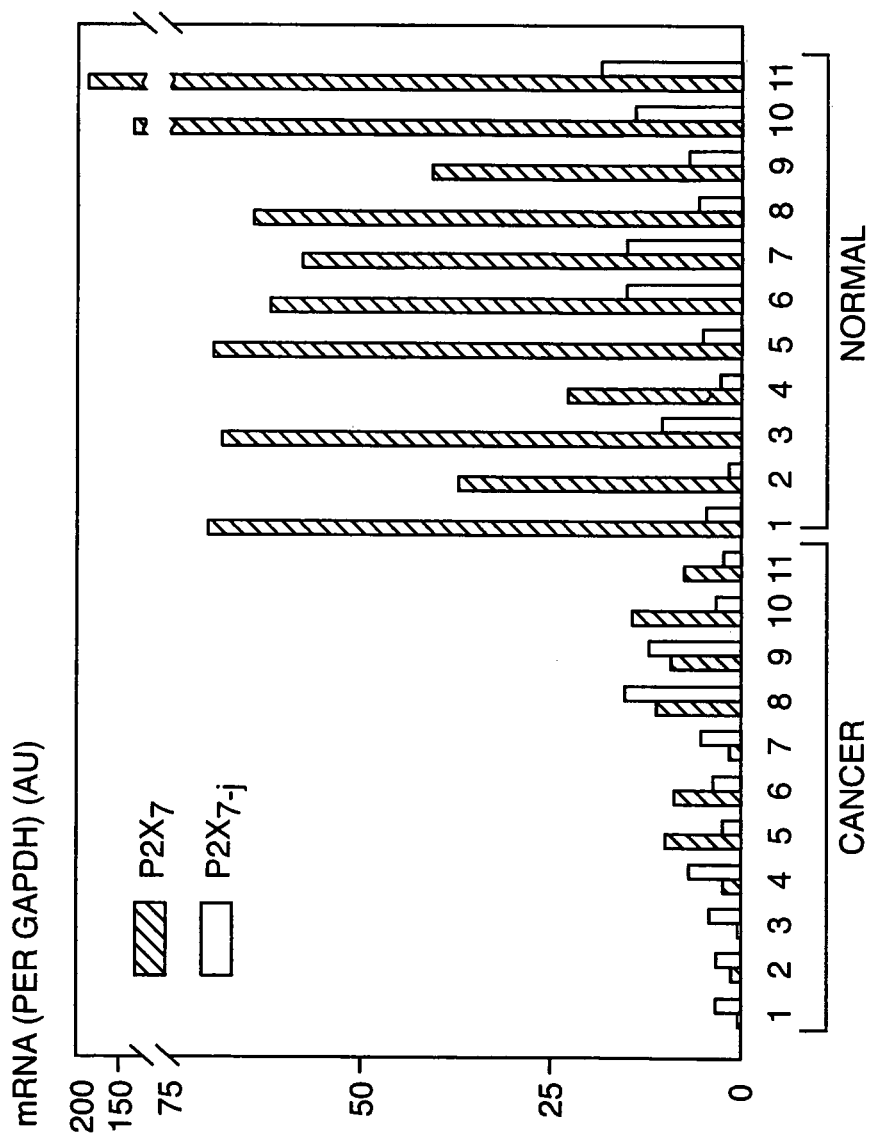

FIG. 25 illustrates example results of an analysis of P2X$_7$ and P2X$_{7-j}$ mRNA levels as determined by Real-Time RT-PCR and normalized in each sample to mRNA of GPDH in uterine tissues obtained from women with cancer of the lining of the uterus (endometrium). Shown are results in 11 women (numbered 1 to 11), and in all women both normal cancer (designated Cancer) and normal uterine tissues surrounding the cancer (designated Normal) were obtained. P2X$_7$: Filled bars. P2X$_{7-j}$: Empty bars.

Figure 26A:
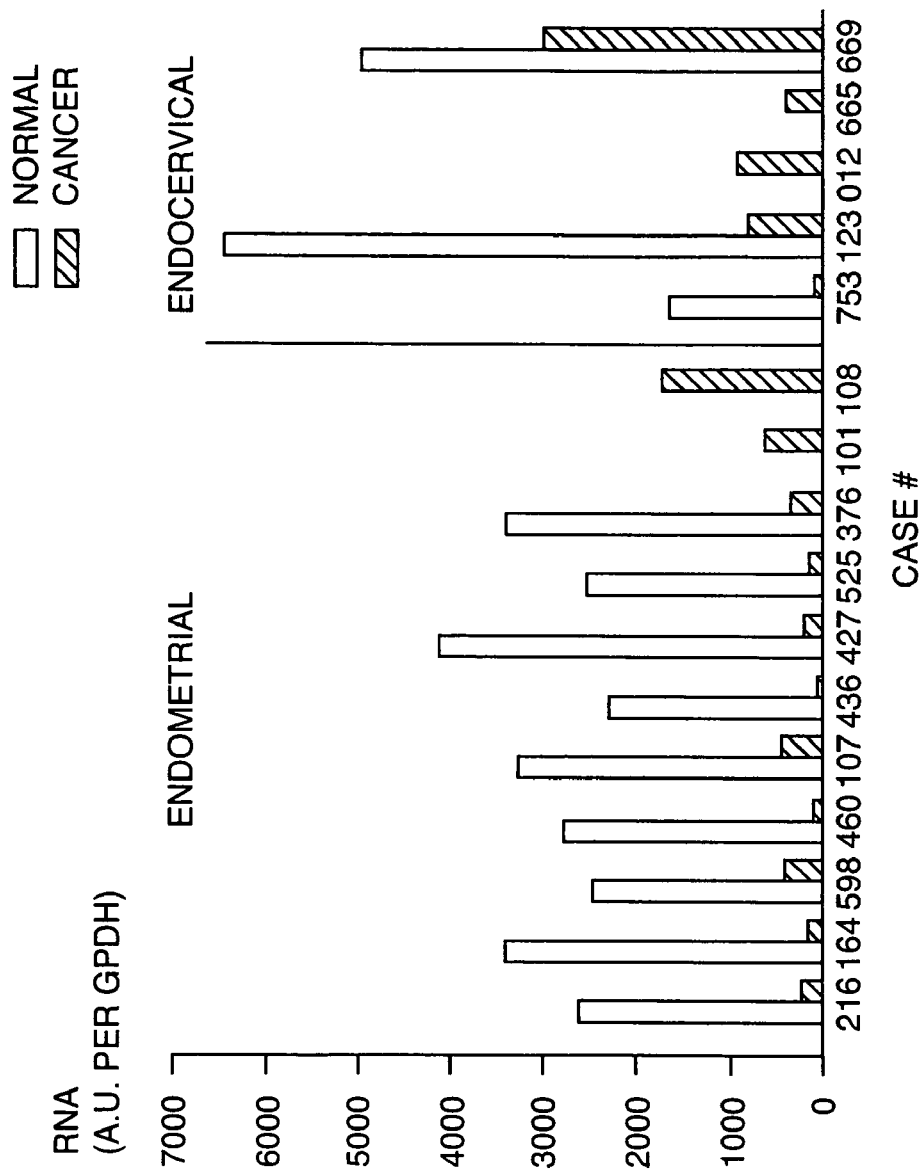
Figure 26B:
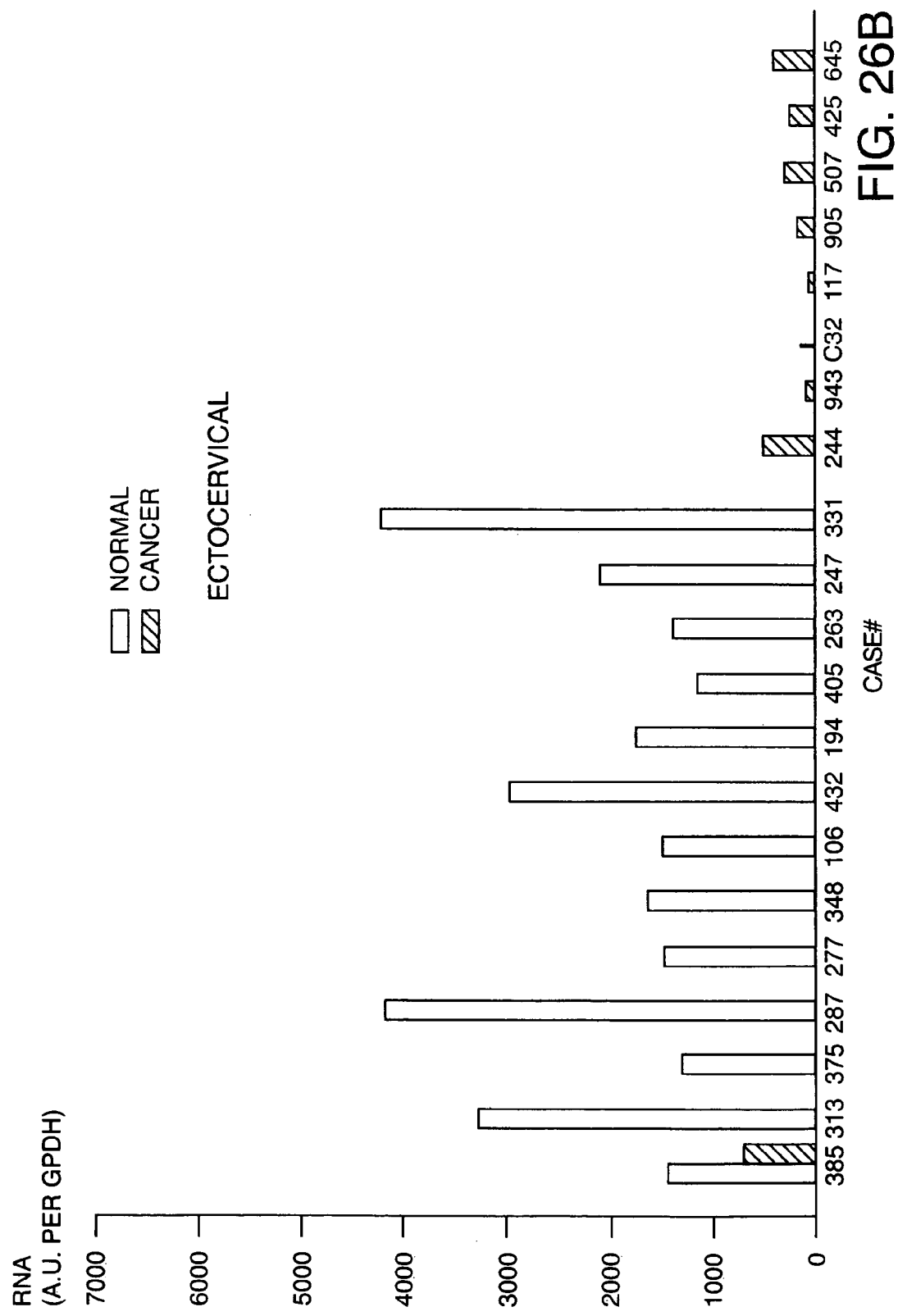

FIGS. 26A-B illustrates example results of an analysis of P2X$_7$ mRNA levels as determined by Real-Time RT-PCR and normalized in each sample to mRNA of GPDH in uterine tissues obtained from women with either normal (open bars) or cancer tissues (filled bars) of the lining of the uterus (endometrium), lining of the inner part of the cervix (endocervix), and from the lining of the outer part of the cervix (ectocervix). Case numbers (#) refer to patients identifying code number. In some women both normal and cancer were obtained.

FIG. 27 illustrates example results of $P2X_7$ and tubulin protein levels by Western analysis using commercially available anti $P2X_7$-receptor antibody that recognizes the C-terminus. In each Panel the symbols N and C refer respectively to normal and cancer tissues. Panel A shows example results from endometrial tissues. Panel B shows example results from ectocervical tissues. Panel C shows example results from ectocervical tissues. Numbers above the Panels refer to the woman's identification code. Horizontal underline numbers indicate that normal and cancer tissues were obtained from the same patient. Vertically placed numbers indicate single cases, namely that either normal or cancer tissue was obtained from that patient.

Figure 28A:
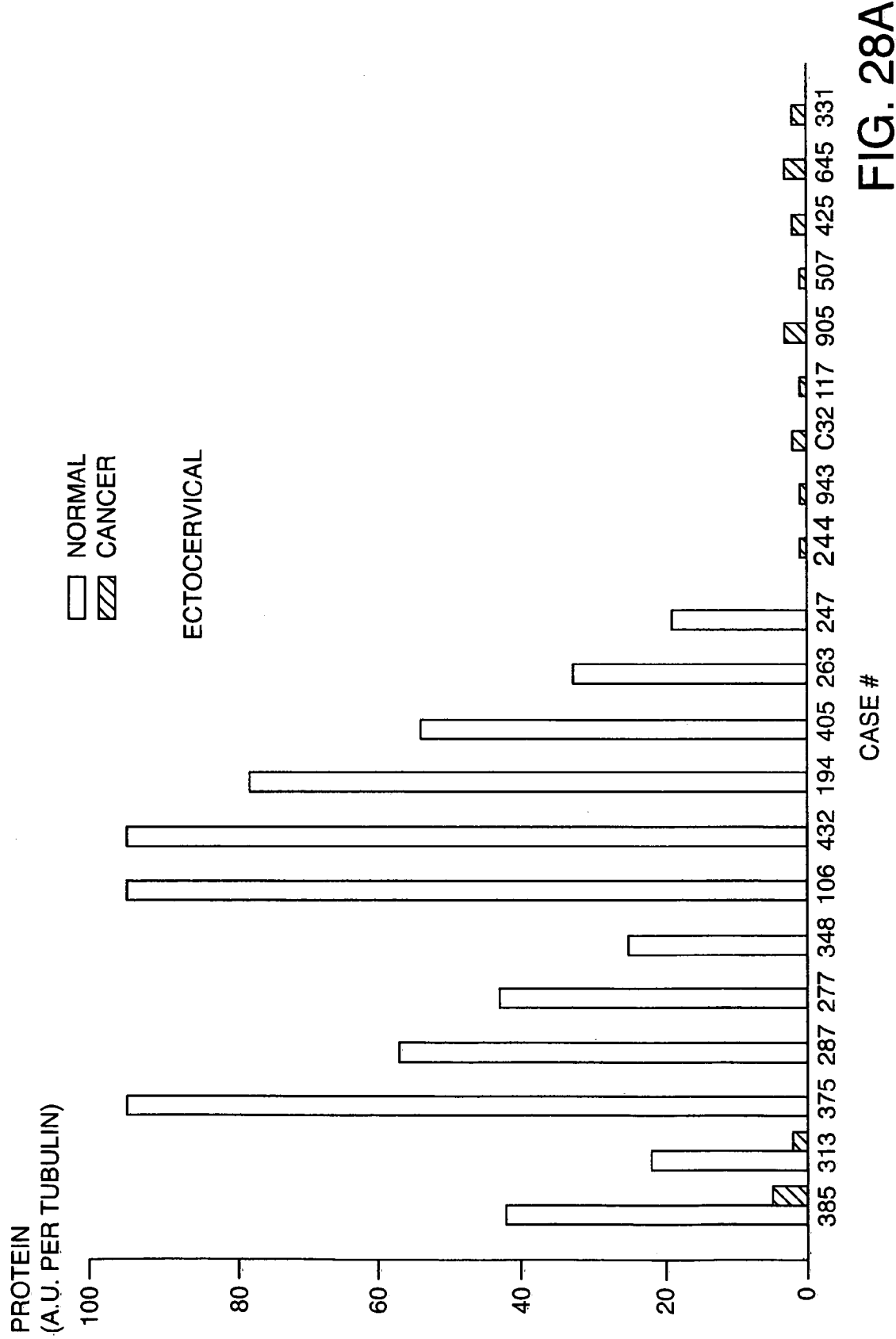
Figure 28B:
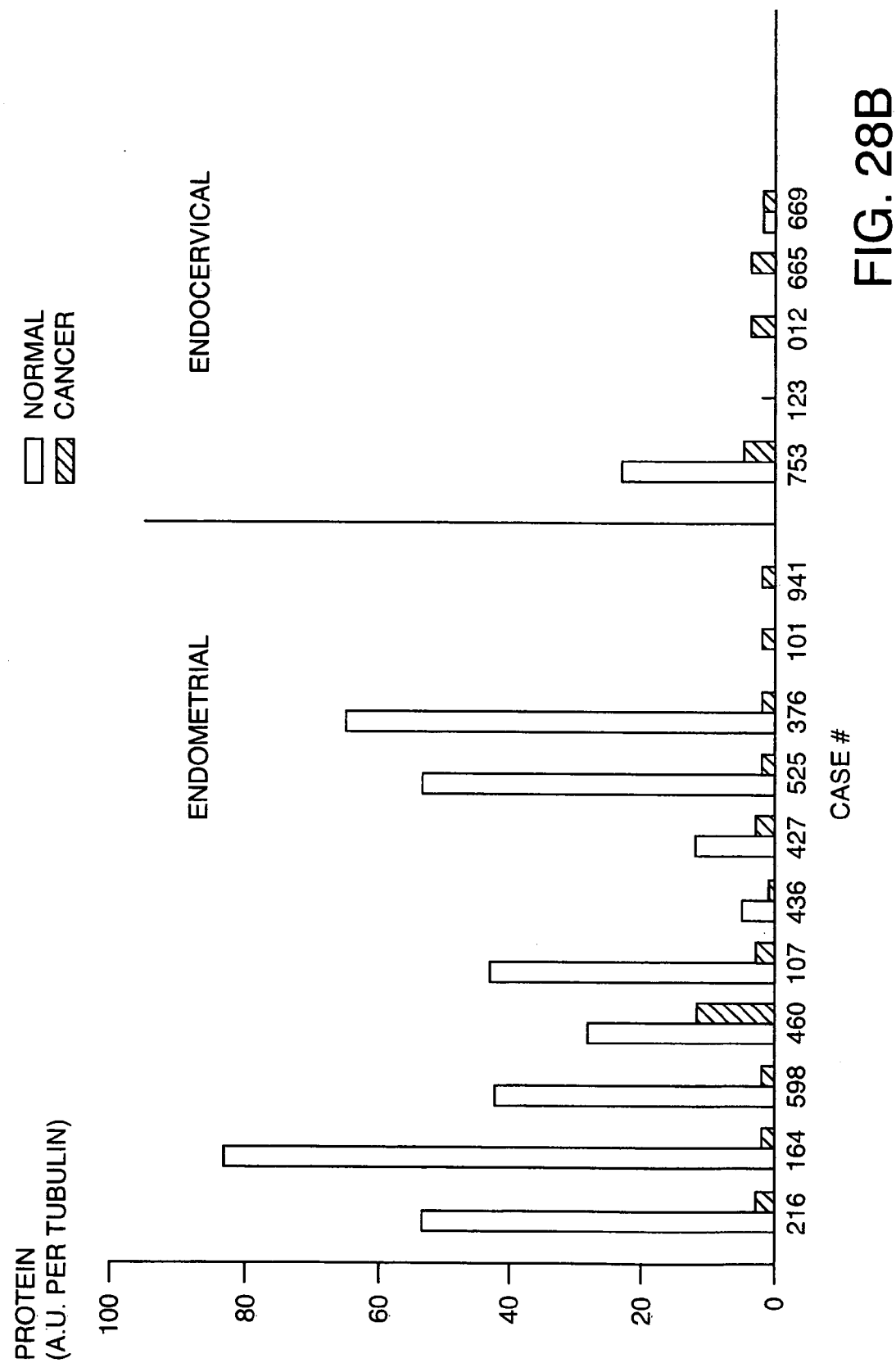

FIGS. 28A-B illustrates example results of an analysis of the $P2X_7$ protein levels from FIG. 27. In each case the density of the $P2X_7$ immunoreactivity band was normalized to the respective tubulin immunoreactivity.

Figure 29:
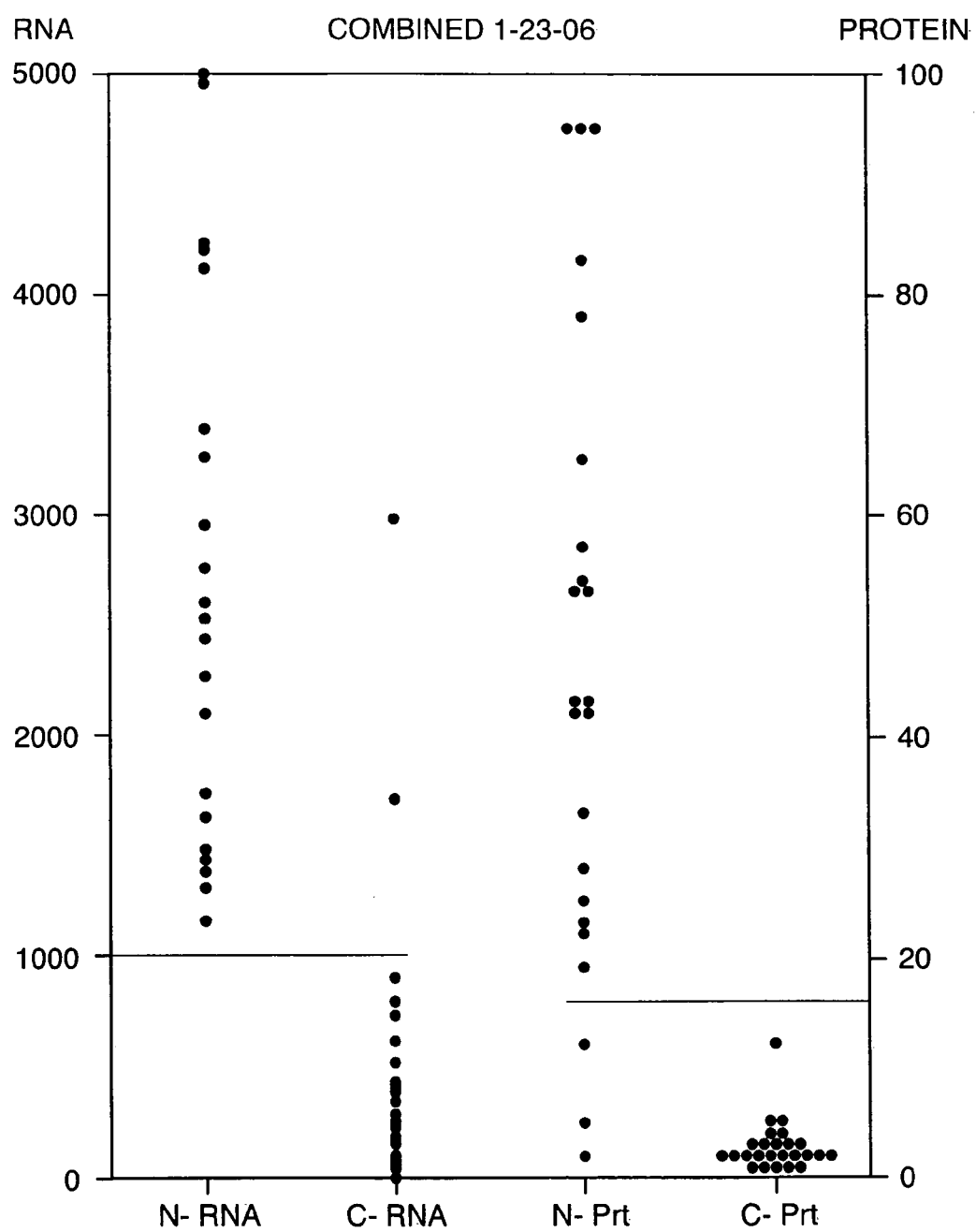

FIG. 29 illustrates a composite of the example data shown in FIG. 26 and FIG. 28 for mRNA $P2X_7$/GPDH (RNA) in normal (N) and cancer (C) samples (two left lanes), and for protein $P2X_7$/tubulin (Prt) in normal (N) and cancer (C) samples (two fight lanes). Each dot represents a single independent measurement. The horizontal bars indicate examples of arbitrarily determined cutoff points for the RNA and Protein data in an attempt to differentiate levels of cancer versus normal tissues.

FIG. 30 illustrates an example of statistical analysis of the mRNA $P2X_7$/GPDH data from FIG. 29.

FIG. 31 illustrates an example of statistical analysis of the protein $P2X_7$/tubulin data from FIG. 29.

FIG. 32 illustrates example of statistical analysis of the mRNA $P2X_7$/GPDH data and the protein $P2X_7$/tubulin data from FIG. 29.

FIG. 33 illustrates an example of an embodiment useful for differentiation of normal and cancer cells. Panel A: Demonstrates epidermal growth factor receptor (EGFR) expression. Panel B: Demonstrates $P2X_7$ expression. Panel C: Demonstrates a composition of EGFR and $P2X_7$ expression. Panel D: Presents identical data as FIG. 36B, except that the cancer cell nuclei are identified with the letter "C".

Figure 34:
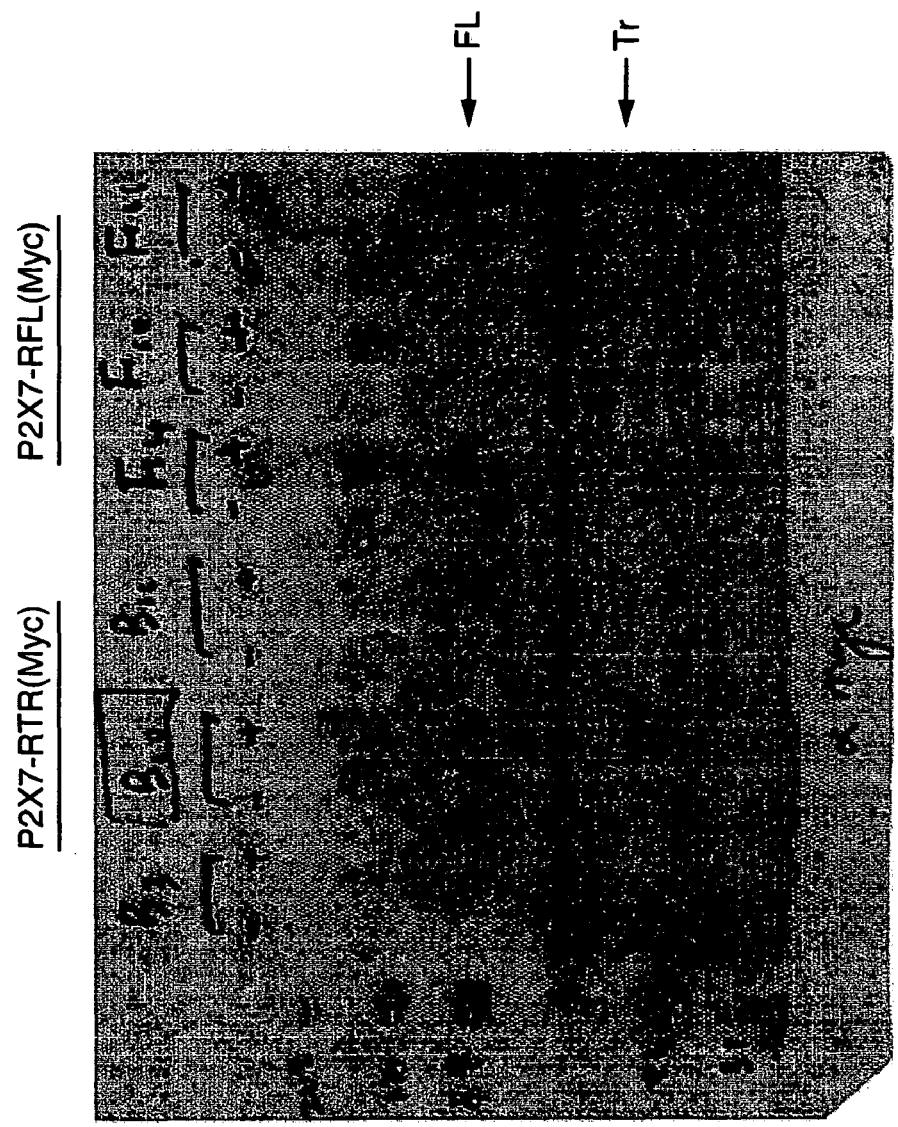

FIG. 34 illustrates example results of immunoblotting experiments using antibodies against a myc tag to probe extracts from MDCK cells expressing either $P2X_7$-$R_{FL}$(Myc) or $P2X_7$-$R_{TR}$(Myc) under the control of a promoter inducible by doxycycline.

FIG. 35 illustrates example results of antibody staining for $P2X_7$ protein in fixed HEK-293 cells expressing either $P2X_7$ (Panels A, B, & C) or $P2X_{7-j}$ (Panels D, E, & F). Panels A and D: $P2X_7$ antibody stain+catenin. Panels B and E: $P2X_7$ antibody stain. Panels C and F: Catenin.

Figure 36:
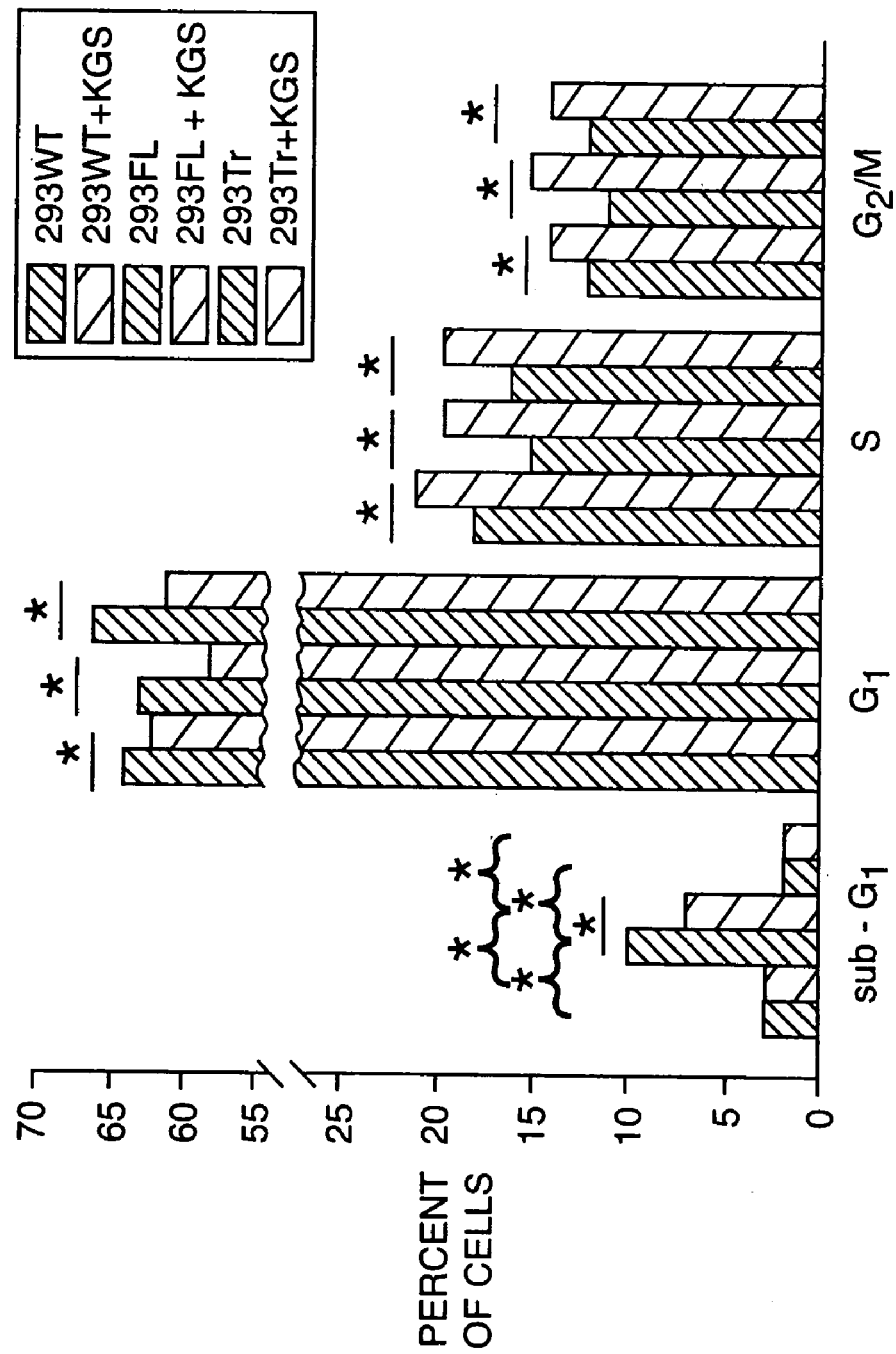

FIG. 36 illustrates example results of cell proliferation and apoptosis in HEK-293 cells, HEK-293 cells expressing $P2X_7$-$R_{FL}$, and HEK-293 cells expressing $P2X_7$-$R_{TR}$. The * in the figure indicates p<0.01 for comparison of the indicated data (Analysis by ANOVA).

Figure 37:
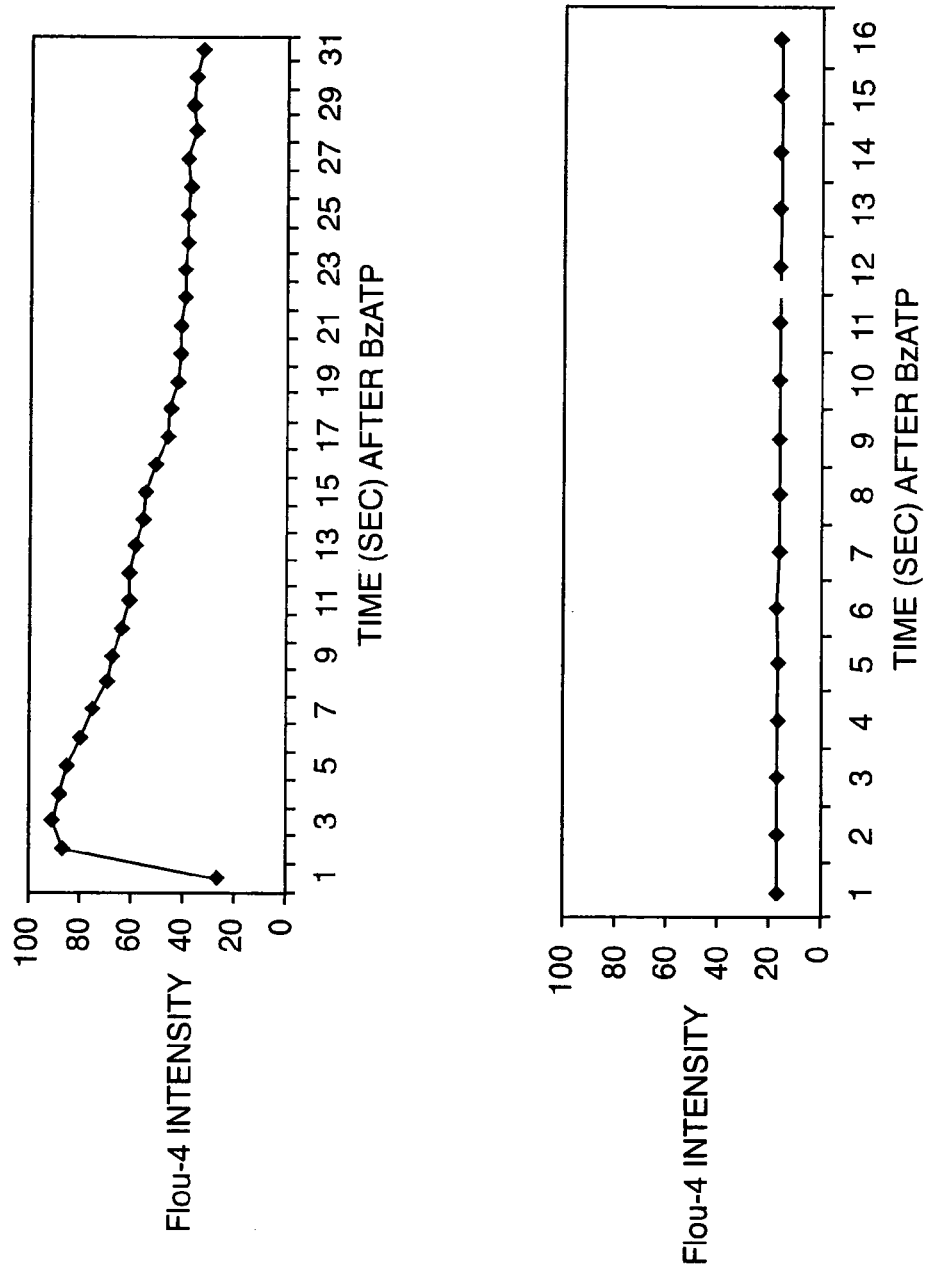

FIG. 37 illustrates example results of BzATP-stimulated channel activation of $P2X_7$-$R_{FL}$ and $P2X_7$-$R_{TR}$.

Figure 38:
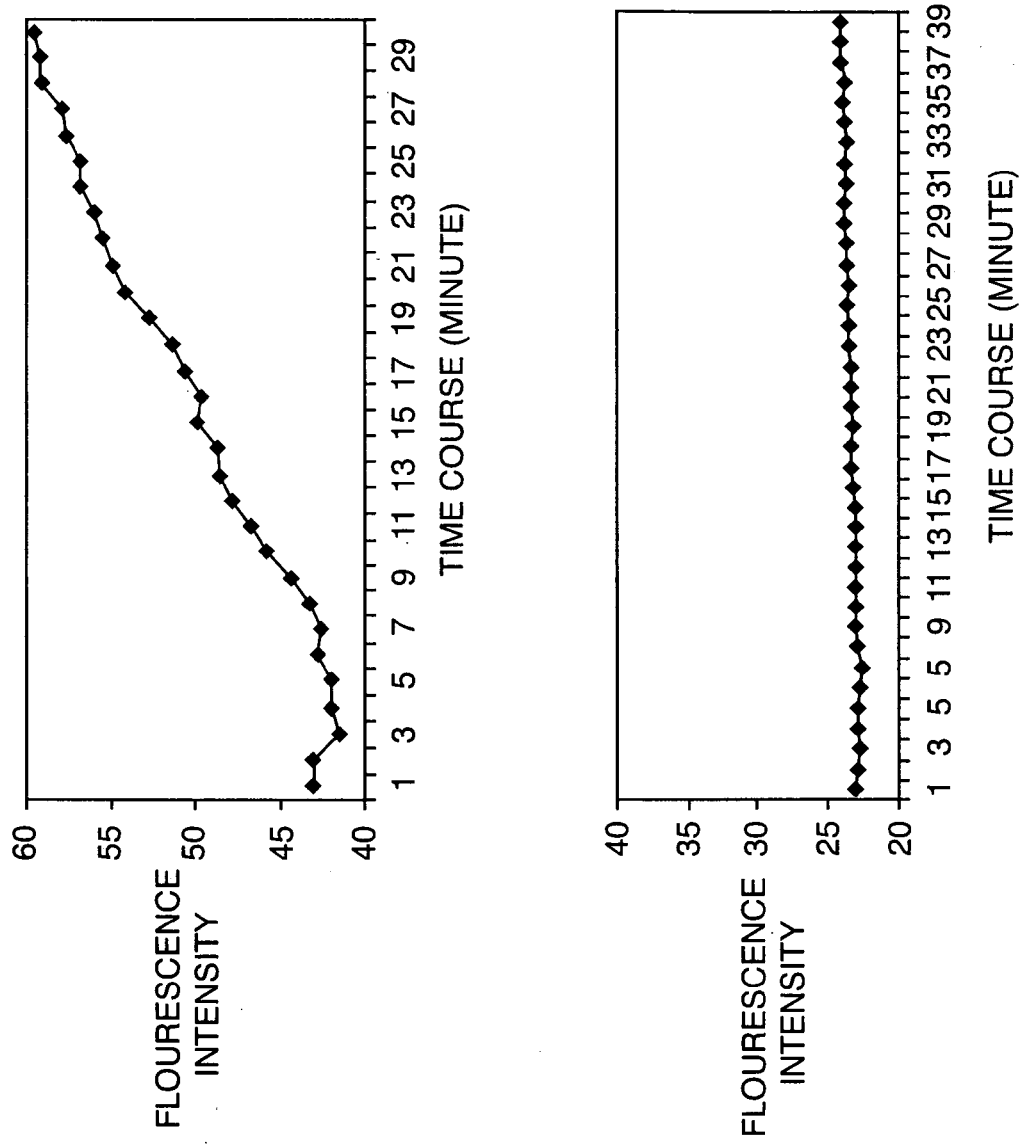

FIG. 38 illustrates example results of BzATP-stimulated pore activation of $P2X_7$-$R_{FL}$ and $P2X_7$-$R_{TR}$. Top Panel: Demonstrating an increase in fluorescence after exposure to BzATP in HEK293 cells transfected with $P2X_7$-$R_{FL}$ receptor protein. Bottom Panel: Demonstrating a lack change in fluorescence after exposure to BzATP in HEK293 cells transfected with $P2X_{7-j}$-$R_{TR}$ receptor protein.

FIG. 39A-B shows one embodiment of a $P2X_7$ receptor nucleic acid sequence (SEQ ID NO:3) and corresponding amino acid sequence (SEQ ID NO:4). A transmembrane segment and an exon are marked.

FIG. 40 shows one embodiment of a $P2X_{7-j}$ receptor nucleic acid sequence (SEQ ID NO:5) and corresponding amino acid sequence (SEQ ID NO:6). A transmembrane segment and an exon are marked.

Figure 41:
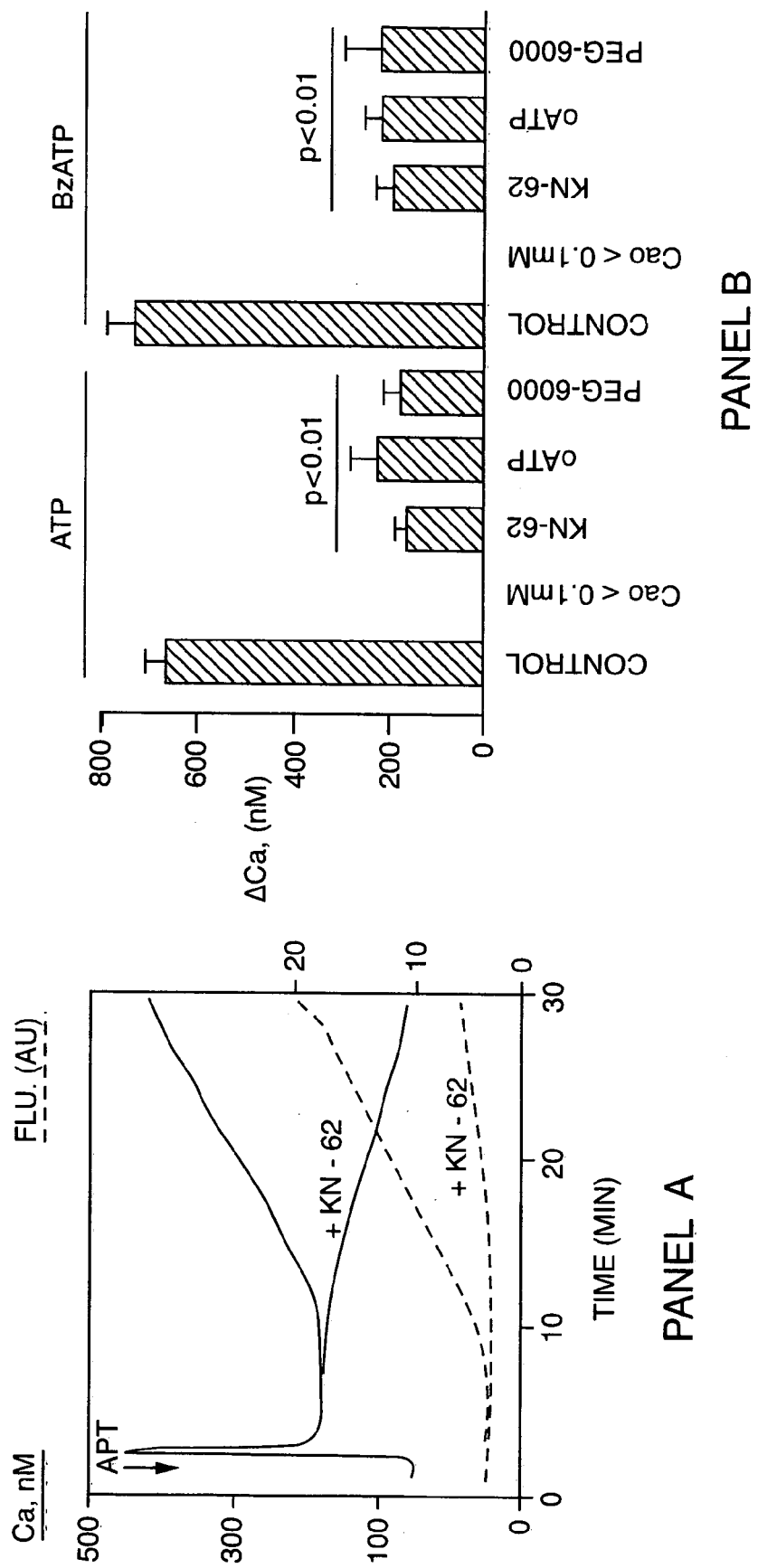
Figure 41:
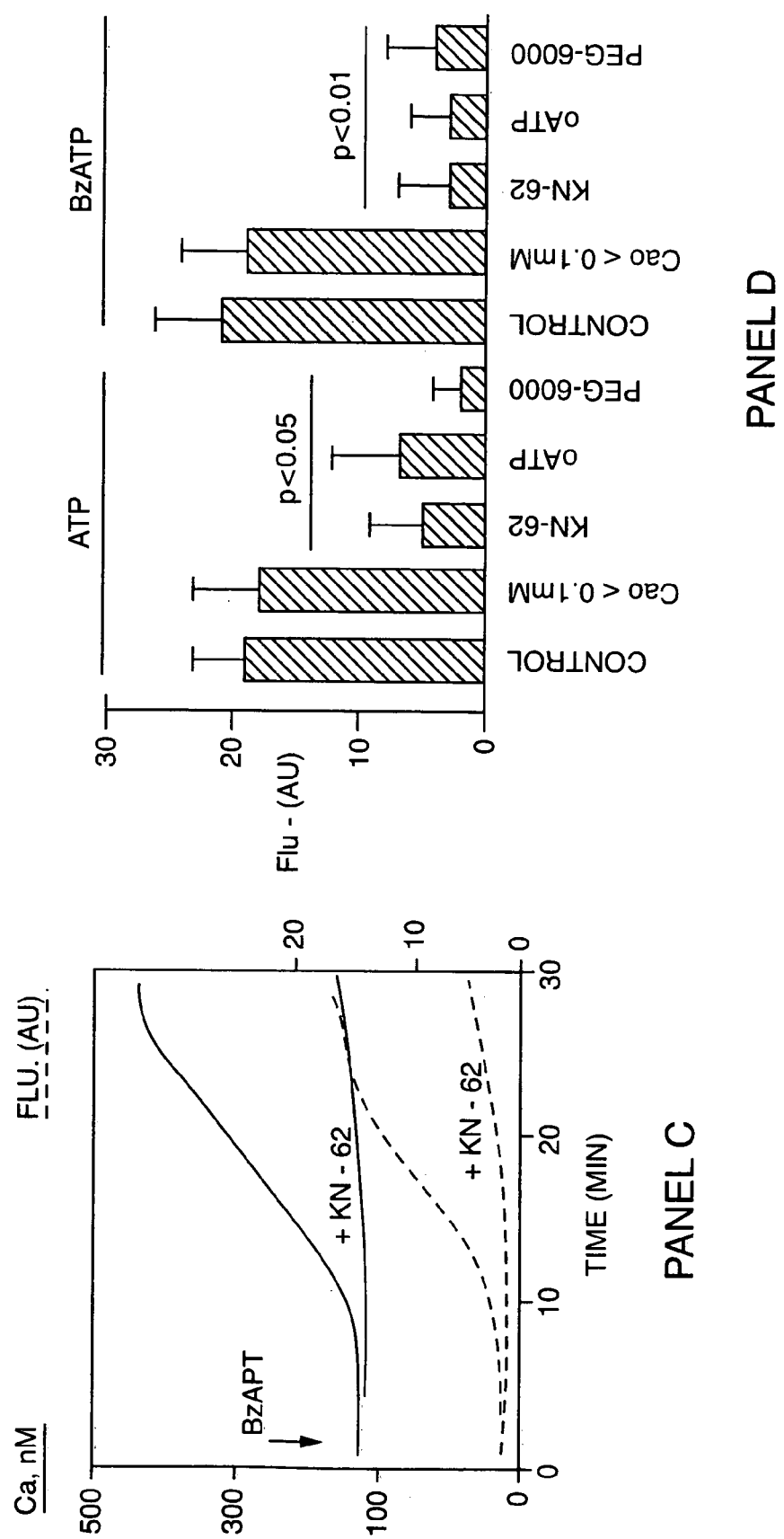

FIG. 41 presents exemplary data of net increases in $Ca_i$ and in ethidium bromide fluorescence in response to ATP or BzATP in CaSki cells attached on filters for six (6) days.

Panel A & Panel B: The effects of ATP (250 µM) on levels of cytosolic calcium ($Ca_i$, solid lines) and influx of ethidium bromide (EB) (EB fluorescence=broken lines as arbitrary units, AU).

Panel C & Panel D: The effects of BzATP (100 µM) (arrows) on levels of cytosolic calcium ($Ca_i$, solid lines) and influx of ethidium bromide (EB) (EB fluorescence=broken lines as arbitrary units, AU).

Each Point=mean±standard deviation (N=3-5).

$Ca_o$ was lowered to <0.1 mM by adding 1.2 mM EGTA. KN-62, oATP and PEG-6000 were added at 100 nM, 75 µM, and 1 mM, respectively 10-15 min prior to adding ATP. $\Delta Cai$ increase above baseline for the late sustained increase in $Ca_i$ was determined 30 minutes after adding ATP in cells pretreated with 75 µM suramin or pyridoxal phosphate-6-azophenyl-2',4-disulfonic acid (PPADS) to block the transient acute increases in $Ca_i$.

Figure 42:
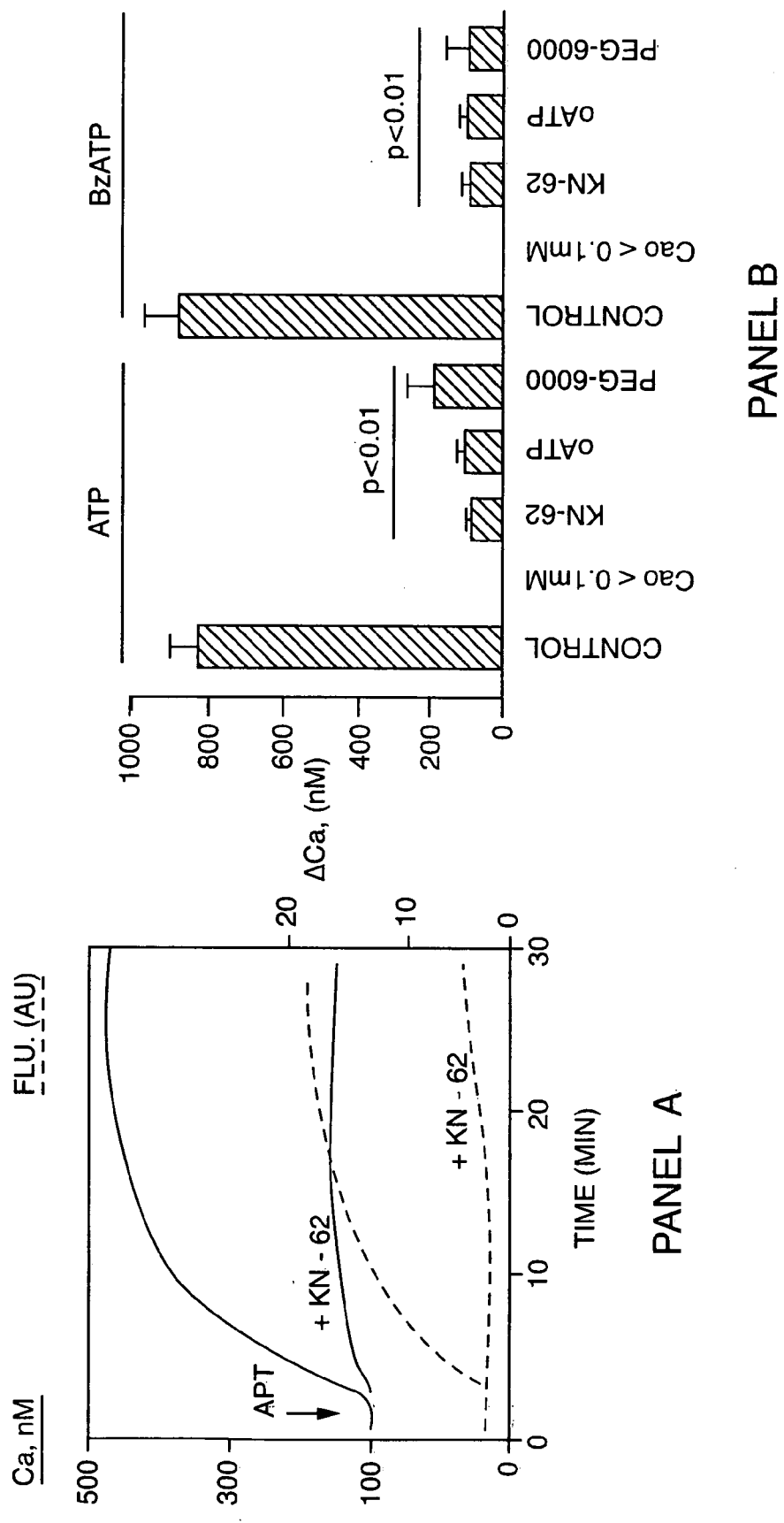
Figure 42:
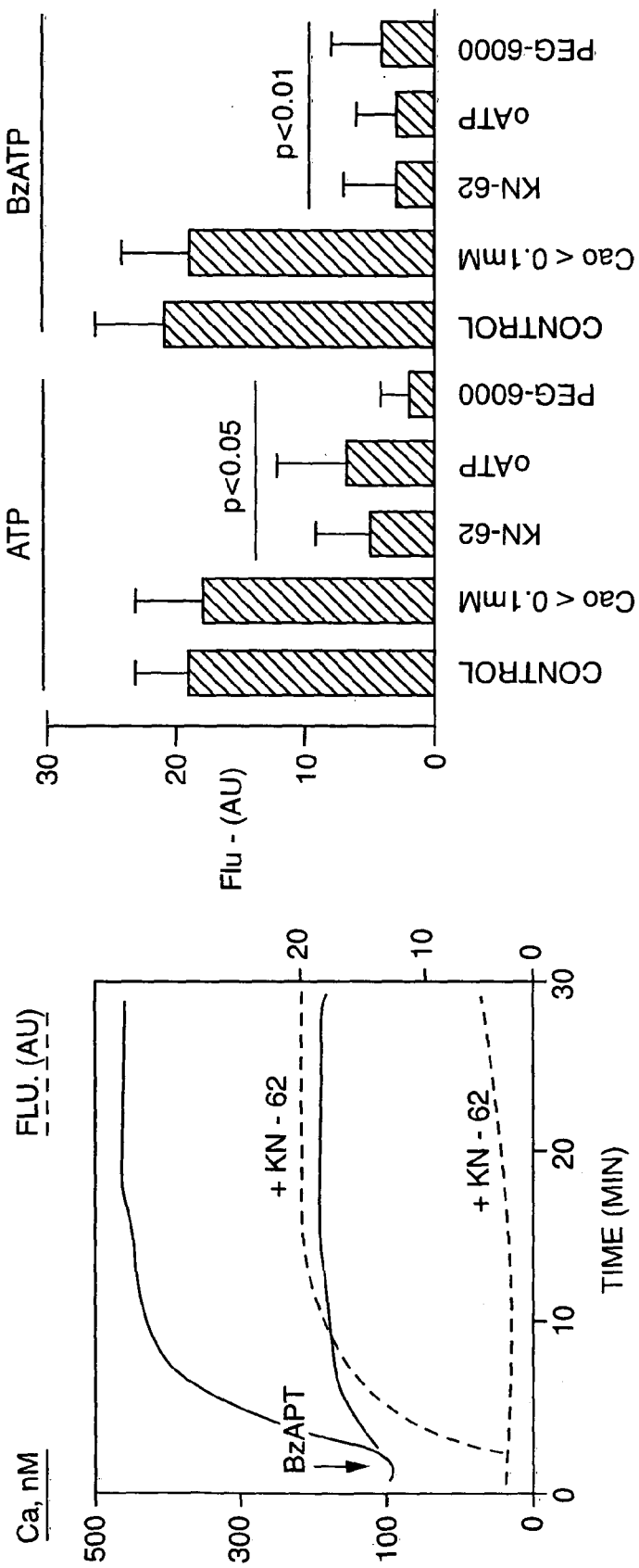

FIG. 42 presents exemplary data showing the effects of ATP (Panel A & Panel B) and BzATP (Panel C & Pane D) (arrows) on levels of $Ca_i$ (solid lines) and influx of ethidium bromide (EB fluorescence; broken lines) in HEK-293-hP2XT-R cells attached on filters for 3 days.

FIG. 43 presents exemplary data showing the reversibility and concentration dependence of ATP cytosolic calcium transport.

Panel A demonstrates the reversibility of ATP effect. Six-Day, fura-2 loaded CaSki cells attached on filters were treated with 250·M ATP and at different time intervals the bathing solutions were replaced with fresh medium. Experiments were repeated 3-7 times with similar trends.

Panel B demonstrates the concentration dependent effect of ATP (filled circles) and BzATP (empty circles) on $Ca_i$ and ethidium-bromide fluorescence in Day-6 CaSki cells attached on filters. $\Delta Cai$ for the late sustained increase in $Ca_i$ (solid lines) were determined 30 minutes after adding ATP in cells pre-treated for 15 min with 75 µM suramin and PPADS. Changes in fluorescence 30 minutes after adding ethidium bromide (broken lines).

FIG. 44 demonstrates the detection, cellular distribution and isolation of one embodiment of a $P2X_7$ receptor protein.

Panel A: Immunostaining of Day-6 CaSki and HEK-293-hP2XT-R cells for the $P2X_7$ receptor protein (×20). CaSki cells were treated 30 minutes prior to staining with one of indicated concentrations of ATP. +Ag: co-incubation with the $P2X_7$ antigen.

Panel B: Cellular distribution of the $P2X_7$-receptor in Day-6 CaSki cells as determined by confocal laser scanning microscopy (×40):

a) co-incubation of the anti P2X7 receptor antibody with the P2X7 antigen;

b) nuclear staining;

c) immunostaining with the anti-$P2X_7$-receptor antibody;

d) immunostaining plus anti-$P2X_7$ receptor antibody.

Panel C. Western immunoblot analysis of P2X$_7$ receptor protein:
  a) total homogenates from Day-6 cultured CaSki;
  b) total homogenates from HEK-293 cells.

Experiments with HEK-293 cells utilized either the wild-type, cells transfected with β-arrestin-2-GFP, or cells transfected with the full-length human P2X$_7$ receptor alone or in combination with β-arrestin-2-GFP. The experiments were repeated 2-5 times with similar trends.

Figure 45:
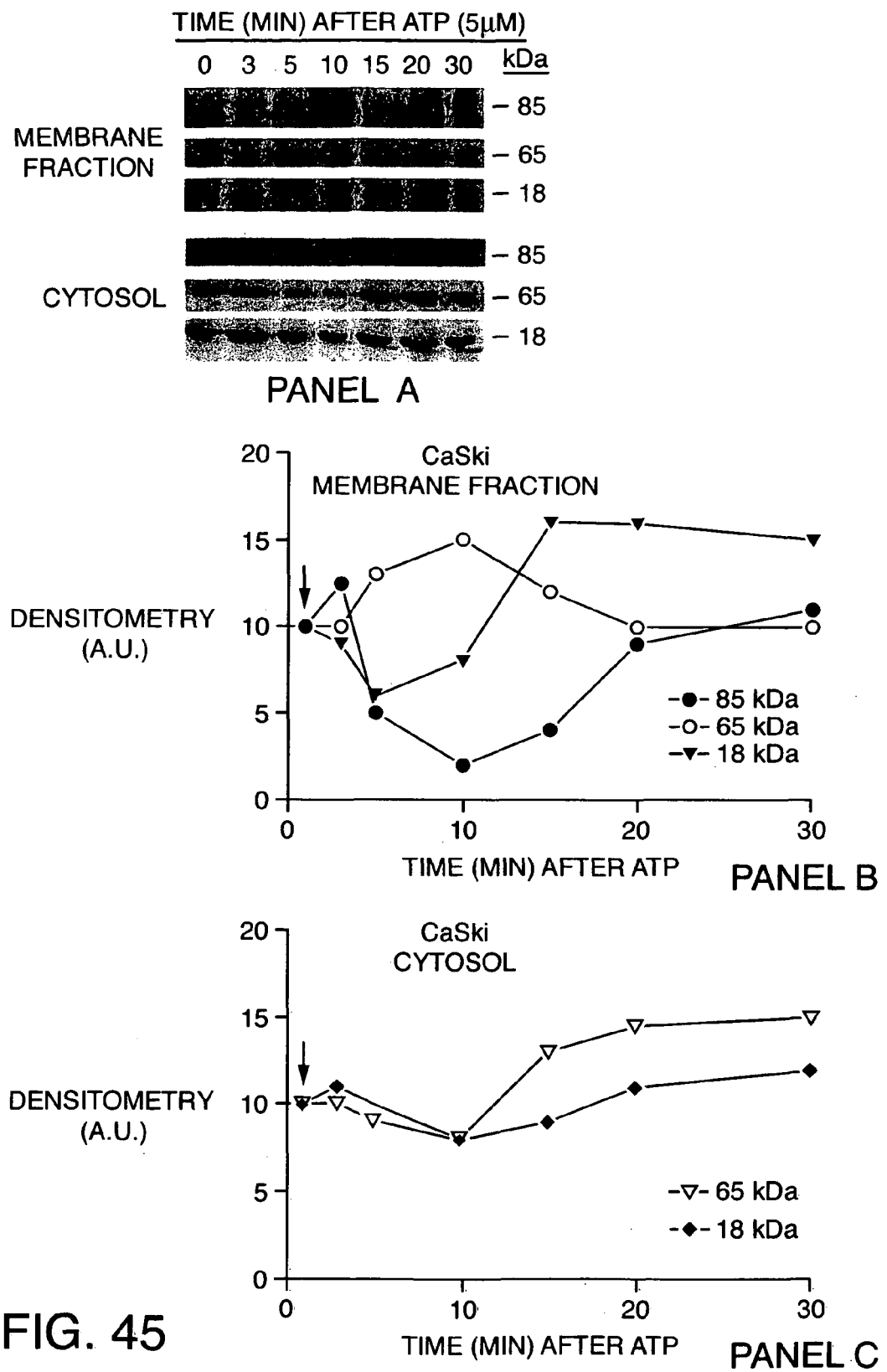

FIG. 45 presents exemplary data regarding the distribution and amounts of P2X$_7$ receptor isoforms.

Panel A: ATP effects on the distribution of P2X$_7$ receptor isoforms in the plasma membrane and cytosol. Day-6 CaSki were treated with 250 μM ATP, and at time intervals of 0 to 30 min after treatment membrane-enriched and cytosolic fractions were prepared. Samples of 15 μg protein were fractionated in gel electrophoresis and assayed by Western immunoblot analysis for the P2X$_7$ receptor. The experiments were repeated twice with similar trends.

Panels B & C: Densitometry analysis of the data in Panel A. Each isoform within the density levels were normalized to the level of expression at time t=0 prior to adding the ATP.

FIG. 46 presents exemplary data showing ATP effects on the distribution of P2X$_7$ receptor isoforms in the plasma membrane and cytosol of HEK-293-hP$_2$X$_{T-R}$ cells. The experiments were repeated twice with similar trends and data analysis were performed in accordance with FIG. 45. Panel A: A time course of 85, 65 and 18 kDa protein expression following exposure to BzATP in both the membrane and cytosol fractions. Panel B: A densitometry scan of the membrane fraction gels of Panel A. Panel C: A densitometry scan of the cytosol fraction gels on Panel A.

FIG. 47 presents exemplary data showing ATP effects on the distribution of P$_2$X$_7$ receptor isoforms in the plasma membrane and cytosol of HEK-293-c-Myc-hP$_2$X$_7$-R cells. The experiments were repeated twice with similar trends and data analysis were performed in accordance with FIG. 45 except that Western immunoblots utilized anti c-Myc antibody. Panel A: A time course of 85, 65 and 18 kDa protein expression following exposure to BzATP in both the membrane and cytosol fractions. Panel B: A densitometry scan of the membrane fraction gels of Panel A. Panel C: A densitometry scan of the cytosol fraction gels on Panel A.

FIG. 48 presents exemplary data showing ATP-induced phosphorylation of the P2X$_7$ receptor.

Panel A: $^{32}$P: Day-6 CaSki cells were labeled with [$^{32}$P] orthophosphate, and treated with (+) or without (−) 250 μM ATP for 5 minutes. Cell lysates were fractionated on gel electrophoresis and immunoprecipitated with the anti P2X$_7$ antibody. IB: Western immunoblots with anti-P2X$_7$ antibody of parallel protein samples.

Panel B: Day-6 CaSki cells were treated with 250 μM ATP; at time intervals of 0 to 30 minutes. Cell lysates were then immunoprecipitated in a mixture of antibodies containing anti-phosphotyrosine PY20 and P99 antibodies, anti-phosphoserine (PS), and anti-phosphothreonine (PT) antibodies, and immunoblotted with the anti-P2X$_7$ antibody.

Panel C: Day-6 CaSki cells were treated for 1 minute with ATP at concentrations ranging from 0 to 500 μM. Cells lysates were immunoprecipitated with the indicated anti-phospho-antibodies alone or in combination, and immunoblotted with the anti-P2X$_7$ antibody. The experiments were repeated twice with similar trends.

Figure 49:
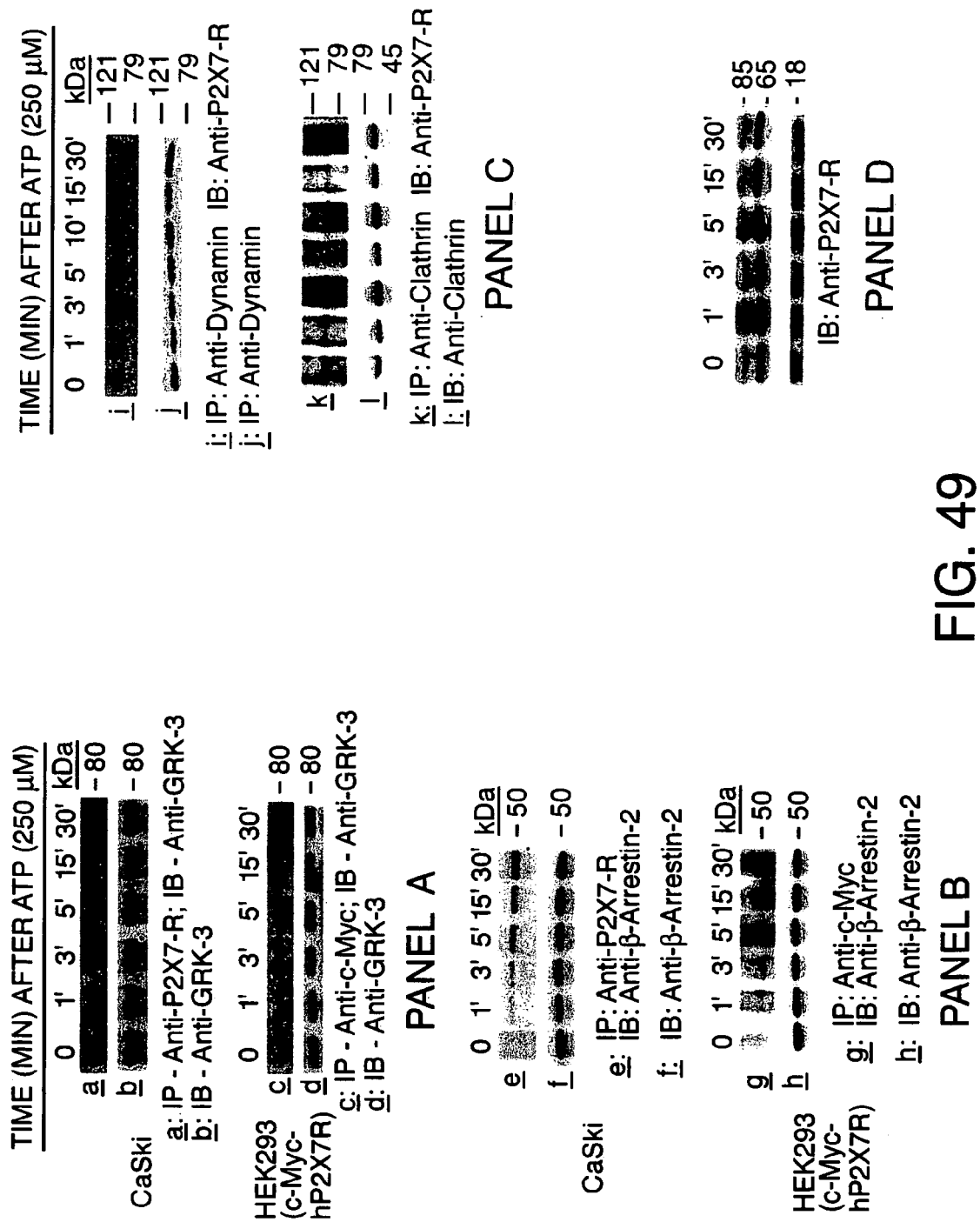

FIG. 49 presents exemplary data showing ATP-induced co-localization of the P2X$_7$ receptor:

Panel A: GRK-3; Panel B: β-arrestin-2; Panel C: dynamin and clathrin. Day-6 CaSki cells (Panels A, B, & C) or HEK-293-c-Myc-hP2XT-R cells (Panels A & B) were treated with 250 μM ATP, and at time intervals of 0 to 30 minutes after treatment cell lysates were immunoprecipitated/immunoblotted. Panel D: Effects of treatment with ATP on total cellular levels of the P2X$_7$ receptor forms in Day-6 CaSki cells. Each experiment was repeated 2-3 times with similar trends.

FIG. 50 presents exemplary data demonstrating ATP-induced recruitment of β-arrestin-2 into sub-membranous regions:
  Panel A: CaSki cells were transfected with β-arrestin-2-GFP and analyzed by real-time confocal microscopy:
    a) Phase images;
    b) Nuclei staining;
    c-e). Fluorescence images at excitation wavelength of 488 nm (×20) at baseline (c), and 3 minutes (d) and 5 minutes (e) after adding 250 μM ATP.
  The experiment was repeated three times with similar trends.
  Panel B: 20× magnification of HEK-293-hP2X7-R cells co-transfected with β-arrestin-2-GFP: a) Nuclei staining; b) Fluorescence at excitation wavelength of 488 nm. 40× magnification: c) HEK-293 cells transfected with β-arrestin-2-GFP only: d) HEK-293 cells transfected with β-arrestin-2-GFP after treatment with 250 μM ATP; e) HEK-293-hP2X7-R cells transfected with β-arrestin-2-GFP. Panel C: HEK-293-hP2X7-R cells co-transfected with β-arrestin-2-GFP and treated either with 10 μM angiotensin (a-c), 10 μM UTP; (d-f): and 250 μM ATP (g-i). Real-time confocal laser microscopy was used to determine fluorescence at excitation wavelength of 488 at baseline (a, d, & g), or 5 minutes (b, e, & h) and 10 minutes (c, f, & i) after treatments (20× magnification). The experiments were repeated 2-3 times with similar trends.

FIG. 51 presents exemplary data showing the effects of EGF and epinephrine (Epi) on number of CaSki cells in culture (Panel A), DNA synthesis (Panel B), and BzATP-induced DNA solubilization (Panel C). In A: *, P<0.01 (EGF vs. Baseline); , P<0.03 [Baseline, Epi vs. C (control)]; *, P<0.03 (EGF, Epi vs. C). In B: *, P<0.01 (EGF vs. Baseline, in both C and Epi groups). In C: *, P<0.01 (BZATP vs. Baseline Control and EGF groups); , P<0.01 (BzATP, Epi vs. Control and EGF groups); *, P<0.03 (BZATP, EGF+EPI vs. Epi groups). Means±SD, three to five independent experiments).

Figure 52:
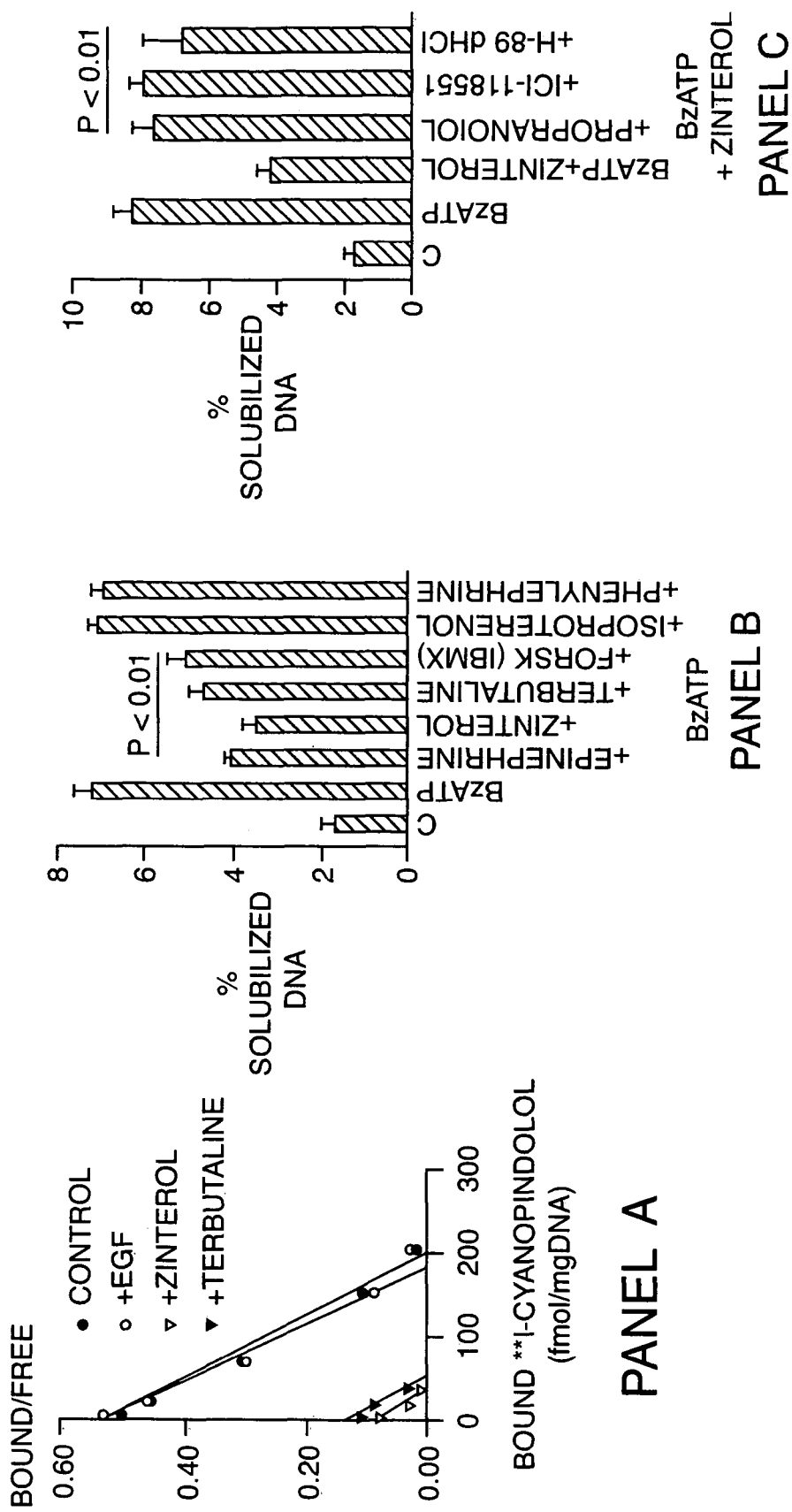

FIG. 52 Panel A: One embodiment of a Scatchard analysis of [$^{125}$I]cyanopindolol binding to CaSki cells, and the effects of EGF, zinterol, and terbutaline. Panel B: Modulation of BzATP-induced DNA solubilization by adrenoceptor agonists and by activators of adenylyl cyclase forskolin (Forsk., in the presence of 3-isobutyl-1-methylxanthine). Panel C: Modulation of zinterol-dependent inhibition of BzATP-induced DNA solubilization by β2-adrenoceptor antagonists and by the protein kinase A inhibitor H-89 dihydrochloride (H-89-dHC1). Data in B and C are Means±SD of three to four independent experiments. *, P<0.01 (BzATP+Zintero] vs. BZATP).

Figure 53:
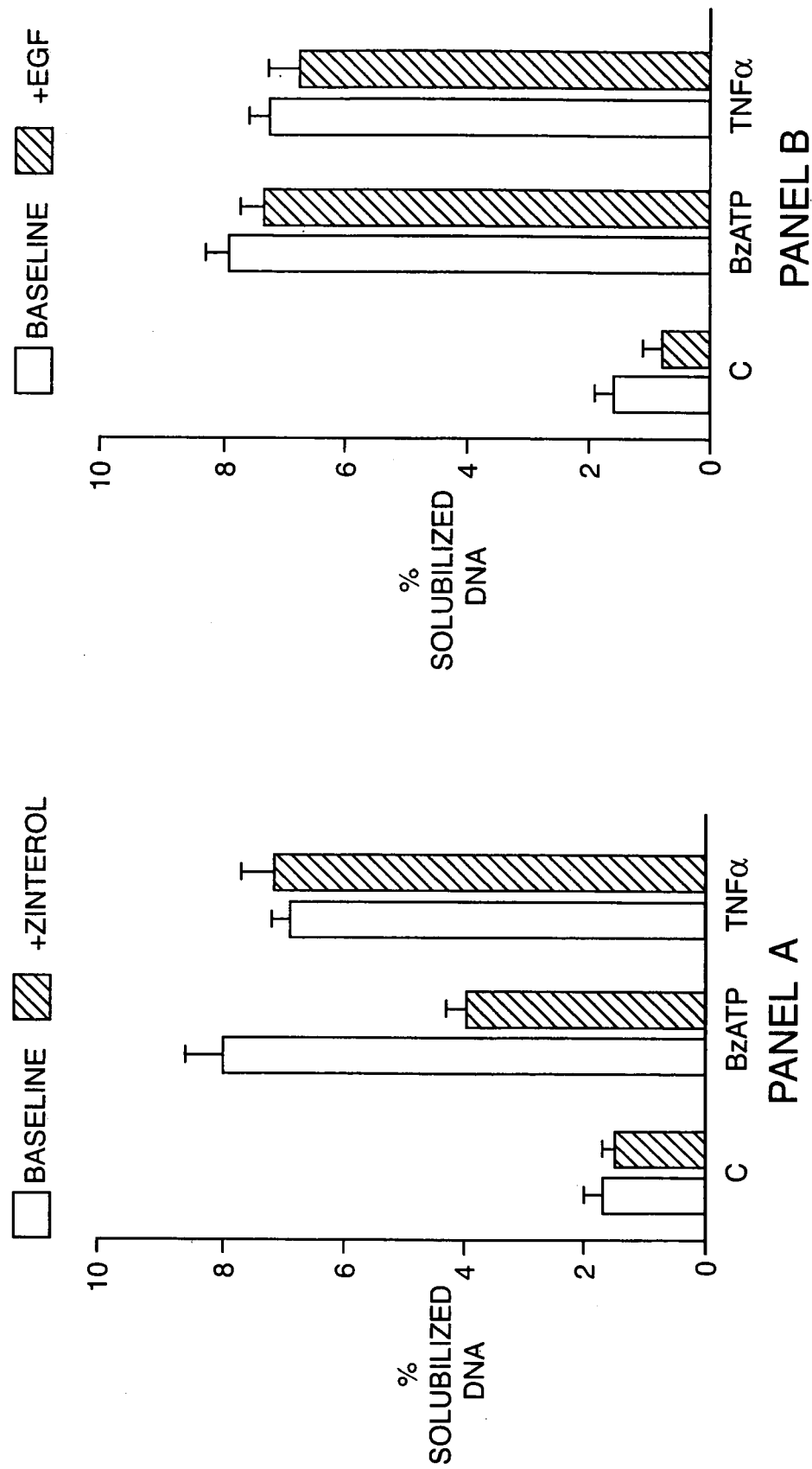

FIG. 53 presents exemplary data showing the effects of zinterol (Panel A) and EGF (Panel B) on DNA solubilization induced by BzATP and by TNFα. Data are Means±SD of three independent experiments. *, P<0.01 (BzATP group, Zinterol vs. Baseline).

FIG. 54 presents exemplary data showing EGF and Epi modulation of: Panel A: BzATP-induced changes in cytosolic calcium (Ca$_i$). Panel B: BzATP-induced in flux of ethidium bromide (B) in CaSki cells. AU=Arbitrary Units of fluorescence (Flu.) Insets: Increases in Cai and intracellular ethidium bromide fluorescence thirty (30) minutes after BzATP addition. KN-62 was added at 100 nM fifteen (15) minutes before adding BzATP. * P<0.01 (Epi v. Control and EGF groups); ** P, 0.03 (EGF+Epi and KN-62 v. Epi).

Figure 55:
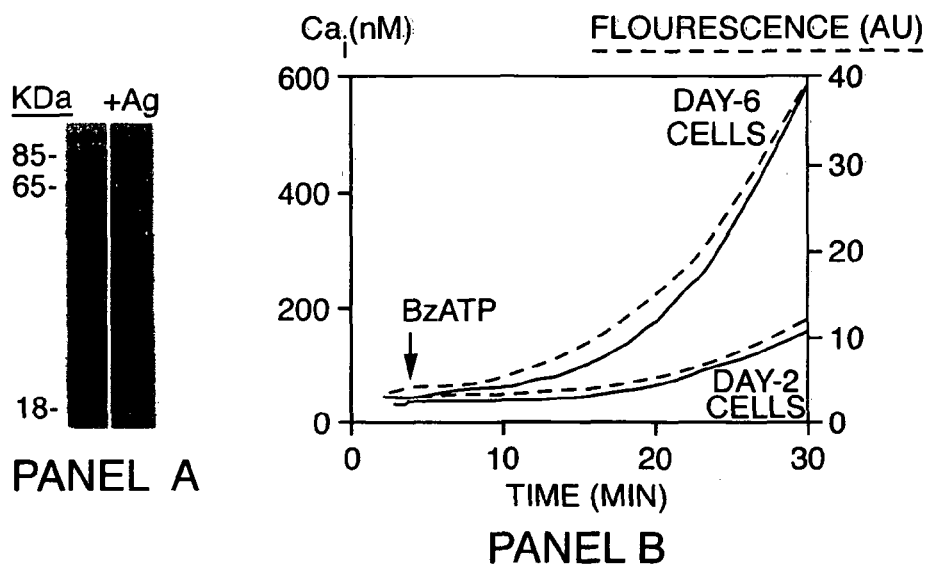

FIG. 55. Panel A: Western immunoblot analysis of $P2X_7$ receptor protein using total homogenates from Day-6 cultured CaSki cells. +Ag denotes coincubation with the $P2X_7$ antigen. Panel B: Effects of length in culture on BzATP-induced influx of $Ca^{2+}$ (solid lines, determined in terms of the increase in $Ca^{2+}$, and on BzATP-induced influx of ethidium bromide (broken lines). Panel C: Effects of incubation of CaSki-cell lysates in vitro with N-glycosidase F. The filled and empty bars represent the densitometric ratio of the 65-kDa/85-kDa forms before and after treatment with N-glycosidase F, respectively. Panel D: Effects of day in culture, and of treatments with EGF and Epi on the cellular expression of the $P2X_7$ receptor. Western immunoblot analysis was done on total homogenates of CaSki cells grown on filters for 2 or 6 days. Where indicated, cells were treated with EGF, epinephrine, or both.

DETAILED DESCRIPTION OF THE INVENTION

The present invention is related to cancer screening, diagnosis, and treatment. In one embodiment, a cell may be screened for the presence of a truncated $P2X_7$ mRNA and/or protein. In another embodiment, reagents reactive with a defective $P2X_7$ protein are provided in a kit. In another embodiment, patients are treated by increasing the amount and/or activity of a functional $P2X_7$ protein.

I. The P2X Receptor/Protein Family

A. Overview

The $P2X_7$ receptor belongs to the P2X receptor sub-family of P2 nucleotide receptors, which are membrane-bound, ligand-operated $K^+$, $Na^+$, $Ca^{2+}$ permeable channels that function as homo- or hetero-multimeric complexes. Nieke et al., "$P2X_1$ and $P2X_3$ receptors form stable trimers: a novel structural motif of ligand-gated ion channels" *EMBO J* 17:3016-3028 (1998); and Torres et al., "Identification of a domain involved in ATP-gated ionotropic receptor subunit assembly. *J Biol Chem* 274:6653-6659 (1999). Activation of the $P2X_7$ receptor can stimulate various cell-specific signaling cascades including, but not limited to, the adenosine triphosphate pathway. Dubyak et al., "Signal transduction via P2-purinergic receptors for extracellular ATP and other nucleotides" *Am J Physiol* 265:C577-C606 (1993).; and Ralevie et al., "Receptors for purines and pyrimidines" *Pharmacol Rev* 50:413-492 (1998). Effects unique to the receptor are the induction of membrane fusion and blebbing associated with microvesicle generation (Di Virgilio et al., "Cytolytic P2X purinoceptors" *Cell Death Differ* 5:191-199 (1998); and Di Virgilio et al., "Nucleotide receptors: an emerging family of regulatory molecules in blood cells" *Blood* 97:587-600 (2001)), interleukin-1β processing and secretion (Humphreys et al., "Induction of the P2z/$P2X_7$ nucleotide receptor and associated phospholipase D activity by lipopolysaccharide and IFN-γ in the human THP-1 monocytic cell line" *J Immunol* 157:5627-5637 (1996); and MacKenzie et al., "Rapid secretion of interleukin-1β by microvesicle shedding" *Immunity* 15:825-834 (2001)) and opening of membrane pores. (Murgia et al., "Characterization of the cytotoxic effect of extracellular ATP in J774 mouse macrophages" *Biochem J* 288:897-901 (1992); and Suh et al., "$P2X_7$ nucleotide receptor mediation of membrane pore formation and superoxide generation in human promyelocytes and neutrophils" *J Immunol* 166:6754-6764 (2001)). Epithelial cells of the female lower reproductive tract express the $P2X_7$ receptor, and in human cervical epithelial cells activation of the receptor induces apoptosis by a mechanism that involves calcium-dependent activation of the mitochondrial pathway. Bardini et al;. "Distribution of P2X receptor subtypes in the rat female reproductive tract at late pro-oestrus/early oestrus" *Cell Tissue Res* 299:105-113 (2000); and Wang et al., "$P2X_7$-receptor mediated apoptosis of human cervical epithelial cells" *Am J Physiol Cell Physiol* 287:C1349-C1358 (2004)). Apoptosis plays an important role in the regulation of cell cycle and control of neoplastic transformation. Ellis et al., "Mechanisms and functions of cell death" *Annul Rev Cell Biol* 7:663-698 (1991). To solve the problem of whether a dysfunction of apoptosis could be associated with cervical dysplasia and cancer, the present invention contemplates that the $P2X_7$ receptor may mediate apoptosis of cervical cells.

The function of a $P2X_7$ receptor is believed to depend on receptor expression and intracellular distribution. Ralevie et al., "Receptors for purines and pyrimidines" *Pharmacol Rev* 50:413-492 (1998). In one embodiment, the present invention contemplates that human cervical epithelial cells expressing endogenous $P2X_7$ receptor protein is comparable to $P2X_7$ receptor protein expression in a heterologous system of HEK-293 cells transfected with the full-length human $P2X_7$ receptor (HEK-293-h$P2X_7$-R cells). In both types of cells, stimulation of the receptor caused plasma membrane pore formation. In both types of cells, treatment with ATP decreased transiently the 85 KDa form of the $P2X_7$ receptor in the plasma membrane, and increased the $P2X_7$ receptor protein level in the cytosol. These effects were followed by an increase of an 18 KDa P2X receptor form both in the plasma membrane and in the cytosol, and are therefore compatible with internalization, degradation and recycling. Treatment with ATP also increased phosphorylation of the receptor, and increased binding of the 85 KDa form to the G-protein coupled receptor kinase 3 (GRK-3), β-arrestin-2, and dynamin. Feng et al., "ATP stimulates GRK-3-phosphorylation and b-arrestin-2-dependent internalization of the P2X7 receptor". *Am J Physiol Cell Physiol.* 288(6):C1342-C1356 (2005). Although it is not necessary to understand the mechanism of an invention, it is believed that these data could be important for our understanding of $P2X_7$ receptor activation, compartmentalization and signal transduction.

It is further believed that $P2X_7$ receptors are generally membrane-bound, ligand-operated, or ligand-gated ion channels that can be activated in vivo by ATP and possibly by other ligands or agonists. Receptors that bind ATP may be called purinergic receptors. When activated, these receptors generally become permeable to ions like $Na^+$, $K^+$, $Ca^{2+}$, and possibly others. Repeated or prolonged activation by ATP, and possibly other ligands, may make the receptors permeable to larger ions (i.e., for example, ethidium bromide). In the repeatedly or prolonged activation state, the receptor-related channels may be called pores rather than channels. Evidence exists that $P2X_7$ receptors, when activated by agonists, may mediate signaling of different cellular processes in certain cell types, including, but not limited to, apoptosis.

B. Compositions

In one embodiment, the present invention contemplates a $P2X_7$ receptor comprising a short intracellular N-terminus, two transmembrane segments, an extracellular loop domain containing a ligand-binding domain, and a C-terminus. In one embodiment, a $P2X_7$ receptor protein shares an approximate 40-45% amino acid identity with other P2X proteins, but appears to be structurally distinct at the C-terminus, which extends for an additional 100-200 amino acids compared to other P2X receptors. FIG. 1.

The wild type (i.e., for example, full length) $P2X_7$ receptor is referred to herein either as the $P2X_7$, $P2X_7$-$R_{FL}$ or the $P2X_7$-WT (which designations are hereinafter used interchangeably). A truncated form of the $P2X_7$ mRNA and protein has been discovered. The truncated $P2X_7$ mRNA appears to be a splice variant of the full-length $P2X_7$ receptor, and it is designated $P2X_{7-j}$ or $P2X_7$-$R_{TR}$ (which designations are hereinafter used interchangeably). In one embodiment, a $P2X_{7-j}$ mRNA may include at least one nucleotide sequence that is different than the nucleotide sequence in $P2X_7$ mRNA, and may lack other nucleotide sequences. In one embodiment, a $P2X_{7-j}$ receptor protein may include at least one amino acid sequence that is different than an amino acid sequence in $P2X_7$ receptor protein, and may lack other amino acid sequences.

Example nucleotide sequences of the coding regions of both $P2X_7$ (left) and $P2X_{7-j}$ (right) and the corresponding amino acid sequences of the proteins are presented, wherein blocks of amino acids are underlined that represent transmembrane segments of the protein. See FIGS. 2, 39, and 40.

In one embodiment, a $P2X_{7-j}$ protein-encoding sequence (i.e., for example, a $P2X_{7-j}$ nucleotide sequence) differs from the $P2X_7$ protein-encoding sequence (i.e., for example, a $P2X_7$ nucleotide sequence). Most of the eighth coding exon, except for the last "A" in $P2X_7$ is missing in $P2X_{7-j}$. See FIG. 2A; portion underlined with dotted line of $P2X_7$, on the left. The coding sequence of $P2X_{7-j}$ then continues with the ninth coding exon. Although it is not necessary to understand the mechanism of an invention, it is believed that the last A of the eighth coding exon provides a shift in the translation reading frame (i.e., for example, a frameshift mutation) in the coding sequence of $P2X_{7-j}$ as compared to $P2X_7$. In one embodiment, a frameshift mutation provides for a sequence of the last 10 amino acids of $P2X_{7-j}$ that is not present in $P2X_7$ (see last ten amino acids in $P2X_{7-j}$ sequence on the right; IRQVLQGKQC (SEQ ID NO:1). In one embodiment, a frameshift mutation produces an in-frame stop codon, resulting in the $P2X_{7-j}$ protein being shorter than the $P2X_7$ protein. (See FIG. 2C, boxed TGA in $P2X_{7-j}$ illustration on the right). In one embodiment, a sequence for truncated $P2X_{7-j}$ has been filed with the GeneBank Accession Number DQ399293.

Figure 3:
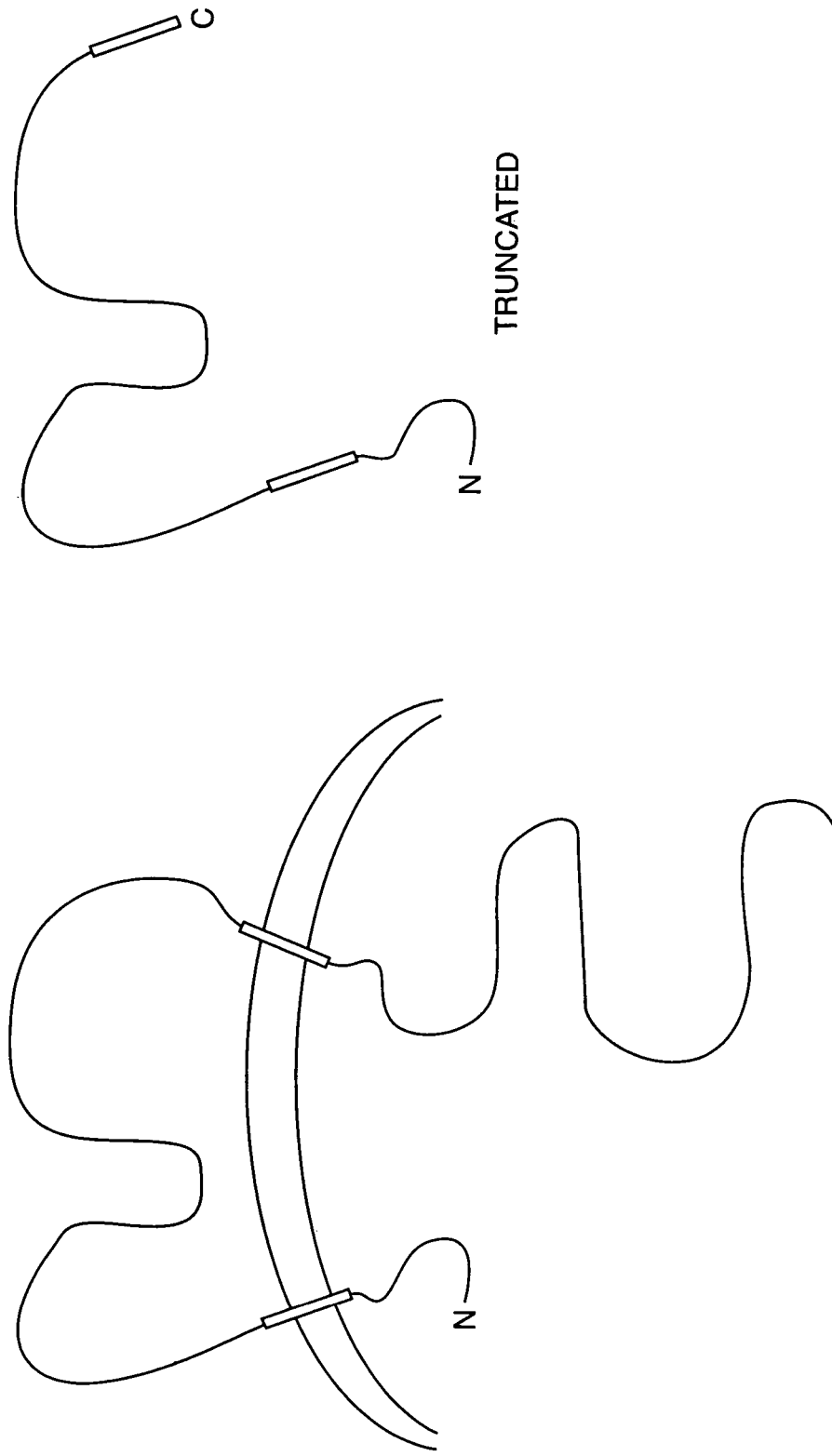
FIG. 3 illustrates example predicted structures of the P2X$_7$ (left) and P2X$_{7-j}$ (right) proteins.

In one embodiment, a $P2X_7$ receptor protein comprises a short intracellular N-terminus, two transmembrane segments, an extracellular loop containing a ligand-binding domain, and a C-terminus. In one embodiment, a $P2X_{7-j}$ receptor protein lacks a second transmembrane segment and a C-terminus having 100% identity to $P2X_7$. In one embodiment, a $P2X_{7-j}$ receptor protein comprises a short sequence of C-terminal amino acids that are absent in a $P2X_7$ receptor protein. See FIG. 3.

In one embodiment, the present invention contemplates a method comprising detecting $P2X_{7-j}$ and/or $P2X_7$ mRNAs by reverse transcription-polymerase chain reaction (RT-PCR). In one embodiment, primers and conditions to perform the RT-PCR are described in FIG. 4. In one embodiment, the method comprises collecting RNAs from various cells, reverse transcribing the RNA, and assaying produced cDNA under conditions capable of determining whether $P2X_{7-j}$ and $P2X_7$ mRNAs are present in the cells.

C. Subcellular Localization

Antibody staining for $P2X_7$ proteins in fixed HEK-293 cells expressing either $P2X_7$ or $P2X_{7-j}$ was performed, thereby determining the subcellular location of the $P2X_{7-j}$ protein as compared to the $P2X_7$ protein. See FIG 9. HEK-293 cells lack endogenous expression of P2X receptors, consequently, HEK-293 cells were transfected with expression vectors expressing either $P2X_7$ or $P2X_{7-j}$. See FIG. 9; Panels A, B, & C and Panels D, E, & F, respectively). Fluorescent antibody specific for $P2X_7$ (Panels B and E); ii) an antibody specific for alpha-catenin, which stains the cell membrane (Panels C and F); and iii) both $P2X_7$ and alpha-catenin (Panels A and B).

Figure 9:
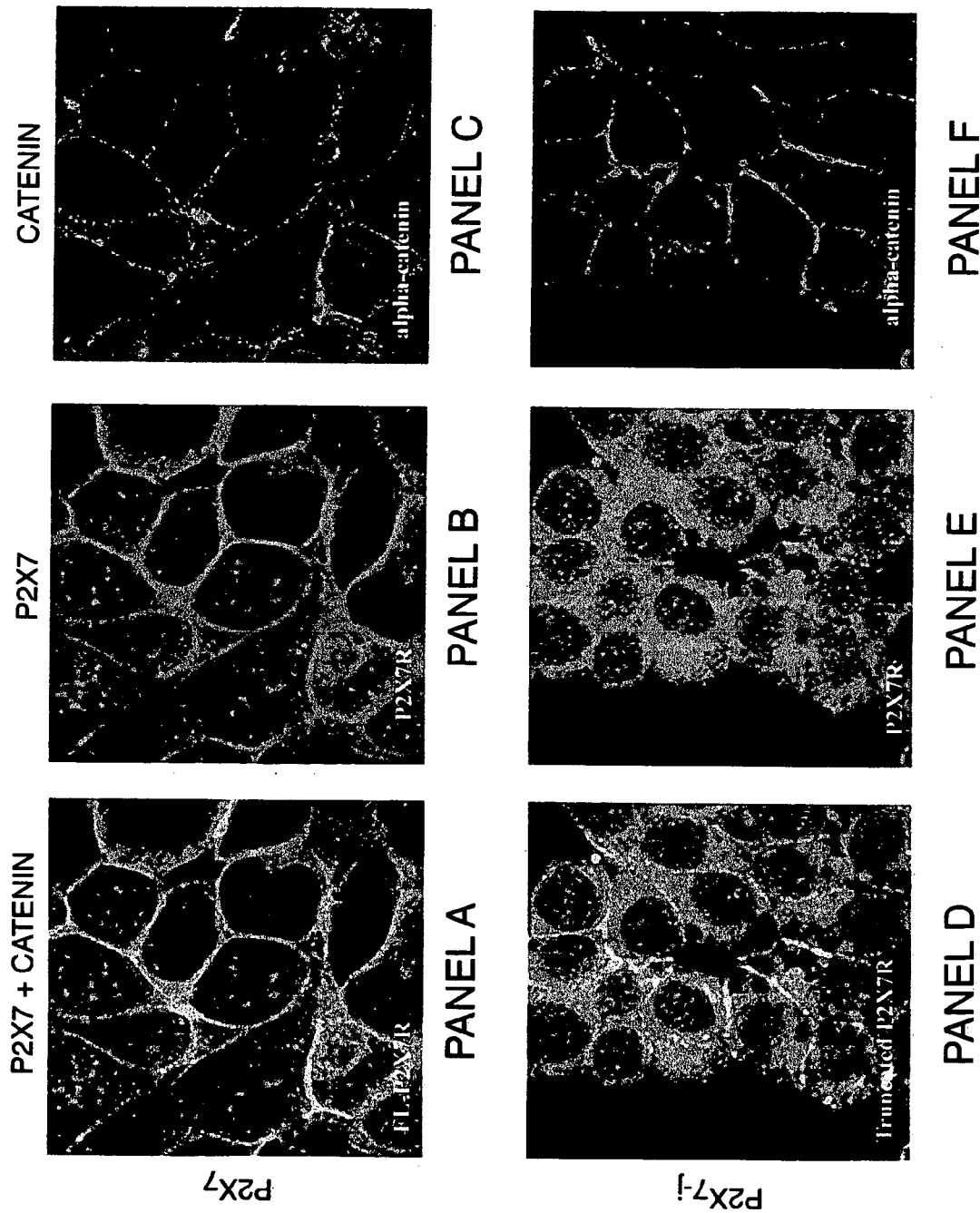
FIG. 9 illustrates example results of antibody staining for P2X$_7$ protein in fixed HEK-293 cells expressing either P2X$_7$ or P2X$_{7-j}$.

The staining results show that $P2X_7$ protein was located within the cellular plasma membrane (FIG. 9, Panel B). The alpha-catenin staining pattern was similar to the staining for $P2X_7$. (FIG. 9, Panels C and F). In summary, the staining results indicate that while some of the $P2X_{7-j}$ protein was located in the cell cytoplasm, a portion of the $P2X_{7-j}$ receptor protein was localized within the plasma membrane. FIG. 9, Panel E).

Figure 10:
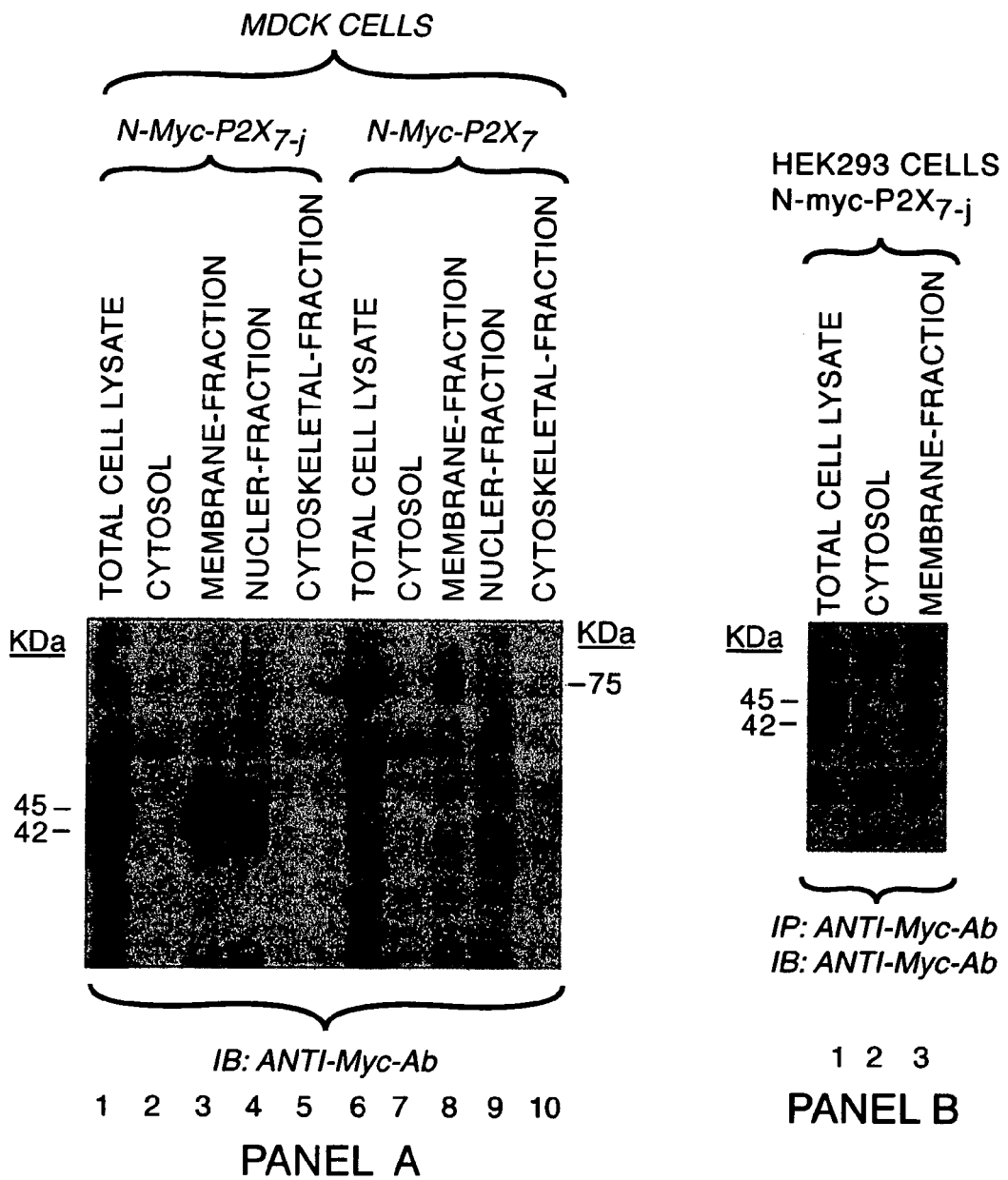
FIG. 10 illustrates example results of the cellular compartments where the P2X$_7$ and the P2X$_{7-j}$ proteins are expressed.

Antibody staining for either $P2X_{7-j}$(Myc) or $P2X_7$(Myc) receptor proteins expressed in transfected MDCK cells (induced by doxycycline) also identified similar intracellular localizations as in the HEK-293 cells. (FIG. 10, Panel A: Lanes 1-5; Lanes 6-10, respectively). Total homogenates (TH) of the MDCK cells were further fractionated using Proteo-Extract-Subcellular Proteome Extraction kit (EMD Biosciences, Inc. San Diego, Calif.) into fractions enriched with cytosol, plasma-membrane, nuclear material, or cytoskeleton. All fractions were thereafter immunoblotted with antimyc antibody. Like the HEK-293 cells, the $P2X_{7-j}$ specific 42-45 kDal proteins were localized in both the plasma membrane and nuclear fractions (FIG. 10, Panel A, Lanes 3 and 4, respectively). Similarly, the $P2X_7$ specific 75 kDal protein(s) were localized mainly in the plasma membrane fraction. (FIG. 10, Panel A, Lane 8).

Antibody staining for the $P2X_{7-j}$ proteins in the cytosolic and membrane fractions of HEK-293 cells expressing the $P2X_{7-j}$(Myc) was further assayed. FIG. 10, Panel B. Cell extracts were first immunoprecipitated with anti-myc antibody to increase the intensity of the signal and then immunoblotted with anti-myc antibody. The data show that $P2X_{7-j}$ specific 42-45 kDal proteins were localized mainly in the plasma membrane fraction. (FIG. 10, Panel B, Lane 3).

Collectively, the data suggest that both $P2X_7$ and $P2X_{7-j}$ proteins localize predominantly in the plasma membrane, although when compared to the $P2X_7$ receptor protein a greater portion of the $P2X_{7-j}$ receptor proteins are found in cytosolic and perinuclear locations.

II. $P2X_7$ And $P2X_{7-j}$ As Cancer Markers

In one embodiment, the present invention contemplates that wild-type $P2X_7$ RNA and/or protein alone, or in combination with the truncated $P2X_7$ RNA and/or receptor protein, may be a marker for cancer cells. In one embodiment, detection of the $P2X_7$ and/or the $P2X_{7-j}$ is capable of diagnosing the presence of cancer cells in a subject and/or determining the probability that cancer cells may develop in a subject at some later time. In one embodiment, a low $P2X_7$ RNA and/or receptor protein level provides a cancer diagnosis in a patient. In one embodiment, a high $P2X_{7-j}$ RNA and/or receptor protein level provides a cancer diagnosis in a patient. In one embodiment, detection of $P2X_7$ and/or $P2X_{7-j}$ RNAs and/or receptor proteins are useful to provide a prognosis. In one embodiment, a low $P2X_7$ RNA and/or receptor protein tissue level diagnoses an epithelial cancer. In one embodiment, a high $P2X_{7-j}$ RNA and/or receptor protein tissue level diagnoses an epithelial cancer. In one embodiment, epithelial cell cancers may include, but are not limited to, breast, prostate, gastrointestinal, and skin cancers. In one embodiment, a low $P2X_7$ RNA and/or receptor protein tissue level diagnoses a cervical epithelial cancer. In one embodiment, a high $P2X_{7-j}$ RNA and/or receptor protein tissue level diagnoses a cervical epithelial cancer.

In one embodiment, detecting $P2X_7$ and/or the $P2X_{7-j}$ RNA and/or receptor protein provides a screening tool for cancer. In one embodiment, the screening is performed to detect cervical cancer in a subject, wherein assaying for $P2X_7$ and/or the $P2X_{7-j}$ RNA and/or receptor protein is assayed in conjunction with a Pap test.

In some embodiments, the present invention contemplates methods comprising detecting cancer, screening for cancer, diagnosing cancer, and the like, using cell samples from a patient at risk for cancer. Cell samples may be obtained from a subject by a variety of different methods including, but not limited to, tissue biopsies, blood samples, serum samples, plasma samples, saliva samples, and fecal samples.

In some embodiments, the present invention contemplates methods comprising detecting cancer, screening for cancer, diagnosing cancer, and the like, using detection and/or quantification of $P2X_7$ and/or the $P2X_{7-j}$ RNA and/or receptor protein in cells from a sample from a subject. In one embodiment, a method comprises detecting and quantifying a P2X receptor variant using reverse transcriptase polymerase chain reaction (RT-PCR). In one embodiment, detection of $P2X_7$ and/or the $P2X_{7-j}$ protein(s) in cells from a sample comprise reagents having specificity for $P2X_7$. In one embodiment, reagents include, but are not limited to, antibodies, antibody fragments, and the like, that specifically bind to $P2X_7$ proteins. In one embodiment, the reagents comprise specific binding for $P2X_7$ and/or the $P2X_{7-j}$ receptor proteins. In one embodiment, a second protein may react with either $P2X_7$ and/or $P2X_{7-j}$ receptor proteins. Although it is not necessary to understand the mechanism of an invention, it is believed that protein properties like, size of the protein and/or intracellular location of the protein, for example, may be used to distinguish $P2X_{7-j}$ from $P2X_7$.

In one embodiment, the present invention contemplates a method comprising diagnosing and prognosticating cancer using relative expression levels of $P2X_{7-j}$ and $P2X_7$ proteins in cells. In some embodiments, reagents (i.e., for example, antibodies) are used to perform a variety of detection assays directed to $P2X_7$ and/or the $P2X_{7-j}$ receptor proteins. In one embodiment, such detection assays may include, but are not limited to, immunofluorescence staining of cells, immunoblotting and/or immunoprecipitation of extracts from cells, flow cytometry, other immunoassays including enzyme-linked immunoabsorbent assay (ELISA), and others.

In addition to methods that directly detect $P2X_7$ proteins, methods that detect function of $P2X_7$ proteins may be used. For example, assays that test cells in a sample for ability to undergo apoptosis, to form channels and/or to form pores, may be used to infer a lack or decrease in $P2X_7$ or the presence of $P2X_{7-j}$.

In some embodiments, $P2X_7$ and $P2X_{7-j}$ receptor proteins are expressed in certain cancer cells including, but not limited to, human cervical cancer epithelial cells, squamous cell carcinoma skin cells, breast cancer epithelial cells, prostate cancer epithelial cells, and others. In other embodiments, $P2X_7$ and $P2X_{7-j}$ receptor proteins are not expressed or expressed at low levels in tissues including, but not limited to, normal cervical tissue, normal keratinocytes, normal cells from blood and lymph, and others. Although it is not necessary to understand the mechanism of an invention, it is believed that $P2X_7$ and $P2X_{7-j}$ receptor proteins in cancer cells may not reach the cell membrane and, instead, may accumulate and remain located within the cytoplasm of the cell whereby these cytosolic $P2X_7$ and $P2X_{7-j}$ receptor proteins are, in general, functionally defective. In one embodiment, a cytosolic $P2X_{7-j}$ receptor protein fails to mediate cellular apoptosis, thereby permitting the growth of a cancerous cell.

Immunoblots of membrane extracts from human cervical cancer cell lines (CaSki, HeLa, HT3, and SiHa), as well as human normal cervical tissues (patients numbers are shown above the lanes) were probed with an anti-$P2X_7$ receptor antibody. $P2X_7$ receptor protein is expressed to a greater extent and $P2X_{7-j}$ receptor protein is expressed to a lesser extent in normal cervical tissues when compared to cancer cervical cells. FIG. 19. The position of the full-length (FL) $P2X_7$ and truncated (TR) $P2X_{71}$ are marked with arrows.

Immunoblots of extracts of human cervical cancer cell lines (CaSki, HeLa, HT3); extracts of human normal cervical tissues (patients numbers are shown above the lanes); and extracts of other cells, including SCC9 (cell line derived from squamous cell carcinoma of the skin), primary cultures of human skin cells (keratinocytes [N. Ker]), $MCF_7$ (human breast cancer cell line), PC3 (human prostate cancer cell line), and J3 (human lymphoma cell line) were also probed with the anti-$P2X_7$ receptor antibody. A greater expression of $P2X_7$ receptor protein and lower expression of $P2X_{7-j}$ receptor protein was observed in normal cervical tissues when compared to cervix cancer cells. Further, a greater expression of $P2X_7$ receptor protein and lower expression of $P2X_{7-j}$ receptor protein was observed in the normal skin cells when compared to the skin cancer cells. On the other hand, a lower expression of $P2X_7$ receptor protein and higher expression of $P2X_{7-j}$ receptor protein were observed in the MCF7, PC3, and J3 cancer cell lines. FIG. 20.

These results support the hypothesis that cancer cells may express higher levels of the $P2X_{7-j}$ receptor protein and/or lower levels of the $P2X_7$ receptor protein when compared to normal cells. Although it is not necessary to understand the mechanism of an invention, it is believed that the data explains why cancer cells resist apoptosis (i.e., cells having high $P2X_{7-j}$ receptor protein levels are apoptotic-deficient, and cells having high $P2X_7$ receptor protein levels are pro-apoptotic).

Immunostaining of human normal, pre-cancer, and cancer tissues using commercially available anti $P2X_7$-antibody that recognizes the $P2X_7$ C-termini was performed. FIG. 24. The plasma membranes in Panels A-D are significantly thus indicating that, in normal ectocervix tissues, the anti $P2X_7$-receptor antibody stains mainly the basal levels of the epithelium. As the degree of dysplasia progressed from mild (Panel E) to moderate (Panel F), to high-grade (Panel G), and to invasive cancer (Panel H), the immunoreactivity with the anti-$P2X_7$-receptor antibody decreased. This finding suggests that as cervical tissues progress through the neoplastic process, levels of the $P2X_7$ receptor ($P2X_7$-WT) decrease.

An analysis of uterine cervix tissues obtained from women with a normal endometrium (normal) and with endometrial cancer (cancer) was also performed. FIG. 25. A total of 11 women were studied and from each woman tissues were obtained from the cancer areas and from normal areas surrounding the cancer. Tissues were homogenized and mRNA levels of $P2X_7$ (filled bars) and $P2X_{7-j}$ (empty bars) were tested by Real-Time RT-PCR and normalized in each tissue by mRNA levels of the constitutive GPDH. The results show that the mRNA levels of the $P2X_{7-j}$/GPDH were similar in the normal and cancer tissues. In contrast, mRNA levels of the $P2X_7$/GPDH were significantly higher in normal than in cancer tissues.

Although not wishing to be bound by theory, a possible conclusion is that in cancer cells $P2X_{7-j}$ can compete more effectively with the $P2X_7$ because the levels of the $P2X_7$ are low. In contrast, in normal cells P2X$_7$ levels are high and the P2X$_{7-j}$ can have only a minimal effect.

A larger analysis of uterine tissues for mRNA levels of the P2X$_7$/GPDH was also performed. FIGS. 26A-B. Normal (empty bars) and cancer (filled bars) endometrial, endocervical and ectocervical samples were obtained from the women whose identifying code is shown at the bottom of the drawings. The figures shows a tendency for the P2X$_7$/GPDH mRNAs ratio to be higher in normal than in cancer tissues.

Analysis of uterine tissues for P2X$_7$ protein showed a tendency for the P2X$_7$ protein to be higher in normal than in cancer tissues. FIG. 27, Panels A-C. Normal (N) and cancer (C) endometrial, endocervical and ectocervical samples were obtained from the women whose identifying code is shown at the bottom of the drawings. Membranes were probed with the anti-P2X$_7$ antibody (for P2X$_7$ protein determinations) and then reprobed with anti-tubulin antibody to determine expression of the constitutive protein tubulin.

Analysis of the ratio of P2X$_7$/tubulin proteins, as determined by densitometry, of the bands in FIG. 27 showed a tendency for the P2X$_7$/tubulin proteins ratio to be higher in normal than in cancer tissues. FIG. 28.

A comparative composite of the P2X$_7$/GPDH mRNA (FIGS. 26A-B) and P2X$_7$/tubulin protein ratios (FIGS. 28A-B) is presented for clarity. FIG. 29. The left two columns are the individuals P2X$_7$/GPDH mRNAs levels obtained for normal (N-RNA) and cancer (C-RNA) tissues. The right two columns are the individuals P2X$_7$ / tubulin proteins levels obtained for normal (N-Pr 0 and cancer (C-Prt) tissues. There were a total of 36 and 15 mRNA samples and 25 and 23 protein samples, respectively of Cancer and Normal samples. For the P2X$_7$/GPDH mRNAs, the data showed a putative cut-off point of 1000 arbitrary units to differentiate cancer from normal uterine tissues, with sensitivity of 94% and specificity of 100% (p<0.0001; see FIGS. 30 and 32 for detailed analysis). For the P2X$_7$/tubulin proteins levels, the data showed a putative cut-off point of 15 arbitrary units to differentiate cancer from normal uterine tissues, with sensitivity of 100% and specificity of 87% (p<0.0001, see FIGS. 31 and 32 for detailed analysis).

In one embodiment, the present invention contemplates a method comprising detecting and quantifying P2X$_7$ mRNA and/or receptor protein levels for use as a biomarker that differentiates between normal uterine cells and cancerous uterine cells.

Although it is not necessary to understand the mechanism of an invention, it is believed that as protein levels of the wild-type P2X$_7$-receptor (P2X$_7$) decrease, the constitutively present P2X$_{7-j}$ may be capable of competing with the P2X$_7$-WT and block its effect. Further, it is also believed that this altered P2X$_7$/PxX$_{7-j}$ receptor protein level ratio could lead to and/or augment the neoplastic process.

In some embodiments, a diagnostic method measures cellular levels of P2X$_7$ and P2X$_{7-j}$ RNA and/or receptor protein either alone, or in combination with other markers, to discern normal versus abnormal (dysplasia and cancer) cells.

In some embodiments, a therapeutic method comprises overexpression of P2X$_7$ receptor protein to induce apoptosis and/or cell death. In one embodiment, P2X$_{7-j}$ receptor protein expression in abnormal cells (i.e., for example, cancer cells) prevents either competitive inhibition and/or blockade by a P2X$_7$ receptor protein.

In some embodiments, the present invention contemplates methods and reagents for therapy of cancer. In one embodiment, a therapeutic method comprises up-regulation of P2X$_7$ receptor protein expression in cancer and/or premalignant cells. In one embodiment, a gene encoding P2X$_7$ may be introduced into cells expressing P2X$_{7-j}$, wherein said gene overexpresses P2X$_7$ receptor protein, thereby inducing cellular apoptosis. In one embodiment, a therapeutic method comprises directly administering a P2X$_7$ receptor protein to cells not expressing P2X$_{7-j}$.

A variety of methodologies, may be used to introduce the genes into cells. For example, methods like transfection or infection of cells with expression vectors may be used. One method of introducing genes into cells in a human, for example, may be more efficient and more efficacious when the target cells are epithelial cells due, at least in part, to the availability/exposure of these cells in the body. In one embodiment, vectors may be directly applied to the surface of epithelial cells to facilitate entry of the vectors into the cells and expression of the P2X$_7$ therein.

In some embodiments, a therapeutic method comprises introducing a vector encoding P2X$_7$ to into cells. In one embodiment, a therapeutic method comprises administering a P2X$_7$-R$_{FL}$ receptor protein to a cell.

There are a variety of methods known in the art for introducing proteins into cells. In one method, proteins are coupled or fused to short peptides that direct entry into cells. One such group of peptides are called protein transduction domains. Methods using these protein transduction domains may be called protein transduction or protein therapy. Another method for introducing proteins into cells may use lipid carriers. For example, a lipid carrier comprises proteins that are associated with liposomes and are able to enter cells when the liposomes enter or fuse with cells. Other methods of introducing proteins into cells are known. Microinjection and electroporation are two such methods. Other methods are known. In one embodiment, administration of agents, like specific drugs, to cells to stimulate production of endogenous P2X$_7$, stimulate activation of existing P2X$_7$ and the like, may be used.

In one embodiment, the present invention contemplates a therapeutic or preventative method comprising a down-regulation of P2X$_{7-j}$ receptor protein expression in cancer cells or premalignant cells. In one embodiment, the P2X$_{7-j}$ down-regulation is achieved by administering specific inhibitors of P2X$_{7-j}$ and/or P2X$_{7-j}$ mRNA splicing techniques. In other embodiments, down-regulation methods include, but are not limited to, antisense methods, or RNAi methods (e.g., using siRNAs) to inhibit expression of P2X$_{7-j}$.

In one embodiment, anti-P2X$_{7-j}$ therapeutics may use administration of reagents specific for P2X$_{7-j}$ protein. One type of reagent may be an antibody. Various example forms of the antibodies, including humanized or protease-conjugated forms, may be used.

III. Cell Proliferation And Apoptosis

Although it is not necessary to understand the mechanism of an invention, it is believed that one biological role of P2X$_7$ receptors is mediation of apoptosis. Apoptosis comprises a biological mechanism of regulated cell death whereby abnormal (i.e., for example, cancerous and/or premalignant cells) cells are eliminated from the body. It is further believed that one of the mechanisms by which cancer is believed to progress is through defective apoptosis whereby cancer cells fail to undergo apoptosis and are not eliminated.

In one embodiment, the present invention contemplates that the relative expression of P2X$_{7-j}$ compared to the P2X$_7$ render cells susceptible to a diminished degree of apoptosis. In one embodiment, cancer cells express higher levels of the apoptotic deficient P2X$_{7-j}$ receptor protein and/or lower levels of the pro-apoptotic P2X$_7$ receptor protein when compared to normal (i.e., for example, non-cancerous and/or non-premalignant) cells.

Figure 2D:
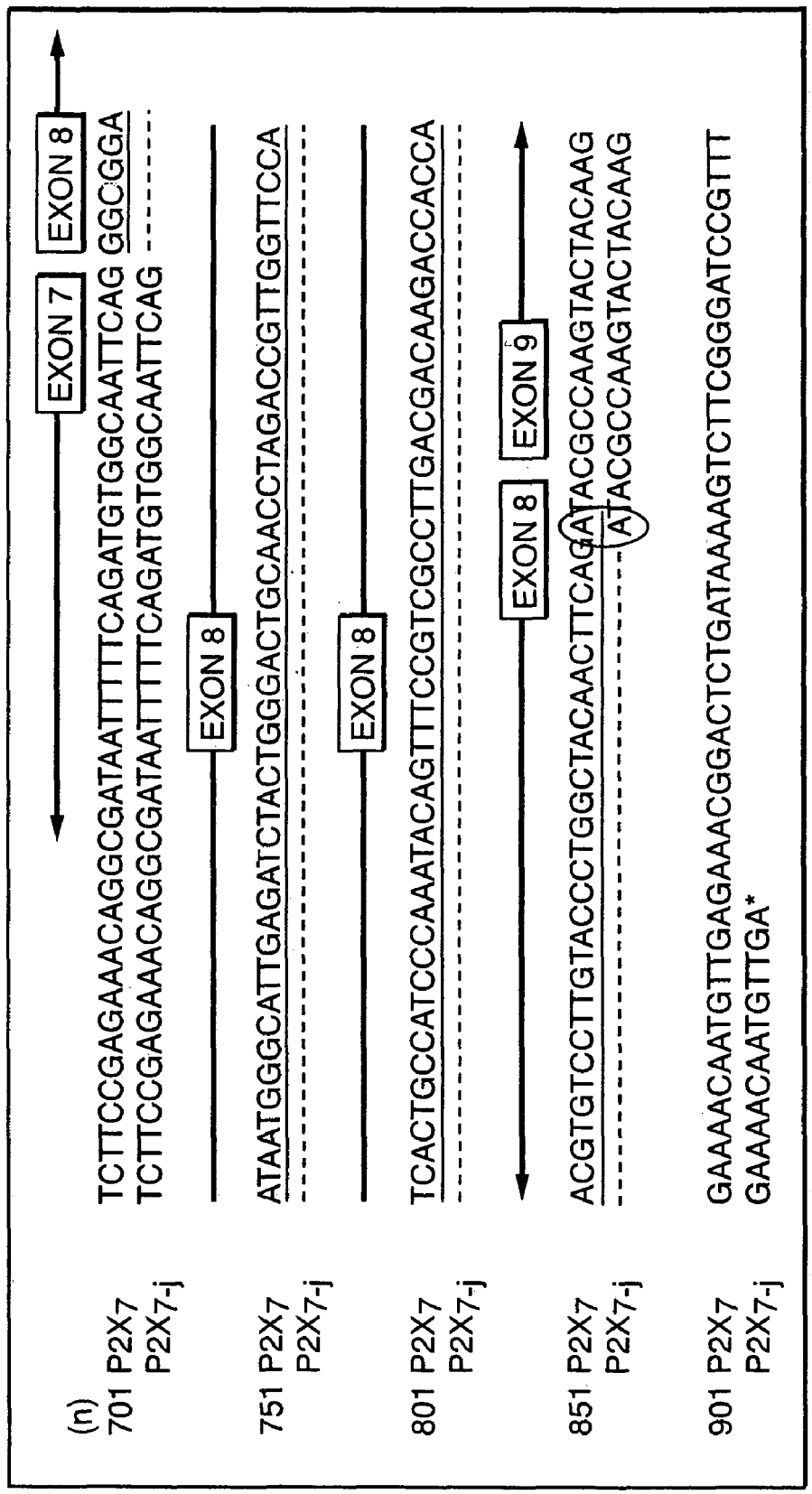
Figure 2E:
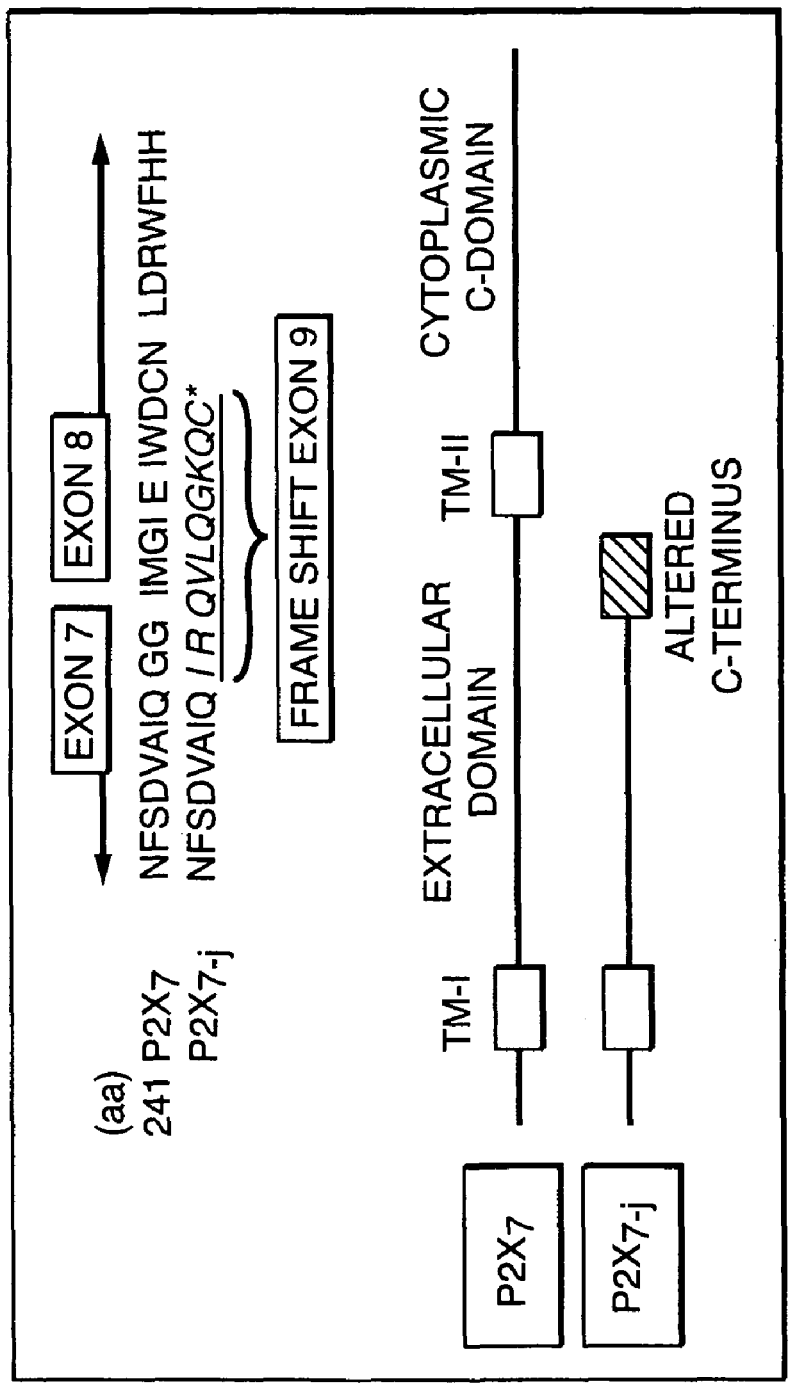

In one embodiment, a method comprises assaying cells in a cell sample obtained from a subject for the presence of a P2X$_7$ protein, or RNA that encodes a P2X$_7$ protein, that lacks the ability of the wild-type P2X$_7$ protein to facilitate apoptosis in certain cells. In one embodiment, a P2X$_7$ receptor protein lacking and/or is defective in apoptotic ability comprises a truncated P2X$_7$ protein. In one embodiment, a truncated P2X$_7$ protein includes, but is not limited to, P2X$_7$ or P2X$_7$-R$_{TR}$. FIGS. 2A-B and 2C, respectively.

In one embodiment, the present invention contemplates reagents that comprise reactivity with a P2X$_7$ protein that is lacking or defective in apoptotic ability. In one embodiment, a reagent includes, but is not limited to, an antibody, or antisera containing antibodies, that is reactive with an apoptotic-defective P2X$_7$ protein. In one embodiment, the antibody or antisera containing antibodies is not reactive with wild-type P2X$_7$. In one embodiment, one or more antibodies reactive with all or part of an amino acid sequence that includes IRQVLQGKQC (SEQ ID NO:1) is disclosed. In one embodiment, the present invention contemplates a kit comprising, among other reagents, one or more reagents for detecting a P2X$_7$ protein that are lacking or defective in apoptotic ability.

In one embodiment, a treatment method may facilitate increasing the amount and/or activity of a wild-type P2X$_7$ protein or a P2X$_7$ protein that is capable of contributing to apoptosis. In one embodiment, a treatment method may facilitate increasing the amount and/or activity of one or more RNAs encoding a wild-type P2X$_7$ protein or a P2X$_7$ protein that is capable of contributing to apoptosis. In one embodiment, a treatment method may facilitate decreasing the amount and/or activity of an apoptotic-defective P2X$_7$ protein. In one embodiment, a treatment method may facilitate decreasing the amount and/or activity of one or more RNAs encoding an apoptotic-defective P2X$_7$ protein. In one embodiment, a treatment method for decreasing the amount and/or activity of an apoptotic-defective P2X$_7$ protein may include the use of at least one antibody capable of specifically binding to an apoptotic-defective P2X$_7$ protein. In one embodiment, an antibody may specifically bind to all or part of an amino acid sequence that comprises IRQVLQGKQC (SEQ ID NO:1).

In some embodiments, the present invention contemplates pharmaceutical compositions that may include one or more of these antibodies or other reagents that bind to apoptotic-defective P2X$_7$ proteins.

Figure 15A:
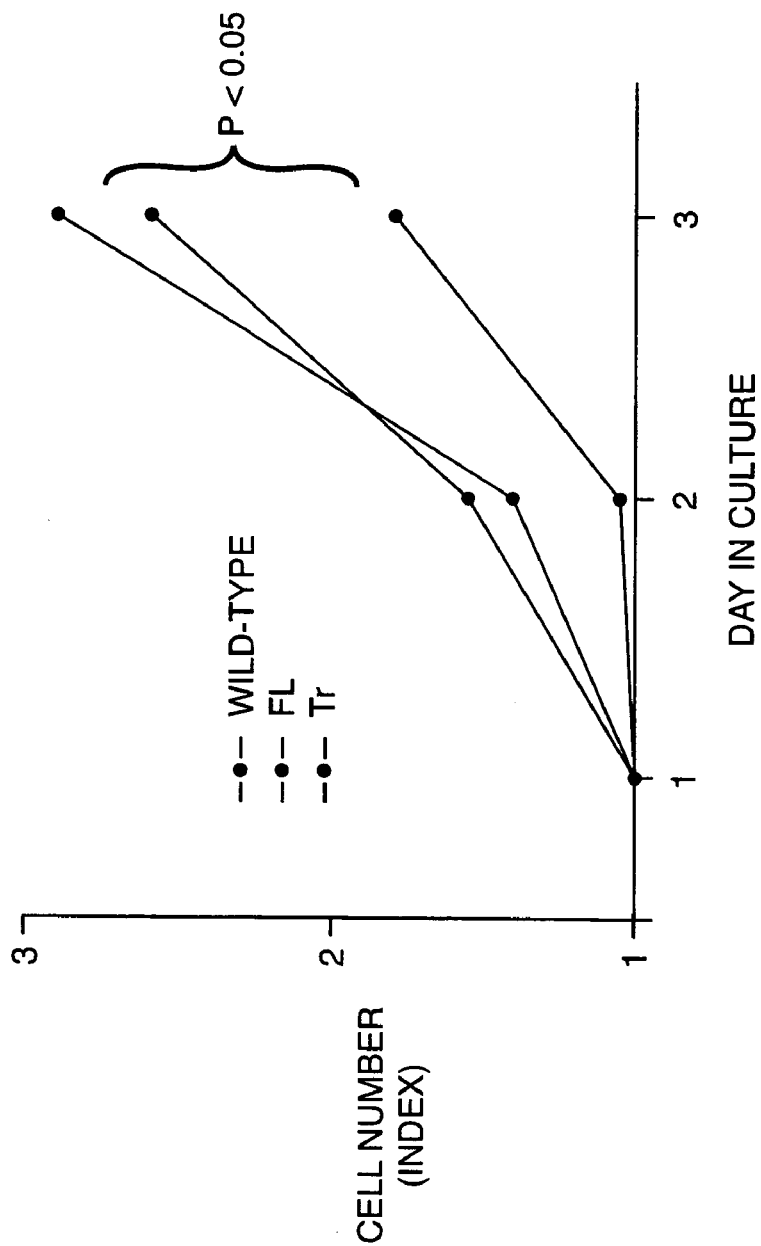
FIG. 15A illustrates example results of cell number index for HEK-293 cells, HEK-293 cells expressing P2X7-RFL, and HEK-293 cells expressing P2X7-RTR grown in culture.

Alterations in cell number for HEK-293 cells, HEK-293 cells expressing P2X$_7$-R$_{FL}$, and HEK-293 cells expressing P2X$_7$-R$_{TR}$ grown in culture were studied. FIG. 15A. The three cells lines were grown in culture and viable cells were counted for a period of 3 days. The data are presented as cell number index versus days in culture. The results show that HEK-293 cells and HEK-293 cells expressing P2X$_7$-R$_{TR}$ protein increased in number at similar rates. In contrast, HEK-293 cells expressing P2X$_7$-R$_{FL}$ protein increased in number at a significantly slower rate. Although it is not necessary to understand the mechanism of an invention, it is believed that these data may indicate that the presence of P2X$_7$-R$_{FL}$ protein, but not P2X$_7$-R$_{TR}$ protein, may affect the growth or survival characteristics of cells. For example, a P2X$_7$-R$_{FL}$ receptor protein may facilitate cellular apoptosis (infra).

Cell number in a culture of MDCK cells and HEK-293 cells expressing P2X$_7$ or P2X$_{7-j}$ proteins were also determined. FIG. 15, Panels A & B. Over a period of four days in culture there was a steady growth of MDCK cells in culture as is evident by an increase in the cell-number index. However, cell number was lower in doxycycline-treated MDCK expressing the P2X$_7$. Although not wishing to be bound by theory, one possible explanation is that ATP, which is constitutively secreted by cells and is present in the extracellular fluid at concentrations that suffice to activate the P2X$_7$-receptor have activated the doxycycline-induced P2X$_7$-receptor in those cells, and activation of the P2X$_7$-receptor slowed the growth of cells.

A. Adenosine Triphosphate Regulation Of P2X

The cell number of wild-type HEK-293 cells and of HEK-293 cells expressing P2X$_{7-j}$ protein increased to a greater degree than that of HEK-293 cells expressing the P2X$_7$ protein. FIG. 15A. Treatment with 100 micromolar BzATP significantly decreased further the growth of HEK-293-P2X$_7$ cells but had no significant effect on wild-type HEK-293 cells and on HEK-293-P2X$_{7-j}$ cells.

Although not wishing to be bound by theory, these data may indicate that the presence of P2X$_7$ protein, but not P2X$_{7-j}$ protein, may affect the growth or survival characteristics of cells. For example, a P2X$_7$ receptor protein may facilitate cellular apoptosis.

Figure 16:
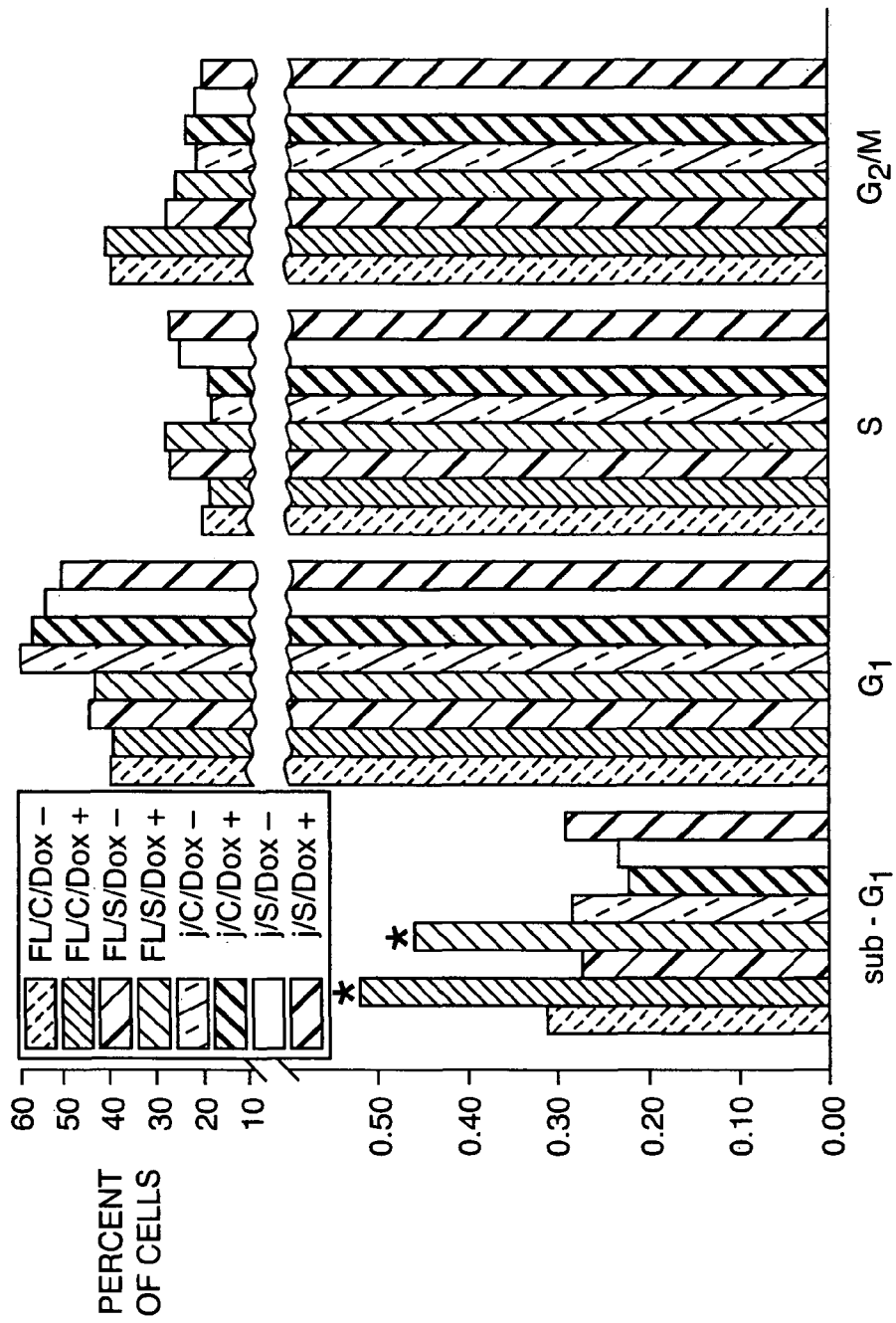
FIG. 16 illustrates example results of cell-cycle, cell proliferation, and apoptosis analysis in MDCK cells expressing P2X$_7$(Myc) or P2X$_{7-j}$(Myc) under the control of a promoter inducible by doxycycline (Panel A); and HEK-293 cells, HEK-293 cells expressing P2X$_7$, and HEK-293 cells expressing P2X$_{7-j}$(Panel B). The * or ** in the figure indicate p<0.01 for comparison of the indicated data (Analysis by ANOVA). FL denotes the Full-Length P2X$_7$ protein; j denotes the truncated P2X$_{7-j}$ protein; C denotes control; S denotes serum plus KGS; Dox denotes doxycycline; 293 wild-type denotes HEH-293; and BzP denotes BzATP.
Figure 16:
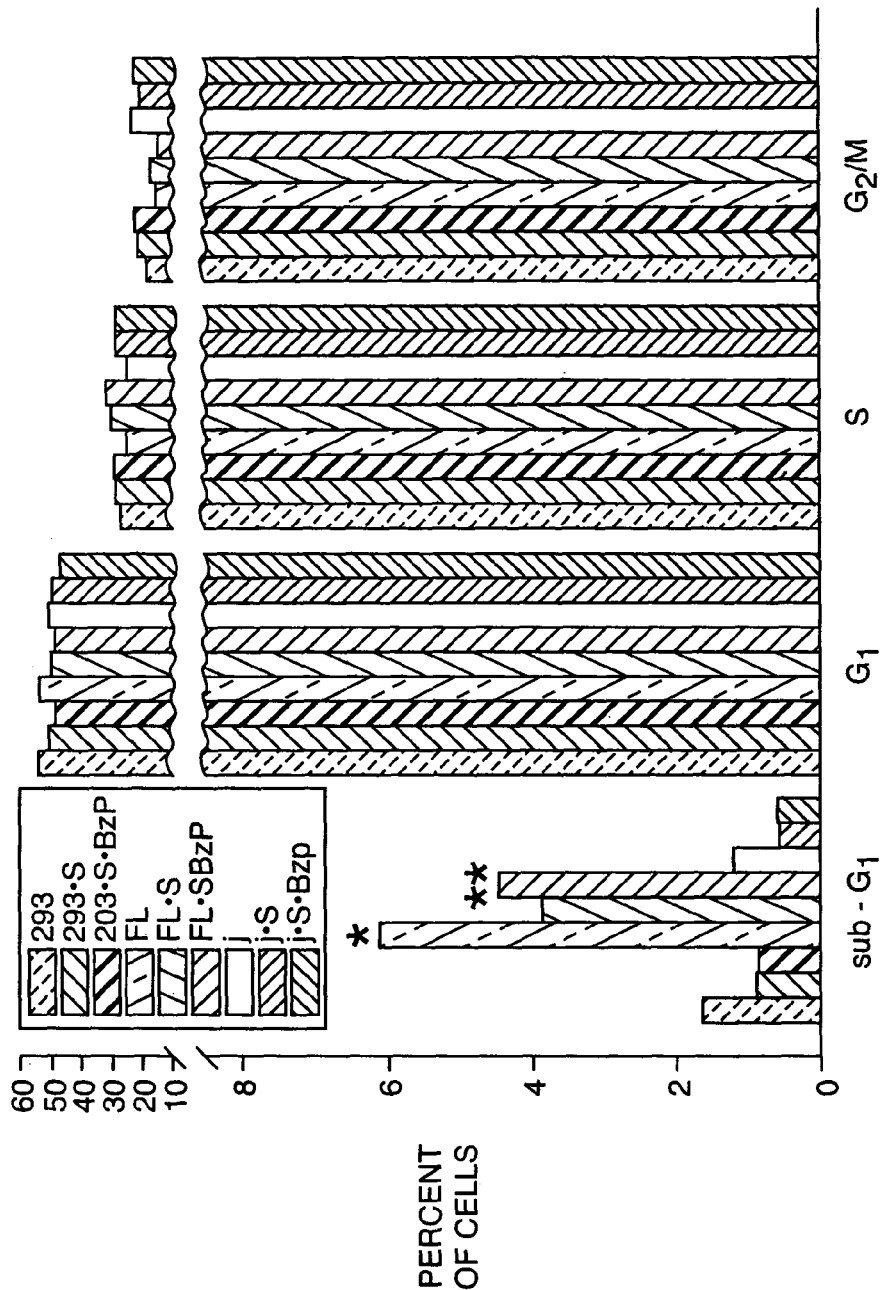

Cell proliferation and apoptosis was studied in MDCK cells and HEK-293 cells expressing the P2X$_7$ or the P2X$_{7-j}$. FIGS. 16, Panels A and B, respectively. Although it is not necessary to understand the mechanism of an invention, it is believed that P2X$_7$ proteins may control cell proliferation and/or cellular apoptosis as it relates to the cell cycle and various growth factors. Cells were shifted to serum-free medium to place the cells into a semiquiescent state, therefore synchronizing the cells. After 6 hours in the serum-free medium, the cells were then synchronously stimulated into the cell cycle by addition of serum-free medium containing 1:500 defined keratinocyte-SFM growth supplement (KGS) from bovine pituitary extract (GIBCO, Cat. 10784-015) for 18 hours. Control cells had no KGS. The cells were then fixed in methanol, treated with RNase, DNA was stained with propidium iodide, and cells were analyzed for DNA content by flow cytometry. DNA histograms were analyzed for the percentage of cells in the various cell cycle phases. Cell cycle phases analyzed were sub-G1, G1, S, and G2+M. The data showed that the KGS stimulated all of the tested cells into the cell cycle, leading to DNA synthesis (S phase) and cell division (M phase). FIG. 16. These data suggest that expression of neither the P2X$_7$ nor P2X$_{7-j}$ proteins keep cells from proliferating, as measured by entry into the cell cycle. Although it is not necessary to understand the mechanism of an invention, it is believed that because expression of the P2X$_7$ protein does not inhibit cellular proliferation, this indicates that the decrease in cell number of cells expressing P2X$_7$ protein was due to cellular apoptosis and not inhibition of cellular proliferation. The results also indicate that cells were undergoing apoptosis, as cells with a sub-G1 DNA content generally are apoptotic cells. These results indicate that a greater percentage of cells expressing P2X$_7$ were apoptotic than cells expressing P2X$_{7-j}$ or cells expressing no P2X$_7$. Although not wishing to be bound by theory, the explanation for greater apoptosis in the cells expressing P2X$_7$ may be that ATP secreted by cells contributes to apoptosis in the cells expressing P2X$_7$. Sensitivity to apoptosis is also likely increased by deprivation of certain growth factors, as shown by the increased apoptosis of cells expressing P2X$_7$ when not growth-stimulated by KGS. Stimulation of cells into the cell cycle generally is known to rescue cells from apoptosis.

Figure 17:
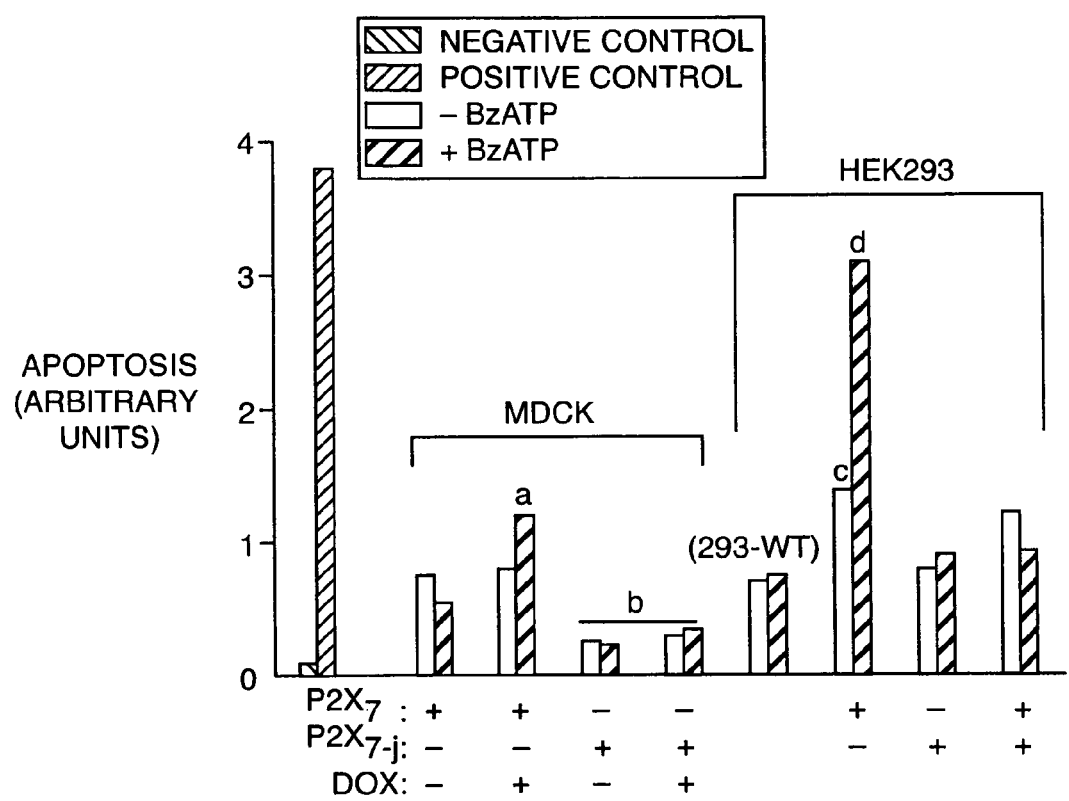
FIG. 17 illustrates example results of spontaneous, or 2'-3'-O-(4-benzoylbenzoyl)adenosine 5'-triphosphate (BzATP)-stimulated apoptosis in MDCK cells expressing P2X$_7$(Myc) or P2X$_{7-j}$(Myc) under the control of a promoter inducible by doxycycline; wild-type HEK-293 cells (293-WT), HEK-293 cells expressing P2X$_7$ (293-FL), and HEK-293 cells expressing P2X$_{7-j}$ (293-Tr). BzATP is a non-hydrolyzable analog of ATP.

Baseline and BzATP-induced apoptosis in MDCK cells and in HEK-293 cells expressing P2X$_7$ and P2X$_{7-j}$ proteins were studied. FIG. 17. The data show that P2X$_{7-j}$ receptor protein functions to mediate apoptosis in relation to the $P2X_7$ protein when activated by BzATP. Cells were treated with BzATP (50 micromolar) to activate the $P2X_7$ receptors. Apoptosis was quantified using Cell Death Detection ELISA-PLUS photometric enzyme-immunoassay that determines cytoplasmic histone-associated-DNA-fragments (mono and oligonucleosomes) after spontaneous or induced cell death (Roche, Cat. No. 1774425, 96 tests). Doxycycline treated MDCK-$P2X_7$ cells showed increased apoptosis following exposure to BzATP. Baseline apoptosis in HEK-293-$P2X_7$ cells was greater than in wild-type HEK-293 cells, and treatment with BzATP further increased this baseline apoptosis. Expression of the $P2X_{7-j}$ proteins either had no effect (HEK-293 cells) or may have decreased apoptosis (MDCK cells). Co-expression of $P2X_7$ plus the $P2X_{71}$, in HEK-293 cells resulted in reduced apoptosis when compared to cells expressing only the $P2X_7$. Although it is not necessary to understand the mechanism of an invention, it is believed that these results suggest that the $P2X_{7-j}$ blocks $P2X_7$-mediated apoptosis. These data further indicate that the $P2X_{7-j}$ protein is defective in its ability to mediate cellular apoptosis as compared to $P2X_7$ protein (having consistency with the data presented in FIG. 16). Further it is believed that these data may explain the decrease in call number in cells expressing $P2X_7$ protein, versus cell number in cells expressing the $P2X_{7-j}$ protein or cells not expressing $P2X_7$ proteins, due to apoptosis of a subset of cells in the population of cells expressing the $P2X_7$ protein (as seen in FIGS. 15 & 15A). These data may also indicate that the decrease in cell number in cells expressing $P2X_7$-$R_{FL}$ protein, versus cell number in cells expressing $P2X_7$-$R_{TR}$ protein, or cells not expressing $P2X_7$ protein, was due to apoptosis of a subset of cells in the population of cells expressing $P2X_7$-$R_{FL}$ protein.

Cellular proliferation and apoptosis were compared in HEK-293 cells, HEK-293 cells expressing $P2X_7$-$R_{FL}$, and HEK-293 cells expressing $P2X_7$-$R_{TR}$. Growing HEK-293 cells (293WT) and HEK-293 cells stably expressing either $P2X_7$-$R_{FL}$ (293FL) or $P2X_7$-$R_{TR}$ (293Tr) proteins were shifted to serum-free medium to place the cells into a semi-quiescent state, therefore synchronizing the cells. FIG. 36. After 6 hours in the serum-free medium, the cells were then synchronously stimulated into the cell cycle by addition of serum-free medium containing 1:500 defined keratinocyte-SFM growth supplement (KGS) from bovine pituitary extract (GIBCO, Cat. 10784-015) for 18 hours. This KGS supplement contained epidermal growth factor (EGF). Control cells had no KGS. The cells were then fixed in methanol, treated with RNase, DNA was stained with propidium iodide, and cells were analyzed for DNA content by flow cytometry. DNA histograms were analyzed for the percentage of cells in the various cell cycle phases. Cell cycle phases analyzed were sub-G1, G1, S, and G2+M. The results show that the EGF in the KGS stimulated all of the tested cells into the cell cycle, leading to DNA synthesis (S phase) and cell division (M phase). These data indicate that expression of neither the $P2X_7$-$R_{FL}$ nor $P2X_7$-$R_{TR}$ proteins keep cells from proliferating, as measured by entry into the cell cycle. Although it is not necessary to understand the mechanism of an invention, it is believed that because expression of the $P2X_7$-$R_{FL}$ protein does not inhibit cellular proliferation, this further indicates that the decrease in cell number of cells expressing $P2X_7$-$R_{FL}$ protein was due to apoptosis and not inhibition of proliferation (cf FIG. 10). The results are further believed to indicate that the cells are undergoing apoptosis, because cells with a sub-G1 DNA content generally are apoptotic cells. These results indicate that a greater percentage of cells expressing $P2X_7$-$R_{FL}$ were apoptotic than cells expressing $P2X_7$-$R_{TR}$ or cells expressing no $P2X_7$. However, an alternative explanation for greater apoptosis in the cells expressing $P2X_7$-$R_{FL}$ may be that ATP secreted by cells contributes to apoptosis in the cells expressing $P2X_7$-$R_{FL}$. It is further believed that, sensitivity to apoptosis is also likely increased by deprivation of serum growth factors, as shown by the increased apoptosis of cells expressing $P2X_7$-$R_{FL}$ when not growth-stimulated by KGS. Stimulation of cells into the cell cycle generally is known to rescue cells from apoptosis.

A schematic illustration of a growth/survival experiment demonstrates a selection of BzATP-resistant cells. FIG. 22. Even in apparently homogenous populations of cells, there may be subtle differences among cells in the populations. Therefore, an apparently homogenous cell population may have, or be made up of, various cell subpopulations or cell isoforms. Application of specific selective pressures to the cell population may result in certain of the subpopulations responding differently than other of the subpopulations. One example of application of a selective pressure to which certain cell subpopulations respond differently than others. An initial cell population comprises at least two subpopulations, that have not yet been treated with BzATP. FIG. 22, Panel A. The cells represented by filled circles are those sensitive to BzATP. BzATP treatment of these sensitive cells will either inhibit proliferation of the cells and/or cause the cells to undergo apoptosis (i.e., a negative selection pressure). Cells represented by open circles are those resistant to BzATP. BzATP treatment of these resistant cells will not affect proliferation or cause apoptosis (i.e., a positive selection pressure). After treatment with BzATP, the cell population contains different proportions of the BzATP-sensitive and BzATP-resistant subpopulations. FIG. 22, Panel B. Although it is not necessary to understand the mechanism of an invention, it is believed that proliferation of the BzATP-sensitive cells has been inhibited, or apoptosis of the cells has occurred, in response to the BzATP. In contrast, it is further believed that cellular proliferation of the BzATP-resistant cells has not been affected, and the number of BzATP cells, therefore, has significantly increased as a proportion of the total cells in the population. This type of process may be called cell selection.

Growth of various cell lines expressing $P2X_7$ and/or $P2X_{7-j}$ in the presence or absence of BzATP was performed to determine how $P2X_7$ receptors may affect cell selection over time. FIG. 23. HEK-293 cells expressing $P2X_7$, HEK-293 cells expressing $P2X_{7-j}$, or HeLa cells, which express both $P2X_7$ and $P2X_{7-j}$ were separately grown in culture, in the presence or absence of 50 micromolar BzATP for seven (7) days. At various time points, samples of the cells were taken and examined for expression of $P2X_7$ and/or $P2X_{7-j}$ protein by immunoblotting using a $P2X_7$-specific antibody. This antibody was obtained from Alomone Labs (Jerusalem, Israel) and was reactive with the extracellular domain of $P2X_7$ protein. Amino acids 136-152 of the mouse $P2X_7$ receptor (KKGWMDPSKGIQTGRC; (SEQ ID NO:7)) were used as the antigen to prepare the antibody. A labeled secondary antibody was used to visualize reactive protein bands. By layering equal amounts of total protein (15 micrograms) it was possible to compare the relative expression of the $P2X_7$ and/or $P2X_{7-j}$ proteins by the cells.

The results for the HEK-293 cells, expressing the $P2X_7$ protein, show that after each day of treatment with BzATP expression of the $P2X_7$ protein was less than in cells not treated with BzATP. (FIG. 23, upper Panel) This indicates a negative selection pressure in the presence of BzATP. There was, however, significant $P2X_7$ protein expression in cells not treated with BzATP, thereby indicating a positive selection pressure. This result suggests that the beginning population of HEK-293 cells expressing the $P2X_7$ protein contained at least two subpopulations one sensitive to BzATP and one resistant to BzATP. Treatment of the cells with BzATP resulted in selection of the BzATP-resistant subpopulation. Growth and/or survival of the BzATP-sensitive subpopulation was selected against in the presence of BzATP. As was shown earlier, this result is likely due to induction of apoptosis in the BzATP-sensitive subpopulation by BzATP.

The results in HEK-293 cells expressing $P2X_{7-j}$ protein show that continuous treatment with BzATP did not decrease the expression of the $P2X_{7-j}$ protein. (FIG. 23, middle Panel). This indicates no selection pressure in the presence of BzATP. This result suggests that $P2X_{7-j}$ protein expression does not affect cell selection in the presence of BzATP. As was shown earlier, cells expressing $P2X_{7-j}$ protein are relatively resistant to BzATP-induced apoptosis.

HeLa cells are a line of transformed cervical cancer cells and have been shown to express both $P2X_7$ and $P2X_{7-j}$ proteins. The results show that, after seven (7) days of treatment with BzATP, the expression of $P2X_7$ protein was significantly decreased, while the expression of the $P2X_{7-j}$ protein remained stable. (FIG. 23, lower Panel) This indicated that at least some of the cells expressing $P2X_7$ protein are undergoing a negative selection pressure in presence of BzATP. As discussed, this result is likely due to induction of apoptosis in at least some of the cells expressing full-length $P2X_7$ protein.

In summary, these data may indicate that treatment with a $P2X_7$ agonist can cause a negative selection pressure against cells expressing $P2X_7$, thereby providing a selective advantage to cells expressing $P2X_{7-j}$. Although it is not necessary to understand the mechanism of an invention, it is believed that that because $P2X_{7-j}$ expression may be limited to cancer cells, the results may suggest how these cells come to predominate in tumors.

Although not wishing to be bound by theory, the most likely explanation for the baseline decrease in call number in cells expressing the $P2X_7$ is of apoptosis induced by ATP. ATP is secreted by cells constitutively to the extracellular milieu, and it results in apoptosis by an autocrine-paracrine mechanism that involves the $P2X_7$ receptor system. Similarly, treatment with BzATP activates the $P2X_7$ receptor and augments the apoptosis. The data in FIG. 16 and FIG. 17 indicate that expression of the $P2X_{7-j}$, on the other hand, does not enhance apoptosis, but may in fact result in an increase in cell number. The data in FIG. 16 and FIG. 17 also explain the changes in cell number observed in FIG. 23. Thus, expression of the functional $P2X_7$ is associated with increased apoptosis and will lead to decreased cell number. In contrast, expression of the $P2X_{7-j}$ does not lead to increased apoptosis and therefore does not lead to a decrease in cell number. Although it is not necessary to understand the mechanism of an invention, it is believed that that the $P2X_{7-j}$ receptor protein is a non-functional form of the $P2X_7$ receptor protein. Furthermore, cells transfected with the $P2X_{7-j}$ cDNA increased in cell number and in cells cotransfected with the $P2X_7$ plus the $P2X_{7-j}$ cDNA the levels of apoptosis were lower than in cells transfected only with the $P2X_7$ cDNA, it is possible that the $P2X_{7-j}$ competes with the $P2X_7$ and blocks its action.

Figure 18:
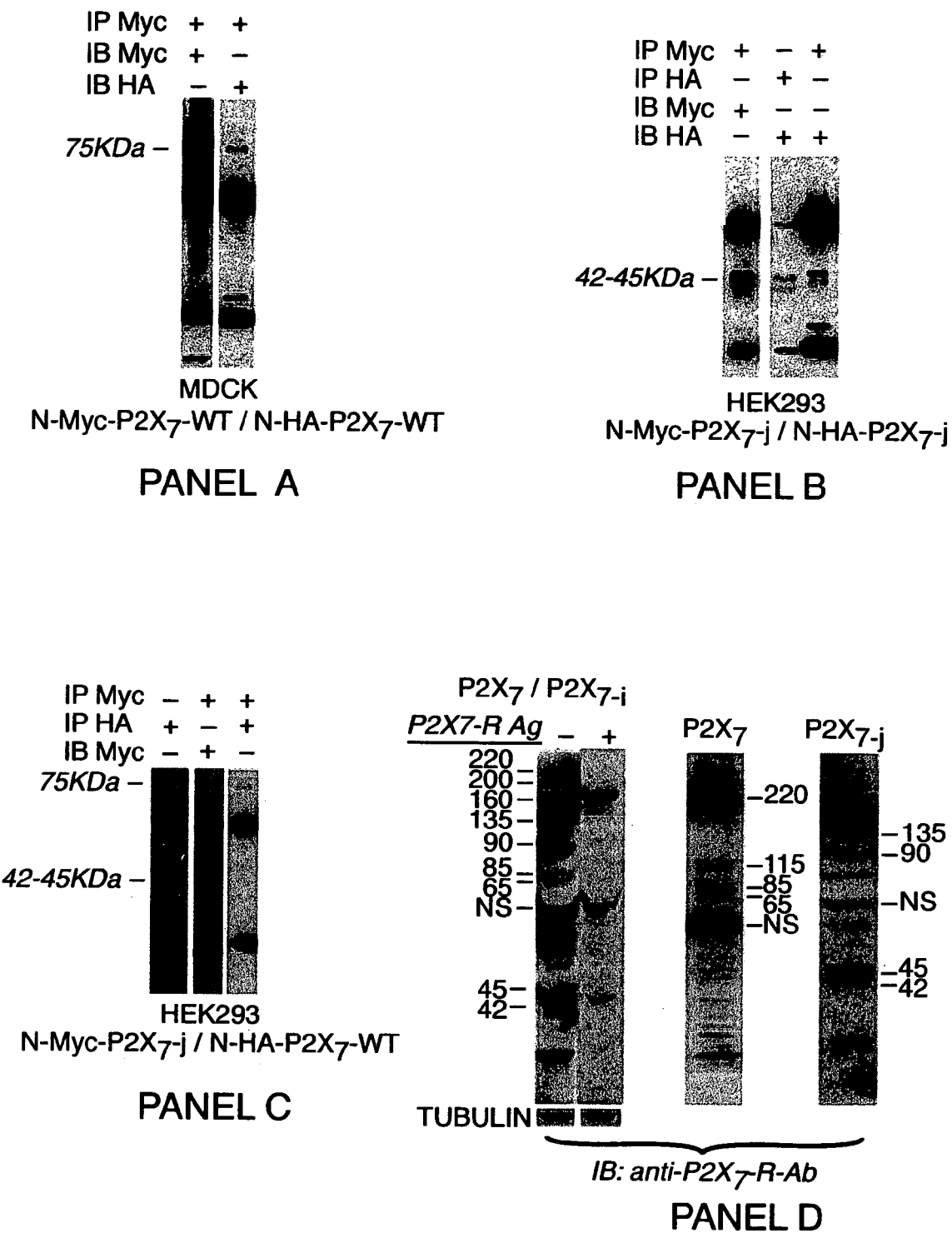
FIG. 18 illustrates example results of gel electrophoresis protein separation experiments that studied the oligomerization properties of the P2X$_7$ and the P2X$_{7-j}$ receptors.

This conclusion is supported by the oligomerization experiments in FIG. 18. As discussed above, the $P2X_{7-j}$ competes with the $P2X_7$ for oligomerization, so that in the relative excess of the $P2X_{7-j}$ or in the relative absence of the $P2X_7$, the $P2X_7$ receptor complexes will be dominated by the inactive $P2X_{7-j}$. This should render the $P2X_7$ system unresponsive to ATP, and will abrogate the ATP-related apoptosis. The net cellular effect would favor cell growth, and may lead to cell overgrowth and contribute to the development and spread of cancer.

B. Epinephrine Inhibition Of $P2X_7$—Mediated Apoptosis

Proper function the epithelia of the female genital tract depends on coordinated growth and differentiation of the epithelial cells, and deviations from these well-controlled functions can cause infertility and lead to dysplasia and cancer. The uterine cervical epithelium is maintained by a balance between proliferation of the basal layer of cells, and death of cells in upper layers. Our current state of knowledge suggests three levels of growth-control of cervical epithelial cells: proliferation, controlled by mitogenic signals [e.g. estrogen and epidermal growth factor (EGF)] vs. growth inhibitory factors (e.g. TGFb); Jacobberger et al. "Transforming growth factor β regulation of epidermal growth factor receptor in ectocervical epithelial cells" *Exp Cell Res* 220: 390-396 (1995); terminal differentiation, controlled mainly by estrogen; Vijayalakshmi et al., "Estradiol-regulated transamidation of keratins by vaginal epithelial cell transglutaminase" *Exp Cell Res* 214:358-366 (1994); and senescence of cells evading growth control and terminal differentiation due to the erosion of telomeres Mandelblatt, "Squamous cell of the cervix, immune and HPV: is cervical age-related neoplasm?" *Adv Exp Med Biol* 330:13-26 (1993). Recently it was reported that growth of human cervical epithelial cells is also regulated by apoptosis; the effect involves predominantly the P2X7 receptor as its proximal signaling arm, and it uses the mitochondrial apoptotic pathway. Wang et al., "P2X7-receptor mediated apoptosis of human cervical epithelial cells" *Am Physiol Cell Physiol* 287:C1349-C1358 (2004). However, relatively little is known about regulation of these effects and the mechanisms involved. Because apoptosis functions to eliminate abnormal cells and dysregulation of apoptotic cell-death has been implicated in the premature death of cells, loss of tissue, aging, states of disease, and neoplastic transformation, elucidation of these data could be important for our understanding of cervical cell biology and tumorigenesis. Ellis et al., "Mechanisms and functions of cell death" *Annu Rev Cell Biol* 7:663-698 (1991); and Ashkenazi et al., "Death receptors: signaling and modulation" *Science* 281:1305-1308 (1998).

Both EGF and epinephrine are added routinely to cultures of squamous epithelial cells to enhance cell-growth. Gorodeski et al., "Human uterine cervical epithelial cells grown permeable support—a model for the study of differentiation and transepithelial transport" *Differentiation* 56:107-118 (1994); and Sime et al., "Method for the growth of equine airway epithelial cells in culture" *Res Vet Sci* 62:30-33 (1997).

EGF and members of the EGF receptor family influence cell survival predominantly by stimulating proliferation, including of human cervical epithelial cells. Wells "EGF receptor" *Int Biochem Cell Biol* 31:637-643 (1999). Until recently, no mechanistic explanation was given for the growth promoting effect of epinephrine. Recently we found that epinephrine increases the number of human cervical epithelial cells in culture, and that EGF potentiates the epinephrine effect. Because epinephrine, in contrast to EGF alone, inhibited apoptosis of cervical cells, we hypothesized that EGF, in addition to its mitogenic role, also potentiates epinephrine antiapoptotic effect. The specific objective of the present study was to understand the mechanisms of EGF and epinephrine antiapoptotic effects.

The results suggest that the epinephrine effect is mediated by β2-adrenoceptor-dependent inhibition of $P2X_7$ receptor pore formation. The results also suggest a dual role for EGF: as mitogen, using the MAPK/MAPK kinase (MAPK/MEK)

signaling pathway, and as facilitator of epinephrine effect. We also found that the effect of EGF involves facilitated, phosphoinositide 3-kinase (PI3K)-dependent inhibition of β2-adrenoceptor internalization, and facilitated β2-adrenoceptor recycling, thereby increasing the level of β2-adrenoceptors in the plasma membrane. These findings underscore a novel signaling network that could be a general paradigm for functional communication between the receptor tyrosine kinases (RTKs), the G protein-coupled receptors (GPCRs), and the purinergic $P2X_7$ receptor.

C. Estrogen Mediation Of $P2X_7$ Induced Apoptosis

Shifting cultured cervical cells to low calcium attenuated baseline apoptosis and abolished $P2X_7$ receptor-induced apoptosis, suggesting that both are mediated by $P2X_7$ receptor-induced calcium influx and depend on increases in cytosolic calcium. Wang et al., "Antiapoptotic Effects Of Estrogen In Normal And Cancer Human Cervical Epithelia Cells" *Endocrinol.* 145:5568-5579 (2004). The only condition found to induce sustained increases in cytosolic calcium in human cervical epithelial cells was ligation of the $P2X_7$ receptor. ATP, the naturally occurring ligand of the $P2X_7$ receptor, is constitutively secreted by cervical cells and is present in the extracellular fluid at concentrations that suffice activation of the receptor. Wang et al., "$P2X_7$-receptor mediated apoptosis of human cervical epithelial cells" *Am Physiol Cell Physiol* 287:C1349-C1358 (2004). These data are compatible with autocrine-paracrine regulation of apoptosis whereby cervical cells regulate activation of the $P2X_7$ receptor by secreting ATP into the extracellular fluid.

Two mechanisms have been identified by which cancer cervical cells may evade $P2X_7$ receptor-induced apoptosis. The late sustained increases in cytosolic calcium in response to activation of the $P2X_7$ receptor were smaller in cancer cells than in normal cells. In addition, in the cancer cervical cells, CaSki, the anti-apoptotic Bcl-2, was up-regulated in response to estrogen. The former would entail lesser proapoptotic signal, whereas the latter an increased antiapoptotic mechanism, and both could act in concert to block $P2X_7$ receptor/calcium-induced apoptosis. Whether those mechanisms contribute to the neoplastic transformation of cervical epithelial cells in vivo is at present unknown.

Estrogen may be involved in the modulation of apoptosis. Estrogen blocked baseline and $P2X_7$ receptor-induced apoptosis in hECEs, ECE16-1, HT3, and CaSki cells. The effect of estrogen involved transcription and protein translation, but it did not depend on cell-cycle phase or the state of cell differentiation, indicating that the antiapoptotic effect of estrogen is unrelated to its mitogenic function. The specificity profile of estrogen action supports interaction with specific response elements but lack of inhibition by tamoxifen ICI-182780, and progesterone does not support activation of the traditional nuclear estrogen receptor(s). Because the time course of apoptosis assays required 9 h of treatment with ATP or BzATP, it was difficult to pinpoint the direct time-related perturbation by estrogen. Nevertheless, the present data suggest effects as early as 1-3 h after adding the hormone.

In contrast to HT3 and CaSki cells, treatment of SiHa and Hela cells with 17β-estradiol had no effect on the $P2X_7$ receptor-induced apoptosis, despite the fact that both types of cells express specific binding sites for the hormone. SiHa and Hela cells may have evolved mechanisms that resist estrogen modulation of $P2X_7$ receptor-induced apoptosis. One of the mitochondrion-related antiapoptotic mechanisms in cancer cells is Bcl-2. Cervical cancer cells such as CaSki, Siha, and Hela express Bcl-2, and the protein plays a role in the regulation of apoptosis. In CaSki cells, estrogen upregulated Bcl-2, suggesting it is an antiapoptotic mechanism of estrogen.

On the other hand in SiHa and Hela cells, we did not find estrogen regulation of Bcl-2, suggesting that SiHa and Hela cells have lost the capacity for estrogen up-regulation of Bcl-2. One possible explanation is the loss of apoptosis regulation. An alternative explanation is of already submaximal Bcl-2 activity, with no additional effect by estrogen.

In both hECEs and CaSki cells, treatment with estrogen blocked $P2X_7$ receptor-induced activation of caspase-9. However, the regulation of upstream signaling proximal to the caspase-9 differed significantly between the two types of cells. In the normal hECEs, treatment with estrogen did not affect directly mitochondrial swelling in response to $Ca^{2+}$ or the expression of Bcl-2, suggesting that estrogen regulation of apoptosis involves steps proximal to the mitochondrion. Estrogen did block BzATP-induced calcium influx, suggesting that the latter is the main cellular mechanism of the antiapoptotic effect of estrogen in normal cervical cells.

In contrast to hECEs, in the cancer CaSki cells, estrogen had only a mild effect on BzATP-induced calcium influx, but it up-regulated expression of Bcl-2. The Bcl-2/Bcl-xL and Bax/Bak family proteins control directly mitochondrial apoptotic pathways, and up-regulation of Bcl-2/Bcl-xL activity or down-regulation of Bax/Bak activity blocks release of cytochrome C and the downstream mitochondrial-dependent activation of caspases. In this regard the up-regulation of Bcl-2 is most likely the mechanism that explains the attenuation of $Ca^{2+}$-induced mitochondrial swelling in CaSki mitochondrial preparations.

In the normal cervix, estrogen may function as an antiapoptotic agent and that the effect involves blocking $P2X_7$ receptor-induced calcium influx. Lack of estrogen, such as after menopause, can stimulate thinning of the cervical-vaginal epithelia for two main reasons: the loss of estrogen mitogenic effect and the loss of estrogenic antiapoptotic influence. The other facet of this hypothesis is that as antiapoptotic agents estrogens could promote the growth of cervical cancer. This could potentially be the mechanism by which chronic exogenously administered estrogens induce cervical and vaginal squamous carcinogenesis in HPV-16 transgenic mice.

III. In Vitro Transfection And Expression Of $P2X_7$ Or $P2X_{7-j}$

In some embodiments, the present invention contemplates therapeutic and/or preventative methods comprising transfecting a cell with a gene encoding a $P2X_7$ receptor whereby cellular apoptosis is increased. In one embodiment, the cellular apoptosis is increased in a cancer and/or a premalignant cell.

Detection of $P2X_{7-j}$ and/or $P2X_7$ mRNAs was performed in transfected cells using RT-PCR, wherein the transfected cells comprise wild-type HEK-293 and MDCK cells that normally lack endogenous expression of P2X receptors. HEK-293 cells were transfected with expression vectors encoding either $P2X_7$ or $P2X_{7-j}$ to establish cells expressing the $P2X_7$ and $P2X_{7-j}$ proteins. CaSki cells were also examined using standard cell transfection techniques. CaSki cells are a line of transformed cells that retain phenotypic characteristics of human endocervical epithelial cells, and are a useful model to study cervical cell functions. MDCK cells were transfected with expression vectors encoding either $P2X_7$ or $P2X_{7-j}$ under the control of a promoter inducible by doxycycline.

Figure 5:
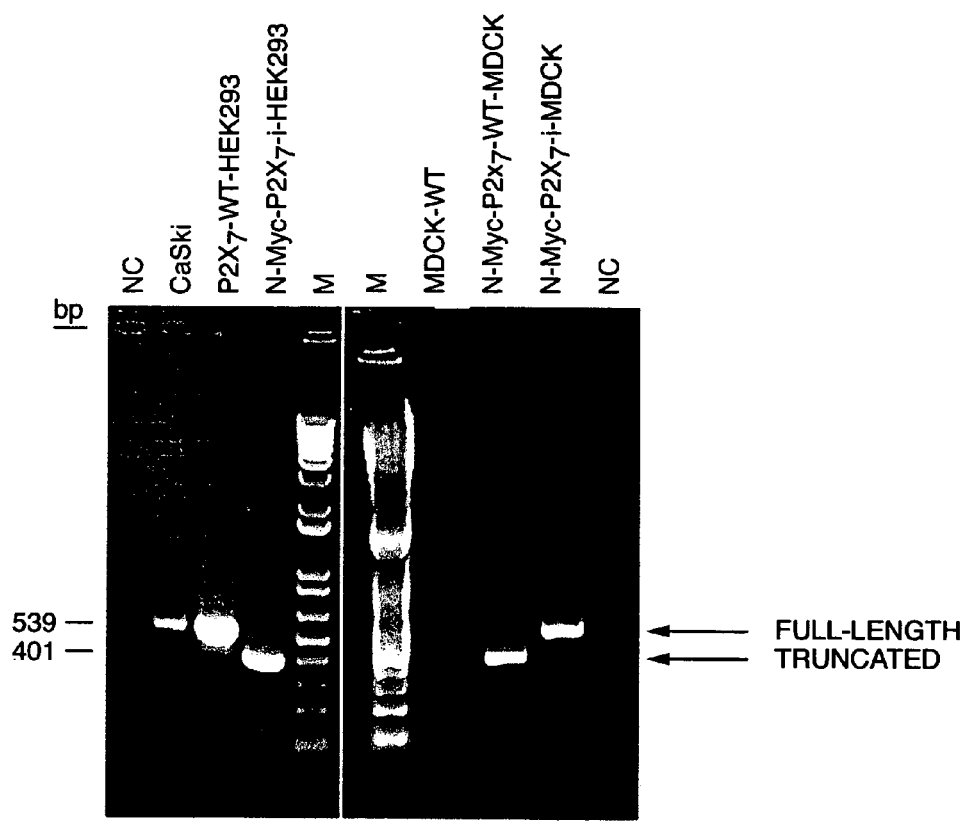
FIG. 5 illustrates example results of a study to detect P2X$_{7-j}$ and/or P2X$_7$ mRNAs in cells using RT-PCR.

The results show that the HEK-293 transfected with the $P2X_7$ expression vectors express $P2X_7$ mRNAs. The RT-PCR assay produces gel bands that can be distinguished based on size. HEK-293 cells transfected with the $P2X_{7-j}$ encoding vector produced a band of smaller size than other HEK-293 cells transfected with the $P2X_7$ encoding vector. Similarly, MDCK cells transfected with the $P2X_{7-j}$ encoding vector produced a band of smaller size than other MDCK cells transfected with the P2X$_7$ encoding vector. These data illustrate that mRNAs from genes encoding P2X$_7$ and P2X$_{7-j}$ were distinguishable using the RT-PCR assay. The results also show that CaSki cells expressed both P2X$_7$ and P2X$_{7-j}$. The RT-PCR results indicate that the levels of P2X$_{7-j}$ mRNA in CaSki cells may have been less than the levels of P2X$_7$ mRNA. FIG. 5.

Figure 6:
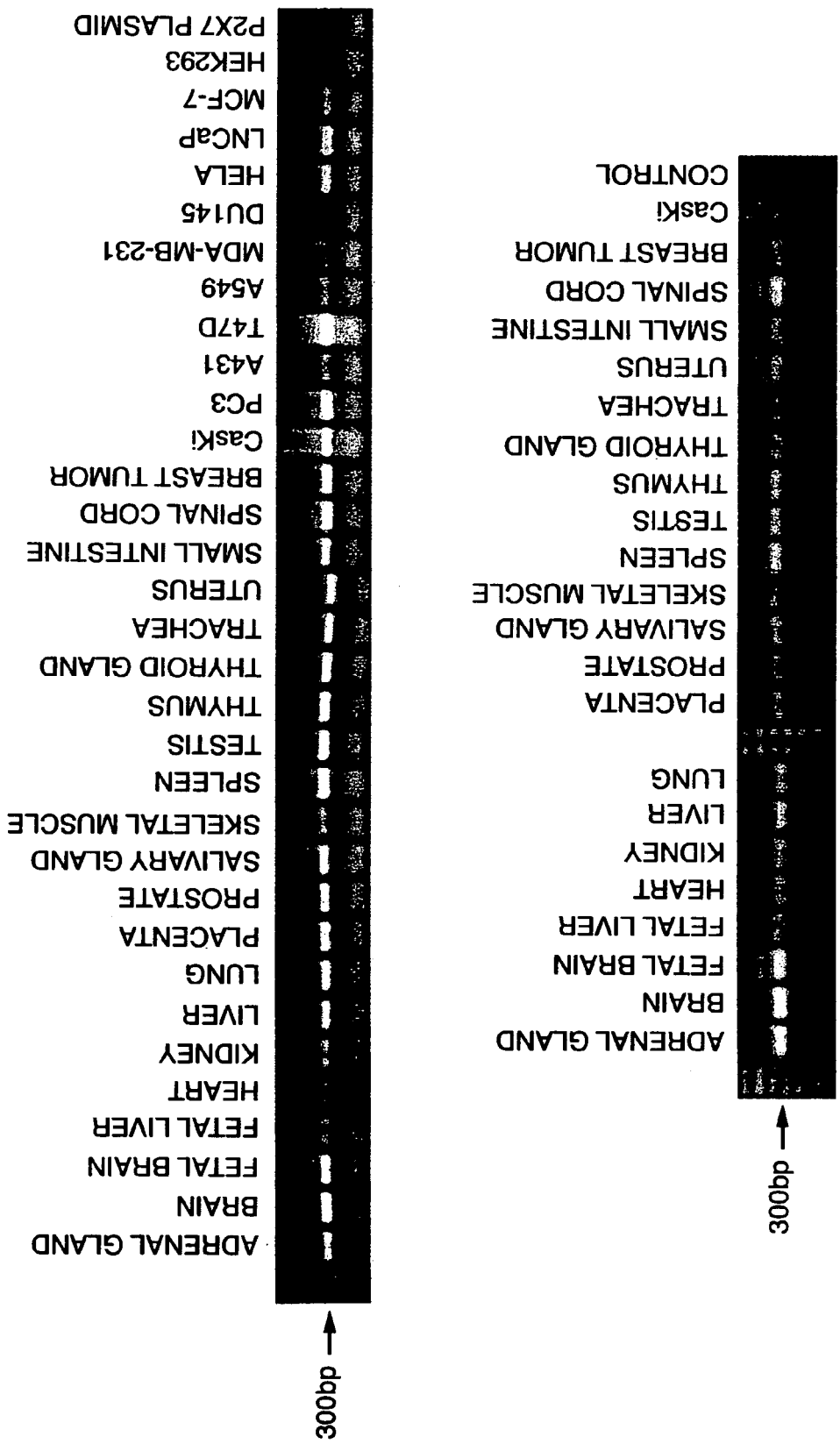
FIG. 6 illustrates example results of a study to detect P2X$_{7-j}$ mRNAs in a variety of human tissues and cancer cell lines using RT-PCR.

Detection of P2X$_{7-j}$ mRNAs in a variety of human tissues and cancer cell lines using RT-PCR was performed. FIG. 6. The results show that P2X$_{7-j}$ mRNA was expressed in a variety of normal human tissues as well as in various human cancer cell lines.

Immunoblotting experiments using antibodies against a myc tag to probe extracts from MDCK cells expressing either P2X$_7$-R$_{FL}$(Myc) or P2X$_7$-R$_{TR}$(Myc) under the transcriptional control of a promoter inducible by doxycycline was performed. FIG. 34. MDCK cells were transfected with doxycycline-inducible expression vectors encoding either P2X$_7$-R$_{FL}$(Myc) or P2X$_7$-R$_{TR}$(Myc). Independent clones of MDCK cells transfected with P2X$_7$-R$_{TR}$(Myc) (indicated as B cells in FIG. 34) and with P2X$_7$-R$_{FL}$(Myc) (indicated as F cells in FIG. 34) were obtained. The clones were grown and either induced (+ in FIG. 34) or not induced (− in FIG. 34) with doxycycline. Extracts were made and analyzed by immunoblotting using an antibody specific for the short amino acid sequence from the myc protein. The results showed that P2X$_7$-R$_{FL}$ protein was expressed in the F clones after induction with doxycycline. The results also show that P2X$_7$-R$_{TR}$ protein was expressed in the B clones, to varying degrees, after induction with doxycycline. Again, these data show that the P2X$_7$-R$_{FL}$ and P2X$_7$-R$_{TR}$ proteins can be expressed and detected in cells using different antibodies allowing the approximation of P2X receptor protein sizes (i.e., for example, approximately 40-45 kDal for the P2X$_7$-R$_{TR}$ protein; and approximately 65-75 kDal for the P2X$_7$-R$_{FL}$ protein).

Figure 7:
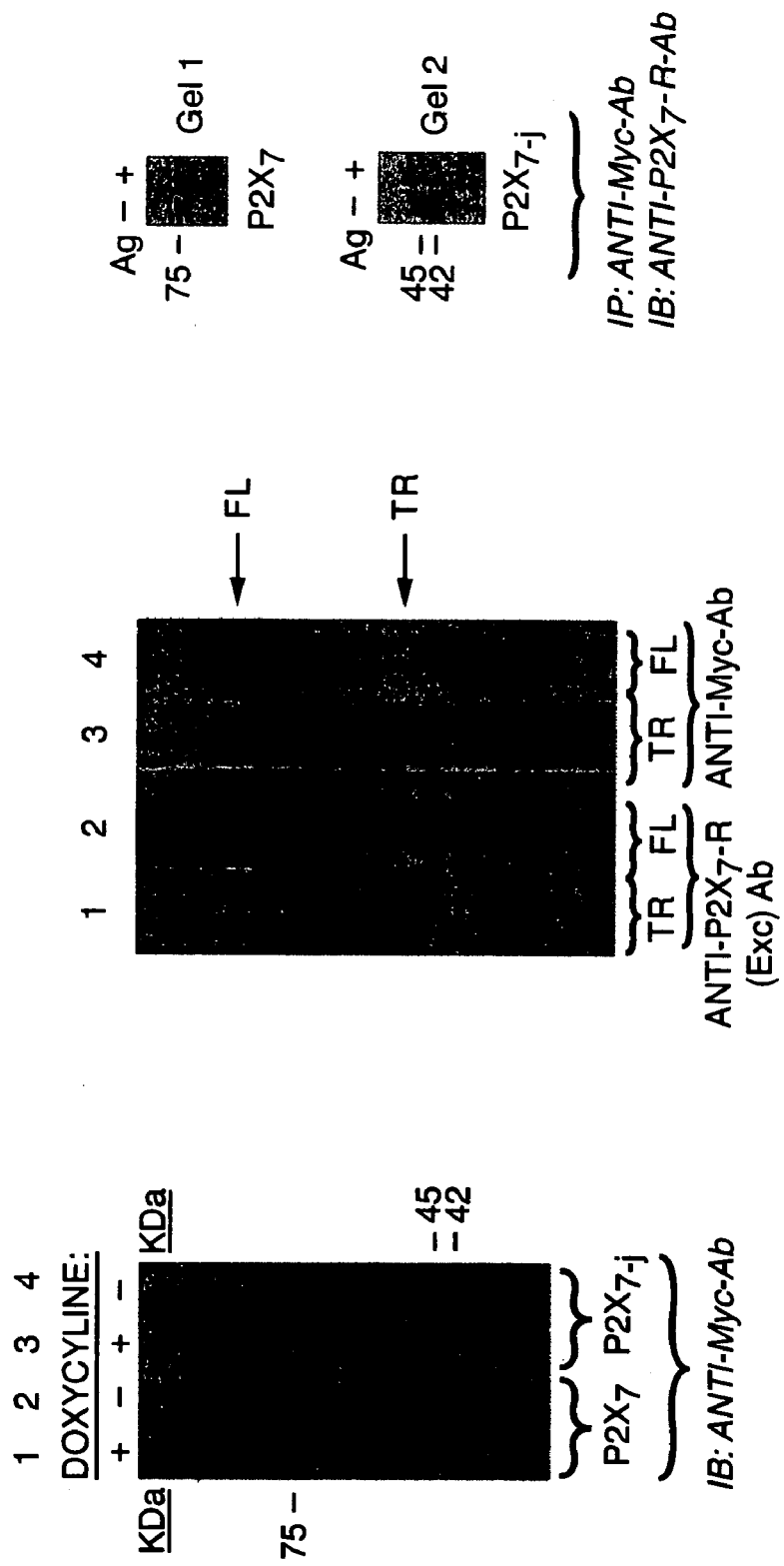
FIG. 7 illustrates example results of immunoprecipitation of cell extracts from Madin Darby canine kidney (MDCK) cells expressing P2X$_7$(Myc) or P2X$_{7-j}$ (Myc) under the control of a promoter inducible by doxycycline using antibodies against a myc tag and subsequent immunoblotting analysis of the immunoprecipitates using anti-P2X$_7$ or anti-myc antibodies.

Immunoprecipitation of cell extracts from Madin Darby canine kidney (MDCK) cells expressing either P2X$_{7-j}$(Myc) or P2X$_7$(Myc) using antibodies against a myc tag and subsequent immunoblotting analysis of the immunoprecipitates using anti-P2X$_7$ or anti-myc antibodies determined whether P2X$_7$ proteins could be expressed and detected in cells. FIG. 7. MDCK cells lack endogenous expression of P2X$_7$ and, consequently, the MDCK cells were transfected with expression vectors encoding either P2X$_7$ or P2X$_{7-j}$. The expression vectors were constructed such that the encoded P2X$_7$ proteins were fused or tagged at their N-terminus with a short amino acid sequence from the myc protein, to which there is a commercially available antibody. The expression vectors were also constructed such that the encoded P2X$_7$ proteins were under transcriptional control of a promoter regulated by doxycycline. The corresponding encoded mRNAs and proteins are, therefore, referred to as P2X$_7$(Myc) and P2X$_{7-j}$(Myc). The cells were grown and extracts were made. The extracts were then immunoprecipitated using an antibody specific for the myc amino acid sequence. The immunoprecipitated proteins were separated by SDS-polyacrylamide gel electrophoresis and were then blotted to a membrane. The membranes were then probed with one of two antibodies. One antibody was an anti-P2X$_7$ antibody (Alomone Labs, Jerusalem, Israel), reactive with the extracellular domain of the P2X$_7$ protein. A peptide comprising amino acids 136-152 of the mouse P2X$_7$ receptor (KKGWMDPSKGIQTGRC; (SEQ ID NO:7)) was used as the antigen to produce this antibody. This antibody reacts with both full-length and truncated P2X$_7$ proteins. The other antibody was the antibody specific for the myc amino acid sequence.

Immunoblotting experiments using antibodies against a myc tag to probe extracts from MDCK cells expressing either P2X$_7$(Myc) or P2X$_{7-j}$(Myc) under the transcriptional control of a promoter inducible by doxycycline were performed. MDCK cells were transfected with doxycycline-inducible expression vectors encoding either P2X$_7$(Myc) or P2X$_{7-j}$(Myc). Cells were grown and either induced (+ in FIG. 7) or not induced (− in FIG. 7) with doxycycline. Extracts were made and analyzed by immunoblotting using an antibody specific for the short amino acid sequence from the myc protein. The results in show, that in extracts of cells transfected with the expression vector encoding P2X$_7$(Myc) and treated with doxycycline, a band of about 75 kiloDaltons (kDal) was detected by probing the membrane with the anti-myc antibody. FIG. 7, Panel A, Lane 1. This lane was not detected if the cells were not previously treated with the doxycycline, because lack of treatment with doxycycline failed to induce translation of the protein from the transfected cDNA. FIG. 7, Panel A, Lane 2. This result therefore suggests that the 75 kDal band in FIG. 7, Panel A, Lane 1 is a de novo product of the P2X$_7$(Myc) cDNA with which the MDCK cells were transfected. The results in FIG. 7, Panel A, Lane 3 show that in extracts of cells transfected with the expression vector encoding P2X$_{7-j}$(Myc) and treated with doxycycline, at least two protein bands between about 42-45 kilo Daltons (kDal) were detected by probing the membrane with the anti-myc antibody. These bands were not detected in extracts of cells that were not previously treated with the doxycycline. (FIG. 7, Panel A, Lane 4). This suggests that the 42-45 kDal bands are de novo products of the P2X$_{7-j}$(Myc) cDNA with which the MDCK cells were transfected. FIG. 7, Panel A, Lane 3. The 75 kDal band was detected with the anti-myc antibody in extracts of MDCK cells transfected with the expression vector encoding P2X$_7$(Myc) and treated with doxycycline. FIG. 7, Panel B, Lane 4. This 75 kDal band was detected in the same cells extract by probing the membrane with the anti-P2X$_7$ antibody. FIG. 7, Panel B, Lane 2. The 42-45 kDal bands detected with the anti-myc antibody in extracts of MDCK cells transfected with the expression vector encoding P2X$_{7-j}$(Myc) (designated as Tr, Truncated) and treated with doxycycline. FIG. 7, Panel B, Lane 3. The 42-45 kDal bands were detected in the same cells extract by probing the membrane with the anti-P2X$_7$ antibody (FIG. 7, Panel B, Lane 1).

The other major bands in the lanes probed with the anti-myc or the anti-P2X$_7$ antibodies in FIGS. 7, Panels A-B are likely the heavy and/or light chains of the anti-myc antibody used for immunoprecipitation which was detected by the secondary antibody used to probe the membrane, or other non-specific reactions with the antibodies.

The expression of the 75 kDal band in extracts of MDCK cells transfected with the expression vector encoding P2X$_7$(Myc), and of the 42-45 kDal bands in extracts of MDCK cells transfected with the expression vector encoding P2X$_{7-j}$(Myc) were determined. FIG. 7, Panel C; Gel 1 & Gel 2, respectively. In both cases, the bands were detected in cells extract by probing the membranes with the anti-P2X$_7$ antibody. Both the 75 kDal band and the 42-45 kDal band detection was inhibited and/or abolished if the protein (antigen) that was used to generate the anti-P2X$_7$ antibody was added to the reaction mixture prior to exposing it to the anti-P2X$_7$ antibody (designated in FIG. 7, Panel C as +Ag [antigen]). These results indicate that the 75 kDal band (for the P2X$_7$ cells), and the 42-45 kDal bands (for the P2X$_{7-j}$ cells) represent bands specifically detected by the anti-P2X$_7$ antibody.

Collectively, the data in FIG. 7, Panels A-C show that MDCK cells can express the $P2X_7$ and $P2X_{7-j}$ proteins, that the proteins can be detected, and the approximate sizes of the proteins can be determined.

Figure 8:
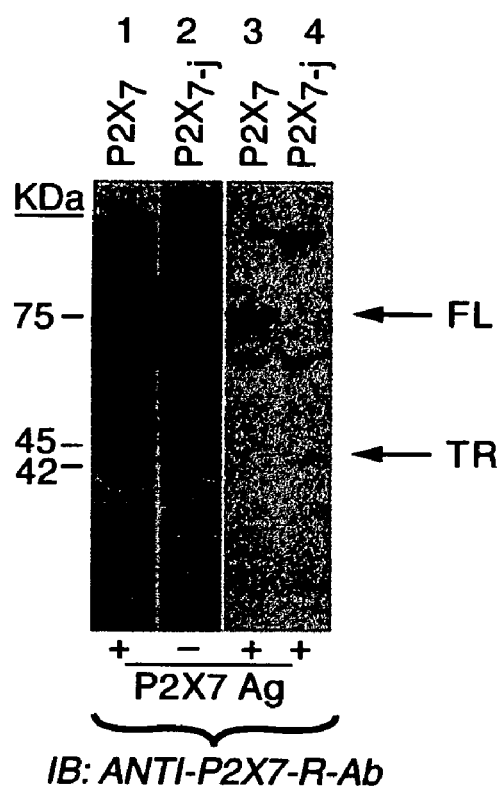
FIG. 8 illustrates example results of immunoblotting experiments using antibodies against a myc tag to probe extracts from HEK293 cells expressing either P2X$_7$, P2X$_{7-j}$, or P2X$_{7-j}$ (Myc) using antibodies against anti-P2X$_7$ or a myc tag.

Western immunoblots using extracts of HEK-293 transfected with an expression vector encoding $P2X_7$. Western immunoblot using extracts of HEK-293 transfected with an expression vector encoding $P2X_{7-j}$ was also determined. FIG. 8 Lane 2 The membranes in both cases were probed with the anti-$P2X_7$ antibody in the absence (FIG. 8, Lanes 1 and 2), or in the presence (FIG. 8, Lanes 3 and 4), of the $P2X_7$ antigen. The pointed arrow designated FL (full-length) points to a 75 kDal band that is expressed in HEK-293-$P2X_7$ cells and completely abolished by prior exposure to the $P2X_7$ antigen. The pointed arrow designated Tr (Truncated) points to a cluster of 42-45 kDal proteins that is expressed in HEK-293-$P2X_{7-j}$ cells and is nearly completely abolished by prior exposure to the $P2X_7$ antigen. These data confirm the findings in MDCK cells suggesting that the translated product of the $P2X_7$ cDNAs are a protein(s) of about 75 kDal, and the translated product of the $P2X_{7-j}$ cDNAs are proteins of about 42-45 kdal.

The data in FIGS. 7 and 8 show that the $P2X_7$ and $P2X_{7-j}$ proteins can be expressed by cells, can be detected in cells by different antibodies and indicate the approximate protein sizes (40-45 kDal for the $P2X_{7-j}$ protein; 65-75 kDal for the $P2X_7$ protein).

IV. Cation Channel Gating And Pore Regulation

In one embodiment, the present invention contemplates a method comprising a P2X receptor protein variant that has altered regulation of cation channel gating and pore regulation. In one embodiment, the P2X receptor protein comprises the $P2X_{7-j}$ receptor protein.

BzATP-stimulated channel activation was studied using either the $P2X_7$-$R_{FL}$ or $P2X_7$-$R_{TR}$ receptor protein. FIG. 37. As discussed earlier, activation of $P2X_7$ receptors provides influx of selected cations through the ATP-activated channel provided by the $P2X_7$ protein. HEK-293 cells expressing either $P2X_7$-$R_{FL}$ or $P2X_7$-$R_{TR}$ were loaded with the calcium-sensitive dye Fluo-4 and treated with BzATP. Calcium entry into the cells via the $P2X_7$ channel after BzATP activation was measured in terms of changes in Fluo-4 fluorescence. The results show that $P2X_7$-$R_{FL}$ was able to form a channel in response to BzATP treatment while $P2X_7$-$R_{TR}$ was not able to form a channel in response to BzATP treatment. Therefore, in addition to its defective ability to mediate apoptosis, these data indicate that $P2X_7$-$R_{TR}$ is also defective in its ability to form an ATP-gated channel.

BzATP-stimulated pore activation was studied using either $P2X_7$-$R_{FL}$ and $P2X_7$-$R_{TR}$ receptor protein. FIG. 38. As discussed earlier, activation of $P2X_7$ receptors also induces influx of larger ions through the ATP-activated pore provided or mediated by the $P2X_7$ protein. HEK-293 cells expressing either $P2X_7$-$R_{FL}$ or $P2X_7$-$R_{TR}$ were treated with BzATP in the presence of ethidium bromide. Fluorescence of ethidium was measured after BzATP activation as a measure of ethidium bromide entry into the cells via the $P2X_7$-mediated pore. The results show that $P2X_7$-$R_{FL}$ was able to form a pore in response to BzATP treatment while $P2X_7$-$R_{TR}$ was not able to form a pore in response to BzATP treatment. In addition to $P2X_7$-$R_{TR}$'s defective ability to mediate apoptosis, and defective ability to form an ATP-gated channel, these results indicate that $P2X_7$-$R_{TR}$ is defective in its ability to mediate formation of an ATP-induced pore.

Figure 11:
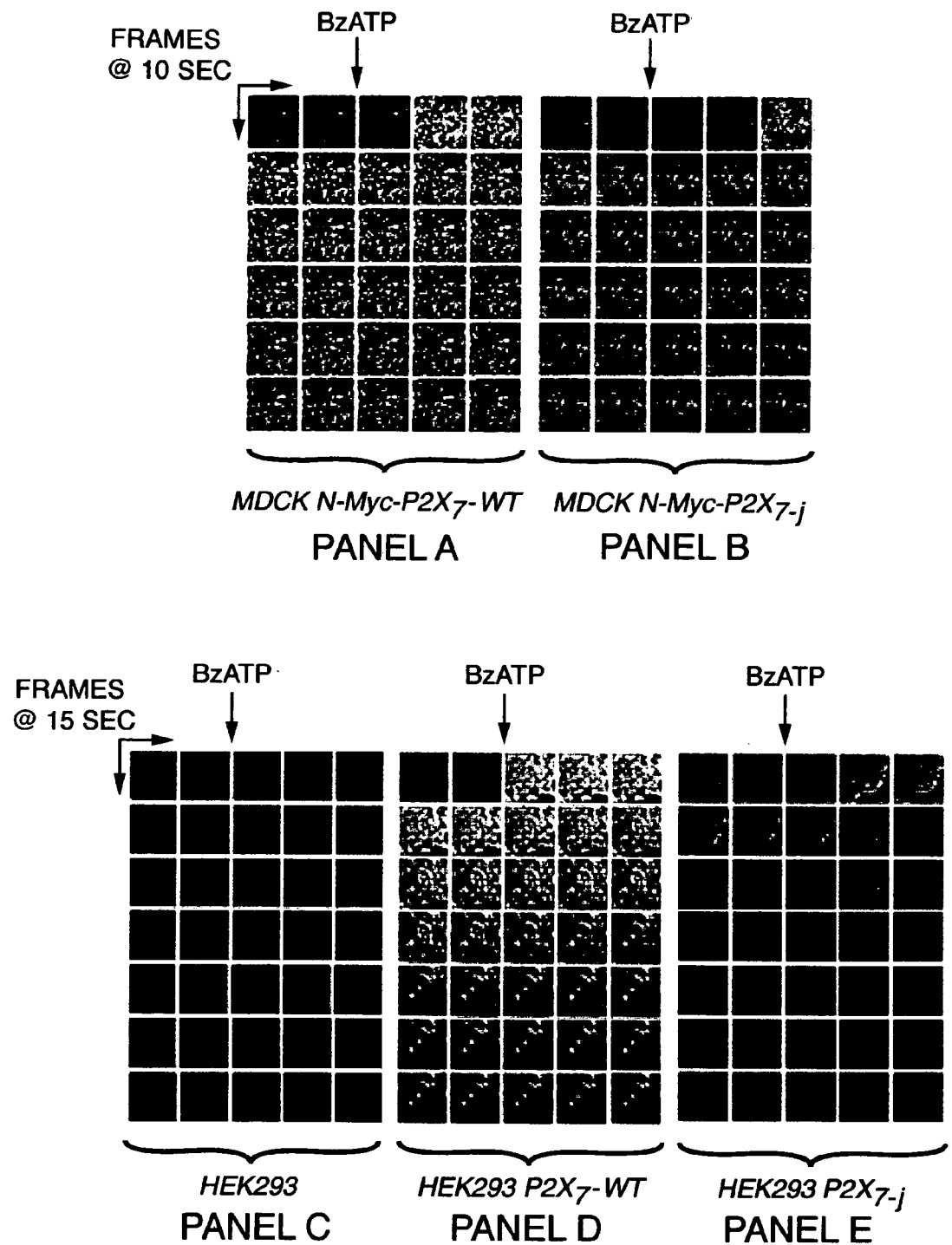
FIG. 11 illustrates example results of the effects of transfections with P2X$_7$ and P2X$_{7-j}$ cDNAs in MDCK cells (Panels A, B) and in HEK293 cells (Panels C-E) on the receptor properties of the P2X$_7$ and P2X$_{7-j}$ proteins using fluorescence microscopy. Receptor properties of the P2X$_7$ and P2X$_{7-j}$ receptors were determined in terms of acute changes in intracellular (cytosolic) calcium in response to treatment with 2'-3'-O-(4-benzoyl)adenosine 5'-triphosphate (BzATP). The direction of the pictures in each Panel is left to right, and then up-down. Panel A is of MDCK-P2X$_7$ cells; Panel B of MDCK-P2X$_{7-j}$ cells; Panel C of wild type HEK-293 cells; Panel D of HEK-293-P2X$_7$ cells; Panel E of HEK-293-P2X$_{7-j}$ cells.

2'-3'-O-(4-benzoyl-benzoyl)adenosine 5'-triphosphate (BzATP) stimulated channel activation of $P2X_7$ and $P2X_{7-j}$ was determined. FIG. 11. As discussed earlier, activation of $P2X_7$ receptors provides influx of selected cations through the ATP-activated channel provided by the $P2X_7$ protein. MDCK or HEK-293 cells expressing either $P2X_7$ or $P2X_{7-j}$ were loaded with the calcium-sensitive dye Fluo-4 and treated with 100 micromolar of BzATP. Calcium entry into the cells via the $P2X_7$ channel after BzATP activation was measured in terms of changes in Fluo-4 fluorescence. The results show that in MDCK-$P2X_7$ cells (FIG. 11, Panel A) and in HEK-293-$P2X_7$ cells (FIG. 11, Panel D) treatment with BzATP increased acutely the Fluo-4 signal, indicating influx of calcium and increased levels of cytosolic calcium following opening of the $P2X_7$ channels. A significantly smaller response, or no response was seen in the other types of cells.

Figure 12:
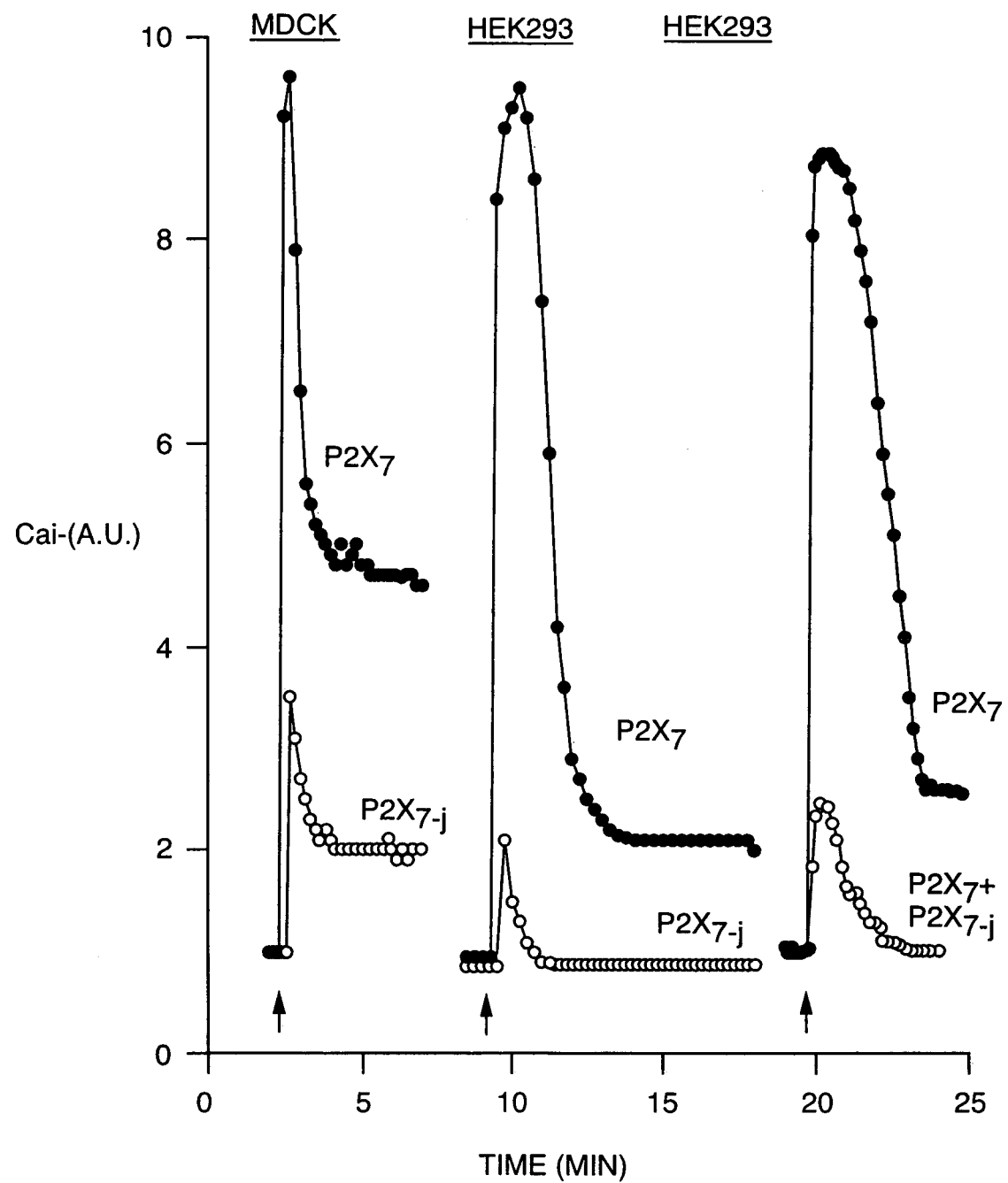
FIG. 12 illustrates example results of the receptor properties of the P2X$_7$ and P2X$_{7-j}$ by summarizing quantitatively the changes in cytosolic calcium from experiments such as in FIG. 11. The left Panel are MDCK cells transfected with the P2X$_7$ or P2X$_{7-j}$ cDNAs. The middle Panel are HEK293 cells transfected with the P2X$_7$ or P2X$_{7-j}$ cDNAs. The right Panel are HEK293 cells transfected with the P2X$_7$ plus the P2X$_{7-j}$ cDNAs.

A quantification of the changes in cytosolic calcium after BzATP exposure provided data that was similar to that presented in FIG. 11. FIG. 12. The calcium responses to BzATP were significantly smaller in MDCK-$P2X_{7-j}$ cells compared to MDCK-$P2X_7$ cells (FIG. 12, left Panel), and in HEK-293-$P2X_{7-j}$ cells compared to HEK-293-$P2X_7$ cells (FIG. 12, middle Panel), and significantly smaller in $P2X_7$ plus $P2X_{7-j}$ HEK-293 cells compared to $P2X_7$ HEK-293 cells (FIG. 12, right Panel).

Although it is not necessary to understand the mechanism of an invention, it is believed that the results suggest a diminished receptor capacity of the $P2X_{7-j}$ compared to the $P2X_7$ and that a co-expression of the $P2X_{7-j}$ blocks the receptor activity of the $P2X_7$ protein.

Figure 13:
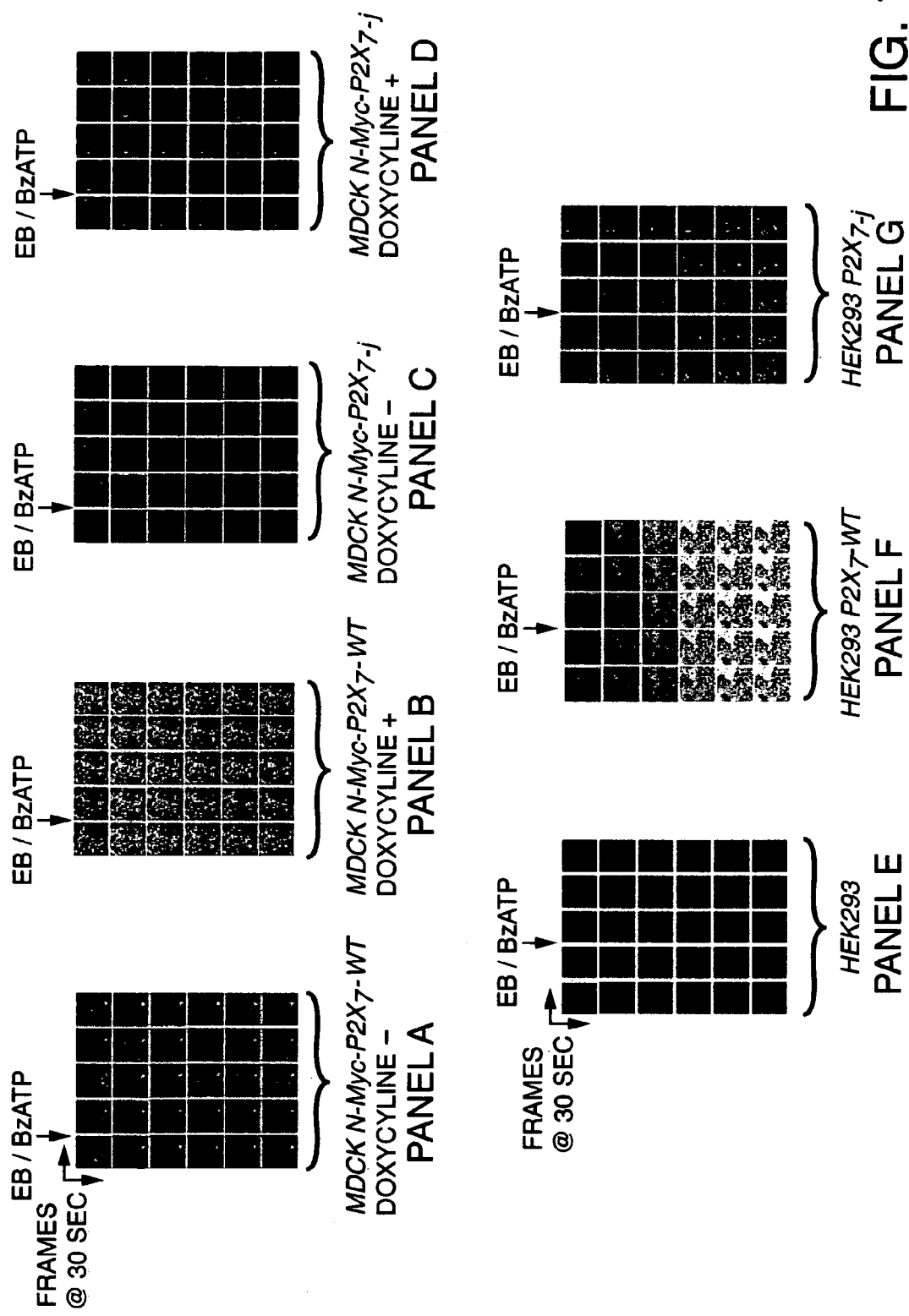
FIG. 13 illustrates example results of the effects of transfections with P2X$_7$ and P2X$_{7-j}$ cDNAs on the property of P2X$_7$ or P2X$_{7-j}$ receptors pore formation in MDCK cells (Panels A-D) and in HEK293 cells (Panels E-G) using fluorescence microscopy. Pore formation of the P2X$_7$ and P2X$_{7-j}$ receptors was determined in terms of acute entry into the cells of the dye ethidium bromide in response to treatment with BzATP. Panel A is of MDCK-P2X$_7$ cells not treated with doxycycline; Panel B of MDCK-P2X$_7$ cells treated with doxycycline; Panel C of MDCK-P2X$_{7-j}$ cells not treated with doxycycline; Panel D of MDCK-P2X$_{7-j}$ cells treated with doxycycline; Panel E of wild type HEK-293 cells; Panel F of HEK-293-P2X$_7$ cells; Panel G of HEK-293-P2X$_{7-j}$ cells.

BzATP-stimulated pore activation of $P2X_7$ and $P2X_{7-j}$ receptor proteins was also determined. FIG. 13. MDCK cells or HEK-293 cells expressing either $P2X_7$ or $P2X_{7-j}$ were treated with BzATP in the presence of ethidium bromide. Fluorescence of ethidium bromide was measured after BzATP activation (100 micromolar) as a measure of ethidium bromide entry into the cells via the $P2X_7$-mediated pore. Results in seven Panels (A-G) each composed of 30 exposures of cells placed on a glass slide. The direction of the pictures in each Panel is left to right, and then up-down. The results show that in doxycycline-treated MDCK-$P2X_7$ cells and in HEK-293-$P2X_7$ cells treatment with BzATP increased ethidium bromide signaling, indicating influx of ethidium bromide through opened $P2X_7$ pores. FIG. 13, Panel B and Panel F, respectively. A significantly smaller response, or no response was seen in the other types of cells.

Figure 14:
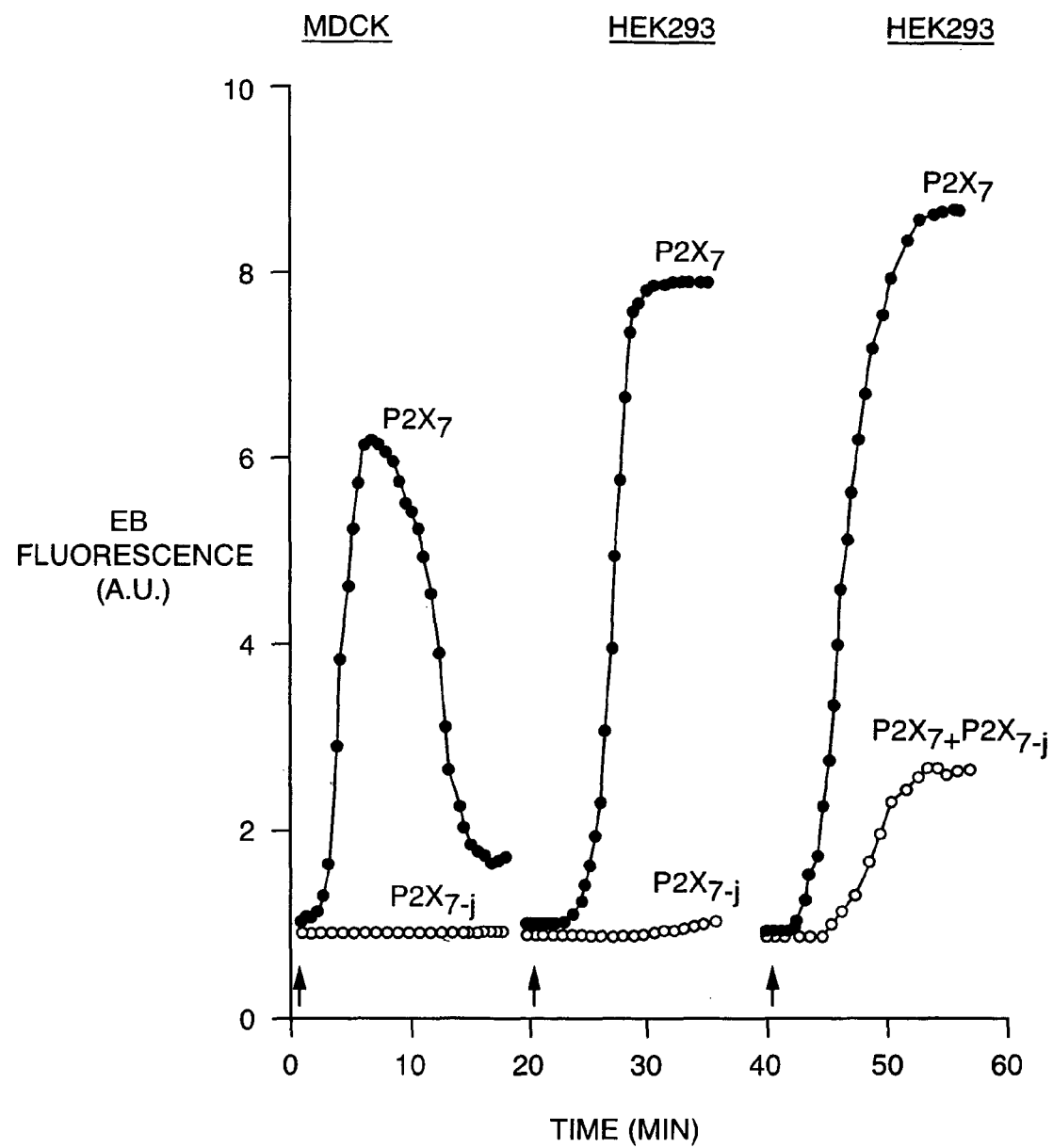
FIG. 14 illustrates example results of pore formation properties of the P2X$_7$ or P2X$_{7-j}$ receptors by summarizing quantitatively the data from FIG. 13 of the acute entry into cells of the dye ethidium bromide. The left Panel are MDCK cells transfected with the P2X$_7$ or P2X$_{7-j}$ cDNAs. The middle Panel are HEK293 cells transfected with the P2X$_7$ or P2X$_{7-j}$ cDNAs. The right Panel are HEK293 cells transfected with the P2X$_7$ plus the P2X$_{7-j}$ cDNAs.

A quantification of the changes in ethidium bromide signaling from experiments similar to those in FIG. 13 was then calculated. FIG. 14. The ethidium bromide signaling responses to BzATP were significantly smaller in doxycycline-treated MDCK-$P2X_{7-j}$ cells compared to doxycycline-treated MDCK-$P2X_7$ cells (FIG. 14, left Panel), and in HEK-293-$P2X_{7-j}$ cells compared to HEK-293-$P2X_7$ cells (FIG. 14, middle Panel). In HEK-293 cells transfected with both the $P2X_7$ plus $P2X_{7-j}$ cDNA and expressing the $P2X_7$ plus $P2X_{7-j}$ proteins the ethidium bromide responses to BzATP were significantly smaller in $P2X_7$ plus $P2X_{7-j}$ HEK-293 cells compared to $P2X_7$ HEK-293 cells (FIG. 14, right Panel).

Although it is not necessary to understand the mechanism of an invention, it is believed that the results in FIGS. 13 and 14 show that $P2X_7$ was able to form pores in response to BzATP treatment while $P2X_{7-j}$ was not able to form pores in response to BzATP and that co-expression of the $P2X_{7-j}$ blocks the capacity of the $P2X_7$ protein to form pores.

Overall, the above results suggest that in addition to its defective capacity as receptor, the $P2X_{7-j}$ is defective in its ability to mediate formation of ATP-induced pores, and when co-expressed with the $P2X_7$, it blocks $P2X_7$ protein receptor and pore formation capacities. (FIGS. 11-14).

V. Oligomerization

Although it is not necessary to understand the mechanism of an invention, it is believed that $P2X_7$ receptor monomers may combine (i.e., for example, oligomerize) to form multiple units that then mediate the specific biological actions of the receptor. Previous studies suggest that the $P2X_7$ receptor may function as a three unit complex (i.e., for example, a homotrimer).

MDCK cells were transfected with cDNA of the $P2X_7$ receptor protein to which a Myc tag was attached in the N-terminus (N-Myc-$P2X_7$-WT), and further co-transfected with cDNA of the $P2X_7$ receptor protein to which a HA tag was attached in the N-terminus (N-HA-$P2X_7$-WT). Following treatment with doxycycline (to induce translation of the N-Myc-$P2X_7$-WT and N-HA-$P2X_7$-WT proteins), cells were homogenized, and immunoprecipitated with an antibody against the Myc and then immunoblotted with an antibody directed against the HA. FIG. 18, Panel A, Right Lane shows positive immunoreactivity at 75 KDa, indicating that two types of molecules have interacted, those tagged with Myc and those tagged with HA. In other words, the $P2X_7$ WT molecules form homooligomers. FIG. 18, Panel A, Left Lane shows a control experiment. A similar experiment was performed with HEK293 cells transfected with N-Myc-$P2X_{7-j}$ cDNA and further co-transfected with N-HA-$P2X_{7-j}$ cDNA, suggesting that the truncated $P2X_{7-j}$ can also undergo homooligomerization. FIG. 18 Panel B. HEK293 cells transfected with N-Myc-$P2X_{7-j}$ cDNA and further co-transfected with N-HA-$P2X_7$ cDNA suggests that the wild-type $P2X_7$-receptor and the truncated $P2X_{7-j}$ can undergo heterooligomerization. FIG. 18, Panel C.

A modified protocol provides additional evidence that $P2X_7/P2X_7$ protein molecules form homooligomers; $P2X_{7-j}/P2X_{7-j}$ protein molecules form homooligomers; and $P2X_7/P2X_7$ protein molecules form heterooligomers. FIG. 18, Panel D. The electrophoretic separation of the protein molecules was done on a 6-8% gels (in contrast to the more traditional 10-12% gels) as was shown in FIGS. 7, 8, and 10. Separation of proteins in 6-8% gels allows better detection and separation of high molecular weights proteins Immunoblot of extracts from HEK-293-$P2X_7$ cells probed with the anti-$P2X_7$ receptor antibody confirms that the Full-Length 75 kDal $P2X_7$ protein is, in fact, a complex of a native non-glycosylated 65 kDa protein and a heavier glycosylated 85 kDal protein. Although it is not necessary to understand the mechanism of an invention, it is believed that glycosylation is a process by which cells attach carbohydrate groups to proteins in order to facilitate their transport to the plasma membrane. The 65/85 kDal forms were also detected in HEK293 cells expressing the $P2X_{7-j}$ plus the $P2X_7$ proteins.

In HEK293 cells expressing the $P2X_7$ alone, the 85-65 kDal form, a major 220 kDal specific $P2X_7$, as well as a minor 115 kDal form immunoreactivity could be detected. FIG. 18, Panel D, Middle Lane. Although not wishing to be bound by theory, the 220 kDal form could be a complex of three $P2X_7$ molecules, namely a $P2X_7$ homotrimer ($[P2X_7]_3$). The 115 kDal form could be either a partially degraded form or a denatured $P2X_7$ homodimer. In HEK293 cells expressing the $P2X_{7-j}$ alone, a 42-45 kDal monomeric form and a 135 kDal form were detected. The 135 kDal form is compatible with a complex of three $P2X_{7-j}$ molecules, namely a $P2X_{7-j}$ homotrimer ($[P2X_{7-j}]_3$). Another 90 kDal form in those cells could be possibly a denatured homodimer. FIG. 18 Panel D, right lane. In HEK293 cells co-expressing the $P2X_7$ plus the $P2X_{7-j}$, a 85-65 kDal form (i.e., $P2X_7$ monomers), a 42-45 kDal form (i.e., $P2X_{7-j}$ monomers), and four other specific forms were observed, which could be abolished by prior incubation with the $P2X_7$ antigen. Additionally, a major 135 kDal form, which could possibly be a $[P2X_{7-j}]_3$ homotrimer; an intermediate form of 160 kDal, possibly a $[P2X_{7-j}]_2/[P2X_7]$ heterotrimer; a 220 kDal, possibly a $[P2X_7]_3$ homotrimer; and a minor form of 200 kDal, possibly a $[P2X_7]_2/[P2X_{7-j}]$ heterotrimer were also observed. FIG. 18, Panel D, Left two lanes.

Semi-quantitative analysis by densitometry of the 135, 160, 220, and 200 kDal bands revealed a ratio of 70:15:10:5, respectively. Although not wishing to be bound by theory, this suggests relative expression such as $[P2X_{7-j}]_3 \gg\!\!\gg\!\!> [P2X_{7-j}]_2/[P2X_7] > [P2X_7]_3 > [P2X_7]_2/[P2X_{7-j}]$. Since the $P2X_{7-j}$ protein alone is inactive, as was shown above, these data predict that co-expression of the $P2X_7$ plus the $P2X_{7-j}$ would favor formation of complexes that are composed predominantly of the non-functional $P2X_{7-j}$ protein. Although not wishing to be bound by theory, this could be the molecular mechanism by which co-expression of the $P2X_{7-j}$ blocks $P2X_7$ actions, as was shown above.

These data lend support to the hypothesis that $P2X_7$ receptor function depends on the relative expression of the $P2X_7$ and the $P2X_{7-j}$. Low levels of the $P2X_{7-j}$ or high levels of the $P2X_7$ protein will favor formation of functional, $P2X_7$-dominated oligo-trimers. In contrast, high levels of the $P2X_{7-j}$ or low levels of the $P2X_7$ protein will favor formation of non-functional, $P2X_{7-j}$ dominated oligotrimers.

VI. Antibodies

In one embodiment, the present invention contemplates reagents that bind specifically to $P2X_7$ proteins. In one embodiment, the reagent that binds to $P2X_7$ proteins binds specifically to $P2X_{7-j}$. In one embodiment, the reagent is an antibody. In one embodiment, the antibody binds to at least part of the amino acid sequence, IRQVLQGKQC (SEQ ID NO:1)(see FIG. 2 and FIG. 21) or an amino acid sequence containing or connected to IRQVLQGKQC (SEQ ID NO:1). Although it is not necessary to understand the mechanism of an invention, it is believed that this is the amino acid sequence that is present in $P2X_{7-j}$ but is not present in $P2X_7$. These reagents may be used for diagnostic and/or prognostic methods.

Antibodies that bind to all or part of the amino acid sequence may be made in a variety of ways. In one embodiment, polyclonal antibodies are made by using all or part of the IRQVLQGKQC (SEQ ID NO:1) amino acid sequence as an antigen that is injected into an animal (i.e., for example, immunization). Serum obtained from the animal at some later time may contain antibodies specifically reactive with $P2X_{7-j}$. In one embodiment, monoclonal antibodies are made using all or part of the same amino acid sequence. Other methods may be used to produce antibodies.

The present invention contemplates monoclonal, polyclonal, and humanized antibodies to P2X receptor proteins. In some embodiments, the antibodies are specific for a $P2X_{7-j}$ receptor protein, wherein said protein has a C-terminal region comprising SEQ ID NO:1.

Monoclonal antibodies useful in this invention may be obtained, for example, by well known hybridoma methods. U.S. Pat No. 6,866,845 to Ward et al. (herein incorporated by reference). In one embodiment, an animal is immunized with a preparation containing a C-terminal truncated $P2X_7$ receptor protein. A fused cell hybrid is then formed between antibody-producing cells from the immunized animal and an immortalizing cell such as a myeloma. In one embodiment, antibodies of the present invention are produced by murine hybridomas formed by fusion of mouse myeloma, or a hybridoma which does not secrete antibody, with murine spleen cells which secrete antibodies obtained from mice immunized against C-terminal truncated P2X$_7$ receptor protein.

In some embodiments, mice are immunized with a primary injection of C-terminal truncated P2X$_7$ receptor protein, followed by a number of boosting injections. During or after the immunization procedure, sera of the mice may be screened to identify mice in which a substantial immune response to the C-terminal truncated P2X$_7$ receptor protein has been evoked. From the selected mice, spleen cells are obtained and fusions are performed. Suitable fusion techniques include, but are not limited to, the Sendai virus technique or the polyethylene glycol method. Kohler et al., *Nature* 256:495 (1975); and Kennet, R. H., In: Monoclonal Antibodies, Hybridoma—A New Dimension in Biological Analysis Plenum Press, NY (1980).

The hybridomas are then screened for production of anti-P2X$_7$ receptor protein antibodies. Suitable screening techniques include, but are not limited to, solid phase radioimmunoassay. A solid phase immunoadsorbent is prepared by coupling P2X$_7$ receptor proteins to an insoluble matrix. The immunoadsorbent is brought into contact with culture supernatants of hybridomas. After a period of incubation, the solid phase is separated from the supernatants, then contacted with a labeled antibody against murine immunoglobulin. Label that is associated with the immunoadsorbent indicates the presence of hybridoma products reactive with P2X$_7$ receptor proteins.

In preferred embodiments the monoclonal anti-P2X$_7$ receptor protein antibodies are produced in large quantities by injecting anti-P2X$_7$ receptor protein antibody producing hybridoma cells into the peritoneal cavity of mice and, after an appropriate time, harvesting acites fluid from the mice which yield a high titer of homogenous antibody. The monoclonal antibodies are isolated therefrom. Alternatively, the antibodies are produced by culturing anti-P2X$_7$ receptor protein antibody producing cells in vitro and isolating secreted monoclonal anti-P2X$_7$ receptor protein antibodies from the cell culture medium directly.

Another method of forming antibody-producing cells is by viral or oncogenic transformation. For example, a B-lymphocyte which produces anti-P2X$_7$ receptor protein specific antibody is infected and transformed with a virus, such as the Epstein-Barr virus, to give an immortal antibody-producing cell. Kozbon et al., *Immunol. Today* 4:72-79 (1983).

The present invention also contemplates anti-P2X$_7$ receptor protein polyclonal antibodies. Polyclonal antibodies can be prepared by immunizing an animal with a crude preparation of C-terminal truncated P2X$_7$ receptor proteins, or purified C-terminal truncated P2X$_7$ receptor proteins (i.e., for example, isolated). The animal is maintained under conditions whereby antibodies reactive with the components of the peptides are produced. Elzaim, et al., *Infect. Immun.* 66:2170-2179 (1998). Typically the animal is "boosted" by additional immunizations to increase the antibody titer. In one method, blood is collected from the animal upon reaching a desired titer of antibodies. The serum containing the polyclonal antibodies (antisera) is separated from the other blood components. The polyclonal antibody-containing serum may be further separated into fractions of particular types of antibodies (e.g. IgG or IgM) or monospecific antibodies can be affinity purified from polyclonal antibody containing serum. In another method, the immunized animal is a bird. In this method antibodies (IgY) are collected from egg yolks. The egg yolk is separated from the yolk lipid and non-antibody proteinaceous matter, recovering the IgY anti-C5a antibodies in purified form. U.S. Pat. No. 4,357,272 to Polson and U.S. Pat. No. 5,904,922 to Carroll (both herein incorporated by reference).

The present invention also contemplates humanized antibodies (i.e. substantially non-immunogenic antibodies). Such antibodies are particularly useful in treating human subjects. Chimeric and 'reshaped' humanized anti-P2X$_7$ receptor protein antibodies may be produced according to techniques known in the art. U.S. Pat. No. 5,585,089 to Queen et al. (herein incorporated by reference); and Kettleborough et al., *Protein Engineering*, 4:773-783 (1991). In one embodiment, humanized anti-P2X$_7$ receptor protein chimeric antibodies are produced using a combinatorial approach. U.S. Pat. No. 5,565,332 to Hoogenboom et al.; and U.S. Pat. No. 5,658,727 to Barbas et al. (both herein incorporated by reference). The present invention also contemplates single polypeptide chain binding molecules which have binding specificity and affinity substantially similar to the binding specificity and affinity of the light and heavy chain aggregate variable region of an anti-P2X$_7$ receptor protein antibody. U.S. Pat. No. 5,260,203 to Ladner et al. (herein incorporated by reference).

VII. Pharmaceutical Administration

The present invention contemplates pharmaceutical formulations and/or compositions including racemic or optically pure compounds that may be comprised in, but not limited to, powders, capsules, oral or intrapulmonary liquids, tablets, coated tablets, caplets, troches, dispersions, sustained release formulations suspensions, solution, patches and liquids. Young, U.S. Pat. No. 6,369,113 (hereby incorporated by reference). Alternatively, the formulations contemplated in the present invention may be administered intra-nasally. Houdi et al., U.S. Pat. No. 6,150,420 (hereby incorporated by reference).

The above formulations and/or compositions may benefit from increasing the solubility of the drug and/or protein during delivery to improve absorption. Hydrophilic drugs are usually easily soluble in the natural aqueous environment of a mammal. Hydrophobic drugs, however, are often difficult to dissolve in a manner that provides a steady and predictable delivery to the target organ. Common solubilizers for hydrophobic drugs include, but are not limited to, compounds that contain alcohols, glycols, or esters. Usually, the problem of solving the solubility of hydrophobic drugs involves mixtures containing triglyceride suspensions or colloids. These preparations are acceptable for topical administration but have obvious practical deficiencies when considering the oral or intrapulmonary or intravenous routes. In one embodiment, the present invention contemplates a formulation comprising hydrophobic and hydrophilic surfactants that coat a standard drug delivery device. In one non-limiting example, a drug formulation having the hydrophobic/hydrophilic coating is known to dissolve prior to the dispersal of the drug and provides an immediate environment that is highly favorable to solubilizing the drug to facilitate its absorption. Patel et al., U.S. Pat. No. 6,294,192 (hereby incorporated by reference).

The present invention contemplates embodiments having controlled delivery formulations. One example of a controlled delivery formulations is a semi-permeable homopolymer and copolymer film that is water-insoluble, yet water-permeable, and retains an active ingredient within an internal matrix. Preferably, the formulation contains a "water-permeability-modifying agent" within the polymers that changes the rate of osmosis through the polymer. This characteristic thereby controls the exit of the releasable active ingredient retained within the polymer film with the aid of an osmotic enhancing agent. Specifically, an osmotic enhancing agent is a water-soluble material having a high molar water solubility which is capable of achieving, in solution, an osmotic pressure greater than that of the surrounding aqueous environment. These films may be incorporated into standard pharmaceutical preparations such as, but not limited to, tablets, subdermal implants, suppositories, and capsules. Baker et al., U.S. Pat. No. RE33,994 (hereby incorporated by reference).

VIII. Kits

In another embodiment, the present invention contemplates kits for the practice of the methods of this invention. The kits preferably include one or more containers containing an antibody of this invention. The kit can optionally include a non-cancerous cell culture to be utilized as a control. The kit can optionally include a second antibody having reactivity to an antibody of this invention. The kit can optionally include a pharmaceutically acceptable excipient and/or a delivery vehicle (e.g., a liposome). The antibodies may be provided suspended in the excipient and/or delivery vehicle or may be provided as a separate component which can be later combined with the excipient and/or delivery vehicle. The kit may optionally contain additional therapeutics to be co-administered with the antibodies.

The kits may also optionally include appropriate systems (e.g. opaque containers) or stabilizers (e.g. antioxidants) to prevent degradation of the antibodies by light or other adverse conditions.

The kits may optionally include instructional materials containing directions (i.e., protocols) providing for the use of antibodies in the diagnosis, detection, and/or treatment of cancer within a mammal. In particular the disease can include any one or more of the disorders described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

The following examples are merely illustrative in nature and are not intended as limiting embodiments of the present invention.

Example 1

Expression of P2X$_7$ and P2X$_{7-j}$ by Normal and Cancer Human Cervical Cells

Human cervical cancer cell lines HT3, SiHa, HeLa and CaSki, as well as five normal human cervical tissues (patients #106, 120, 130, 136 and 153) were used in this example experiments. To perform the experiments, the cell lines were grown in culture. Extracts were prepared from the cell lines and from the tissues. Equivalent amounts of total proteins from the cell extracts and tissues were loaded onto and separated by SDS-polyacrylamide gel electrophoresis and then transferred to a membrane support. The membrane was probed using a polyclonal antibody specific for P2X$_7$. The antibody was obtained from Aiomone Labs (Jerusalem, Israel) and was reactive with the extracellular domain of P2X$_7$ proteins and is therefore specific for detection of the P2X$_7$ and P2X$_{7-j}$ proteins. Amino acids 136-152 of the mouse P2X$_7$ receptor (KKGWMDPSKGIQTGRC; (SEQ ID NO:7) were used as the antigen to prepare the antibody. A labeled secondary antibody was used to visualize reactive protein bands.

The results (FIG. 19) show that all of the tested cells and tissues, both cancer and normal, expressed P2X$_7$ protein. The level of expression of the P2X$_7$ protein was greater in the normal tissues than in the cancer cell lines (see pointed arrow in FIG. 19 with the designation FL, Full-length).

The results (FIG. 19) additionally show that all of the cervical cancer cell lines (HT3, SiHa, HeLa and CaSki) expressed P2X$_{7-j}$ protein to varying degrees (see pointed arrow in FIG. 19 with the designation Tr, Truncated). P2X$_{7-j}$ protein was minimally expressed in 4 out of 5 normal cervical cell clones. Only the #136 normal cervical tissue had detectable P2X$_{7-j}$ protein expression.

The results (FIG. 19) suggest that P2X$_{7-j}$ protein may be preferentially expressed in cancer cells, one type of cancer cell being epithelial cancer cells.

The results (FIG. 19) also suggest that P2X$_7$ protein may be preferentially expressed in normal cells, one type of normal cell being epithelial cells.

Example 2

Expression of P2X and P2X$_{7-j}$ by Normal and Cancer Human Cells

This study was similar to the study described in Example 1, except that additional cells were tested. As in the earlier study, cervical cancer cell lines HT3, HeLa and CaSki were used. Additional lines used include SCC9 cells, which are human squamous skin carcinoma cells; MCF$_7$ cells, which are human breast epithelial cancer cells; PC3, which are human prostate epithelial cancer cells; and 3J, which are human lymphoma cells. Additionally, normal human cervical tissues #237 and 277 were used, as were normal human keratinocyte cells. The cells were grown, extracts made from the cells and the tissues and immunoblotting performed using the P2X$_7$ antibody, as described above for the study described in Example 1.

The results (FIG. 20) showed that all of the cancer cells (HT3, HeLa, CaSki, SCC9, MCF7 and PC3) expressed at least low levels of P2X$_{7-j}$ protein (see pointed arrow in FIG. 20 with the designation Tr, Truncated). The human lymphoma cell line, 3J, expressed only minimal P2X$_{7-j}$ protein. Additionally, normal cervical tissues #237 and 277, and normal keratinocytes, expressed only minimal P2X$_{7-j}$ protein.

The results (FIG. 20) also showed that all types of cells and tissues expressed the P2X$_7$ protein (see pointed arrow in FIG. 20 with the designation FL, Full-length). However, the level of P2X$_7$ protein expression was greater in the normal cervical tissues and normal keratinocytes than in the cancer cells.

These results (FIG. 20) further suggest that the P2X$_{7-j}$ protein may be preferentially expressed in cancer cells, one type of cancer cell being epithelial cancer cells, and that the P2X$_7$ protein may be preferentially expressed in normal cells, one type of normal cell being epithelial cells.

Example 3

Expression of P2X$_7$ and P2X$_{7-j}$ by Normal and Cancer Human Cells

Tissues of normal and invasive uterine endometrial, endocervical, and ectocervical cancers were collected from different women and stained with the polyclonal anti P2X$_7$ antibody. The data showed that the levels of P2X$_{7-j}$ proteins are low and similar across normal and cancer tissues. In contrast, levels of the P2X$_7$ protein are high in normal tissues and low in cancer tissues. Using assays that determined specifically only the P2X$_7$ protein yielded mRNA and Protein methods that could distinguish normal tissues from cancer tissues with high precision (FIG. 29 through FIG. 32).

Although not wishing to be bound by theory, methods that will target the relative P2X$_7$/P2X$_{7-j}$ mRNA and protein expression may also distinguish normal tissues from cancer tissues with high precision.

Example 4

Expression of P2X$_7$ and P2X$_{7-j}$ by Normal, Pre-Cancer and Cancer Human Cells Tissues of normal, precancerous (low-grade, moderate-grade, and high-grade dysplasia), and invasive uterine cervical cancer were collected from different women and stained with the polyclonal anti P2X$_7$ antibody.

As the degree of cervical abnormality progressed from mild (FIG. 24, Panel E) to moderate (FIG. 24, Panel F) to high-grade dysplasia (FIG. 24, Panel G) and to invasive cancer (FIG. 24, Panel H), the immunoreactivity with the anti P2X$_7$-receptor antibody decreased. The data in FIG. 24 also suggest that the immunoreactivity with the anti P2X$_7$ receptor antibody was markedly reduced in high-grade dysplasia (FIG. 24, Panel G) and invasive cancer (FIG. 24, Panel H), compared to normal tissues (FIG. 24, Panel C), low-grade dysplasia (FIG. 24, Panel E), and moderate dysplasia (FIG. 24, Panel F).

Although not wishing to be bound by theory, the likely explanation is that the total immunoreactivity is determined by the interaction of the anti P2X$_7$-receptor antibody with the P2X$_7$ and P2X$_{7-j}$ proteins present in the tissue. According to the example shown in FIG. 27 and FIGS. 28A-B, and already discussed above, the levels of P2X$_{7-j}$ proteins are low and similar across normal and cancer tissues. In contrast, levels of the P2X$_7$ protein are high in normal tissues and low in cancer tissues. Since the anti P2X$_7$-receptor antibody that was used interacts with both the P2X$_7$ and P2X$_{7-j}$ proteins, the results in FIG. 24 indicate that as the degree of pre-cancer severity increases from low-grade through high-grade dysplasia, the amount of P2X$_7$ protein expression decreases. This enables the use of quantification of the P2X$_7$ and P2X$_{7-j}$ proteins to differentiate not only normal from cancer uterine tissues (as discussed above), but also low-grade dysplasia and moderate-dysplasia of the cervix from high-grade dysplasia and invasive cancer.

Example 5

Differentiation of Dispersed Normal and Cancer Cells

FIG. 33 illustrates an example of a possible use of the data for better differentiation of dispersed normal and cancer cells. This example is relevant to conditions that employ the methodology of Cytological Evaluation of Specimens, in which single or clumped cells are obtained, dispersed into solution, then placed on a glass slide, and are used for histological or biochemical evaluation using one of different available methods. One example in particular refers to the Pap smear test, which is used in women for early detection of cervical lesions and cancer.

In the example illustrated in FIG. 33, two types of dispersed cells were co-cultured on a glass slide: Normal Human Keratinocytes (skin cells) and skin human Squamous Carcinoma Cells (SCC). Cells on the slide were then co-incubated with two antibodies: anti EGFR and anti P2X$_7$-receptor. Secondary staining for light microscopy visualization was done as previously described. Feng et al, *Am J Physiol* 288:C1342 (2005). In FIG. 33, the EGFR was stained green; the P2X$_7$ red; and cell nuclei blue. The EGFR (epidermal growth factor receptor) is a marker of cancer cells. Cancer epithelial cells (e.g. the SCC) express higher levels of the EGFR than normal cells (previously shown by others). Cancer epithelial cells express lower levels of the P2X$_7$ (shown for the first time in FIG. 29). Therefore, combining the staining may enable better differentiation of cancer from normal cells, since cancer cells will predominantly stain with the anti EGFR antibody while normal cells will predominantly stain with the anti P2X$_7$ antibody.

FIG. 33 (Panel A) illustrates the expression of EGFR. FIG. 33 (Panel B) illustrates expression of the P2X$_7$. FIG. 33 (Panel C) illustrates a composite of the EGFR plus P2X$_7$ staining. FIG. 33 (Panel D) is similar to FIG. 33 (Panel B) except that nuclei of cancer cells are marked with the letter C. Using either of the antibodies alone would make it relatively difficult to differentiate the SCC cancer cells from the normal keratinocytes. However, the combined staining significantly improves the ability to distinguish the two groups of cells.

Example 6

Production and Partial Characterization of an Antibody Specific P2X$_{7-j}$ Protein A peptide with an amino acid sequence beginning at amino acid number 239 and ending with amino acid number 258 of the P2X$_{7-j}$ protein was synthesized. The peptide comprises the amino acid sequence GDNFSDVAIQIRQVLQGKQC (SEQ ID NO:8)(See FIG. 2). After synthesis and purification, the peptide was linked to Keyhole Limpet Hemocyanin (KLH). The KLH-linked peptide was used to immunize a rabbit. Before immunization (day 0), preimmune serum was taken from the rabbit. After the preimmune serum was obtained, the animal was immunized with the peptide in complete Freunds Adjuvant. On day 14, a second immunization with the peptide in incomplete Freunds Adjuvant was performed, followed by similar immunizations on days 35 and 56. Serum was obtained from the rabbit on day 66 and tested for reactivity against P2X$_7$, as described below.

Immunoblotting was used to test the rabbit serum for reactivity against P2X$_7$ proteins. Extracts from HEK-293 cells expressing P2X$_7$-R$_{TR}$(Myc) were used to test for serum reactivity against P2X$_{7-j}$ protein (FIG. 21, lanes 2 and 5). Extracts from HEK-293 calls expressing P2X$_7$ were used to test for serum reactivity against P2X$_7$ protein (FIG. 21, lanes 1 and 4). After separation of proteins in the extracts by SDS-polyacrylamide electrophoresis, the proteins were transferred to a membrane. The membrane was then probed with either the preimmune serum from the rabbit (FIG. 21, lanes 4 and 5) or with the immune serum collected on day 66 (FIG. 21, lanes 1 and 2). A labeled secondary antibody was used to visualize reactive protein bands.

The results (FIG. 21) indicated that the antibodies in the immune rabbit serum identified a number of protein bands in extracts from cells expressing P2X$_{7-j}$ protein (lane 2). The band at around 40 kdal is believed to identify P2X$_{7-j}$ protein. None of these bands were generally present in extracts made from cells expressing P2X$_7$ protein (lane 1). No protein bands were generally present when preimmune serum was used to probe the same extracts (lanes 4 and 5). These data indicate that antibodies specific for P2X$_{7-j}$ protein, that are not reactive with P2X$_7$ protein, have been generated.

While example compositions, methods, and so on have been illustrated by description, and while the descriptions are in considerable detail, it is not the intention of the applicants to restrict or in any way limit the scope of the application. It is, of course, not possible to describe every conceivable combination of components or methodologies for purposes of describing the compositions, methods, and so on described herein. Additional advantages and modifications will readily appear to those skilled in the art. Therefore, the invention is not limited to the specific details and illustrative examples shown and described. Thus, this application is intended to embrace alterations, modifications, and variations that fall within the scope of the application. Furthermore, the preceding description is not meant to limit the scope of the invention.

Example 7

In vitro Transfection Of P2X Receptor Genes

Cell Culture Techniques and Transfections

CaSki and HEK-293 cells used in the experiment were obtained from the ATCC. CaSki cells are a line of transformed cells that retain phenotypic characteristics of human endocervical epithelial cells, and are a useful model to study cervical cell functions. Gorodeski et al., "Maintenance of in vivo-like keratin expression, sex steroid responsiveness and estrogen receptor expression in cultured human ectocervical epithelial cells" *Endocrinology* 126:399-406 (1990); Gorodeski et al., "Human uterine cervical epithelial cells grown on permeable support a new model for the study of differentiation and transepithelial transport" *Differentiation* 56:107-118 (1994). HEK-293 cells lack endogenous expression of P2X receptors and are frequently used for heterologous expression of the receptors. The HEK-293 cells were maintained in a medium composed of MEM supplemented with 10% fetal calf serum, 2 mM L-Glutamine, 5 mM sodium pyruvate, 100 U/ml penicillin, and 100 µg/ml streptomycin (Gibco, Los Angeles, Calif.). For experiments, cells were shifted to modified Ringer solution, composed of (mM) NaCl (120), CaCl$_2$ (1.2), MgSO$_4$ (1.2), KCl(5), NaHCO$_3$ (10 mM), before equilibration with 95% O$_2$/5% CO$^2$), N-(2-Hydroxyethyl) piperazine-N'-(2-ethanesulphonic acid) (HEPES) (10), glucose (5), and 0.1% bovine serum albumin.

For transfections, the full length human P2X$_7$ receptor (*Homo Sapiens* purinergic receptor P2X, ligand-gated ion channel, 7 [P2RX$_7$], mRNA human [NM_002562](48) was cloned into pcDNA-6 vector with subdloning sites Eco RI and Not I, along with a c-Myc epitope tag attached at the N-terminus of the P2X$_7$ gene. The plasmid DNA was transfected into HEK-293 cells by GenePorter reagent (Gene Therapy Inc, San Diego, Calif.) according to the manufacturer instructions.

The plasmid contained the construct of the fusion protein β-Arrestin-2 and Green-Fluorescence-Protein (GFP) (β-Arrestin-2-GFP, µg/µl). Oakley et al., "Molecular Determinants Underlying the Formation of Stable Intracellular G Protein-coupled Receptor-β-Arrestin Complexes after Receptor Endocytosis" *J Biol Chem* 276:19452-19460 (2001). Transfections in CaSki cells utilized 3 µg β-Arrestin-2-GFP plasmid DNA per 100 mm dish, and were carried out with the GenePorter II reagent following company (GTS) instruction. Transfections were performed 48 hours prior to the experiment in dishes with cells confluence of about 70%. A similar method was used for co-transfection of HEK-293 cells with the P2X$_7$ receptor and the β-Arrestin-2-GFP, with a mixture of the two plasmids (3 µg for each per 100 mm dish).

The method of fluorescence experiments of attached cells was described. Gorodeski et al., "A novel fluorescence chamber for the determination of volume changes in human CaSki cell cultures attached on filters" *Cell Biochem Biophys* 29:307-332 (1998). Changes in cytosolic calcium (Ca$_i$) were determined in fura-2 loaded cells. For experiments with the nuclear stain Ethidium Bromide (MW 394 Da), the agent was added to the perfusing solutions from a concentrated (100×) stock at a final concentration of 5 µM. Upon influx into cells, the dye binds to nuclear chromatin and elicits specific fluorescence. Changes in fluorescence were measured on-line at the 518/605 um wavelengths (excitation/emission). Agents and solutions were added to both the luminal and subluminal solutions.

Immunostaining Technique

Light microscopy experiments were conducted on cells grown on glass coverslips. Cells were washed with PBS, and fixed with fresh 2% paraformaldehyde in PBS for 10 min at room temperature. After washes with PBS, cells were permeabilized in PBS containing 0.05% NP-40 for 10 min at room temperature, incubated for 30 min at room temperature in blocking solution (PBS, 1% bovine serum albumin, 5% goat serum), and incubated overnight at 4° C. in the same solution with the polyclonal rabbit anti-P2X$_7$ receptor antibody. Cells were washed once with the blocking solution and once with PBS, and incubated with HRP-labeled goat anti-rabbit IgG, heavy and light chain peroxidase (Calbiochem, San Diego, Calif.) at a dilution of 1:2000 for 30 min at room temperature.

The reaction was visualized by Fast-Red (Dako; dakocvtomation.com) and nuclear staining was done with hematoxylin according to standard methods. Confocal laser scanning microscopy experiments were done on cells cultured on Transwell filters (Costar Corporation, Cambridge, Mass.) or on Millicell-CM filters (Millipore, Bedford, Mass.). Cells were fixed in cold methanol for 15 minutes at room temperature, immersed in blocking buffer (3% bovine serum albumin, 0.1% Triton X-100 in PBS) for 30 minutes at room temperature, and incubated overnight at 4° C. in the same solution with the polyclonal rabbit anti-P2X$_7$ receptor antibody. After three washes with PBS, cells attached on the filter were incubated with FITC-labeled anti-rabbit IgG secondary antibodies for 1 h at room temperature. The filters were mounted in Vestashield with DAPI (Vector H-1200). Immunolocalization was observed by using Zeiss MRC 1024 confocal laser scanning microscope. Representative fields were selected, and images were processed using Adobe Photoshop soft-ware package.

Western Blot Analysis

The post-nuclear supernatant of cells was prepared in lysis buffer (50 mM Tris-HCl, pH 6.8, 1% CHAPS, 5 mM EDTA, pH 8.0) containing 50 ptg/ml PMSF, 10 µg/ml of Benzamidine, 10 µg/ml of Bacitracine, 10 µg/ml of Leupeptin, and 2 µg/ml of Aprotinin. Aliquots normalized to 15 µg protein were loaded on SDS-polyacrylamide gels, fractionated in gel electrophoresis (PAGE) and blotted by Western analysis. Receptor polypeptides were visualized using 1.5 µg/ml of rabbit anti-P2X$_7$ antibody. Anti-rabbit peroxidase-conjugated secondary antibody was used for visualization (ECL kit, Santa Cruz Biotechnology, Santa Cruz Calif.).

Cell-Fractionation by the Freeze/Thaw Method

Cells were washed and released with cold Hank's Balanced Salt Solution (HBSS) using HBSS containing 5 mM EDTA, 50 µg/ml PMSF, 10 µg/ml Benzamidine, 10 µg/ml Bacitracine, 10 µg/ml Leupeptin, and 2 µg/ml Aprotinin. The cell suspension was centrifuged at 380 g, and the pellet was resuspended in cold and sterile 0.25 M sucrose solution containing the protease inhibitors and re-centrifuged at 380 g for 5 minutes. Cells were resuspended in 10 ml of the same solution, dispersed into single cells by repeat pipetting, and centrifuged at 380 g for 5 minutes. The pellet was resuspended in 1/10 volume of HME buffer (50 mM Hepes, pH 7.4, 12.5 mM $MgCl_2$, 1.5 mM EGTA; and the protease inhibitors) plus 5 mM EDTA and vortexed. After incubation at −75° C. for 1 hr the pellet was thawed out at room temperature, and the freeze/thaw procedure was repeated two additional times. After spinning at 380 g for 5 minutes the supernatant containing cytosol and plasma membranes was collected and centrifuged at 13,500 g for 20 minutes. After spinning, the supernatant (cytosol) was collected, and the pellet (membranes-enriched fraction) was resuspended in 100 µl of HME plus 10% glycerol. Protein concentration was estimated using the Bio-Rad protein assay kit.

Phosphorylation Assays.

CaSki cells were shifted for 1 hour to phosphate-free DMEM containing 10 mM HEPES, pH 7.4 at 37° C., and treated with 100 µCi/ml [$^{32}$P]orthophosphate (PerkinElmer Life Sciences, Boston Mass.) plus 1 µg/ml microcystin L-R (Calbiochem, San Diego, Calif.) to label the ATP pool. After treatments with ATP, cells were washed with ice-cold PBS, lysed in lysis buffer as described below, and processed by immunoprecipitation with polyclonal rabbit anti-$P2X_7$ antibody. Samples containing equal amounts of protein were resolved on 10% polyacrylamide gels and dried under vacuum. Radioactive bands were visualized by Phosphorimager® (Molecular Dynamics [Amersham], Piscataway, N.J.) and by exposure to x-ray film.

Immunoprecipitation and Immunoblotting Assays

Following treatments, cells collected from 100 mm culture dish were lysed in lysis buffer (1% Triton X-100, 0.5% Nonidet $P2X_7$ P40, 10 mM DTT, 5 mg/ml aprotinin, 5 mg/ml leupeptin, 100 mg/ml bacitracin, 100 mg/ml benzamidine, 2 mM Na-orthovanadate, 150 mM NaCl, 5 mM EDTA, 50 mM NaF, 40 mM sodium pyrophosphate, 50 mM $KH_2PO_4$, 10 mM sodium molybdate, and 20 mM Tris-HCl, pH 7.4), and samples were normalized by adjusting total protein level in each sample to 500 µg. For experiments using the antiphosphotyrosine/serine/threonine antibodies, the composition of the lysis buffer was 1% Triton X-100, 50 mM NaCl, 60 mM n-Octyl-B-D-Glucoside, 5 mM EDTA, 50 mM HEPES pH 7.5 plus the mixture of protease inhibitors. Lysis was carried out at 4° C. for 20 min; the mixture was spun at 10,000 g for 15 min, and lysates were immunoprecipitated with the primary antibody first for 1-3 hours and then precleared with protein A/G-agarose overnight at 4° C. Immune complexes were washed thrice with RIPA buffer (20 mM Tris-HCl, 150 mM NaCl, 1 mM EDTA, 10 mM DTT, 1% Triton X-100, pH 8.0) and separated on a 4% to 12% linear gradient SDS-acrylamide Laemmli gels. Immunoblotting and immunostaining was performed as described above.

Confocal Microscopy

CaSki cells transfected with the β-arrestin-2-GFP, or HEK-293 cells co-transfected with the full-length human $P2X_7$-receptor and the β-arrestin-2-GFP were plated on 35-mm glass-bottom culture dishes (MatTek Corporation, Ashland, MA). Dishes contained a centered, 1 cm well formed from a glass coverslip sealed hole in the plastic. Two hours before experiments the medium was replaced with serum-free medium supplemented with 10 mM HEPES. The distribution of the β-arrestin-2-GFP was visualized before and after treatment with the agonist by real-time confocal microscopy. Imaging of the β-arrestin-2-GFP fluorescence in the same cells was performed on a Zeiss laser-scanning confocal microscope (LSM-510) using a heated (37° C.) microscope stage. Barak et al., "A beta-arrestin/green fluorescent protein biosensor for detecting G protein-coupled receptor activation" *J Biol Chem* 272:27497-27500 (1997).

Images were collected sequentially before and after treatment with agonist for 0-30 min at 37° C. using single line excitation (488 nm).

Densitometry

Using AGFA Arcus II scanner (AGFA, New York N.Y.) and Un-Scan-It gel automated digital software (Silk Scientific, Orem Utah).

Statistical Analysis of the Data

Data are presented as mean±standard deviation and significance of differences among means was estimated by Student's t-test. Trends were calculated using GB-STAT V5.3 (Dynamic Microsystems Inc., 1995, Silver Spring, Md.) and analyzed with ANOVA.

Chemicals and Supplies

Fura-2/AM and Ethidium Bromide were obtained from Molecular Probes (Eugene, Oreg.). All other chemicals, unless specified otherwise, were obtained from Sigma Chemical (St. Louis, Mo.).

Antibodies

The anti $P2X_7$ receptor pAb was from Alomone Laboratories (Jerusalem, Israel), which was raised against the purified peptide (C)KIRK EFPKT QGQYS GFKYP Y (SEQ ID NO:9) corresponding to residues 576-595 of rat $P2X_7$ with an additional N-terminal cysteine. Torres et al., "Identification of a domain involved in ATP-gated ionotropic receptor subunit assembly. *J Biol Chem* 274:6653-6659 (1999). The following were from Santa Cruz Biotechnology (Santa Cruz, Calif.): anti-c-Myc mAb, anti-GRK-3 pAb, anti β-arrestin-2 mAb, anti-dynamin mAb, and anti-clathrin mAb. Anti-phosphotyrosine PY20 and P99, anti-phosphoserine, and anti-phosphothreonine mAbs were obtained from Transduction Laboratories (BD Biosciences, San Jose, Calif.).

Results

Stimulation of the $P2X_7$-Receptor Induces Plasma-Membrane Pore Formation:

Treatment of CaSki cells attached on filters with ATP induced a transient calcium mobilization and acute calcium influx. Gorodeski G. I., "Expression regulation and function of P2X4 receptor in human cervical epithelial cells" *Am J Physiol* 282:C84-C93 (2002); and Gorodeski G. I., "Regulation of transcervical permeability by two distinct P2-purinergic receptor mechanisms" *Am J Physiol* 282:C75-C83 (2002). In the continued presence of ATP, there was also a slow and sustained increase in cytosolic calcium ($Ca_i$) that began about 10 min after adding the ATP. FIG. 41, Panel A.

The late slow increase in $Ca_i$ was blocked by lowering extracellular calcium to <0.1 mM, indicating calcium influx, and attenuated by pretreatment with 1 [N,O-bis(5-isoquinolinesulfonyl)-N-methyl-L-tyrosyl]-4-phenylpiperazine (KN-62), oxidized ATP (oATP), or with polyethylene-glycol 6000 (PEG-6000). FIG. 41, Panel B. From among different ATP agonists only the $P2X_7$-receptor agonist 2',3'-0-(4-benzoyl-benzoyl)-adenosine 5'-triphosphate (BzATP) could induce the late $Ca_i$ increase. FIG. 41, Panel C. To determine whether the late sustained calcium influx is the result of $P2X_7$-receptor-pore formation, CaSki cells were treated with ATP or with BzATP in the presence of ethidium bromide. Dubyak et al., "Signal transduction via P2-purinergic receptors for extracellular ATP and other nucleotides" *Am J Physiol* 265:C577-C606 (1993). Under baseline conditions there were no changes in fluorescence at 518/605 nm (excitation/emission), but treatment with ATP or with BzATP increased the fluorescence indicating increased nuclear binding of ethidium bromide and suggesting influx of ethidium bromide. FIG. 41, Panels A-D. The ethidium bromide effect correlated in time with the $Ca_i$ changes), and was also attenuated by KN-62, oATP and PEG-6000. (FIG. 41, Panel A & Panel C, Panel D, respectively). However, lowered extracellular calcium had no effect on the ATP-or BzATP-induced influxes of ethidium bromide. (FIG. 41 Panel D).

In wild-type HEK293 cells attached on filters treatment with ATP did not produce significant change in $Ca_i$ or influx of ethidium bromide (not shown). Similarly, in HEK-293-$hP2X_7$-R cells ATP did not induce $Ca_i$ transients, nor did the nucleotide UTP have any appreciable effect on $C_i$ levels (not shown), effectively ruling out involvement of a putative $P2Y_2$ receptor in the $Ca_i$ increase. cf: Sehachter et al., "HEK293 human embryonic kidney cells endogenously express the $P2Y_1$ and $P2Y_2$ receptors" *Neuropharmacology* 36:1181-1187 (1997). In contrast, in HEK-293-$hP2X_7$-R cells ATP and BzATP induced sustained $C_i$ increase and influx of ethidium bromide. FIG. 42, Panels A & C. Both effects could be inhibited by KN-62, oATP, and PEG-6000, and the former blocked by lowering extracellular calcium to <0.1 mM. FIG. 42, Panels B & D. Both effects correlated in time. FIG. 42, Panels A & C. But in HEK-293-$hP2X_7$-R they began earlier than in CaSki cells. Collectively, these results suggest that in CaSki cells and in HEK-293-$hP2X_7$-R cells activation of the $P2X_7$ receptor induces $Ca^{2+}$-independent pore formation.

The late ATP-induced calcium influx could be prevented if CaSki cells were washed and reincubated in fresh medium 1 to 7 minutes after treatment. Washes at later times resulted in partial or no effect on the responses. FIG. 43, Panel A. Increasing $Mg^{2+}$ in the extracellular fluid from 1 mM to 5 mM did not significantly affect the magnitude of the ATP-induced late prolonged increase in $Ca_i$ (not shown) suggesting that in contrast to other types of cells, the active ligand for the $P2X_7$ receptor is not the tetra-basic acid $ATP^{4-}$. In both types of cells, the effects of ATP and BzATP were concentration dependent. Increases in $Ca^i$ and in ethidium bromide fluorescence began with low micromolar concentrations of the ligands, and increased with higher added amounts of the nucleotides. FIG. 43, Panel B. While the dose response curves did not reach saturation even at millimolar concentrations of the ligands, the data confirm that BzATP produces more potent and efficacious effects than ATP. FIG. 42 Panel B.

Expression of the $P2X_7$ Receptor Protein

Immunofluorescence staining of CaSki and HEK-293-$hP2X_7$-R cells using the Alomone polyclonal rabbit Anti-$P2X_7$ receptor antibody revealed diffuse, uniform and homogenous speckled cellular decoration that could be blocked by pre-incubation with the $P2X_7$ receptor antigen. FIG. 44, Panel A. Confocal laser scanning microscopy provided a more detailed analysis of the $P2X_7$ receptor cellular distribution in CaSki cells. FIG. 44 Panel B. Specific granular staining along the plasma membrane (i.e., for example, a patchy staining in the cytoplasm), and in some cells, staining in clumps confined to the nucleus. Western immunoblot analysis of total homogenates from CaSki cells revealed specific reactivity to 85 KDa, 65 KDa, and 18 KDa forms that could be blocked by pre-incubation with the $P2X_7$ receptor antigen. FIG. 44, Panel C. Previous studies showed that the 85 KDa is the mature and functional form of the $P2X_7$ receptor, residing mainly in the plasma membrane. Wang et al., "EGF facilitates epinephrine inhibition of $P2X_7$-receptor mediated pore formation and apoptosis: a novel signaling network" *Endocrinology* 146:164-174 (2005). The 65 KDa is the native form of the $P2X_7$ receptor corresponding to the reported $P2X_7$ receptor 70 KDa isoform, while the 18 KDa is a degradation product. Ramirez et al., "P2X purinergic receptor channel expression and function in bovine aortic endothelium" *Am J Physiol* 282:H2106-H2116 (2002).

The $P2X_7$ receptor antibody did not stain untransfected HEK293 cells or HEK-293 cells transfected with GFP-β-arrestin-2 fusion protein alone (not shown). In homogenates of HEK-293-$hP2X_7$-R cells specific immunoreactivity to 85 KDa, 65 KDa, and 18 KDa forms of $P2X_7$ receptor was found; similar to CaSki cells. FIG. 44, Panel C. Co-transfection of HEK-293-$hP2X_7$-R cells with GFP-β-arrestin-2 had no effect on the expression of the three $P2X_7$ receptor forms. FIG. 44, Panel C.

Re-Distribution of the $P2X_7$ Receptor

Although it is not necessary to understand the mechanism of an invention, it is believed that the above data suggests a compartmentalization of the $P2X_7$ receptor. Further, both CaSki and in HEK-293-$hP2X_7$-R cells the 85 KDa form was expressed mainly in the plasma-membrane enriched fraction. Assays utilizing the anti-$P2X_7$ receptor antibody did not detect expression of the 85 KDa form in the cytosol. (FIG. 45 and FIG. 46. The 65 KDa and 18 KDa forms were expressed in both the plasma-membrane enriched fraction and in the cytosol. Western blots in homogenates of HEK-293 cells transfected with the full-length human $P2X_7$ receptor tagged with c-Myc epitope at the N-terminus of the $P2X_7$ gene (HEK-293-c-Myc-$hP2X_7$-R cells), using the anti c-Myc antibody, revealed immunoreactivity at 85 KDa and 65 KDa in both the plasma membrane and cytosolic fractions, but did not detect specific 18 KDa staining. FIG. 47).

To determine the degree of which ligand binding induces re-distribution of the receptor, Day-6 CaSki cells were immunostained with the anti-$P2X_7$ receptor antibody at different time intervals after treatment with ATP. Thirty minutes after treatment with 10 µM ATP receptor staining remained diffuse, uniform and relatively homogenous. In cells treated with 50 µM or with 250 µM ATP, the staining became non-uniform, coarse, and condensed towards perinuclear regions of the cells. In control slides, (i.e., processed in the presence of the $P2X_7$ receptor antigen) no significant morphological changes could be discerned. FIG. 44, Panel A.

Although it is not necessary to understand the mechanism of an invention, it is believed that these results indicate that the ATP-induced changes in $P2X_7$ receptor staining are not the result of changes in cell structure, but rather represent specific changes in receptor distribution. For example, in CaSki cells, treatment with ATP stimulated a transient decrease in the level of the 85 KDa form in the membrane-enriched fraction, with a parallel transient increase in the 65 KDa form. Maximal effects were observed 10 min after treatment with ATP, with gradual return to baseline levels after about 20 min. About 15 min after treatment with ATP there was an increase in the densities of the 18 KDa isoform in the membrane-enriched fractions, and of the 65 KDa and 18 KDa forms in the cytosol. Those increases persisted throughout the 30 min of the experiment. FIG. 45.

In HEK-293-$hP2X_7$-R cells, treatment with ATP stimulated transient decrease in the 85 KDa and 65 KDa forms in the membrane-enriched fraction. Maximal effects were observed 3 to 5 min after the treatment, with gradual return to baseline levels after about 15 min. In the membrane-enriched fraction, ATP stimulated also a gradual increase in the 18 KDa form that began 10 min after the treatment and persisted throughout the 30 min of the experiment. ATP also stimulated biphasic change in the 65 KDa and 18 KDa forms in the cytosol. First, a transient increase peaked at about 10 min after adding ATP. Second, a decrease to sub-baseline levels was seen that persisted for at least 30 minutes. FIG. 46. In HEK-293-c-Myc-hP2X$_7$-R cells, treatment with ATP stimulated transient decreases in the 85 KDa and 65 KDa forms in the membrane-enriched fraction, with reciprocal transient increases in the 85 KDa and 65 KDa forms in the cytosol. FIG. 47.

Although it is not necessary to understand the mechanism of an invention, it is believed that that treatment with ATP increases the P2X$_7$ receptor 85 KDa form and decreases the 18 KDa form in the plasma membrane, and increases the levels of the three receptor forms in the cytosol. It is further believed that the main differences between the effects in CaSki cells and in HEK-293-hP2X$_7$-R cells are faster effects in HEK-293-hP2X$_7$-R cells, and an increase in the plasma membrane in CaSki cells of the 65 KDa form in contrast to a decrease in HEK-293-hP2X$_7$-R cells.

Mechanism of Internalization of the P2X$_7$ Receptor

A. Phosphorylation

To determine whether ligand binding induces phosphorylation of the P2X$_7$ receptor, the intracellular ATP pool of CaSki cells was labeled by incubation of cells with [$^{32}$P] orthophosphate. After treatment with ATP, cell lysates were immunoprecipitated with the anti-P2X$_7$ antibody. Autoradiography at baseline conditions prior to ATP revealed some phosphorylation of the 65 kDa form and negligible phosphorylation of the 85 kDa form. Treatment with ATP increased phosphorylation of the 85 kDa form by at least 10 fold, with no significant effect on the 65 kDa form as determined by Western immunoblots. Further, there were no significant changes in total receptor content after treatment with ATP, suggesting that the 85 kDa form of the P2X$_7$ receptor is the preferred target of phosphorylation. FIG. 48, Panel A.

To determine the mechanism of ATP-induced phosphorylation of the 85 kDa form, CaSki cells were treated with 250 µM ATP for different time intervals of 0 to 30 min. Cell lysates were immunoprecipitated in a mixture containing anti-phosphotyrosine PY20 and P99 antibodies, anti-phosphoserine, and anti-phosphothreonine antibodies. Immunoblotting with the anti-P2X$_7$ antibody revealed negligible specific immunoreactivity at 85 KDa at 0 min, which increased already at 0.5 min, and disappeared at 5 to 10 min after treatment with ATP. FIG. 48, Panel B.

To better understand what residues of the 85 kDa form are phosphorylated, CaSki cells were treated for 1 min with ATP at concentrations ranging from 0 to 500 µM; cell lysates were immunoprecipitated with anti-phospho antibodies alone or in combination, and immunoblotted with the anti-P2X$_7$ antibody. Immunoprecipitates with anti-phosphotyrosine PY20 and anti-phosphoserine antibodies revealed maximal immunoreactivity in cells treated with 5 µM ATP, with a gradual decrease in cells treated with higher concentrations of the nucleotide. FIG. 48, Panel C.

Immunoprecipitates with anti-phosphothreonine antibodies, alone or in combination with antiphosphotyrosine PY20 and anti-phosphoserine revealed a lesser degree of immunoreactivity at 5 µM ATP that increased with higher concentrations of ATP. These results indicate that low concentrations of ATP (5 µM) sufficed to stimulate phosphorylation of the P2X$_7$ receptor 85 kDa form on tyrosine and serine residues, while ATP at higher concentrations tended to block the effect. In contrast, phosphorylation of the 85 kDa form on threonine residues increased with ATP, and it also increased ATP requirements for phosphorylation of the 85 kDa form on tyrosine and serine residues in combination.

B. Involvement of GRK-3

Phosphorylation of GPCRs by G-protein-coupled-receptor kinases (GRKs) is often required for binding of β-arrestin and the consequent initiation of receptor endocytosis. Luttrell et al., "The role of 13-arrestins in the termination and transduction of G-protein-coupled receptor signals" *J Cell Sci* 115: 455-465 (2002). The role of GRK phosphorylation is to increase the affinity of the receptor for arrestins. Lohse et al., "Receptor specific desensitization with purified proteins. Kinase dependence and receptor specificity of β-arrestin and arrestin in the β2-adrenergic receptor and rhodopsin systems" *J Biol Chem* 267:8558-8564 (1993); and Lohse et al. β-arrestin: a protein that regulates β-adrenergic receptor function. *Science* 248:1547-1550 (1990). In preliminary experiments we found that CaSki and HEK-293 cells constitutively express GRK-2 and GRK-3, and the latter also GRK-5 and GRK-6 (not shown). To determine whether, and which, GRK phosphorylates the P2X$_7$ receptor, lysates of ATP-treated CaSki cells were immunoprecipitated with anti-P2X$_7$ antibody and immunoblotted with commercially available anti-GRK antibodies. The immunoblots revealed specific immunoreactivity only to anti-GRK-3 antibody at about 80 KDa 1 to 3 min after adding ATP. This immunoreactivity increased in a time-related manner for at least 30 min after ATP. FIG. 49, Panel A, (a).

A similar effect was seen in HEK-293-c-Myc-hP2X$_7$-R cells. FIG. 49, Panel A, (c). However, in CaSki cells the association between the P2X$_7$ receptor and GRK-3 persisted for at least 30 min after adding ATP than in the latter (15 min). FIG. 49, Panel A. In both types of cells, immunoblots with anti-GRK-3 antibody revealed no significant change in total cellular GRK-3 protein. FIG. 49, Panels A, (b) & A, (d). Similarly, treatment with ATP did not significantly affect total cellular levels of the P2X$_7$ receptor 85 KDa, 65 KDa, and 18 KDa forms. FIG. 49, Panel D.

C. Recruitment of β-arrestin-2

GRK-mediated phosphorylation of GPCRs leads to recruitment of β-arrestins to the plasma membrane; β-arrestin binding to the phosphorylated GPCR both uncouples the receptor from heterotrimeric G proteins and targets them to clathrin-coated pits for endocytosis. β-arrestin-1, and β-arrestin-2 are ubiquitously expressed proteins, and preliminary results showed expression of both in CaSki and in HEK-293 cells. There are three potential β-arrestin-2 binding motifs in the P2X$_7$ receptor sequence, T357YSS, T508TS, and S540TNS, but until recently little was known about the involvement of β-arrestins in P2X$_7$ receptor activation. Oakley et al., "Molecular Determinants Underlying the Formation of Stable Intracellular G Protein-coupled Receptor-µ-Arrestin Complexes after Receptor Endocytosis" *J Biol Chem* 276:19452-19460 (2001). To determine whether and which β-arrestin associates with phosphorylated P2X$_7$ receptor, lysates of CaSki cells treated with ATP were immunoprecipitated with the anti-P2X$_7$ antibody and immunoblotted with anti β-arrestin-1 and β-arrestin-2 antibodies. The immunoblots revealed specific immunoreactivity only to β-arrestin-2 at about 50 KDa, which began 1 minute after adding the nucleotide and increased in a time-related manner for at least 30 min after treatment. FIG. 49, Panel B, (e). A similar effect was seen in HEK-293-c-Myc-hP2X$_7$-R cells. FIG. 49, Panel B, (g). In both types of cells immunoblots with anti β-arrestin-2 antibody revealed no significant change in total cellular β-arrestin-2 protein. FIGS. 9 Panel B, (f) & (h).

This finding was confirmed with the secondary method of real-time confocal laser microscopy. The experiments utilized CaSki cells overexpressing β-arrestin-2 tagged with GFP, and HEK-293-hP2X$_7$-R cells co-transfected with the β-arrestin-2-GFP. Cells transfected with P2X$_7$ receptor tagged with the GFP were not used, since tagging a GFP onto the N-terminus or the C-terminus of the P2X$_7$ receptor could affect receptor functionality. Smart et al., "Pore formation is not associated with macroscopic redistribution of P2X$_7$ receptors" *Am J Physiol* 283:C77-C84 (2002). FIG. 50, Panel A demonstrates the feasibility of the method in CaSki cells. In control cells (not transfected with the β-arrestin-2-GFP), no GFP fluorescence was detected (not shown). In contrast, fluorescence was observed in cells transfected with the β-arrestin-2-GFP. Under steady-state conditions the GFP fluorescence (i.e., the β-arrestin-2) was distributed diffusely and homogenously throughout the cytoplasm. FIG. 50, Panel A,(c). Treatment with ATP resulted in re-distribution of GFP fluorescence within 3 minutes of treatment towards cell periphery, suggesting recruitment of the β-arrestin-2 into sub-membranous regions. FIG. 50, panel A, (d) & (e). A similar effect was observed using BzATP (not shown).

To determine more directly P2X$_7$-receptor recruitment of a β-arrestin, HEK-293-hP2X$_7$-R cells were co-transfected with the β-arrestin-2-GFP, to determine in real-time P2X$_7$-receptor mediated changes in β-arrestin-2 redistribution. FIG. 50, Panel B shows the feasibility of the method, and it demonstrates three important points. First, in HEK-293 cells transfected with only the β-arrestin-2-GFP, under steady-state conditions GFP fluorescence was diffuse and homogenous. FIG. 50, Panel B, (c). Second, in those cells treatment with ATP had no significant effect on the GFP fluorescence, ruling out activation of β-arrestin-2 associated ATP receptors. FIG. 50, Panel B, (d).

Third, the GFP fluorescence was not significantly affected by co-transfection with the full-length human P2X$_7$-receptor. FIG. 50, Panel B, (e), and FIG. 50, Panel C, (a,d,g). Transfection with only the P2X$_7$-receptor did not elicit green fluorescence (not shown). This system was used to determine the degree of which stimulation of the P2X$_7$-receptor induces recruitment of β-arrestin-2. Control experiments were treatments with angiotensin or with UTP; the rationale for the former was that HEK-293 cells do not express endogenously angiotensin receptors. UTP was used to determine if activation of the supposedly expressed P2Y2 receptor in HEK-293 cells can contribute to recruitment of β-arrestin-2. Sehachter et al., "HEK293 human embryonic kidney cells endogenously express the P2Y1 and P2Y2 receptors" *Neuropharmacology* 36:1181-1187 (1997).

Neither angiotensin, nor UTP, had a significant effect on the GFP fluorescence. FIG. 50, Panel C, (a-c) & FIG. 50, Panel C, (d-f), respectively). In contrast, treatment with ATP resulted in redistribution of the GFP fluorescence towards cell periphery within 5 min of treatment, and the effect lasted for at least 10 minutes. FIG. 50 Panel C, (g-i). This result suggests that stimulation of the P2X$_7$-receptor induces recruitment of β-arrestin-2 into submembranous regions of the cell.

D. Role of Clathrin and Dynamin

In addition to the initiation of signal transduction events, ligand binding to GPCRs can induce dynamin-dependent receptor endocytosis via clathrin-coated pits. McPherson et al., "Signaling on the Endocytic Pathway. *Traffic* 2:375-384 (2001); and von Zastrow M., "Mechanisms regulating membrane trafficking of G protein-coupled receptors in the endocytic pathway" *Life Sci* 74:217-224 (2003)). To determine whether the re-distribution of the P2X$_7$ receptor after treatment with ATP is associated with dynamin and clathrin, lysates of ATβ-treated CaSki cells were immunoprecipitated with anti-dynamin or with anti-clathrin antibodies, and immunoblotted with the anti P2X$_7$ antibody.

Immunoprecipitates obtained with anti-dynamin antibody revealed specific immunoreactivity to anti P2X$_7$ antibody at about 85 KDa 3 to 5 minutes after treatment with ATP, which returned to baseline levels at 10 to 30 minutes. FIG. 49, Panel C, (i). Immunoprecipitates obtained with anti-clathrin antibody revealed monotonic specific immunoreactivity to anti P2X$_7$ antibody at about 85 Kda. FIG. 49, Panel C, (k). Treatment with ATP had no effect on the cellular levels of dynamin or clathrin. FIG. 49, Panel C, (j) & FIG. 49, Panel C, (l), respectively).

Example 8

Epinephrine Regulation Of P2X$_7$-Mediated Apoptosis

Cell Cultures

The experiments used CaSki cells, a line of transformed cervical epithelial cells that were obtained from the ATCC (Manassas, Va.) and were previously characterized as stably expressing phenotypic characteristics of human cervical epithelial cells. Cells were grown and subcultured in RPMI-1640 supplemented with 8% fetal calf serum, 0.2% NaHCO3, non-essential amino acids (0.1 mM), L-glutamine (2 mM), penicillin (100 U/ml), streptomycin (100 μg/ml), and gentamycin (50 ml) at 37° C. in a 91% O2-9% CO humidified incubator. Cultures were routinely tested for mycoplasma. Preliminary experiments were conducted on cells plated on culture plates, and definitive experiments were repeated on cells plated on filters. Filters were either Anocell (Anocell-10, Oxon, UK, obtained through Sigma Chemicals, St. Louis, Mo.), Transwell (Costar Corporation, Cambridge, Mass.), or Millicell-CM (Millipore, Bedford, Mass.). Filters were coated on their upper (luminal) surface with 3-5 μg/cm collagen type IV and incubated at 37° C. overnight. The remaining collagen solution was aspirated, and the filter was dried at 37° C. Before plating, both sides of the filters were rinsed three times with Hanks' balanced salt solution (HBSS). Cells were plated on the upper surface of the filter at 3×10 cells/cm$^2$. By plating at this high density, the cultures become confluent and polarized within 12 h after plating. All solutions and agents were added to both the luminal and subluminal bathing solutions. DNA synthesis DNA synthesis was measured by [$^3$H]thymidine incorporation. Six hours before assays, cells attached on filters were labeled for 4 h with 1 μM methyl-[$^3$H]-thymidine (1 μCi/ml; specific activity, 87 Ci/mmol; Amersham, Piscataway, N.J.) and maintained for 2 additional hours in medium devoid of radioactive thymidine. After labeling, the cells were washed several times in ice-cold PBS, lysed in 200/μl 0.1 N NaOH, and precipitated in 2 ml ice-cold 10% trichloroacetic acid for 2 d at 4° C. The radioactivity [dpm/mg protein, determined by Bio-Rad (Hercules, Calif.) Protein Assay solution] of triplicated samples was determined by scintillation counting (LS1801 scintillation counter; Beckman, Fullerton, Calif.).

DNA Solubilization Assay

Twenty-four hours before the end of the experiment, cells were labeled with [$^3$H]thymidine (specific activity, 93 Ci/mmol; 5 μCi/1×10$^6$ cells) for 16 h. The medium was removed, and cells were washed three times with fresh medium lacking [$^3$H]thymidine and were incubated in the same medium for an additional 6 h. At the end of incubation, the supernatant was stored, and cells were lysed in 0.5 ml lysis buffer (10 mM Tris-HCl, pH 7.5; plus 1 mM EDTA-0.2% Triton X-100) for 1 h at 4° C. The intact chromatin was separated from the fragmented DNA by 5 min centrifugation at 4° C. in Eppendorf microcentrifuge at 12,000×g. The supernatant (lysate) was stored, while the pellet was resuspended in 0.5 ml of 1% sodium dodecyl sulfate (SDS). The radioactivity contained in the supernatants, lysates; and pellets was counted in a scintillation counter, and DNA fragmentation was calculated as: [% Solubilized DNA]=([cpm supernatant+cpm lysates]/[cpm supernatant+cpm lysate+cpm pellet])×100.

Binding Studies

Binding studies of the adrenoceptors and the EGF receptor used a similar method. Two hundred fifty microliters of binding medium (serum-free DMEM, 0.1% BSA, 10 mM HEPES) containing 10-1000 μM of the radioligand were added to the apical container of the filter, and 500/μl of the same solution to the basolateral container; parallel tubes contained an additional 200-fold excess radioinert ligand. The cells were then incubated at 4° C. for 3 h; at the completion of incubations cells were washed three times with ice-cold HBSS containing 0.1% BSA. Cells were solubilized in 0.2 N NaOH, and the bound ligand was separated on glass fiber filters (Whatman, GF/C, Tonawanda, N.Y.) by vacuum filtration. The associated radioligand was counted either in a β-scintillation counter (for [$^3$H] associated ligands) or in a γ-counter (for 125I] associated ligands). The following radioligands were used: [$^3$H]prazosin and [$^3$H]tamsulosin (α-adrenoceptor radioligand) and [$^{125}$I]cyanopindolol [β-adrenoceptor radioligand] (all at 1 μCi/ml; specific activity, about 90 Ci/mmo]; Amersham), and [$^{125}$I]EGF (5 μCi/ml; specific activity, about 100 Ci/mmol; Biomedical Technology, Stoughton, Mass.). The α- and β2-adrenoceptor radioinert ligands were phenylephrine and zinterol (Sigma Chemicals). Human recombinant EGF was from R&D Systems (Minneapolis, Minn.). Specific receptor binding was expressed per milligram DNA, and data were analyzed by Scatchard plot.

Fluorescence Changes

For measurements of cytosolic calcium, cells on filters were incubated with 7 μM fura-2/acetoxymethyl ester plus 0.25% pluronic F12. Measurements of fluorescence were conducted in a custom-designed fluorescence chamber. In this apparatus, a filter with cells is placed horizontally in an enclosed dark chamber maintained at a fixed temperature, under conditions that permit selective perfusion of the luminal (0.2 ml) and subluminal compartments (0.5 ml) at rates of 1-1.5 ml/min. Cells were illuminated over the apical surface, and the intensity of the emitted light from the apical surface was measured. Agents were added to the luminal and subluminal solutions, and changes in cytosolic calcium were determined by switching the excitation filters to record the maximal (340/510 nm excitation/emission) and minimal (380/510 nm) fluorescence. Levels of cytosolic calcium were determined by the formula $[Ca^{2+}]_i$ (nM)=$[(R-R_{min})/(R_{max}\times R)]\times K_d-(S_{f2}/S_{b2})$, where $[Ca^{2+}]_i$ is the level of cytosolic calcium, R is the ratio of fluorescence excitation measurements at 340 to 380 nm, $R_{min}$ and $R_{max}$ are the experimentally determined minimum and maximum calcium measurement ratios, 340 nm to 380 nm respectively, $K_d$ is the dissociation constant for fura-2 (224 μM), and $S_{f2}/S_{b2}$ is the ratio of fluorescence value at 380 nm excitation determined at $R_{min}$ (0 calcium) and $R_{max}$ (maximal calcium). Maximal calcium fluorescence was obtained by adding 10 μM ionomycin in the presence of 10 mM $CaCl_2$, and minimal calcium fluorescence was obtained by competing calcium from fura-2 with 2.5 mM $MnCl_2$. This method was also used for experiments with the nuclear stain ethidium bromide (molecular mass, 394 Da). Ethidium bromide was added to the perfusing solutions from a concentrated stock (×100) at a final concentration of 5 μM. Upon influx into cells, the dye binds to nuclear chromatin and elicits specific fluorescence. Changes in fluorescence were measured on-line at wavelengths 518/605 nm (excitation/emission).

Western Blot Analysis

The post-nuclear supernatant of cells was solubilized in lysis buffer (50 mM Tris-HCl, pH 6.8; 1% 3-[(3-cholamidopropyl)dimethyl-ammonio]-1-propanesulfonate; 5 mM EDTA, pH 8.0) containing 50/ug/ml phenylmethylsulfonylfluoride, 10 μg/ml benzamidine, 10 μg/ml bacitracine, 10 μg/ml leupeptin, and 2 μg/ml aprotinine. Aliquots (about 45/μl), normalized to 15 μg protein, were loaded on 10% polyacrylamide SDS gel, and vertical electrophoresis was conducted at 50 mA for 1.5 h. Gels were transferred onto Immobilon membrane (Millipore) at 200 V for 1.5 h, membranes were blocked in 5% milk, and receptor polypeptides were visualized using 1.5 μg/ml rabbit anti-P2X antibody at 4° C. overnight. Membranes were washed three times in PBS and fluorescent stained for 1 minute using an enhanced chemiluminescence kit of anti-rabbit peroxidase-conjugated secondary antibody (Santa Cruz Biotechnology, Santa Cruz, Calif.). For protein deglycosylation, 20 μg total lysate proteins containing 1% SDS was denatured by heating for 5 minutes at 100° C. The mixture was incubated overnight at room temperature after addition of U fresh N-glycosidase F (GlycoTech, Rockville, Md.) in 20 mM Tris-HCl, pH 7.5, containing 1 mM EDTA and 50 mM NaCl. Samples were analyzed by Western blot as described above.

Cellular cAMP

Cellular cAMP was assayed in total homogenates of cells attached on filters. For assays, cells were incubated in HEPES:buffered Krebs-Ringer's bicarbonate buffer (pH 7.4) containing 1 mg/ml BSA and 2.5 mM glucose (Krebs bicarbonate Ringer) at 37° C. for 30 minutes. The reactions were terminated by adding 12% trichloroacetic acid (1:1 vol/vol). Cells were scraped off the filters and centrifuged at 3,000×g for 15 rain. Supernatants were extracted with 2 ml water-saturated diethylether three times. The concentration of cAMP in the aqueous phase was determined in duplicate by RIA using a commercially available kit (Amersham).

β2-Adrenoceptor Internalization (Endocytosis) Assays

Fifteen minutes before assays, cells were shifted to ice-cold medium and labeled with 1 μCi/ml [$^{125}$I]cyanopindolol for 30 min at 4° C. After three washes with ice-cold medium lacking the radioligand, cells were shifted to fresh, warm (37° C.) medium and treated with 1 μM zinterol. At time intervals of 0,15, 30, and 60 minutes, cells were washed with ice-cold medium. Surface-bound and internalized β2-adrenoceptors were distinguished. Briefly, cells were washed three times with ice-cold HBSS to remove unbound radioactivity. Cultures were then incubated for 10 minutes at 4° C. in 0.2 M acetic acid plus 0.5 M NaCl (pH 2.5) (250 and 500 μl, respectively, in the apical and basolateral containers of the filter). The filters were then rinsed with 250 and 500 μl, respectively, of the same solution, and the washes (defined as the surface bound fraction) were collected. The remaining cell-associated radioactivity was removed by incubating the cells for 60 minutes at 37° C. with 1 N NaOH. The percent membrane bound [$^{125}$I]cyanopindolol was determined relative to membrane bound [$^{125}$I]cyanopindolol in cells not exposed to zinterol.

β2-Adrenoceptor Recycling Assays

Fifteen minutes before assays, cells were shifted to ice-cold medium and labeled with 1 µl, Ci/ml [$^{125}$I]cyanopindolol for 30 minutes at 4° C. After three washes with ice-cold medium lacking the radioligand, cells were incubated at 4° C. for 15 minutes with 1 µM zinterol, and then shifted to 37° C. and incubated for an additional 60 min in the same medium. At the completion of incubation, cells were washed three times at 37° C. with the same medium, lacking zinterol, to remove unbound zinterol, and internalized processed zinterol was released into the medium. After the wash, cells were incubated further at 37° C. for 0, 0.5, 3, 4, 8, 16, and 24 h, and the amount of membrane bound [$^{125}$I]cyanopindolol was determined as above. Data about recycled receptor are presented in terms of percent control bound [$^{125}$I]cyanopindolol (compared with cells not exposed to zinterol).

Densitometry

Densitometry was done using AGFA Arcus II scamper (AGFA, New York, N.Y.) and Un-Scan-It gel automated digital software (Silk Scientific, Orem, Oreg.).

Statistical Analysis of the Data

Data are presented as means (±SD), and significance of differences among means was estimated by Student's test. Trends were calculated using GB-STAT V5.3, 1995 (Dynamic Microsystems Inc., Silver Spring, Md.) and analyzed with ANOVA.

Chemicals and Supplies

Ethidium bromide and fura-2/AM were obtained from Molecular Probes (Eugene, Oreg.). Benzyloxy-vallne-alardne-aspartate-O-methylfluoromethylketone (zVAD-FM-K) was from Calbiochem (La Jolla, Calif.). All other chemicals, unless specified otherwise, were obtained from Sigma Chemicals. The anti-P2X receptor pAb was from Alomone Laboratories (Jerusalem, Israel).

Results

Effects of epinephrine and EGF on proliferation and apoptosis of cervical cells

Near-confluent cultures of CaSki cells on filters were shifted for 14 hours to serum-free medium supplemented with 1% BSA and were treated in the same medium with 0.2 nM EGF, 2 nM epinephrine, or both for an additional 24 h. At the completion of treatments, cells were harvested off the filters and counted. Treatments with EGF or with epinephrine alone increased the number of cells in culture. FIG. 51, Panel A. However, treatment with EGF plus epinephrine increased cell number more than did each drug alone suggesting that EGF facilitates the effect of epinephrine.

EGF, but not epinephrine, increased [$^3$H]thymidine incorporation. FIG. 51, Panel B. The effects of EGF and epinephrine on apoptosis were determined in terms of modulation of changes in DNA solubilization induced by the P2X$_7$ receptor-specific agonist 2',3'-O-(4-benzoylbenzoyl)-ATP (BzATP). Treatment with 100 µM BzATP for 9 h increased DNA solubilization significantly from the baseline level of 1.9% to 7.8%. Pretreatment for 24 h with 0.2 nm EGF alone had little effect on the BzATP-induced apoptosis. FIG. 51, Panel C. In contrast, pretreatment for 24 h with 2 nM epinephrine decreased DNA solubilization to 4.6%, and cotreatment with EGF facilitated the epinephrine effect (2.9%). The control for this experiment was zVAD-FMK, a pan-caspase inhibitor that was added 30 min before assays at a concentration of 50/ZM. Treatment with zVAD-FMK decreased the BzATP induced DNA solubilization to levels that were lower than baseline apoptosis (about 1.4%).

Collectively, these data indicate that epinephrine increases cell number by attenuation of apoptosis, whereas EGF has a dual role: as mitogen, and as facilitator of epinephrine anti-apoptotic effect.

Involvement of the β2-adrenoceptor mechanism.

The low concentration of epinephrine that inhibited apoptosis (2 nM) suggested an effect mediated by adrenergic receptor(s). Binding assays revealed no specific binding of the α-adrenoceptor radioligands [$^3$H]prazosin or [$^3$H]tamsulosin (not shown), ruling out expression of functional α-adrenoceptors. In contrast, CaSki cells bound, with high affinity, the β-adrenoceptor radioligand [$^{125}$I]cyanopindolol and the binding activity was about 15 fmol/mg DNA (~10, 000 receptors/cell). FIG. 52, Panel A, Kd~0.3 nM). The radiolabel could be displaced by coincubation with the β2-adrenoceptor ligands zinterol and terbutaline, but not with the β1-adrenoceptor ligand isoproterenol (data not shown). These data indicate that CaSki cells express the β2-adrenoceptor.

Pretreatment for 24 h with either zinterol or terbutaline (1 µM) inhibited BzATP-induced apoptosis. FIG. 52, Panel B. Similarly, pretreatment for 14 h with 10 µM forskolin [in the presence of 0.5 mM of the phosphodiesterase inhibitor 3-isobutyl-1-methylxanthine, to activate directly adenylyl cyclase] also inhibited BzATP-induced apoptosis. In contrast, pretreatments with 10 µM of the β1-adrenoceptor ligand isoproterenol or with 100 µM of the α1-adrenoceptor ligand phenylephrine had no effect on BzATP-induced apoptosis. Cotreatment for 24 h with either 10 µM propranolol (β3-adrenoceptor antagonist); 100 nM ICI 118,551 (β2-adrenoceptor antagonist), or 30 µM of H-89 dihydrochloride (protein kinase A inhibitor) blocked the zinterol (1 µM)-induced inhibition of BzATP-induced apoptosis. FIG. 52, Panel C.

Collectively, these data indicate that epinephrine-dependent attenuation of BzATP-induced apoptosis is mediated by the β2-adrenoceptor. The data also suggest that the effect involves cAMP and protein kinase A as downstream mediators.

Modulation of the Mitochondrial Pathway.

Apoptosis can be induced by the cell-surface receptor and/or mitochondrial pathways. The former usually involves the Fas and TNF mechanisms followed by activation of caspase-8. The mitochondrial pathway involves the release of cytochrome-c and activation of caspase-9. The cell surface receptor and mitochondrial-dependant pathways integrate at the level of the effector caspases, so that activation of caspases 9 and 8 triggers the nonreversible execution of apoptosis by caspases 6, 7, and 3.

In CaSki cells, apoptosis induced by ligation of the P2X7 receptor mechanism involves predominantly the mitochondrial pathway. CaSki cells were treated with either 100 µM BzATP for 9 h or with 10 µM TNFα, for 14 h, and effects on DNA solubilization were determined. Either of these two agents significantly increased DNA solubilization. FIG. 53. Pretreatment for 24 h with 1 µM zinterol inhibited BzATP-induced increase in DNA solubilization, but it had no effect on the increase in DNA solubilization induced by TNFα. FIG. 53, Panel A. Pretreatment for 24 h with 0.2 nM EGF alone had no significant effect on BzATP- or TNFα-induced increase in DNA solubilization. FIG. 53, Panel B.

Inhibition of P2X7 Receptor Pore Formation.

The P2X$_7$ receptor is unique in its ability to form pores in the plasma membrane in the continued presence of the ligand. Plasma membrane pore formation depends on the long C terminus of the receptor, and oligomerization of neighboring molecules is believed to cause progressive dilatation of the pore to a diameter of approximately 4 mn and an increase in the permeation path to molecules of molecular mass of 400-900 Da. In its final size, the pore is relatively permeable to $Ca^{2+}$, but it remains selective to other cations and is impermeable to anions. Uncontrolled influx of $Ca^{2+}$ and the sustained increases in cytosolic calcium are believed to trigger the apoptotic mitochondrial pathway.

Fura-2-loaded CaSki cells were attached on filters housed in a fluorescence chamber. Under these conditions, treatment with BzATP induced 1-[N,O-bis(5-isoquinolinesulfonyl)-N-methyl-L-tyrosyl]-4-phenylpiperazine (KN-62)-sensitive, time-dependent sustained $Ca^{2+}$ influx that began about 10 min after adding the ligand. FIG. 54 Panel A. EGF alone had no significant effect, and pretreatment with epinephrine attenuated the BzATP-induced increase in cytosolic calcium FIG. 54, Panel A, inset. Pretreatment with epinephrine plus EGF attenuated the BzATP-induced increase in cytosolic calcium to a degree that was observed in cells treated with the $P2X_7$ receptor modifier KN-62.

Cells attached on filters were also treated with BzATP in the presence of ethidium bromide (molecular mass, 394 Da). Under baseline conditions, there were no changes in fluorescence at 518/605 nm (excitation/emission), indicating no influx of ethidium bromide. Treatment with BzATP resulted in time-related increase in the fluorescence, indicating nuclear binding of ethidium bromide and suggesting that the nucleotide induced influx of ethidium bromide. FIG. 54, Panel B. The increase in fluorescence began about 10 min after adding the agonist, and it correlated with the sustained increase in cytosolic calcium. Compare FIG. 54, Panel A and 54, Panel B. Similar to the effect on cytosolic calcium, the BzATP-induced influx of ethidium bromide could be blocked by pretreatment with KN-62. FIG. 54, Panel B, inset. Pretreatment with EGF alone had no significant effect; pretreatment with epinephrine attenuated the BzATP-induced influx of ethidium bromide, and pretreatment with epinephrine plus EGF inhibited the BzATP-induced influx of ethidium bromide, similar to the effect of KN-62. FIG. 54 Panel B, inset. Collectively, these data suggest that epinephrine inhibited ligation-induced $P2X_7$ receptor pore formation; EGF alone had no significant effect, but it facilitated the effect of epinephrine.

Modulation of P2X7 Receptor Expression.

Expression of the $P2X_7$ receptor protein was analyzed using the Alomone polyclonal rabbit anti-$P2X_7$ receptor antibody as the primary antibody. This antibody was raised against the purified peptide (C)KIRK EFPKT QGQYS GFKYPY (SEQ ID NO:10). Western immunoblot analysis of total homogenates from CaSki cells revealed specific reactivities to 85-kDa, 65-kDa, and 18-kDa forms that were abolished in the presence of the antigen used to raise the antibody. FIG. 55, Panel A. The 65-kDa is most likely the native form of the $P2X_7$ receptor corresponding to the reported $P2X_7$ receptor 70-kDa isoform, whereas the 18-kDa is a degradation product.

The levels of BzATP-induced $Ca^{2+}$ reflux and of BzATP-induced influx of ethidium bromide were greater in ceils cultured for 6 days than in cells cultured for 2 days. FIG. 55, Panel B. Length in culture also affected the levels of the $P2X_7$ receptor forms: in Day-2 cells, the predominant form was the 65-kDa; in contrast, in Day-6 cells, the levels of the 85-kDa and 18-kDa forms were greater than in Day-2 cells. FIG. 55, Panel D, left lanes). These results suggest that the mature and functional form of the $P2X_7$ receptor protein is the 85-kDa form.

Incubation in vitro of cell lysates with N-glycosidase F showed a decrease in the density of the 85-kDa form along with an increase in the density of the 65-kDa form. FIG. 55, Panel C. Densitometry analysis of two experiments indicates that the ratio of 65-kDa/85-kDa increased more than 3-fold after treatment in vitro with N-glycosidase F. These data indicate that the 85-kDa form is the glycosylated form of the $P2X_7$ receptor. Pretreatment of CaSki cells with EGF alone had only mild effect on the levels of the $P2X_7$ receptor forms, increasing mainly the 18-kDa form in Day-6 cells. Pretreatment of d-2 cells with epinephrine decreased the 65-kDa form; whereas in Day-6 cells, it decreased the 85-kDa and 65-kDa forms and increased the 18-kDa form. Cotreatment of Day-2 cells with EGF plus epinephrine increased the 18-kDa form 50-fold; cotreatment of Day-6 cells decreased the 85-kDa form and increased the 18-kDa isoform 35-fold. In addition, in Day-6 cells, treatment with epinephrine plus EGF resulted in the appearance of an intermediate form of 75-kDa.

Collectively, these data indicate that EGF facilitates epinephrine-induced decrease of the glycosylated 85-kDa form of the $P2X_7$ receptor, and of $P2X_7$ receptor degradation. The data also suggest that EGF, acting in concert with epinephrine, induces deglycosylation of the $P2X_7$ receptor.

---

We claim:

1. An isolated $P_2X_7$ protein comprising SEQ ID NO:6, wherein said SEQ ID NO: 6 comprises an altered C-terminus, wherein said terminus comprises IRQVLQGKQC (SEQ ID NO:1).

2. The protein of claim 1, wherein said protein is encoded by a nucleic acid sequence comprising SEQ ID NO: 5.

3. The protein of claim 2, wherein said nucleic acid sequence comprises a frameshift mutation.

4. The protein of claim 3, wherein said nucleic acid sequence encodes a truncated protein.

* * * * *